United States Patent [19]
Gomez et al.

[11] Patent Number: 5,952,334
[45] Date of Patent: Sep. 14, 1999

[54] CARBOCYCLIC COMPOUNDS

[75] Inventors: Jose Ruiz Gomez; Jose Marie Bueno Calderon; Silvestre Garcia-Ochoa Dorado; Maria T. Fraile Gabaldon; Julia C. Pichel; Jose Fiandor Roman; Domingo Gargallo Viola; Juan C. Cuevas Zurita; Jose L. Lavandera Diaz; Sophie Huss, all of Madrid, Spain

[73] Assignee: Glaxo Wellcome S.A., Spain

[21] Appl. No.: 09/081,090

[22] Filed: May 19, 1998

Related U.S. Application Data

[63] Continuation of application No. 08/669,441, filed as application No. PCT/EP95/04331, Nov. 6, 1995, Pat. No. 5,854, 280.

[30] Foreign Application Priority Data

Nov. 8, 1994 [EP] European Pat. Off. .............. 94500173
Nov. 8, 1994 [EP] European Pat. Off. .............. 94500175

[51] Int. Cl.$^6$ ........................ A01N 43/54; A01N 43/02; A01N 43/64
[52] U.S. Cl. ........................ 514/269; 514/149; 514/183; 514/383; 514/430; 514/456; 514/450
[58] Field of Search ..................... 549/90, 396; 514/430, 514/456, 183, 149, 269, 450, 383

[56] References Cited

FOREIGN PATENT DOCUMENTS

WO 98/10782 3/1998 WIPO .

OTHER PUBLICATIONS

Patent Abstracts of Japan vol. 18, No. 485 (C–1248), 1994 JP,A,06 157582 Banyu Pharmaceut. Co. Ltd. Jun. 1994.
Patent Abstracts of Japan vol. 11, No. 119 (C–436), 1987 JP,A,62 040292 Sankyo Co. Ltd. Feb. 1987.
Helvetica Chimcia Acta, vol. 54, No. 119, Basel, CH pp. 1178–1190, XP002000182 Hauser D. and Sigg H.P.: "Isolierung und Abbau von Sordarin".

Primary Examiner—Amelia Owens
Attorney, Agent, or Firm—Nixon & Vanderhye

[57] ABSTRACT

A compound of formula

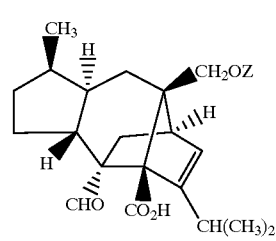

(I)

wherein Z is a tetrahydro-pyrano group selected from

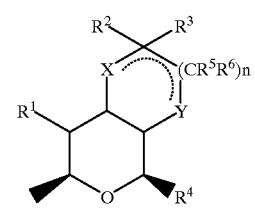

(a)

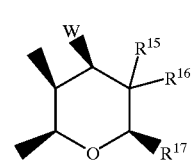

(b)

having antifungal activity in combination with other antifungal agents.

6 Claims, No Drawings

CARBOCYCLIC COMPOUNDS

This a continuation of application Ser. No. 08/669,441, filed Oct. 18, 1996, now U.S. Pat. No. 5,854,280, which is a 371 of PCT/EP95/04331, filed Nov. 6, 1995.

This invention relates to novel sordarin derivatives having antifungal activity, to processes for their preparation, to pharmaceutical compositions containing them and to their use in medicine, more particularly in the prevention or treatment of diseases in animals, including humans, caused by fungal infection.

British Patent Specification No. 1,162,027 describes the preparation of an antibiotic, SL2266, by the cultivation of the strain NRRL 3196 of the fungus species *Sordaria araneosa*. SL 2266, later named sordarin, is reported to have fungistatic activity. The same research group also described in Helvetica Chimica Acta (1971), 51, 119–120 the degradation of sordarin to sordaricin. Published Japanese Patent Application No. J6 2040292A describes the preparation of an antibiotic, zofimarin, which is reported to have antifungal activity.

Sordarin, sordaricin and zofimarin may be represented by formula (A) below

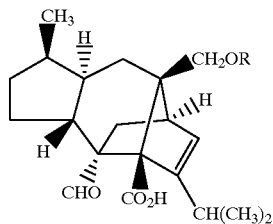
(A)

where
OR as

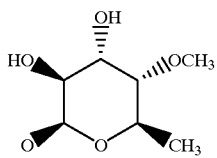

describes sordarin;
OR as OH describes sordaricin; and
OR as

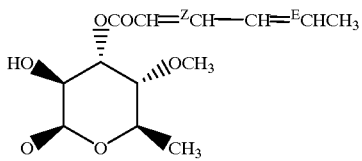

describes zofimarin.

Although sordarin and zofimarin exhibit antifungal activity, both compounds are only moderately active and have limited spectra of action when tested against a battery of fungal organisms. We now describe hereinafter a novel group of fungicidal sordarin derivatives which exhibit excellent antifungal activity and a broad spectrum of action. Thus, according to a first aspect of the present invention, we provide compounds of formula (I)

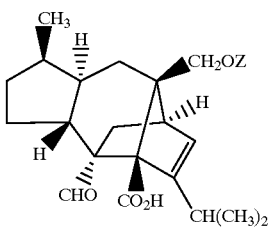
(I)

wherein Z is a tetrahydro-pyrano group selected from

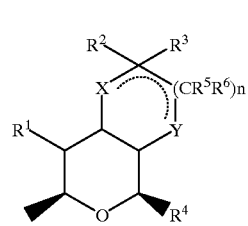
(a)

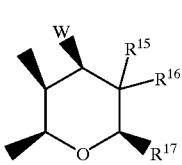
(b)

and pharmaceutically acceptable salts and solvates (e.g. hydrates) or metabolically labile derivatives thereof, wherein $R^1$ represents hydrogen, halogen, hydroxyl, $C_{1-4}$alkoxy or acyloxy;

$R^2$ and $R^3$ may each independently represent hydrogen, $C_{1-6}$alkyl or $C_{1-4}$alkoxy $C_{1-4}$alkyl or $R^2$ and $R^3$ may together with the carbon atom to which they are attached represent C=O, C=S or $C_{3-8}$cycloalkyl;

$R^4$ represents hydrogen or $CH_2R^7$ (where $R^7$ is hydrogen, hydroxyl, $C_{1-4}$alkoxy or a group $OCOR^8$ in which $R^8$ is $C_{1-4}$alkyl or aryl);

$R^5$ and $R^6$ may each independently represent hydrogen, $C_{1-6}$alkyl or $C_{1-4}$alkoxy $C_{1-4}$alkyl or $R^5$ and $R^6$ may together with the carbon atom to which they are attached represent C=O, C=S or $C_{3-8}$cycloalkyl;

n represents zero or 1;

X and Y may each independently represent oxygen, sulphur or $CR^9R^{10}$ (where $R^9$ and $R^{10}$ may each independently represent hydrogen, $C_{1-6}$alkyl, $C_{1-4}$alkoxy or $C_{1-4}$alkoxyC$_{1-4}$alkyl or $R^9$ and $R^{10}$ may together with the carbon atom to which they are attached represent C=O C=S, $C_{3-8}$cycloalkyl or C=CHR$^{11}$ where $R^{11}$ represents hydrogen or $C_{1-4}$alkyl); or when X or Y is oxygen and n is zero then —Y—CR$^2$R$^3$— or —X—CR$^2$R$^3$— respectively may also represent —N=CR$^3$— or —NR$^{12}$—CR$^2$R$^3$— (where CR$^2$ and R$^3$ are C=O and R$^{12}$ is $C_{1-4}$alkyl an acyl group COR$^{13}$ where $R^{13}$ is $C_{1-6}$alkyl) or when Y is oxygen and n is zero X may be represent the group $CR^{11}$ (wherein $R^{11}$ has the meanings defined above) which is attached to the pyran ring by a double bond;

$R^{15}$ represents hydrogen, halogen, azido, $C_{1-6}$alkyl, hydroxy, $C_{1-6}$alkoxy (optionally substituted by 1 or 2 hydroxy or a ketal thereof or 1 or 2 $C_{1-3}$ alkoxy groups), arylC$_{1-4}$alkoxy, C$_{3-6}$ alkenyloxy, a group OCOR$^{18}$ (where R$^{18}$ is arylC$_{1-4}$alkoxy or a C$_{1-10}$alkyl group optionally containing one or two double bonds) or C$_{1-6}$alkoxycarbonyl C$_{1-4}$alkoxy, and R$^{16}$ represents hydrogen or R$^{15}$ and R$^{16}$ may together with the carbon atom to which they are attached represent C=O or C=CH$_2$;

R$^{17}$ represents CH$_2$R$^{19}$ where R$^{19}$ is hydrogen, hydroxyl, C$_{1-14}$alkoxy or a group OCOR$^{20}$ in which R$^{20}$ is C$_{1-4}$alkyl); and W represents an oxygen or sulphur atom or a CH$_2$ group;

and the dotted line in group (a) indicates the optional presence of an additional bond;

Suitable pharmaceutically acceptable salts of the compounds of formula (I) include inorganic base salts such as alkali metal salts (for example sodium and potassium salts) and ammonium salts and organic base salts. Suitable organic base salts include amine salts such as trialkylamine (e.g. triethylamine), dialkylamine (e.g. dicyclohexylamine), optionally substituted benzylamine (e.g. phenylbenzylamine or p-bromobenzylamine), procaine, ethanolamine, diethanolamine, N-methylglucosamine and tri(hydroxymethyl)methylamine salts and amino acid salts (e.g. lysine and arginine salts).

References hereinafter to a compound of formula (I) includes that compound and its pharmaceutically acceptable salts.

Other salts which are not pharmaceutically acceptable may be useful in the preparation of compounds of formula (I) and these form a further aspect of the invention.

Metabolically labile derivatives of compounds of formula (I) are compounds which are converted in the body to compounds of formula (I). Examples of such derivatives include conventional metabolically labile esters formed from the free carboxylic acid in the molecule.

It is to be understood that the present invention encompasses any individual isomers, including optical isomers, of compounds represented by formula (I) above as well as mixtures thereof, including wholly or partially racemic mixtures thereof.

As used herein, "alkyl" as a group or part of a C$_{1-4}$alkoxy group may be a straight or branched chain. Suitable examples include methyl, ethyl, n-propyl, i-propyl, n-butyl, s-butyl and t-butyl, n-hexyl and n-octyl.

As used herein, the term "aryl" as a group or part of a group means phenyl or heteroaryl each optionally substituted by one or more (e.g. 1, 2 or 3) atoms or groups selected from halogen, hydroxyl, C$_{1-6}$alkyl, C$_{1-6}$alkoxy or C$_{1-4}$alkoxy carbonyl. The heteroaryl group may be a 5- or 6-membered heteroaromatic ring containing one or more heteroatoms selected from nitrogen, oxygen and sulphur. Suitable examples of heteroaryl groups include pyridyl, furyl, thienyl and pyrrolyl.

The term "halogen" means herein fluorine, chlorine, bromine or iodine.

When R$^1$ is an acyloxy group it may represent, for example, a group OCOR$^{13}$ where R$^{13}$ is as defined above.

Examples of C$_{3-8}$cycloalkyl groups include cyclopentyl and cyclohexyl groups.

Examples of X groups include oxygen, CR$^9$R$^{10}$ wherein R$^9$ and R$^{10}$ are each hydrogen, C$_{1-4}$ alkoxy or C$_{1-4}$alkyl or CR$^9$R$^{10}$ represent the group C=O or C=CHR$^{11}$ e.g. C=CH$_2$, or X represents CR$^{11}$.

Examples of suitable Y groups include oxygen or CR$^9$R$^{10}$ wherein R$^9$ is hydrogen, C$_{1-4}$alkoxy or C$_{1-4}$alkyl and R$^{10}$ is hydrogen or C$_{1-4}$alkyl.

When R$^{18}$ is an unsaturated C$_{1-10}$alkyl group it may particularly represent a straight or branched chain C$_{5-8}$alkyl group containing two double bonds, for example —CH=$^Z$CH—CH=$^E$CHCH$_3$.

When R$^{15}$ is a C$_{1-6}$ alkoxy group substituted by hydroxy or alkoxy, this may be for example 2,3-dihydroxy propoxy and the acetone ketal derived therefrom or a 2,3-dimethoxypropoxy group.

R$^{16}$ is preferably a hydrogen atom with R$^{15}$ sited in the α-configuration.

R$^1$ may represent, for example, a hydrogen atom or a hydroxyl group.

R$^2$ may represent, for example, hydrogen or C$_{1-4}$alkyl (e.g. methyl), and R$^3$ may represent, for example, hydrogen, C$_{1-4}$alkyl (e.g. methyl, ethyl or n-propyl) or C$_{1-4}$alkoxyC$_{1-4}$alkyl (e.g. methoxyethyl), or CR$^2$R$^3$ may represent C=O, C=S or C$_{3-8}$cycloalkyl (e.g. cyclopentyl).

R$^4$ may represent, for example, methyl or C$_{1-4}$alkoxymethyl (e.g. methoxymethyl).

R$^5$ and R$^6$ may each independently represent, for example, hydrogen or C$_{1-4}$alkyl (e.g. methyl).

Examples of ring systems represented by

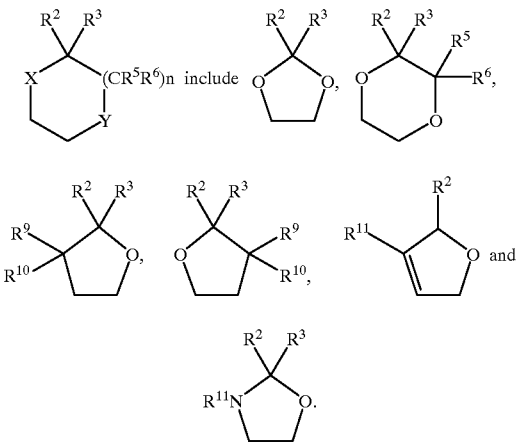

Examples of particular R$^{15}$ groups include halogen (e.g. fluorine), azido hydroxyl, C$_{1-4}$alkoxy, benzyloxy, benzyloxycarbonyloxy, C$_{1-4}$alkoxycarbonyloxy and C$_{1-4}$alkoxyC$_{1-4}$alkoxy (e.g. methoxyethoxy), C$_{1-4}$alkoxycarbonyl-C$_{1-4}$alkoxy, C$_{1-4}$alkylcarbonyloxy, 2,3-dihydroxy propoxy, and the acetone ketal thereof, 2,3dimethoxy propoxy, C$_{3-6}$ alkenyloxy e.g. allyloxy or 3methylallyloxy or R$^{15}$ and R$^{16}$ and the carbon atom to which they are attached represents C=O or C=CH$_2$.

R$^{17}$ may represent, for example, methyl or C$_{1-4}$alkoxymethyl (e.g. methoxymethyl) or hydroxy methyl.

R$^{15}$ preferably represents C$_{1-4}$alkoxy, C$_{3-4}$alkenyloxy, benzyloxy or OCOR$^4$ (where R$^4$ is a C$_{1-4}$alkyl group), especially sited in the α-configuration.

R$^{17}$ preferably represents methyl.

W preferably represents oxygen.

A particular group of compounds of the invention are compounds of formula (I) are those wherein Z is the group.

wherein one of X and Y is oxygen and the other is oxygen or the group CR$^9$R$^{10}$. Within this group more particularly R$^1$ is hydroxyl or hydrogen; X is oxygen, or CR$^9$R$^{10}$ wherein R$^9$ is hydrogen, C$_{1-3}$alkoxy, C$_{1-4}$alkyl and R$^{10}$ is hydrogen or CR$^9$R$^{10}$ represent the group C=O, or C=CHR$^{11}$; Y is oxygen or CHR$_9$ wherein R$^9$ is H or C$_{1-4}$ alkyl, R$^2$ and R$^3$ each independently represent hydrogen, C$_{1-4}$ alkyl e.g. methyl, propyl or C$_{1-4}$alkoxy alkyl e.g. methoxymethyl or R$^2$ and R$^3$ together with the carbon atom to which they are attached represent a cyclopentyl group or the group C=O or C=S; R$^5$ and R$^6$ are each preferably hydrogen.

When R$^1$ represents hydroxyl or C$_{1-4}$alkoxy, the R$^1$ moiety is preferably sited in the axial configuration. However, R$^1$ preferably represents a hydrogen atom.

R$^2$ and R$^3$ may each particularly represent individually hydrogen or C$_{1-4}$alkyl.

R$^4$ preferably represents methyl.

R$^5$ and R$^6$ are each preferably hydrogen.

n preferably represents zero.

Particular ring systems represented by where R$^2$ and R$^3$ are as defined previously and X and Y are each independently oxygen, or CR$^9$R$^{10}$ (where R$^9$ and R$^{10}$ are as defined previously), provided that at least one of X and Y is oxygen or the ring.

Within the ring systems preferred rings are those wherein one of X and Y represents oxygen and the other represents CR$^9$R$^{10}$ (where R$^9$ and R$^{10}$ each independently represent hydrogen or C$_{1-4}$alkyl (e.g. methyl) or CR$^9$R$^{10}$ represent the group C=O or C=CH$_2$) or X and Y both represent oxygen; R2 and R3 represent hydrogen, C$_{1-4}$ alkyl or the group CO.

It is to be understood that the present invention covers all combinations of particular and preferred groups described hereinabove.

A further particular group of compounds of the invention are compounds of formula (I) wherein Z is a group (a) and wherein R$^1$ is hydrogen R$^4$ is methyl;

n is zero and R$^2$ and R$^3$ are hydrogen or C$_{1-4}$ alkyl, X and Y are oxygen or Y is oxygen and X is the group CHR$^9$ wherein, R$^9$ is hydrogen or C$_{1-4}$ alkyl C=O, C=CH$_2$ or X is CH, Y is oxygen, n is zero and R$^2$ and R$^3$ are hydrogen.

A further particular group of compounds of the invention are compounds of formula (I) wherein Z is the group (b).

and pharmaceutically acceptable salts and solvates (e.g. hydrates) thereof, wherein W is oxygen or sulphur and R$^{15}$ is as defined previously. More particularly, W is oxygen and R$^{15}$ is a group selected from C$_{1-4}$alkoxy, benzyloxy or OCOR$^4$ (where R$^4$ is a C$_{1-4}$alkyl group.g. isopropyl or t-butyl), or C$_{3-4}$alkenyloxy, C$_{1-4}$alkoxycarbonylalkoxy.

Specific compounds according the present invention include:

[1R-(1α, 3aβ, 4β, 4aβ, 7β, 7aα, 8aβ)] 8a-[[1S, 7R, 9R]-2,8-Dioxa-9-methyl-4-methylene-cis-bicyclo[3.4.0]-non-7-yl-oxy-methyl]-4-formyl-4,4a,5,6,7,7a,8,8a-octahydro-7-methyl-3-(1-methylethyl)-1,4-methano-s-indacene-3a(1H)-carboxylic acid.

[1R-(1α,3aβ,4β,4aβ,7β,7aα,8aβ)] 8a-[(2,6-dideoxy-3,4-O-isopropylidene-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid;

[1R-(1α,3aβ,4β,4aβ,7β,7aα,8aβ)] 8a-[[1S,4R,7R,9R]-2,8-Dioxa-4,9-dimethyl-cis-bicyclo[3.4.0]-non-7-yl-oxy-methyl]-4-formyl-4,4a,5,6,7,7a,8,8a-octahydro-7-methyl-3-(1-methylethyl)-1,4-methano-s-indacene-3a(1H)-carboxylic acid;

[1R-(1α,3aβ,4β,4aβ,7β,7aα,8aβ)] 8a-[[1S,4S,6R,8R]-2,7-dioxa-4,6-dimethyl-cis-bicyclo[3.4.0]-non-8-yl-oxy-methyl]-4-formyl-4,4a,5,6,7,7a,8,8a-octahydro-7-methyl-3-(1-methylethyl)-1,4-methano-s-indacene-3a(1H)-carboxylic acid;

[1R-(1α, 3aβ, 4β, 4aβ, 7β, 7aα, 8aβ)] 8a-[(2,3-anhydro-6-deoxy-4-O-propyl-β-D-mannopyranosyloxy)methyl]-4-formyl-4,4a,5,6,7,7a,8,8a-octahydro-7- methyl-3-(1-methylethyl)-1,4-methano-s-indacene3a (1H)-carboxylic acid;

[1R-(1α, 3aβ, 4β, 4aβ, 7β, 7aα, 8aβ)] 8a-[(2,3-anhydro-6-deoxy4-O-methyl-β-D-mannopyranosyloxymethyl] 4-formyl-4,4a,5,6,7,7a,8,8a-octahydro-7-methyl-3-(1-methylethyl)-1,4-methano-s-indacene-3a(1H)-carboxylic acid;

and pharmaceutically acceptable salts and solvates (e.g. hydrates) or metabolically labile derivatives thereof.

The compounds of formula (I) are very active fungicides useful in combatting fungal infections in animals, including humans. For example, they may be used in the treatment of fungal infections caused by organisms such as species of Candida (e.g. *Candida albicans, Candida glabrata,* (*Torulopsis glabrata*), *Candida tropicalis, Candida parapsilosis* and *Candida pseudotropicalis*), *Cryptococcus neoformans, Pneumocystis carinii,* Aspergillus Sp (e.g. *Asperaillus flavus* and *Aspergillus fumigatus*), Coccidioides (e.g. *Coccidioides immitis*), Paracoccidioides (e.g. *Paracoccidioides brasiliensis*), Histoplasma (e.g. *Histoplasma capsulatum*) or Blastomyces (e.g. *Blastomyces dermatitidis*). They may also be used to treat other fungal infections caused by species of Candida, Trichophyton, Microsporum or Epidermophyton (e.g. *Trichophyton mentographytes, Trichophyton rubrum, Microsporum canis* or *Epidermophyton floccosum*), or in mucosal infections caused by *Candida albicans.*

Compounds of formula (I) may also be used to treat other infections caused by species of filamentous fungi such as Geotrichum (e.g. *Geotrichum clavatum*), Trichosporon (e.g. *Trichosporon beigelii*), Blastoschizomyces (e.g. *Blastoschizomyces capitatus*), Sporothrix (e.g. *Sporothrix schenckii*), Scedosporium (e.g. *Scedosporium apiosperum*), Cladosporium (e.g. *Cladosporium carrionii*) and *Pityrosporum ovale.*

The compounds of formula (I) may also be used to treat infections caused by protozoa such as Toxoplasma, Cryptosporidium, Leishmania, Tripanosoma, Giardia and Trichomonas.

The in vitro evaluation of the anti-fungal activity of compounds of the invention was performed on liquid or solid medium by the antifungal two-fold serial dilution technique of determining the minimum inhibitory concentration (MIC) of anti-fungal agent that inhibited development of growth after 24 to 48 hours of incubation at 37° C. In practice, a series of agar plates or broth microdilution panels containing two-fold dilutions of anti-fungal agent tested were inoculated with a standard culture of a clinically relevant pathogen, for example, candida albicans. The agar plates or broth microdulution panels were then examined for the presence or absence of growth of the fungus and the appropriate MIC values were noted.

MFC values (defined as the lowest anti-fungal concentration that killed at least 99.9% of the initial inoculum in liquid medium) may also be determined by sub-culturing 0.01 and 0.1 μl of broth from the drug-free control well, the first well containing growth and each clear well on agar plates.

The in vivo evaluation of compounds of formula (I) can be carried out at a series of dose levels by administration (e.g. subcutaneously, orally, intraperitoneally or intravenously) to mice or rats inoculated with a strain of *Candida albicans.* Untreated animals die within 3 to 9 days and the dose level at which the test compound provides 50% protection against the lethal effect of the infection is noted.

In view of their antifungal activity, compounds of formula (I) recommend themselves for the treatment of a variety of fungal infections in human beings and animals. Such infections include superficial, cutaneous, subcutaneous and systemic mycotic infections such as respiratory tract infections, gastrointestinal tract infections, cardiovascular infections, urinary tract infections, CNS infections, candidiasis and chronic mucocandidiasis (e.g. thrush and vaginal candidiasis) and skin infections caused by fungi, cutaneous and mucocutaneous candidiasis, dermatophytoses including ringworm and tinea infections, athletes foot, paronychia, pityriasis versicolor, erythrasma, intertrigo, fungal nappy rash, candida vulvitis, candida balanitis and otitis extema. They may also be used as. prophylactic agents to prevent systemic and topical fungal infections. Use as prophylactic agents may, for example, be appropriate as part of a selective gut decontamination regimen in the prevention of infection in immunocompromised patients (e.g. AIDS patients, patients receiving cancer therapy or transplant patients). Prevention of fungal overgrowth during antibiotic treatment may also be desirable in some disease syndromes or iatrogenic states.

While it is possible that, for use in therapy, compounds of the invention may be administered as the raw chemical, it is preferable to present the active ingredient as a pharmaceutical formulation. The invention thus further provides a pharmaceutical formulation comprising compounds of formula (I) and physiologically acceptable salts thereof together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, implant, rectal, topical, ophthalmic or genito-urinary administration or in a form suitable for administration by inhalation or insufflation.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate or crosscarmellose sodium; or wetting agents such as sodium lauryl sulphate. The tablets which include chewable, dispersible or effervescent tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compositions according to the invention are conveniently delivered in the form of an aerosol spray presentation from pressurised packs with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation the compositions according to the invention may take the form of a dry powder composition, for example a powder mix of the compound and a suitable powder base such as lactose or starch or as a modified physical form of the drug substance alone. The powder composition may be presented in unit dosage form in, for example, capsules or cartridges of e.g. gelatin, or blister packs from which the powder may be administered with the aid of an inhaler or insufflator.

The compositions may take the form of a suppository, e.g. containing a conventional suppository base, or a pessary, e.g. containing a conventional pessary base.

The compositions may also be formulated for topical administration in the form of ointments, creams, gels, lotions, shampoos, powders (including spray powders), pessaries, tampons, sprays, dips, aerosols, drops (e.g. eye, ear or nose drops) or pour-ons. Ointments and creams may, for example, be formulated with an aqueous or oily base with the addition of suitable thickening and/or gelling agents. Ointments for administration to the eye may be manufactured in a sterile manner using sterilised components. Pour-ons may, for example, be formulated for veterinary use in oils containing organic solvents, optionally with formulatory agents, e.g. stabilising and solubilising agents. Pessaries and tampons for vaginal insertion may be formulated using conventional techniques and, where appropriate, may contain an effervescent vehicle. Such compositions may also contain other active ingredients such as corticosteroids, antibiotics or antiparasitics as appropriate.

Liquid preparations for intranasal delivery may take the form of solutions or suspensions and may contain conventional excipients such as tonicity adjusting agents, for example, sodium chloride, dextrose or mannitol; preservatives, for example benzalkonium chloride, thiomersal, phenylethyl alcohol; and other formulating agents such as suspending, buffering, stabilising, dispersing and or flavouring agents.

Transdermal administration may be affected by the design of a suitable system which promotes absorption of the active compound through the skin and would typically consist of a base formulation enclosed within an adhesive stick-on patch comprising backing films, membranes and release liners. Such systems may include absorption enhancers such as alcohols or work by promoting ionotophoresis.

The composition according to the invention may also be formulated as a depot preparation. Such long acting formulations may be administered by implantation (for example subcutaneously or intramuscularly) or by intramuscular injection. Thus, for example, a compound of the invention may be formulated with suitable polymeric or hydrophobic materials (for example as an emulsion in an acceptable oil) or ion exchange resins, or as sparingly soluble derivatives, for example, as a sparingly soluble salt.

When the compositions comprise dosage units, each unit will preferably contain 0.001 mg to 1000 mg, advantageously 0.01 mg to 400 mg, of active ingredient where a compound of the invention is to be administered orally. The daily dosage as employed for adult human treatment will preferably range from 0.001 mg to 5000 mg of active ingredient, most preferably from 0.01 mg to 2000 mg which may be administered in 1 to 4 daily doses, for example, depending on the route of administration and on the condition of the patient and the disease to be treated.

The compound may be administered by intravenous infusion using, for example, up to 50 mg/kg/day of the active ingredient. The duration of treatment will be dictated by the rate of response rather than by arbitrary numbers of days.

Compounds of the invention may also be used in combination with other therapeutic agents, and the invention thus provides, in a further aspect, a combination comprising a compound of the invention together with another therapeutically active agent.

Thus for example the compounds of the invention may be used in combination with one or more other antifungal agents, such as a polienic derivative e.g. (Amphotericin B, Nystatin, a lipid formulation of Amphotericin B) an azole derivative e.g. (Fluconazole, Intraconazole, Ketoconazole, Miconazole, Clotrimazole, ZD-08070, UK-109496), 5-Fluorocytosine, a Pneumocandin or Echinocandine derivative such as Cilofungin, LY-303366, L-733560, and/or one or more immunomodulating agents such as an interferon e.g. (IFN-$\gamma$), interleukine e.g. (IL-1, IL-2, IL-3 and IL-8) and colony stimulating factors, [(G)-CSF, (M)-CSF and (GM)-CSF] and defensines. Particularly advantageous compounds for use with compounds of the invention include Intraconazole, Flucytosine, Fluconazole or Amphotericin B.

When the compounds of the invention are administered in combination with another antifungal agent the compounds of the invention and the other fungal agent can be administered at the recommended maximum clinical dosage or at lower doses.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention. The individual components of such combinations may be administered either sequentially or simultaneously in separate or combined pharmaceutical formulations.

When a compound of the invention is used in combination with a second therapeutic agent against the same condition the dose of each compound may differ from that when the compound is used alone. Appropriate doses will be readily appreciated by those skilled in the art.

According to another aspect of the present invention, we provide a compound of formula (I) or a physiologically acceptable salt thereof or a pharmaceutical composition comprising a compound of formula (I) or a physiologically acceptable salt thereof as defined above for use in therapy, particularly for the treatment of fungal infections in animals (especially humans).

According to another aspect of the present invention, we provide the use of a compound of formula (I) or a physiologically acceptable salt thereof in the manufacture of a medicament for the treatment of fungal infections in a human or non-human animal patient.

According to a further aspect of the present invention, we provide a method of treatment of the human or non-human animal body to combat fungal diseases, which method comprises administering to said body an effective amount of a compound of formula (I) or a physiologically acceptable salt thereof.

It will be appreciated by those skilled in the art that references herein to treatment extend to prophylaxis as well as the treatment of established conditions or infections.

The compounds of the invention may be prepared by the processes described below.

Thus, a general process (A) for the preparation of a compound of formula (I) wherein Z is the group (a) comprises reacting a compound of formula (II)

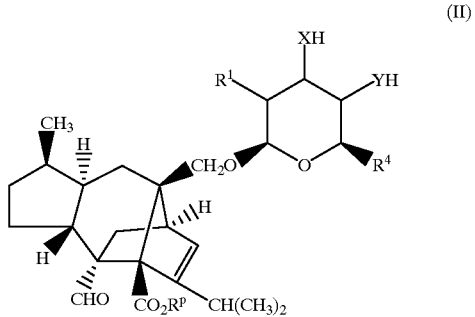

(II)

(in which $R^1$ and $R^4$ are as defined in formula (I) above, $R^p$ is a carboxyl protecting group and X and Y are as defined in formula (I) above, except that X and/or Y cannot represent $CR^9R^{10}$) to form the desired cyclic system, followed by the removal of the carboxyl protecting group.

According to a first embodiment of process (A), a compound of formula (Ia) in which $R^1$ to $R^4$ are as defined in formula (I) above, n is zero and X and Y are both oxygen may be prepared by treating a diol of formula (III)

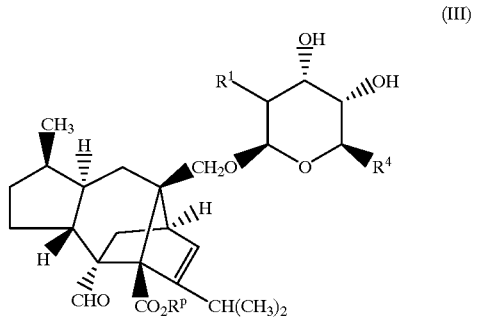

(III)

(in which $R^1$ and $R^4$ are as defined in formula (I) above and $R^p$ is a carboxyl protecting group) with a compound $(L)_2CR^2R^3$ (in which L is a suitable leaving group), followed by the removal of the carboxyl protecting group. When $R^2$ and $R^3$ both represent hydrogen the ring-forming reaction may conveniently be effected by treating a compound of formula (III) with a dihalomethane (e.g. dibromomethane) in the presence of a strong base, such as an alkali metal hydroxide (e.g. sodium hydroxide), preferably under phase transfer conditions, using for example a tetraalkylammonium salt (e.g. tetrabutylammonium bromide), at about ambient temperature. When at least one of $R^2$ and $R^3$ is a $C_{1-6}$alkyl group or a $C_{1-4}$alkoxy$C_{1-4}$alkyl group or $CR^2R^3$ is a $C_{3-8}$cycloalkyl group the ring-forming reaction may conveniently be effected by treating a compound of formula (III)

with a ketal $(RO)_2CR^2R^3$ (wherein R is a $C_{1-6}$alkyl group, e.g. methyl), preferably in the presence of a suitable acid such as p-toluenesulphonic acid or pyridinium p-toluenesulphonate, and in a suitable solvent such as a ketone (e.g. acetone), a nitrile (e.g. acetonitrile) or a halogenated hydrocarbon (e.g. dichloromethane) at about room temperature. Compounds of formula (Ia) in which X and/or Y represents sulphur may be similarly prepared from intermediates corresponding to those of formula (III) in which one or both of the diol hydroxyl groups is replaced by thiol. When $CR^2R^3$ represents C=O or C=S the ring-forming reaction may conveniently be effected by reacting a compound of formula (III) with carbonyldiimidazole or thiocarbonyidiimidazole in a suitable solvent such as a hydrocarbon (e.g. toluene) or an ether (e.g. tetrahydrofuran) under reflux. Alternatively, when $CR^2R^3$ represents C=S the ring-forming reaction may be effected by treating a compound of formula (III) with a tin oxide (e.g. dibutyltin oxide) in a hydrocarbon solvent (e.g. refluxing toluene), followed by the addition of a halothionoformate (e.g. phenyl chlorothionoformate) in a hydrocarbon solvent (e.g. toluene) at about room temperature.

According to a further embodiment of process (A), a compound of formula (I) in which $R^1$ and $R^4$ are as defined in formula (I) above, one of $R^2$ and $R^3$ represents $C_{1-6}$alkyl and the other represents hydrogen, $C_{1-6}$alkyl or $C_{1-4}$alkoxy$C_{1-4}$alkyl, $(CR^5R^6)n$ represents $CR^5R^6$ where $R^5$ and $R^6$ are as defined in formula (I) above and X and Y both represent oxygen may be prepared by treating a diol of formula (III) with a tin oxide (e.g. dibutyltin oxide) in a hydrocarbon solvent (e.g. refluxing toluene), followed by addition of an allylhalide $HalCR^5R^6CR^2=CHR^{14}$ (where $R^{14}$ is hydrogen or $C_{1-6}$alkyl and Hal is halogen, e.g. bromine) and a fluoride salt (e.g. tetrabutylammonium fluoride) in a suitable solvent such as an ether (e.g. tetrahydrofuran), and heating the mixture at a temperature in the range of about 40° to 80° C. to give a compound of formula (IV)

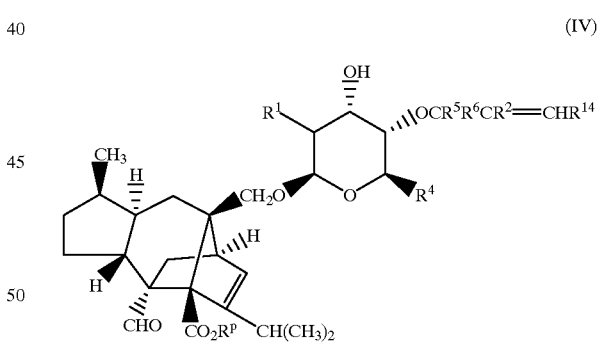

(IV)

which may be converted to the desired compound of formula (Ia) by cyclisation involving an intramolecular electrophilic addition induced by a mercury salt (e.g. mercuric trifluoroacetate) followed by a hydride reduction, for example using a trialkyltin hydride (e.g. tributyltin hydride), and thereafter removing the carboxyl protecting group. The reaction may conveniently be effected at about room temperature in the presence of a suitable solvent such as an ether (e.g. tetrahydrofuran).

In another embodiment of process (A), a compound of formula (Ia) in which $R^1$ to $R^4$ are as defined in formula (I) above, n is zero and one of X and Y represents oxygen and the other is $CR^9R^{10}$ (where one of $R^9$ and $R^{10}$ represents $C_{1-6}$alkyl and the other represents hydrogen, $C_{1-6}$alkyl or $C_{1-4}$alkoxy$C_{1-4}$alkyl or $CR^9R^{10}$ represents $C=CHR^{11}$) may be prepared by treating a compound of formula (III) with a tin oxide (e.g. dibutyltin oxide) in a hydrocarbon solvent (e.g. refluxing toluene) and optionally in the presence of a fluoride salt (e.g. tetrabutylammonium fluoride), and then either adding thereto an allylhalide $HalCR^2R^3CR^9=CHR^{14}$ or an alkynylhalide $HalCR^2R^3C\equiv CR^{11}$ (where $R^{11}$, $R^{14}$ and Hal are as defined previously) or adding the allylhalide or alkynylhalide after protection of one of the diol hydroxyl groups, to give a compound of formula (V)

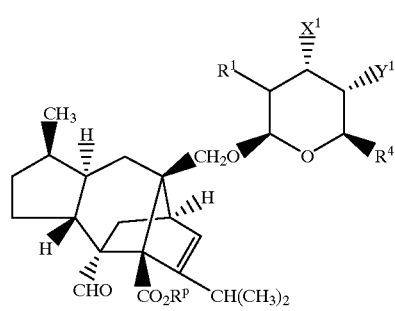

(V)

(where $X^1$ represents OH and $Y^1$ represents $OCR^2R^3CR^9=CHR^{14}$ or $OCR^2R^3C\equiv CR^{11}$, or $X^1$ represents $OCR^2R^3CR^9=CHR^{14}$ or $OCR^2R^3C\equiv CR^{11}$ and $Y^1$ represents a protected hydroxyl group). The cyclisation may be completed by first removing the hydroxyl protecting group, when present, then activating the free hydroxyl group, for example by forming an S-alkyldithiocarbonate (e.g. S-methyldithiocarbonate) and then closing the ring under radical conditions, for example by treating a solution of the activated intermediate in a hydrocarbon solvent (e.g. toluene) under reflux with a hydrogen donor, for example a hydride reducing agent (e.g. a trialkyltin hydride such as tributyltin hydride) in the presence of an activating agent [e.g. azobis(isobutyronitrile)], and thereafter removing the carboxyl protecting group. The formation of an S-alkyldithiocarbonate may conveniently be effected by treating a compound of formula (V) in which one of $X^1$ and $Y^1$ is OH and the other is $OCR^2R^3CR^9=CHR^{14}$ or $OCR^2R^3=CR^{11}$ with a strong alkali metal base (e.g. sodium hydride), in the presence of imidazole, and in a suitable solvent such as an ether (e.g. tetrahydrofuran) at a reduced temperature (e.g. about 0° C.), and then adding carbon disulphide and an alkyl halide (e.g. methyl iodide) at about room temperature.

In a further embodiment of process A a compound of formula (I) wherein Y is oxygen, n is zero, $R^2$ and $R^3$ are hydrogen and X is the group $CR^9R^{10}$ may be prepared by reacting a compound of formula (V) wherein $X^1$ is hydroxyl with triphenylphosphine, iodine and imidazole in a suitable solvent such as tetrahydrofuran to yield the desired 4 iodo derivative (Va). The required ring closure can then be effected under radical conditions such as reaction with a trialkyl tinhydride in a hydrocarbon solvent together with heating.

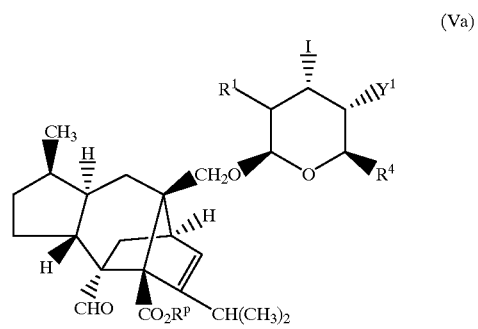

(Va)

In a further emboidment of process A compounds of formula (I) wherein Y is oxygen, X is $NR^{12}$ and the group $CR^2R^3$ is $C=O$ may be prepared by reaction of iodo compound of formula (Va) with sodium hydride and the isocyanate $R^{12}NCO$ in an aprotic solvent such as tetrahydrofuran followed by removal of the carboxyl protecting group.

In a further embodiment of process (A), a compound of formula (I) in which $R^1$ and $R^4$ are as defined in formula (I) above, $R^2$ and $R^3$ each independently represent hydrogen, $C_{1-6}$alkyl or $C_{1-4}$alkoxy$C_{1-4}$alkyl or $CR^2R^3$ represents $C_{3-8}$cycloalkyl, n is zero, and one of X and Y represents $-NR^{12}-$ (where $R^{12}$ is as defined in formula (I) above) and the other represents oxygen may be prepared by N-acylation of a compound of formula (VI)

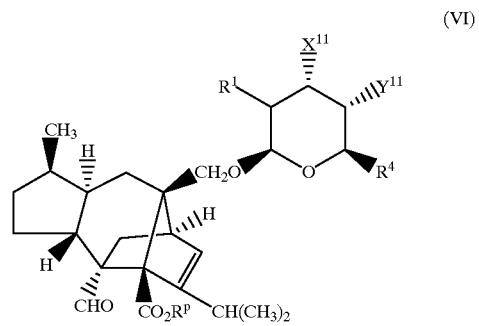

(VI)

(in which one of $X^{11}$ and $Y^{11}$ is OH and the other is $NH_2$) or a protected derivative thereof, for example using an acylhalide such as an acyl chloride under conventional conditions, followed by treating the amide with an aldehyde or ketone $R^2R^3C=O$ or a dialkylacetal $R^2R^3C(OAlkyl)_2$ in the presence of a suitable acid such as p-toluenesulphonic acid or pyridinium p-toluenesulphonate and in a suitable solvent such as a halogenated hydrocarbon (e.g. dichloromethane) at about room temperature, and thereafter removing any protecting groups present.

In another embodiment of process (A), a compound of formula (Ia) in which $R^1$ and $R^4$ are as defined in formula (I) above, n is zero, $-X-CR^2R^3$ or $-Y-CR^2R^3$ represents $-N=CR^3-$ (where $R^3$ is $C_{1-6}$alkyl or $C_{1-4}$alkoxy$C_{1-4}$alkyl), and Y or X remaining is oxygen may be prepared by treating a compound of formula (VI) with an imino ester $R^3C(=NH)OR$ (where R is a $C_{1-6}$alkyl group, e.g. methyl).

Another general process B compounds of formula (I) wherein Z is the group (a) and Y is oxygen, n is zero, $R^2$ nd $R^3$ are hydrogen and X is CH may be prepared by reaction of the compound of formula (VII).

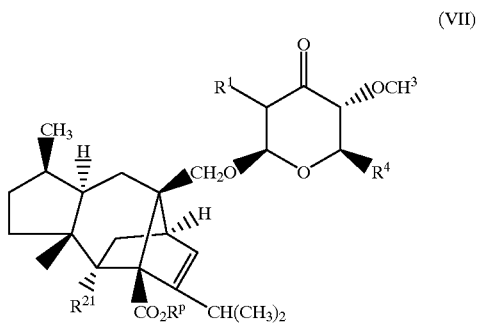

(VII)

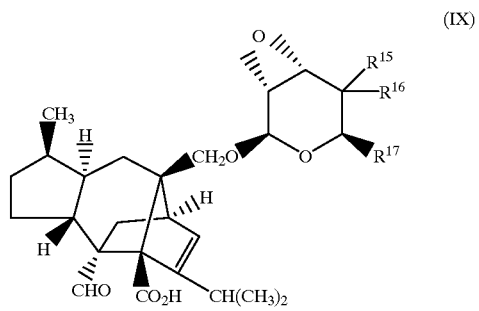

(IX)

wherein $R^{21}$ is the group CHO or a protected derivative thereof, $R^p$ is a protected carboxyl group with a dialkyl diazomethyl phosphonate in the presence of a base such as potassium tert butoxide in an aprotic solvent such as an ether (e.g. tetrahydrofuran followed by the removal of the carboxyl protecting group $R^p$ and if necessary the aldehyde protecting group.

The 4-ketotetrahydropyran derivative (VIII) may be prepared by oxidation of the corresponding 4-hydroxy derivative by conventional means for example by a Swern oxidation.

A general process (C) for the preparation of a compound of formula (I) in which Z is the group (b) and W is oxygen comprises cyclising a compound of formula (VIII)

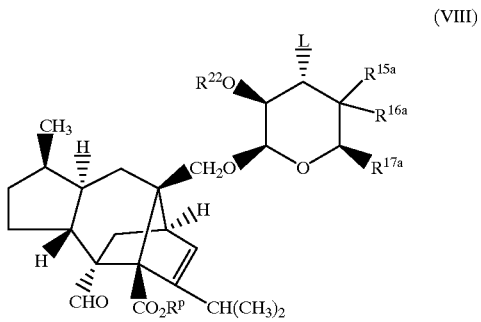

(VIII)

(in which $R^{15a}$, $R^{16a}$ and $R^{17a}$ are as defined for $R^{15}$, $R^{16}$ and $R^{17}$ in formula (I) above or are protected derivatives thereof, $R^p$ is hydrogen or a carboxyl protecting group, L is a suitable leaving group such as an alkyl- or arylsulphonyloxy group and $R^{22}$ is hydrogen or $OR^{22}$ is the same group as defined for L), followed, where necessary, by the removal of any protecting groups present.

The cyclisation reaction may conveniently be effected by treating a compound of formula (VIII) with a strong base such as an alkali metal hydride (e.g. sodium hydride) in a suitable solvent such as dimethylformamide or an ether (e.g. tetrahydrofuran), conveniently at about room temperature. Alternatively, sodium in an alcoholic solvent (e.g. methanol) may be used, especially when $OR^{22}$ is the same group as defined for L. In this instance the base system is added to a solution of a compound of formula (VIII) in a suitable solvent such as a halogenated hydrocarbon (e.g. dichloromethane) and the reaction is conveniently carried out at a temperature of from room temperature to reflux.

Another general process (D) for the preparation of a compound of formula (I) in which W is sulphur comprises treating a compound of formula (IX)

(in which $R^{15}$, $R^{16}$ and $R^{17}$ are as defined in formula (I) above) with a sulphur donor. Thus, for example, the reaction may conveniently be effected by treating a compound of formula (IX) with 5,5-dimethyl-2-thiolo-2-thioxo-1,3,2-dioxaphosphorinane in a solvent such as dimethylformamide, preferably in the presence of a suitable base such as a trialkylamine (e.g. triethylamine) at an elevated temperature (e.g. about 80° to 120° C.).

A compound of formula (IX) may conveniently be prepared from a compound of formula (VIII) in which L is a hydroxyl group and $OR^{22}$ represent a suitable leaving group such as an alkyl- or arylsulphonyloxy group using the conditions described in process (C), followed, where necessary, by the removal of any protecting groups present.

Another general process (E) comprises an interconversion reaction wherein a compound of formula (I) is prepared from a different compound of formula (I) or a protected derivative thereof.

According to a first embodiment of process (E), a carboxyl protected derivative of a compound of formula (I) wherein Z is the group (a) and in which $R^1$ is hydroxyl may be converted to a corresponding compound of formula (I) in which $R^1$ is hydrogen by a procedure comprising (i) forming an S-alkyldithiocarbonate according to the method described previously and (ii) removing this group by treating a solution of the intermediate compound in a hydrocarbon solvent (e.g. toluene) at an elevated temperature (e.g. about 80° to 120° C.) with a hydride reducing agent (e.g. a trialkyltin hydride such as tributyltin hydride), and thereafter removing the carboxyl protecting group.

In a further embodiment of process (E), a compound of formula (I) wherein Z is a group (a) in which $R^1$ is $C_{1-4}$alkoxy and/or $R^4$ is $C_{1-4}$alkoxymethyl may be prepared by alkylating a protected derivative of a compound of formula (I) in which $R^1$ is hydroxyl and/or $R^4$ is hydroxymethyl and any labile groups (e.g. carboxyl and hydroxyl groups) are protected, followed by removal of the protecting groups present. The alkylation may conveniently be effected by initial reaction with a strong alkali metal base (e.g. sodium hydride) and thereafter with an alkyl halide (e.g. methyl iodide). The reaction may be carried out in a suitable solvent such as an ether (e.g. tetrahydrofuran) at a temperature within the range of about 0° to 30° C.

In another embodiment of process (E), a compound of formula (I) in which $R^1$ is acyloxy and/or $R^4$ is $CH_2OCOR^8$ may be prepared by acylating a protected derivative of a compound of formula (I) in which $R^1$ is hydroxyl and/or $R^4$ is $CH_2OH$ and any labile groups (e.g. carboxyl and hydroxyl groups) are protected, followed by removal of any protecting groups present. The acylation reaction may be carried out using conventional methodology, for example by treatment with a carboxylic acid in the presence of an activating agent such as dicyclohexylcarbodiimide and a suitable base such as dimethylaminopyridine, or using an acid halide (e.g. an acid chloride), optionally in the presence of a suitable base such as pyridine or 4-dimethylaminopyridine.

According to a further embodiment of process (E), a compound of formula (I) in which $R^1$ is a hydroxyl group in the equatorial configuration may be prepared from a protected derivative of a compound of formula (I) in which $R^1$ is a hydroxyl group in the axial configuration and any labile groups (e.g. carboxyl, hydroxyl and CHO groups) are protected, followed by removal of any protecting groups present. The isomerisation reaction may conveniently be effected by a two step procedure comprising (i) oxidising the 2'-axial OH to an oxo group by treatment with a suitable oxidising system [e.g. chromium oxide in the presence of pyridine in a solvent such as a halogenated hydrocarbon (e.g. dichloromethane) containing acetic anhydride] and (ii) reducing the oxo group to an equatorial OH group using a suitable reducing agent such as a borohydride (e.g. sodium borohydride). The reduction may conveniently be carried out in a suitable solvent such as an alcohol (e.g. aqueous methanol) at a temperature in the range of about 0° to 10° C.

In another embodiment of process (E), a compound of formula (I) in which $R^1$ is a halogen atom may be prepared from a protected derivative of a compound of formula (I) in which $R^1$ is a hydroxyl group, followed by removal of any protecting groups present. The displacement reaction takes place with inversion of configuration. Thus, for example, an axial OH group may conveniently be converted to an equatorial iodine atom by the addition of iodine to a solution of the starting material in a suitable solvent such as a hydrocarbon (e.g. toluene) in the presence of triphenyl phosphine and iodine, and then heating the mixture (e.g. under reflux).

A fluorine atom may similarly be introduced by treatment with a suitable fluorinating agent such as diethylaminosulphur trifluoride (DAST) in a suitable solvent such as a halogenated hydrocarbon (e.g. dichloromethane) or an aromatic hydrocarbon (e.g. toluene) at about room temperature.

In a further embodiment of process E a compound of formula (I) wherein Y is oxygen, n is zero, $R^1$ and $R^2$ are hydrogen and X is CH, or a protected derivative thereof may be converted into the corresponding compound wherein X s $CH_2$ by reduction with a hydrogen and a suitable catalyst e.g. palladium on charcoal in a suitable solvent followed by removal of a carboxyl protecting group.

In another embodiment of process E a compound of formula (I) wherein Y is oxygen, n is zero, $R^2$ and $R^3$ are hydrogen and X is the group $C=CH_2$ may be converted into the corresponding compound wherein X is the group $C=O$ by oxidation e.g. using osmium tetroxide and sodium periodate.

Similarly compounds of formula (I) wherein Y is oxygen, n is zero, $R^2$ and $R^3$ are hydrogen and X is the group $C=CH_2$ may be converted into the corresponding compound of formula (I) wherein $R^2$ and $R^3$ and the carbon atom to which they are attached represents the group $C=O$ by oxidation e.g. with chromium trioxide in pyridine.

According to a further embodiment of process (E), a carboxyl protected derivative of a compound of formula (I) in which $R^{15}$ is hydroxyl may be converted to a corresponding compound of formula (I) in which $R^{15}$ is halogen by a standard displacement reaction, and thereafter removing the carboxyl protecting group. Thus, for example, the displacement of hydroxyl by a fluorine atom may conveniently be effected with inversion of configuration by adding diethylaminosulphur trifluoride (DAST) to a solution of the starting material in a solvent such as a halogenated hydrocarbon (e.g. dichloromethane). The reaction may conveniently be effected at about room temperature.

In a further embodiment of process (E), a compound of formula (I) in which $R^{15}$ is $C_{1-6}$alkoxy or an optionally substituted alkoxy group and/or $R^{17}$ is $C_{1-4}$alkoxymethyl may be prepared by alkylating a protected derivative of a compound of formula (I) in which $R^{15}$ and/or $R^{17}$ contains a free hydroxyl group and any labile groups (e.g. carboxyl and hydroxyl groups) are protected as appropriate, followed by removal of the protecting groups present. The alkylation may conveniently be effected by initial reaction with a strong alkali metal base (e.g. sodium hydride) and thereafter with an alkyl halide (e.g. methyl bromide). The reaction may be carried out in a suitable solvent such as an ether (e.g. tetrahydrofuran) at a temperature within the range of about 0° to 50° C. Where appropriate, an ammonium salt such as a tetraalkylammonium halide (e.g. tetrabutylammonium iodide) may also be present.

Alternatively, a straight or branched alkyl group may conveniently be introduced in two steps, the first step comprising alkenylation using a suitable alkenylhalide in the presence of a base such as a carbonate (e.g. cesium carbonate) in a solvent such as dimethylformamide at about room temperature, and the second step comprising a hydrogenation procedure in the presence of a palladium catalyst (e.g. 10% palladium on charcoal) at about room temperature.

In another embodiment of process (E), a compound of formula (I) in which $R^{15}$ is $CH_2OCOR^{20}$ or $R^1$ is $OCOR^{18}$ may be prepared by acylating a protected derivative of a compound of formula (I) in which $R^{17}$ is $CH_2OH$ or $R^{15}$ is hydroxyl and any labile groups (e.g. carboxyl and hydroxyl groups) are protected, followed by removal of any protecting groups present. The acylation reaction may be carried out using conventional methodology, for example by treatment with a carboxylic acid in the presence of an activating agent such as dicyclohexylcarbodiimide and a suitable base such as dimethylaminopyridine, or using an acid halide (e.g. an acid chloride), optionally in the presence of a suitable base such as pyridine or dimethylaminopyridine.

According to a further embodiment of process (E), a compound of formula (I) in which $CR^{15}R^{16}$ represents $C=O$ may be prepared by oxidising a protected derivative of a compound of formula (I) in which $R^{15}$ is a hydroxyl group and any labile groups (e.g. carboxyl and hydroxyl groups) are protected, followed by removal of any protecting groups present The oxidation reaction may conveniently be effected by addition of a suitable oxidising agent such as dimethylsulphoxide in the presence of trifluoroacetic anhydride. The oxidation conveniently takes place in the presence of a suitable solvent such as a halogenated hydrocarbon (e.g. dichloromethane) at an elevated temperature (e.g. about 40° to 80° C.).

Compounds of formula (I) wherein $CR^{15}R^{16}$ represent the group $CH=CH_2$ may be prepared by reaction of the corresponding compound of formula (I) or a protected derivative thereof wherein $CR^{15}R^{16}$ is the group $C=O$, with an alkyltriphenyl-phosphonium halide and an alkyllithium in an aprotic solvent such as e.g. tetrahydrofuran.

Compounds of formula (I) wherein $R^{15}$ is an azide group may be prepared from the corresponding compound of formula (I) or a protected derivative thereof wherein $R^{15}$ is a hydroxyl group by reaction with a toluene sulphonyl halide and then treating the resultant toluene sulphonate derivative with an alkali metal azide e.g. lithium azide in an aprotic solvent. e.g. dichloromethane.

Many of the above-mentioned procedures require the removal of one or more protecting groups as a final step to provide the desired compound of formula (I). Thus, a further general process (F) comprises deprotecting a protected derivative of a compound of formula (I). Suitable carboxyl protecting groups and hydroxyl protecting groups for use herein include any conventional protecting group, for example as described in "Protective Groups in Organic Chemistry", Ed. J. F. W. McOmie (Plenum Press, 1973) or "Protective Groups in Organic Synthesis" by Theodora W. Greene (John Wiley and Sons, 1991). Examples of suitable carboxyl protecting groups include arylalkyl groups such as diphenylmethyl, p-methoxybenzyl and silyl groups (e.g. trimethylsilylethyl or t-butyldimethylsilyl). Examples of suitable hydroxyl protecting groups include arylalkyl groups such as p-methoxybenzyl and ester groups such as benzyloxycarbonyl. Aldehyde groups may conveniently be protected in the form of cyclic ketals.

The protecting groups may be removed using conventional techniques. Thus, a diphenylmethyl group may conveniently be removed using trifluoroacetic acid or by hydrogenolysis in the presence of a palladium catalyst (e.g. 10% palladium on charcoal). A benzyloxycarbonyl group may conveniently be removed by hydrogenolysis in the presence of a palladium catalyst (e.g. 10% palladium on charcoal). A p-methoxybenzyl group may conveniently be removed using 2,3-dichloro-5,6-dicyano-1,4-benzoquinone. Silyl groups such as trimethylsilylethyl or t-butyldimethylsilyl may conveniently be removed using fluoride ions. Cyclic ketal groups may conveniently be converted to aldehyde group by the addition of a suitable acid such as hydrochloric acid.

Compounds of formula (II) may conveniently be prepared by reacting a compound of formula (X)

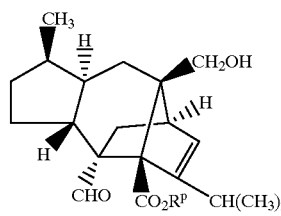

(where $R^p$ is a carboxyl protecting group) with a compound of formula (XI)

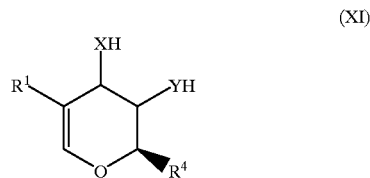

(where $R^1$, $R^4$, X and Y are as defined in formula (II) above) or a protected derivative thereof, followed, where necessary, by removal of any protecting groups present. The reaction may conveniently be effected by heating (X) and (XI) at a temperature in the range of about 40° to 80° C. in a suitable solvent, such as a hydrocarbon (e.g. toluene), in the presence of an acid such as hydrobromic acid-triphenylphosphine.

When XH and YH in formula (XI) represent hydroxyl groups these may conveniently be protected as acyloxy (e.g. acetoxy) groups, with removal of the protecting groups following reaction with a compound of formula (X). Removal of acetoxy protecting groups may conveniently be effected by addition of a suitable base such as an alkoxide (e.g. sodium methoxide) in a suitable solvent such as an alcohol (e.g. methanol) at about room temperature.

The aforementioned reaction is particularly suitable for preparing compounds of formula (II) in which $R^4$ is other than a methyl group. When $R^4$ is methyl it may be more convenient to prepare compounds of formula (II) from 4'-demethylsordarin, a compound of formula (XII)

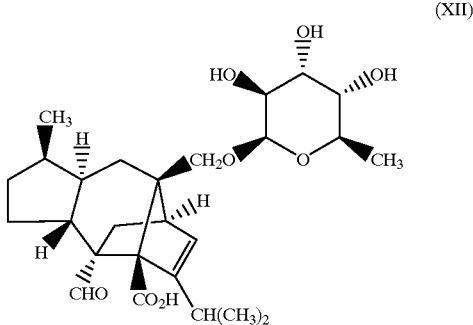

Thus, for example, compounds of formula (III) in which $R^4$ represents methyl may be prepared by protection of the carboxyl group in (XII) using conventional methods, followed, if appropriate, by converting the 2'-axial hydroxyl group to a different $R^1$ group by the interconversion procedures described hereinabove. It may be necessary to protect the 3' and 4' hydroxyl groups when manipulating the 2'-axial hydroxyl group. Protection may conveniently be effected by the formation of an isopropylidene group using a procedure described in the first embodiment of process (A). Subsequent removal of this group to provide the diol function may be achieved by treatment with an acid such as an inorganic acid (e.g. hydrochloric acid).

When the carboxyl group in the compound of formula (XII) is protected with a diphenylmethyl group the protection reaction may conveniently be carried out by treating a solution of the compound of formula (XII) in an alcoholic solvent (e.g. methanol) and/or in a halogenated hydrocarbon (e.g. dichloromethane) with diphenyldiazomethane, conveniently added as a solution in a halogenated hydrocarbon solvent (e.g. dichloromethane).

Compounds of formula (II) wherein X and Y represent oxygen or sulphur may also be prepared by the decarbonylation of a corresponding protected derivative of a compound of formula (I) in which $CR^2R^3$ represents C=O and n is zero. The decarbonylation may conveniently be effected by addition of an alkoxy compound (e.g. CH$_3$ONa) in a suitable solvent such as an alcohol (e.g. methanol).

Compounds of formula (X) may conveniently be prepared from sordaricin using conventional carboxyl group protecting means. Thus, for example, when $R^p$ in a compound of formula (X) represents trimethylsilylethyl this group may be introduced by treating sordaricin with O-[2-trimethylsilyl) ethyl]-N,N'-diisopropylisourea, conveniently in a suitable solvent such as an ether (e.g. tetrahydrofuran) at an elevated temperature (e.g. under reflux). When $R^p$ represents diphenylmethyl this group may be introduced using the methodology described above.

When a hydroxyl group in a carboxyl protected derivative of sordarin or a compound of formula (XII) is protected with a p-methoxybenzyl group this group may be introduced by reaction with a tin oxide (e.g. dibutyltin oxide) in a hydrocarbon solvent (e.g. refluxing toluene), followed by the addition of a p-methoxybenzyl halide in the presence of an fluoride salt (e.g. tetrabutylammonium fluoride). When protected with a benzyloxycarbonyl group, this group may be introduced by reaction with a benzylhaloformate in the presence of a suitable amine base such as 4-dimethylaminopyridine and in a solvent such as a halogenated hydrocarbon (e.g. dichloromethane) or acetonitrile.

The formation of a group L in formula (VIII) where L is an alkyl- or arylsulphonyloxy group and/or a group $R^{22}O$ where $R^{22}O$ is an alkyl- or arylsulphonyloxy group may be effected by reacting a suitably protected derivative of sordarin or a compound of formula (XII) with an alkyl- or arylsulphonyl halide in the presence of a suitable solvent such as pyridine and optionally also comprising an amine base (e.g. 4-dimethylaminopyridine) or in a halogenated hydrocarbon solvent (e.g. dichloromethane) in the presence of a suitable amine base (e.g. 4-dimethylaminopyridine). The reaction may conveniently be carried out at about room temperature. Other groups may be similarly introduced using conventional procedures.

It will be appreciated that it may be appropriate to convert a hydroxyl group to the desired $R^{15}$ group prior to cyclisation according to process (C). Thus, a suitably protected derivative of 4'-demethylsordarin or a compound of formula (II) in which $R^{15a}$ is hydroxyl may be reacted to convert the 4'-hydroxyl group to the desired $R^1$ group using conventional procedures. Thus, for example, conversion to a $C_{1-6}$alkoxy, $C_{1-4}$alkoxy$C_{1-4}$alkoxy or aryl$C_{1-4}$alkoxy group may be effected by conventional alkylation, for example, according to the various methods described hereinabove. Removal of the hydroxyl group to provide a compound in which $R^{15}$ is hydrogen may conveniently be effected in two steps comprising (i) forming an S-alkyldithiocarbonate by treatment with a strong alkali metal base (e.g. sodium hydride), in the presence of imidazole, and in a suitable solvent such as an ether (e.g. tetrahydrofuran) at a reduced temperature (e.g. about 0° C.), and then adding carbon disulphide and an alkylhalide (e.g. methyliodide) at about room temperature and (ii) removing this group by treating a solution of the intermediate compound in a hydrocarbon solvent (e.g. toluene) at an elevated temperature (e.g. about 80° to 120° C.) with a hydride reducing agent (e.g. a trialkyltin hydride such as tributyltin hydride), optionally in the presence of an activating agent [e.g. azobis(isobutyronitrile)]. Conversion to a $C_{2-6}$alkyl group may conveniently be effected by (i) forming an S-alkyldithiocarbonate as described previously (ii) replacing this group with an alkenyl group by reaction with a trialkylalkenyltin compound under the conditions described above for the removal of the S-alkyldithiocarbonate group and (iii) reducing the alkenyl group to an alkyl group by, for example, hydrogenation in the presence of a suitable palladium catalyst (e.g. 10% palladium on charcoal).

Base salts of compounds of formula (I) may be conveniently formed by treating a compound of formula (I) with an appropriate salt or base. Thus, for example, salts may conveniently be prepared by treating a compound of formula (I) with a salt or a base selected from sodium or potassium hydroxide, hydrogen carbonate, carbonate or acetate (e.g. potassium hydroxide, potassium hydrogen carbonate, sodium hydrogen carbonate or potassium acetate), ammonium acetate, calcium acetate and L-lysine as appropriate. The salt may, for example, be prepared by adding the appropriate salt or base (if necessary as an aqueous solution) to a solution or suspension of the compound of formula (I) in a suitable solvent such as an alcohol (e.g. methanol) or dioxane at temperatures of for example 0° C. to 80° C. and conveniently at about room temperature.

Pharmaceutically acceptable salts may also be prepared from other salts, including other pharmaceutically acceptable salts of the compounds of formula (I), using conventional methods.

Metabolically labile esters of compounds of formula (I) may be formed with the carboxyl group present and these may be prepared by conventional processes. Similarly, metabolically labile estersw may also be formed with any free hydroxyl group present in the molecule.

The novel compound of formula (XII) may conveniently be prepared according to the fermentation process described hereinafter or by demethylating sordarin using a biotransformation procedure.

The fermentation process comprises cultivating a microorganism capable of producing the compound of formula (XII) and thereafter isolating the compound of formula (XII) from the culture.

Microorganisms capable of producing the compound of formula (XII) will conveniently be mutant strains of *Sordaria araneosa* which can readily be identified by screening survivors of mutagenesis by analysing a test sample obtained from fermentation of the microorganism using standard methodology. In particular, the microorganism to be conveniently used is a mutant strain of *Sordaria araneosa* deposited in the permanent culture collection of the CAB International Mycological Institute, Genetic Resource Reference Collection, Bakeham Lane, Egham, Surrey TW20 9TY, England. The strain was received by the Institute on 10 Jun., 1994 and was subsequently given the accession number IMI 362184 and dates of acceptance and confirmation of viability of 13 and 21 Jun., 1994 respectively. The Institute is an International Depository authority recognised under the Budapest Treaty. The characteristics thus far identified for IMI 362184 are given in Example 74.

The present invention provides in a further aspect the microorganism IMI 362184 per se and mutants thereof.

Mutants of the IMI 362184 may arise spontaneously or may be produced by a variety of methods including those outlined in Techniques for the Development of Microorganisms by H I Adler in "Radiation and Radioisotopes for Industrial Microorganisms", Proceedings of the Symposium, Vienna 1973, p241, International Atomic Energy authority. Such methods include ionising radiation, chemical methods, e.g. treatment with N-methyl-N'-nitro-N-nitrosoguanidine (NTG), heat, genetic techniques, such as recombination and transformation, and selective techniques for spontaneous mutants.

The preparation of the compound of formula (XII) by fermentation may be effected by conventional means i.e. by culturing a suitable organism in the presence of assimilable sources of carbon, nitrogen and mineral salts, and thereafter isolating the desired product.

Assimilable sources of carbon, nitrogen and minerals may be provided by either simple or complex nutrients. Sources of carbon will generally include glucose, maltose, starch, glycerol, molasses, dextrin, lactose, sucrose, fructose, galactose, myo-inositol, D-mannitol, soya bean oil, carboxylic acids, amino acids, glycerides, alcohols, alkanes and vegetable oils. Sources of carbon will generally comprise from 0.5 to 10% by weight of the fermentation medium. Fructose, glucose and sucrose represent preferred sources of carbon.

Sources of nitrogen will generally include soya bean meal, corn steep liquors, distillers solubles, yeast extracts, cottonseed meal, peptones, ground nut meal, malt extract, molasses, casein, amino acid mixtures, ammonia (gas or solution), ammonium salts or nitrates. Urea and other amides may also be used. Sources of nitrogen will generally comprise from 0.1 to 10% by weight of the fermentation medium.

Nutrient mineral salts which may be incorporated into the culture medium include the generally used salts capable of yielding sodium, potassium, ammonium, iron, magnesium, zinc, nickel, cobalt, manganese, vanadium, chromium, calcium, copper, molybdenum, boron, phosphate, sulphate, chloride and carbonate ions.

Cultivation of the organism will generally be effected at a temperature of from 20° to 40° C., preferably from 20 to 35° C., especially about 25° C., and will desirably take place with aeration and agitation e.g. by shaking or stirring. The medium may initially be inoculated with a small quantity of mycelium and/or spores. The vegetative inoculum obtained may be transferred to the fermentation medium, or to one or more seed stages where further growth takes place before transfer to the principal fermentation medium. The fermentation will generally be carried out in the pH range 3.5 to 9.5, preferably 4.5 to 7.5. It may be necessary to add a base or an acid to the fermentation medium to keep the pH to within the desired range. Suitable bases which may be added include alkali metal hydroxides such as aqueous sodium hydroxide or potassium hydroxide. Suitable acids include mineral acids such as hydrochloric, sulphuric or phosphoric acid.

The fermentation may be carried out for a period of 4–30 days, preferably about 5–15 days. An antifoam may be present to control excessive foaming and added at intervals as required. Carbon and/or nitrogen sources may also be fed into the fermentation medium as required.

The compound of formula (XII) is associated mainly with the cells and may be brought into solution either by addition of an acid and a water-miscible organic solvent, or more preferably by addition of a base (e.g. sodium hydroxide). Cells may be separated from these solutions either by centrifugation, conventional filtration or membrane filtration. The liquor may be optionally thereafter treated with an acid such as sulphuric acid until the pH is below 6 (e.g. about pH 4.5).

The compound of formula (XII) may be isolated and purified by a variety of fractionation techniques, for example adsorption-elution, precipitation, fractional crystallisation, solvent extraction and liquid-liquid partition which may be combined in various ways.

Adsorption onto a solid support followed by elution has been found to be particularly suitable for isolating and purifying the compound of formula (IX). Suitable solid supports include silica; a non-functional macroreticular adsorption resin, for example cross-linked styrene divinyl benzene polymer resins such as CG161 and Amberlite XAD-2, XAD-4, XAD-16 or XAD-1180 resins (Rohm & Haas Limited) or Kastell S112 (Montedison); a substituted styrene-divinyl benzene polymer such as Diaion SP207 (Mitsubishi); an anion exchanger [e.g. IRA-958 or Macro-Prep High Q (BioRad)], an organic solvent-compatible cross-linked dextran such as Sephadex LH20 (Pharmacia UK Limited), or on reverse phase supports such as hydrocarbon linked silica, e.g. $C_{18}$-linked silica.

The compound of formula (XII) may also be isolated and purified by the use of a liquid anion exchanger such as LA2.

Suitable solvents for the elution of the compound of formula (XII) will, of course, depend on the nature of the adsorbent. When using a polymer resin such as XAD-16 water-miscible solvents such as methanol, acetone, isopropanol or acetonitrile in various proportions in water may be particularly suitable.

The presence of the compound of formula (XII) during the extraction/isolation procedures may be monitored by conventional techniques such as high performance liquid chromatography (HPLC) or UV spectroscopy or by utilising the optical rotation or other property of the compound.

Where the compound of formula (XII) is obtained in the form of a solution in an organic solvent, for example after purification by absorption/elution, the solvent may be removed by conventional procedures, e.g. by evaporation, to yield the required compound. If desired, the compound may be further purified by chromatographic techniques such as countercurrent chromatography using a coil extracter such as a multi-layer coil extracter or high performance liquid chromatography or supercritical fluid chromatography on adsorbents such as carbon, alumina, vanadium, polymeric resins or silica, with or without bonded phases. Suitable solvents/eluents for the chromatographic purification/separation of the compound of formula (XII) will of course depend on the nature of the adsorbent. When using a C8 bonded silica, mixtures of acetonitrile and water are particularly suitable. Alternatively, the compound may be further purified by solvent extraction, for example using an appropriate organic solvent such as a ketone (e.g. acetone or methyl ethyl ketone), a halogenated hydrocarbon, an alcohol (e.g. methanol), a diol (e.g. propane-1,2-diol or butane-1,3-diol) or an ester (e.g. methyl acetate or ethyl acetate) In a further alternative, solutions of compound (XII) may be further purified by treatment with adsorbents that selectively remove impurities when added at appropriate levels (e.g. DEAE-cellulose) or by crystallisation (e.g. from a mixture of acetonitrile and water) or using a combination of the above procedures.

The biotransformation of sordarin to 4'-demethylsordarin, the compound of formula (XII), may be effected by incubating sordarin in a culture comprising a suitable organism and sources of carbon and nitrogen, including those sources specified hereinabove, and thereafter isolating the compound of formula (XII) from the culture.

Microorganisms capable of demethylating sordarin at the 4'-position may readily be identified by using a small scale test and analysing a test sample obtained using standard methodology, for example, using HPLC. Examples of microorganisms which have been identified as sordarin demethylators include *Streptomyces capreolus* ATCC 31963, *Streptomyces avermitilis* ATCC 31272, *Streptomyces armentosus* NRRL 3176, *Streptomyces antibioticus* ATCC 31771, *Streptomyces rimosus* ATCC 23955, *Streptomyces platensis* ATCC 29778, *Streptomyces mashuensis* ATCC 23934, *Streptomyces eurythermus* ATCC 14975, *Nocardia orientalis* ATCC 43491 and *Cunninghamella echinulata var elegans* ATCC 36112.

Cultivation of the organism will generally be effected at a temperature of from 20° to 40° C., preferably from 20° to 35° C., especially about 28° C., and will desirably take place with aeration and agitation, e.g. by shaking or stirring. The medium may initially be inoculated with a small quantity of mycelium and/or spores. The vegetative inoculum obtained may be transferred to the fermentation medium or to one or more seed stages where further growth (e.g. over about 1–3 days) takes place before transfer to the principal fermentation medium. The principal fermentation medium will also comprise sordarin and the fermentation will generally be carried out in a pH range of 3.5 to 9.5, preferably 4.5 to 7.5. It may be necessary to add a base or an acid to the fermentation medium to keep the pH to within the desired range. Suitable bases which may be added include alkali metal hydroxides such as aqueous sodium hydroxide or potassium hydroxide. Suitable acids include mineral acids such as hydrochloric, sulphuric or phosphoric acid. Fermentation may be carried out over a period of 2 to 5 days, preferably about 3 days. An antifoam may be present to control excess foaming and added at intervals as required. Carbon and/or nitrogen sources may also be fed into the fermentation medium as required.

The separation and isolation of the compound of formula (XII) from the fermentation broth may be effected by the general procedures previously described. When it is desired to lower the pH of the liquor to below pH 6 (e.g. to about pH 2.5) this may conveniently be achieved by the addition of an acid such as orthophosphoric acid.

It will be appreciated that biotransformation may be effected according to a number of alternative methods. For example, cells may be grown and harvested prior to addition to a solution of sordarin in, for example, buffer, spent fermentation medium or water. It is also feasible that the appropriate enzymes could be isolated and used (with appropriate co-enzymes) or the enzymes cloned and over-expressed.

As stated hereinabove, sordarin and sordaricin are known compounds, which may be obtained using procedures described in the relevant art. Thus, for example, the preparation of sordarin by the cultivation of *Sordaria araneosa* NRRL 3196 (also deposited in the ATCC as ATCC 36386) is described in British Patent Specification No. 1,162,027. Specific examples of the preparation of sordarin using similar procedures are reported hereinafter.

Sordaricin may conveniently be prepared under fermentation conditions similar to those described for preparing sordarin using *Sordaria araneosa* NRRL 3196 or a suitable mutant thereof, with isolation of the desired compound using appropriate chromatographic means. One such mutant has been deposited in the permanent culture collection of the CAB International Mycological Institute, Genetic Resource Reference Collection, Bakeham Lane, Egham, Surrey TW20 9TY, England. The strain was received and accepted by the Institute on 11 Aug., 1994 and was subsequently given the accession number IMI 362947 and a date of confirmation of viability of 19 Aug., 1994. The Institute is an International Depository authority recognised under the Budapest Treaty. The characteristics thus far identified for IMI 362947 are given in Example 75.

The present invention provides in a further aspect the microorganism IMI 362947 per se and mutants therof.

Processes for obtaining mutants of IMI 362947 and its genetic material will be similar to those described hereinabove for the manipulation of IMI 362184.

Sordaricin may also be prepared from sordarin using a biotransformation procedure. The biotransformation may conveniently be effected by incubating sordarin in a culture comprising a suitable organism and sources of carbon and nitrogen, including those sources specified hereinabove, and thereafter isolating sordaricin from the culture.

Microorganisms capable of converting sordarin to sordaricin may readily be identified by using a small scale test and analysing a test sample obtained using standard methodology, for example, using HPLC. We have identified one such microorganism and deposited it with the National Collections of Industrial and Marine Bacteria Limited (NCIMB), 23 St. Machar Drive, Aberdeen AB2 1RY, Scotland. The strain was received by the NCIMB on 4 Aug., 1994 and was the same day accepted for deposit for patent purposes and the viability of the microorganism confirmed. The microorganism, which is a Coryneform species having the characteristics given in Example 76, has been assigned the accession number NCIMB 40675. The NCIMB is an International Depository authority recognised under the Budapest Treaty.

The invention thus provides in another aspect the microorganism NCIMB 40675 per se and mutants thereof.

According to another aspect of the present invention we provide the genetic material of NCIMB 40675 and mutants thereof that participates in the bioconversion of sordarin to sordaricin.

Processes for obtaining mutants of NCIMB 40675 and its genetic material will be similar to those described hereinabove for the manipulation of IMI 362184.

Cultivation of the NCIMB 40675 will generally be effected at a temperature of from 20° to 40° C., preferably from 20° to 35° C., especially about 28° C., and will desirably take place with aeration and agitation, e.g. by shaking or stirring. The medium may initially be inoculated with a small quantity of mycelium and/or spores. The vegetative inoculum obtained may be transferred to the fermentation medium or to one or more seed stages where further growth (e.g. over about 1–3 days) takes place before transfer to the principal fermentation medium. The principal fermentation medium will also comprise sordarin and the fermentation will generally be carried out in a pH range of 3.5 to 9.5, preferably about 7.5. It may be necessary to add a base or an acid to the fermentation medium to keep the pH to within the desired range. Suitable bases which may be added include alkali metal hydroxides such as aqueous sodium hydroxide or potassium hydroxide. Suitable acids include mineral acids such as hydrochloric, sulphuric or phosphoric acid. Fermentation may be carried out over a period of 4 to 8 days, preferably about 6 days. An antifoam may be present to control excess foaming and added at intervals as required. Carbon and/or nitrogen sources may also be fed into the fermentation medium as required.

It will be appreciated that biotransformation may be effected according to a number of alternative methods. For example cells may be grown and harvested prior to addition to a solution of sordarin in, for example, buffer, spent fermentation medium or water. It is also feasible that the appropriate enzymes could be isolated and used or the enzymes cloned and overexpressed.

The separation and isolation of sordaricin from the fermentation broth may be effected by the general procedures previously described. When it is desired to lower the pH of the liquor to about pH 6 this may conveniently be achieved by the addition of an acid such as orthophosphoric acid.

It is to be understood that the fermentation and bioconversion processes described hereinabove for preparing sordaricin represent further aspects of the present invention.

The examples hereinafter illustrate aspects of the present invention and are not intended to limit the invention in any way.

PREPARATION 1

Production of Sordarin

A culture of *Sordaria araneosa* NRRL3196 (ATCC36386) was grown on an agar medium until mature growth occurred. 6 mm diameter plugs of the agar containing the growth were transferred to sterile water or Brain Heart Infusion broth (Oxoid)+10% glycerol and stored at ambient temperature or −140° C. respectively. A suspension containing 2 of these agar plugs was used to inoculate a 250 ml Erlenmyer flask containing 50 ml of medium FS.

| Medium FS | g/L |
| --- | --- |
| Peptone (Oxoid L34) | 10 |
| Malt extract (Oxoid L39) | 21 |
| Glycerol (Glycerine CP) | 40 |
| Junlon 110 (Honeywell & Stein) | 1 |
| Distilled water | |

The culture was incubated at 25° C. for 5 days on a rotary shaker operated at 250 rpm with a 50 mm diameter orbital motion. Aliquots (2 ml) of the developed inoculum were used to inoculate further 250 ml Erlenmyer flasks containing medium FS (50 ml) which were incubated as described above. 80 ml of the bulked shake flask developed inoculum was used to inoculate each of two 7 L fermenters containing 5 L of medium FS. The fermentations were controlled to a temperature of 25 C. The culture was agitated at 400 rpm and aerated at 2 Lpm. After 3 days fermentation, 10 L of culture was used to inoculate a 780 L fermenter containing 500 L of medium SM55VAR.

| SM55VAR | g/L |
| --- | --- |
| Glucidex 32D (Roquette Frere) | 74 |
| Peptone (Oxoid L37) | 10 |
| Proflo (Traders Protein) | 30 |
| Beet molasses | 15 |
| $MgSO_4.7H_2O$ (BDH) | 5 |
| $CaCO_3$ (BDH) | 5 |
| $FeSO_4.7H_2O$ (Sigma) | 2 |
| $ZnSO_4.7H_2O$ (BDH) | 0.04 |
| L-trytophan (Sigma) | 2 |
| PPG2000 (K & K Greef) | 0.5 |
| Silicone 1520 (Dow Corning) | 0.04 |
| Distilled water | |

The fermentation was controlled to a temperature of 25° C. The broth was agitated at 300–350 rpm and aerated at 200 Lpm. 70% (w/v) Meritose (Tunnel Refineries) solution was fed to the culture to maintain a positive residual glucose concentration. Distilled water was fed to maintain a culture volume of 500 L. PPG2000 antifoam was added on demand to control foaming. Whole broth extracts (in aqueous acetonitrile+1% trifluoroacetic acid) were assayed for presence of sordarin by reverse phase HPLC. The culture was harvested after 11 days when the extract of a broth sample indicated a sordarin titre of 0.6 g/L. Fermentation broth was made 0.1M with respect to sodium hydroxide and after storage at ambient temperature overnight was filtered through Dicalite on a rotary vacuum filter (1% Dicalite was added to the broth as filter aid). The filtrate was adjusted to pH 6–7 with concentrated sulphuric acid and the solution was applied to XAD16 resin (10 volumes of filtrate/volume resin). The adsorbent was washed with water and acetone-:water (1:3) in both cases to give a clear effluent before sordarin was eluted with acetone:water (3:1; 2 column volumes collected). Flow rate throughout the process was between 1–2 column volumes/hr. The eluate was concentrated to a small volume (8.5 L). The concentrate was adjusted to pH 3 with phosphoric acid and stood overnight at ambient temperature to allow precipitated sordarin to settle. Supernatant was decanted then centrifuged and the supernatant was discarded. Centrifuge pellets and precipitate were taken up in 75% aqueous acetonitrile to give 3.9 L of a dark brown solution. To this was added 1.0 L 0.2M $NH_4H_2PO_4$ with stirring, and the solution was adjusted to pH 4.0 with phosphoric acid, to give a final volume of 5.0 L with approximate composition 60% acetonitrile –0.1M $NH_4H_2PO_4$. The crude sordarin solution (5.0 L) from above was subjected to preparative HPLC in 10 injections (450–550 ml each) on a column (15 cm×25 cm) of 7 mm Kromasil C8 in mobile phase of 50% acetonitrile –0.1M $NH_4H_2PO_4$, pH 4 (50 L acetonitrile made up to 100 L with water containing 575 g $NH_4H_2PO_4$ and 40 ml $H_3PO_4$), flow-rate 600 ml/min, detection by UV absorbance ($\lambda$ 210 nm).

The fraction eluting between 15.4 and 19.2 min was collected. Pooled fractions from the 10 injections (23 L) were diluted with water to SOL and this solution was pumped back through the Kromasil column at 28 L/h. The column was washed with water (25 L) then eluted with 90% acetonitrile (10 L). The eluate was evaporated to a residue of 1300 ml which was freeze-dried to yield the title compound as a buff powder (105.6 g). MS and NMR analysis of the product showed equivalence with an authentic sample of sordarin.

PREPARATION 2

Production of Sordarin Potassium Salt

*Sordada araneosa* NRRL3196 (ATCC36386) was maintained in Brain Heart Infusion broth (Oxoid) +10% glycerol at –140° C. as described in Preparation 1. A suspension containing 2 agar plugs was used to inoculate a 250 ml Erlenmyer flask containing 50 ml of medium FS. The culture was incubated at 25° C. for 5 days on a rotary shaker operated at 250 rpm with a 50 mm diameter orbital motion. Aliquots (2 ml) of the developed inoculum were used to inoculate further 250 ml Erlenmyer flasks containing medium FS (50 ml) and incubated as described above. 80 ml of the bulked shake flask developed inoculum was used to inoculate each of two 7 L fermenters containing 5 L of medium FS. The fermentations were controlled to a temperature of 25° C. The culture was agitated at 400 rpm and aerated at 2 Lpm. After 3 days fermentation, 10 L of culture was used to inoculate a 780 L fermenter containing 500 L of medium SD1.

| SD1 | g/L |
| --- | --- |
| Meritose (Tunnel refineries) | 22 |
| Lactose | 20 |
| Glucidex 32D (Roquette Frere) | 30 |
| Arkasoy (The British Arkady Co.) | 20 |
| CSL | 20 |
| $FeCl_3.6H_2O$ | 0.05 |
| $NH_4H_2PO_4$ | 5 |
| $ZnSO_4.7H_2O$ (BDH) | 0.1 |
| PPG2000 | 0.5 |
| Distilled water | |

The fermentation was controlled to a temperature of 25° C. The broth was agitated at 350 rpm and aerated at 200 Lpm. Distilled water was fed to maintain a culture volume of 500 L. Whole broth extracts were assayed for presence of sordarin by reverse phase HPLC. The culture was harvested after 6 days when the extract of a broth sample indicated a sordarin titre of 1.3 g/L. A 50 L sample of harvest broth was made 0.1M with respect to sodium hydroxide and stored at 4° C. overnight. Cells were removed by vacuum filtration through a bed of Dicalite adding an additional 2% Dicalite to the broth as filter aid. The filtrate was adjusted to approximately pH 6 with concentrated sulphuric acid. Broth extract was pumped through a bed of Amberchrom CG161 resin at 320 ml/min (0.64 bed volumes per min). The effluent was monitored by HPLC. After 45 min (equivalent to a pumped volume of 14.4 L) sordarin began to break through and pumping was halted. The adsorbent was washed with water (2 L) then 25% v/v acetone in water (2 L). Sordarin was eluted with 75% v/v acetone in water (1.5 L). The 75% v/v acetone eluate was evaporated to about 200 ml by rotary evaporation at 40° C. 200 ml butan-1-ol was added and the evaporation continued until a viscous oil remained (containing some butan-1-ol). The oily residue was extracted with hot methanol (2×500 ml). Extracts were combined, filtered (Whatman no 1 paper) then evaporated at 40 to 45° C. to give a viscous oil. This was extracted with hot acetone (2×500 ml). Acetone extracts were combined, filtered and evaporated to a viscous oil. Propan-2-ol (350 ml) was added and the oil dissolved at 45° C. to give a clear brown solution. A solution of potassium-2-ethylhexanoate (39% w/w solution in propan-2-ol, 54 g) was weighed into a 500 ml conical flask. The sordarin-containing solution in propan-2-ol was poured into the conical flask, the contents mixed, and left to stand for 4 h at room temperature. The solution was seeded with sordarin potassium salt (about 5 mg) and the stoppered flask was stored for 3 days at 4° C. The off-white solid which formed was filtered under vacuum (No 4 sinter funnel) and the filter cake was washed with propan-2-ol (about 20–30 ml). The solid was transferred to a crystallising dish and dried in vacuo over $P_2O_5$ for 16 h to give the title compound (10.5 g).

PREPARATION 3

Production of Sordarin Potassium Salt 500 liters of culture broth was prepared as in Preparation 1. The broth was made 0.1M with respect to sodium hydroxide and after 4 days at 0° C. was filtered through a bed of Dicalite on a rotary vacuum filter. 1% Dicalite was added to the broth as filter aid. The pH of the filtrate was adjusted from pH 9.6 to pH 7.5 with concentrated sulphuric acid. Filtrate (10 L) was adjusted to pH 6 with $H_3PO_4$ and applied to a bed (200 ml) of XAD-16 resin packed in water at a flow-rate of 1–1.5 bed volumes/h. The resin bed was washed with water (1 bed volume) then with 25% aqueous isopropanol (2.5 bed volumes) before elution with neat isopropanol. After a fore-run of 50 ml the isopropanol eluate was collected as 100 ml fractions. Sordarin-rich fractions 2–6 inclusive were pooled and evaporated to half volume. Isopropanol was added to bring the volume back to 500 ml, then the evaporation to half volume repeated to remove residual water by azeotropic distillation. After a third evaporation to half volume the residue was filtered and the filter was washed with isopropanol. To the combined filtrate and washings (400 ml) was added a solution of potassium 2-ethylhexanoate (8 g) in isopropanol (100 ml). The mixture was seeded with sordarin potassium salt and stood for several days at 4° C. whilst a slow crystallisation took place. Crystals were filtered on a No. 3 sinter, washed with a little ice-cold isopropanol and dried in vacuo to yield the title compound as a pale brown powder (4.85 g).

PREPARATION 4

Production of 4'-demethylsordarin (i) IMI 362184 was maintained in Brain Heart Infusion broth (Oxoid) +10% glycerol at −140° C. as described in Preparation 1. A suspension containing 2 agar plugs was used to inoculate a 250 ml Erlenmyer flask containing 50 ml of medium FS. The culture was incubated at 25° C. for 5 days on a rotary shaker operated at 250 rpm with a 50 mm diameter orbital motion. Aliquots (2 ml) of the developed inoculum were used to inoculate further 250 ml Erlenmyer flasks containing medium FS (50 ml) and incubated as described above. 80 ml of the bulked shake flask developed inoculum was used to inoculate each of two 7 L fermenters containing 5 L of medium FS. The fermentations were controlled to a temperature of 25° C. The culture was agitated at 400 rpm and aerated at 2 Lpm. After 3 days fermentation, 10 L of culture was used to inoculate a 780 L fermenter containing 500 L of medium SM55VAR (as described in Preparation 1). The fermentation was controlled to a temperature of 25° C. The broth was agitated at 350 rpm and aerated at 500 Lpm. 70% w/v Meritose (Tunnel Refineries) solution was fed to the culture to maintain a positive residual glucose concentration. Distilled water was fed to maintain a culture volume of 500 L. Whole broth extracts were assayed for presence of 4'-demethylsordarin by reverse phase HPLC. The culture was harvested after 10 days when the extract of a broth sample indicated a 4'-demethylsordarin titre of 0.8 g/L. Fermentation broth was made 0.1M with respect to sodium hydroxide and after 1 hour at ambient temperature was filtered through Dicalite on a rotary vacuum filter (1% Dicalite was added to the broth as filter aid). The filtrate was adjusted to pH 4.5 with concentrated sulphuric acid and the solution was applied to XAD16 resin (20 g product/L resin). The adsorbent was washed with 0.1% phosphoric acid (10 column volumes) and acetonitrile:water 1:4 (6 column volumes) before the product was eluted with acetonitrile:water (1:1; 2 column volumes). Flow rate throughout the process was between 1–2 column volumes/hr. The eluate was concentrated to dryness with the addition of butan-1-ol and the solid was extracted with methanol (12 L) followed by acetone (10 L) at 60° C. Insoluble material was removed at each stage by filtration through a no 3 glass sinter and the extracts concentrated to dryness as before. The solid was crystallised from acetonitrile:water (3:7) before being recrystallised from the same solvent and dried to constant weight over $P_2O_5$ to give the title compound (244.0 g), which by proton NMR analysis showed equivalence with an authentic sample of 4'-demethylsordarin.

(ii) The fermentation procedure in (i) above was followed, and after the broth was made 0.1M with respect to sodium hydroxide this was ultrafiltered through ETNA 10A membrane (10 kDalton cut-off). After diafiltration with water the bulked permeate was a clear solution. After adjustment to pH 5.2, using concentrated sulphuric acid, the permeate was loaded to a column of XAD16 resin at a rate of 2 column volumes per hour to give a final loading of 32 g 4'-demethylsordarin per liter of resin. The column was washed at a rate of 2 column volumes per hour, first with 0.1% v/v phosphoric acid and then with 20% v/v acetonitrile/water (10 column volumes of each). The column was eluted with 65% acetonitrile/water at 2 column volumes per hour. A forerun of 0.75 column volumes was discarded. 85% of the loaded 4'-demethylsordarin was recovered in the next 1.6 column volumes of eluate. The rich eluate was treated by stirring for 5 minutes with 2% w/v of DE52 cellulose, which was removed by filtration. An aliquot of DE52 treated eluate was concentrated to 62% of the original volume (43% acetonitrile) using a rotary evaporator. The concentrated eluate was held at 4° C. for 15 hours to crystallise and the solids formed collected by filtration through a glass sinter. The crystals were washed with four cake volumes of 30% v/v acetonitrile/water and dried at 30° C. in vacuo. The title compound (1.94 g) was recovered from the concentrated eluate as a pale grey solid.

PREPARATION 5

Screen for Microorganisms Capable of Demethylating Sordarin at the 4' Position Microorganisms capable of demethylating sordarin at the 4'-position could be identified by growing them at 28° C.

(bacteria) or 25° C. (fungi) in 10 ml volumes of SB1 (bacteria) or FB1 (fungi) in 50 ml conical flasks shaken at 250 rpm. After 2 days, sordarin was added to a final concentration of 0.5 mg/ml (from a 200 mg/ml stock solution in 80% ethanol) and the flasks were then incubated for a further 3 days. A 500 μl sample of whole culture was mixed in an Eppendorf tube with 500 μl of 80% acetonitrile/2% trifluoroacetic acid and left to extract at room temperature for 30 minutes. The extract supernatant, obtained by centrifuging samples in a microfuge was assayed by isocratic HPLC for the presence of 4'-demethylsordarin. 4'-demethyl sordarin eluted at 3.35 mins with a mobile phase of 35% acetonitrile in water, flow rate 2 ml/min, using a Spherisorb $C_6$ column (5 μm, 15 cm×4.6 mm). By this method, the following microorganisms were identified as sordarin demethylators:

| | |
|---|---|
| Streptomyces capreolus | ATCC 31963 |
| Streptomyces avermitilis | ATCC 31272 |
| Streptomyces armentosus | NRRL 3176 |
| Streptomyces antibioticus | ATCC 31771 |
| Streptomyces rimosus | ATCC 23955 |
| Streptomcyes platensis | ATCC 29778 |
| Streptomyces mashuensis | ATCC 23934 |
| Streptomyces eurythermus | ATCC 14975 |
| Nocardia orientalis | ATCC 43491 |
| Cunninghamella echinulata var elegans | ATCC 36112 |
| SB1 Medium | g/L |
| Arkasoy | 25 |
| Yeast extract | 5 |
| $KH_2PO_4$ | 5 |
| Glucose | 20 |
| Distilled Water | |
| pH 7 | |
| FB1 Medium | |
| Soya oil | 30 |
| Arkasoy | 10 |
| Yeast extract | 5 |
| $K_2HPO_4$ | 5 |
| Glucose | 20 |
| Distilled Water | |
| pH 5.5 | |

PREPARATION 6

Production of 4'-demethylsordarin by Biotransformation of Sordarin 0.3 ml of a spore suspension of *Streptomyces capreolus* ATCC 31963 (in 15% v/v glycerol stored at −20° C.) was inoculated into 30 ml SBI medium in a 250 ml Erlenmeyer flask to give a seed culture which was incubated at 28° C. and 250 rpm on a rotary shaker. After 4 days, 0.5ml of this was used to inoculate 35 ml SB1 in a 250 ml flask which was grown for 48 hours at 28° C., 250 rpm. At this stage, the culture was aliquoted as 10 ml amounts into 50 ml Erlenmeyer flasks which were fed with 5 mg sordarin (from a 200 mg/ml stock solution in ethanol). Incubation was continued for a further 3 days. 80% v/v acetonitrile in water (14 ml) was added to whole broth (14 ml) and the mixture was kept at room temperature and occasionally agitated. After 30 minutes, the cells were removed by centrifugation. Acetonitrile was removed by evaporation and the pH of the aqueous solution was adjusted to 2.5 with orthophosphoric acid. The solution was passed through a column containing Amberlite XAD-16 resin (bed volume 5 ml). The adsorbent was washed sequentially with water (10 ml), 10% v/v acetonitrile in water (20 ml), 30% v/v acetonitrile in water (10 ml), 50% v/v acetonitrile in water (20 ml) and 90% v/v acetonitrile in water (10 ml). Fractions were monitored by HPLC; 4'-demethylsordarin was located in the 50% v/v acetonitrile in water eluate. The fraction containing 4'-demethylsordarin was evaporated to dryness in vacuo at the room temperature and the residue was re-dissolved in 35% v/v acetonitrile in water (15 ml). 4'-demethylsordarin was purified by preparative HPLC:

| | |
|---|---|
| Column | Spherisorb 5 micron $C_6$ 25 cm × 2.5 cm |
| Flow rate | 25 ml/min |
| Detection | UV at 210 nm |
| Mobile Phase | 350 ml acetonitrile made up to 1000 ml with 0.05 M ammonium dihydrogen phosphate in water. pH adjusted to 2.5 with orthophosphoric acid |
| Injection volume | 4.5 ml |

4'-Demethylsordarin was eluted after 10.0 minutes under these conditions. The pooled fractions from four HPLC runs were diluted 1:1 with water then pumped back onto the silica (after washing this with acetonitrile and re-equilibrating with water). The adsorbent was washed with water (200 ml) and adsorbed product was eluted with 95% v/v acetonitrile in water (200 ml). The acetonitrile/water eluate was evaporated to remove organic solvent, and the aqueous solution freeze dried to yield 4'-demethylsordarin (1.5 mg) as a white powder. δ ($^1$,$CDCl_3$); 9.74(s,1H); 6.08(brd,3,1H); 4.70(d, 1.5,1H); 4.16(d,9.5,1H); 4.08(dd,4.5,3.5,1H); 3.88(dd,4.5, 1.5,1H); 3.75(dq,8.5,6,1H); 3.62(d,9.5,1H); 3.68(dd,8.5,3.5, 1H); 2.65(m,1H); 2.34(m,1H); 1.32(d,6,3H); 1.30(d,12.5, 1H); 1.23(m,1H); 1.04(d,7,3H); 0.99(d,7,3H); 0.81(d,7,3H)

PREPARATION 7

Production of Sordaricin

The procedure according to Preparation 1 was followed up to and including the preparative HPLC stage. The fraction eluting between 21.4 and 25.0 min was collected. Pooled fractions from the 10 injections (22 L) were diluted with an equal volume of water and this solution was pumped back through the Kromasil column at 28 L/h. The column was washed with water (20 L) then eluted with 90% acetonitrile (4.5 L). This eluate was combined with the corresponding eluate fraction (4.5 L) from a similar fermentation which had been processed by the same procedure. Combined 90% acetonitrile eluates were concentrated by rotary evaporation until product began to crystallise (volume about 1.6 L). The residue was heated on a 60° C. water bath with addition of the minimum volume of acetonitrile to give a clear solution. The solution was cooled and stored at 4° C. Crystals were filtered on a No.3 sinter and dried in vacuo to yield a brown solid. This was recrystallised from acetonitrile:water (40:60) and the product was filtered, washed with 25% acetonitrile and dried in vacuo to give the title compound (10.7 g). MS and NMR analysis of the product showed equivalence with an authentic sample of sordaricin.

PREPARATION 8

Biotransformation of Sordarin to Sordaricin

A 0.2 ml suspension of NCIMB 40675 was used to inoculate a 250 ml Erlenmyer flask containing 50 ml of nutrient broth (Oxoid) supplemented with 0.2% yeast extract. The culture was incubated at 28° C. for 29 hours on a rotary shaker operated at 250 rpm with a 50 mm orbital motion. Aliquots (1 ml) of the developed. inoculum were used to inoculate further 250 ml Erlenmyer flasks containing 50 ml of double strength nutrient broth (Oxoid) supplemented with 0.1% yeast extract. These were incubated as above for 24 hours. 62 of these flasks were pooled to provide 2.65 liters of developed culture which was added to 30 liters sordarin fermentation filtrate, pH adjusted to 7.5, prepared as in Preparation 1. The reaction was carried out in a 70 liter fermenter at 30° C., agitated at 200 rpm, aeration at 0.5VVM. The pH was controlled to 7.5 by addition of 1N hydrochloric acid. After 6 days, approximately 16 g of sordarin was converted to sordaricin. Biotransformation broth was filtered through Dicalite on a vacuum filter and the bed was washed with water to give 31.5 L filtrate, pH8.2. This was adjusted to pH6.0 with $H_3PO_4$ and pumped through a bed (25 cm×5 cm) of Amberchrom CG161 resin at 290 ml/min. The Amberchrom bed was washed with 0.1% $H_3PO_4$ (2 L) and 25% acetonitrile (4 L) then eluted with 60% $CH_3CN$ (2 L). Eluate was concentrated by rotary evaporation until the onset of crystallisation, then the residue was heated on a 60° C. water bath with additions of the minimum acetonitrile to give a clear solution. This was cooled and chilled at 4° C. overnight. Crystals were filtered, washed with 25% acetonitrile and dried in vacuo to give a brown powder. Crude product was recrystallised from 1 L of acetonitrile:water (40:60), filtered, washed and dried as above to yield sordaricin as pale brown needles (6.15 g).

PREPARATION 9

Biotransformation of Sordarin to Sordaricin

A loopful of surface growth from an agar culture of NCIMB 40675 was used to inoculate a 250 ml Erlenmeyer flask containing 50 ml of nutrient broth (Oxoid) supplemented with 0.2% yeast extract. The culture was incubated for 26 hours at 25° C. on a rotary shaker operating at 250 rpm with a 50 mm diameter throw. 1 ml aliquots of the developed culture were used to inoculate 250 ml Erlenmyer flasks as described above. The flasks were supplemented with pure sordarin in 80% ethanol to give a final concentration of 1.25 mg/ml. The flasks were incubated as above for 8 days, then bulked to give 365 mls of culture broth containing sordarin. Bioconversion mixture was centrifuged to remove NCIMB 40675 cells, and supernatant (350 ml) decanted. To supernatant was added Whatman Partisil P40 ODS-3 (5 ml, pre-wetted with acetonitrile) and the pH of this mixture was adjusted to 4.0 with $H_3PO_4$. Partisil was filtered off on a Buchner funnel and eluted with acetonitrile (100 ml) followed by 75% acetonitrile (100 ml). Combined eluates were-evaporated to an aqueous residue of 10–15 ml. This was heated on a 60° C. water bath and acetonitrile added until a clear solution was obtained, then heating maintained and water added until the solution became cloudy. The mixture was cooled and stored at 4° C. for several days. Crystals were filtered on a No.3 sinter, washed with water and dried in vacuo over $P_2O_5$ to give sordaricin as white needles (92 mg).

PREPARATION 10

Production of Sordaricin

A frozen ampoule of IMI 362947 was used to inoculate 50 ml of seed medium FS in a 250 ml Erlenmeyer flask. This flask was incubated at 25° C. for 6 days on a rotary shaker operated at 250 rpm with a 50 mm diameter orbital action. Aliquots (1 ml) of the developed inoculum were used to inoculate four 250 ml Erlenmeyer flasks containing 50 ml shake-flask production medium SM55/A.

| SM55/A | g/l |
|---|---|
| Maltodextrin MD30E (Roquette Frere) | 120 |
| Beet molasses | 15 |
| Peptone (Oxoid L37) | 10 |
| Proflo (Traders Protein) | 30 |
| L-Tryptophan (Sigma) | 2 |
| $ZnSO_4.7H_2O$ (BDH) | 0.04 |
| $FeSO_4.7H_2O$ (Sigma) | 2 |
| $CaCO_3$ (BDH) | 5 |
| $MgSO_4.7H_2O$ (BDH) | 5 |

Made up in distilled water and autoclaved at 121° C. for 120 minutes.

These cultures were incubated as described above for 7 days. The flask contents were pooled and a 40 ml portion was treated with 1 N sodium hydroxide (4 ml) with occasional agitation at room temperature for 45 minutes. The cells were then removed by centrifugation at 300 rpm for 20 minutes, the supernatant was taken and the pH was adjusted to 3 with 1N hydrochloric acid. The solution was passed through a Bond Elut column (1 g size; C18) and the adsorbent was washed with water (20 ml) then eluted with 90% v/v acetonitrile in water (15 ml). The eluate was evaporated to dryness at room temperature and the residue was taken up in 50% v/v acetonitrile in water (9 ml). Sordaricin was purified by preparative HPLC:

| | |
|---|---|
| Column | Spherisorb 5 micron ODS-2 (25 cm × 2.1 cm) |
| Flow rate | 25 ml/min |
| Mobile phase | 550 ml acetonitrile made up 1000 ml with water, with 1 ml trifluoracetic acid added per liter of mobile phase |
| Detection | 210 nm |
| Injection volume | 4.5 ml |

Sordaricin eluted after 6.0 minutes under these conditions. Fractions containing sordaricin were pooled, acetonitrile was removed by rotary evaporation at room temperature, and the aqueous solution was freeze dried to yield the title compound (8.9 mg) as a white powder.

INTERMEDIATE 1

[1R-(1α,3aβ,4β,4aβ,7β,7aα,8aβ)] 8a-[(6-Deoxy-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of 4'-demethylsordarin (10 g) in methanol (200 ml) was added dropwise at room temperature a 0.35M solution of diphenyldiazomethane (90 ml) in methylene chloride, and the mixture was stirred for 6 hours. The solvent was evaporated to dryness and the residue chromatographed in a silica gel flash column with hexane:ethyl acetate (3:1) as eluent to give the title compound (12.6 g) as a pale yellow foam.

δ ($^1H$, $CDCl_3$): 9.73 (s, 1H, CHO), 6.98 (s, 1H, C$\underline{H}$Ph$_2$), 6.05 (dd, 1H, H-2, J=1.5 and 3.6 Hz), 4.65 (d, 1H, H-1', J=1.5 Hz), 4.09, 3.76 (2d, 2H, 8a-C$\underline{H}_2$, J=9 Hz), 4.01 (m, 1H, H-2'), 3.84 (m, 1H, H-3'), 3.75 (m, 1H, H-5'), 3.69 (m, 1H, H-4'), 2.73 (t, 1H, H-1, J=4.2 Hz).

INTERMEDIATE 2

[1R-(1α,3aβ,4β,4aβ,7β,7aα,8aβ)] 8a-[(6-Deoxy-3,4-O-isopropylidene-β-D-altropyranosyloxy)methyl]-4-formyl-4,4a,5,6,7,7a,8,8a-octahydro-7-methyl-3-(1-methylethyl)-(1H)-1,4-methano-s-indacene-3a(1H)-carboxylic acid, diphenylmethyl ester To a solution of Intermediate 1 (650 mg) in 15 ml of dimethoxypropane:acetone (1:2) was added p-toluensulphonic acid (10 mg). The solution was stirred at room temperature for 1.5 hours, then potassium carbonate (1.0 g) was added, the stirring continued for 30 minutes and the solvent evaporated to dryness. The crude mixture was partitioned between ethyl acetate (50 ml) and water (25 ml), the aqueous phase was extracted with ethyl acetate (2×50 ml), the organic phase was washed with brine, dried over magnesium sulphate and evaporated to dryness. The residue was flash chromatographed on silica gel eluting with ethyl acetate:hexane (1:3) to give the title compound (600 mg) as a white foam.

δ ($^1$H, CDCl$_3$): 9.73 (s, 1H, CHO), 7.45–7.24 (m, 10H, 2Ph), 6.98 (s, 1H, CHPh$_2$), 6.06 (dd, 1H, H-2, J=1.5 and 3.3 Hz), 4.57 (d, 1H, H-1', J=3.0 Hz), 4.30 (dd, 1H, H-3', J=3.6 and 5.7 Hz), 4.07 (d, I H, 8aCH$_2$, J=9.0 Hz), 3.95–3.93 (m, 1H, H-2'), 3.85 (dd, 1H, H-4', J=5.7 and 9.3 Hz), 3.75 (d, 1H, 8aCH$_2$, J=9.0 Hz), 3.44 (dq, 1H, H-5', J$_d$=9.3 Hz, J$_q$=6.3 Hz), 2.73 (t, 1H, H-1, J=3.6 Hz).

INTERMEDIATE 3

[1R-(1α, 3aβ, 4β, 4aβ, 7β, 7aα, 8aβ)] 8a-[(6-Deoxy-3,4-O-(2-pentylidene)-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a suspension of Intermediate 1 (500 mg) and p-toluensulphonic acid (5 mg) in dichloromethane (5 ml) was added 2,2-dimethoxypentane (2 ml). The mixture was stirred at room temperature for 2 hours. Potassium carbonate (150 mg) was added and the stirring continued for 30 minutes. The solvent was evaporated to dryness and the residue flash chromatographed on silica gel eluting with ethyl acetate:hexane (15:85) and (30:70) to give the title compound (474 mg).

δ ($^1$H, CDCl$_3$): 9.73 (s, 1H, CHO), 7.45–7.24 (m, 10H, 2Ph), 6.98 (s, 1H, CHPh$_2$), 6.06 (dd, 1H, H-2, J=1.5 and 3.3 Hz), 4.57 (d 1H, H-1', J=2.1 Hz), 4.30 (dd, 1H, H-3', J=3.9 and 6.0 Hz), 4.04 (d, I H, 8aCH$_2$, J=9.0 Hz), 3.94–3.91. (m, 1H, H-2'), 3.86 (dd, 1H, H-4', J=6.3 and 9.6 Hz), 3.73 (d, 1H, 7aCH$_2$, J=9.0 Hz), 3.45 (dq, 1H, H-5, J$_d$=9.0 Hz, J$_q$=6.0 Hz), 2.72 (t, 1H, H-1, J=3.6 Hz).

INTERMEDIATE 4

[1R-(1α, 3aβ, 4β, 4aβ, 7β, 7aα, 8aβ)] 8a-[(6-Deoxy-3,4-O-(4-methoxy-2-butylidene)-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a suspension of Intermediate 1 (350 mg) and p-toluensulphonic acid (5 mg) in dichloromethane (4 ml) was added 2,2,4-trimethoxybutane (1 ml). The mixture was stirred at room temperature for 1 hour. Potassium carbonate (150 mg) was added and the stirring continued for 30 minutes. The solvent was evaporated to dryness and the residue flash chromatographed on silica gel eluting with ethyl acetate:hexane (3:7) and (4:6) to obtain the title compound (290 mg) in a 3:1 epimer ratio.

δ ($^1$H, CDCl$_3$) signals of the major component: 9.73 (s, 1H, CHO), 7.45–7.20 (m, 10H, 2Ph), 6.98 (s, 1H, CHPh$_2$), 6.06 (dd, 1H, H-2, J=1.5 and 3.6 Hz), 4.57 (d, 1H, H-1', J=2.1 Hz), 4.31 (dd, 1H, H-3', J=3.9 and 6.0 Hz), 4.05 (d, 1H, 8aCH$_2$, J=9.0 Hz), 3.95–3.90 (m, 1H, H-2'), 3.88 (dd, 1H, H-4', J=6.0 and 9.3 Hz), 3.73 (d, 1H, 8aCH$_2$, J=9.0 Hz), 3.51 (t, 2H, CH$_2$O, J=7.2 Hz), 3.50–3.45 (m, 1H, H-5'), 3.33 (s, 3H, CH$_3$O), 2.72 (t, 1H, H-1, J=3.6 Hz).

INTERMEDIATE 5

[1R-(1α, 3aβ, 4β, 4aβ, 7β, 7aα, 8aβ)] 8a-[(6-Deoxy-3,4-O-cyclopentylidene-β-D-altropyranosyloxy)]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a suspension of Intermediate 1 (160 mg) in dichloromethane:1,1-dimethoxycyclopentane (3:1, 4 ml) was added p-toluensulphonic acid (5 mg) and the mixture was stirred at room temperature for 2 hours. Potassium carbonate (1 g) was added and the stirring continued for 30 minutes. The solvent was evaporated to dryness and the residue was flash chromatographed on silica gel eluting with ethyl acetate:hexane (1:4) to obtain the title compound (142 mg).

δ ($^1$H, CDCl$_3$): 9.73 (s, 1H, CHO), 7.45–7.25. (m, 10H, 2Ph), 6.98 (s, 1H, CHPh$_2$), 6.06 (dd, 1H, H-2, J=1.5 and 3.6 Hz), 4.55 (d, 1H, H-1', J=1.8 Hz), 4.17 (dd, 1H, H-3', J=3.0 and 5.1 Hz), 4.08 (d, 1H, 8aCH$_2$, J=9.0 Hz), 3.95 (dt, 1H, H-2', J$_d$=1.8 Hz, J$_t$=3.0 Hz), 3.81 (dd, 1H, H-4', J=5.1 and 9.3 Hz), 3.76 (d, 1H, 8aCH$_2$, J=9.0 Hz), 3.42 (dq, 1H, H-5', J$_d$=9.3 Hz, J$_q$=6.3 Hz), 2.73 (t, 1H, H-1, J=3.9 Hz).

INTERMEDIATE 6

[1R-(1α, 3aβ, 4β, 4aβ, 7β, 7aα, 8aβ)] 8a-[(6-Deoxy-3,4-O-isopropylidene-2-O-(methylthio)thiocarbonyl-β-D-altropyranosyloxy)methyl-4-formyl-4,4a,5,6,7,7a,8,8a-octahydro-7-methyl-3-(1-methylethyl)-1,4-methano-s-indacene-3a(1H)-carboxylic acid, diphenylmethyl ester Intermediate 2 (100 mg) and imidazole (1 mg) were dissolved in dry tetrahydrofuran (4 ml) under nitrogen atmosphere. Sodium hydride (5 mg) was added and the suspension was stirred at room temperature for 0.5 hours. Carbon disulfide (27 μl) was added, the stirring continued for 20 minutes and methyl iodide (18 μl) was added. After 2 hours the reaction was stopped by addition of 1N ammonium chloride (20 ml). The mixture was extracted with ethyl acetate (3×25 ml), the organic phase was washed with brine, dried over magnesium sulphate and the solvent evaporated to dryness. The residue was purified in a flash chromatography column on silica gel eluting with ethyl acetate:hexane (1:9) to give the title compound (110 mg).

δ ($^1$H, CDCl$_3$): 9.71 (s, 1H, CHO), 7.44–7.25 (m, 10H, 2Ph), 6.96 (s, 1H, CHPh$_2$), 6.01 (dd, 1H, H-2, J=1.2 and 3.6 Hz), 6.90 (dd, 1H, H-2', J=2.4 and 5.4 Hz), 4.85 (d, 1H, H-1', J=2.4 Hz), 4.53 (dd, 1H, H-3', J=5.4 and 6.3 Hz), 4.00 (dd, 1H, H-4', J=6.3 and 8.7 Hz), 3.93 (d, 1H, 8aCH$_2$, J=9.3 Hz), 3.65 (dq, 1H, H-5', J$_d$=8.7, J$_q$=6.3 Hz), 2.68 (t, 1H, H-1, J=3.9 Hz), 2.59 (s, 3H, CH$_3$S).

INTERMEDIATE 7

[1R-(1α, 3aβ, 4β, 4aβ, 7β, 7aα, 8aβ)] 8a-[(2,6-Dideoxy-3,4-O-isopropylidene-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester (i) Intermediate 6 (95 mg) was dissolved in dry toluene (5 ml) under nitrogen atmosphere and heated at 110° C. A solution of tributyltin hydride (64 μl) in dry toluene (5 ml) was added dropwise over 1.5 hours with stirring. The heating was continued for another 1.5 hours, methanol (2ml) was added and the solvent evaporated to dryness. Flash chromatography of the residue on silica gel eluting with ethyl acetate:hexane (1:9) gave the title compound (42 mg).

δ ($^1$H, CDCl$_3$): 9.73 (s, 1H, CHO), 7.44–7.25 (m, 10H, 2Ph), 6.98 (1H, s, CHPh$_2$), 6.05 (dd, 1H, H-2, J=1.2 and 3.3 Hz), 4.54 (dd, 1H, H-1', J=2.7 and 9.3 Hz), 4.39 (dt, 1H, H-3', J$_d$=2.7 Hz, J$_t$=3.6 Hz), 4.04 (d, 1H, 8aCH$_2$, J=9.0 Hz), 3.67 (d, 1H, 8aCH$_2$, J=9.0 Hz), 3.65 (dd, 1H, H-4', J=3.6 and 8.7 Hz), 3.44 (dq, 1H, H-5', J$_d$=6.3 Hz, J$_q$=8.7 Hz), 2.75 (t, 1H, J=3.9 Hz).

(ii) A solution of tributyltin hydride (5.5 ml) in dry toluene (150 ml) was degassed with an argon stream for 1 hour and heated to reflux. A solution of Intermediate 6 (6 g) in dry toluene (50 ml) was then added over a period of 2 hours. Heating was continued until the reaction was complete (1.5 hours). Elimination of the solvent under reduced pressure gave a crude which was flash chromatographed over silica gel eluting with hexane and hexane:ethyl acetate (20:1 to 15:1) to afford the title compound (4 g).

INTERMEDIATE 8

[1R-(1α, 3aβ, 4β, 4aβ, 7β, 7aα, 8aβ)] 8a-[(2,6-Dideoxy-3,4-O-(4-methyoxy-2-butylidene)-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 4 (600 mg) in dry tetrahydrofuran (10 ml) at 0° C. and under nitrogen atmosphere were added sodium hydride (30 mg) and imidazole (5 mg). The solution was stirred for 10 minutes and carbon disulfide (147 μl) was added. After 20 minutes methyl iodide (127 μl) was added and the stirring continued for 30 minutes. 1N Ammonium chloride (20 ml) was added and the mixture extracted with ethyl acetate (3×25 ml), the organic phase washed with brine, dried over magnesium sulphate and the solvent evaporated to dryness. The residue was flash chromatographed on silica gel eluting with ethyl acetate:hexane (15:85) to give a white foam. This foam was dissolved in dry toluene (10 ml) under nitrogen atmosphere and a solution of tributyltin hydride (0.46 ml) in toluene (10 ml) was added dropwise over 2 hours at 115° C. The heating was continued for 2 hours. The solvent was evaporated to dryness and the residue purified by flash chromatography on silica gel eluting with ethyl acetate:hexane (15:85) to give the title compound (260 mg) in a epimer ratio of 4:1.

δ ($^1$H, CDCl$_3$): 9.63 (s, 1H, CHO), 7.44–7.20 (m, 10H, 2Ph), 6.99 (s, 1H, CHPh$_2$), 6.06 (dd, 1H, H-2, J=1.2 and 3.3 Hz), 4.53 (dd, 1H, H-1', J=2.7 and 8.7 Hz), 4.42 (dt, 1H, H-3', J$_d$=3.0 Hz, J$_t$=4.2 Hz), 4.03 (d, 1H, 8aCH$_2$, J=9.0 Hz), 3.68 (dd, 1H, H-4', J=5.1 and 9.3 Hz), 3.66 (d, 1H, 8aCH$_2$, J=9.0 Hz), 3.52 (t, 2H, CH$_2$O, J=7.2 Hz), 3.40 (dq, 1H, H-5', J$_d$=6.3 Hz, J$_q$=6.3 Hz), 3.34 (s, 3H, CH$_3$O), 2.74 (t, 1H, H-1, J=4.2 Hz).

INTERMEDIATE 9

[1R-(1α, 3aβ, 4β, 4aβ, 7β, 7aα, 8aβ)] 8a-[(6-Deoxy-3,4-O-thiocarbonyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A mixture of Intermediate 1 (0.500 g) and thiocarbonyldiimidazole (0.270 g) in tetrahydrofuran (10 ml) was refluxed for 6 hours. The solvent was evaporated in vacuo to give a yellow residue which was chromatographed on silica gel flash column eluting with hexane:ethyl acetate (3:1) to give the title compound (0.263 g).

δ ($^1$H, CDCl$_3$): 9.71 (s, 1H, CHO), 7.44–7.26 (m, 10H, 2×Ph), 6.97 (s, 1H, CO$_2$CHPh$_2$), 6.06 (dd, 1H, H-2, J=1.5 and 3.3 Hz), 4.93 (dd, 1H, H-3', J=3.9 and 7.2 Hz), 4.63 (d, 1H, H-1', J=2.1 Hz), 4.61 (dd, 1H, H-4', J=7.2 and 9.3 Hz), 4.12 (m, 1H, H-2'), 4.08 (d, 1H, 8aCH$_2$, J$_{AB}$=9.3 Hz), 3.74 (d, 1H, 8aCH$_2$, J$_{AB}$=9.3 Hz), 3.64 (m, 1H, H-5'), 2.69 (m, 1H, H-1).

INTERMEDIATE 10

[1R-(1α, 3aβ, 4β, 4aβ, 7β, 7aα, 8aβ)] 8a-[(2,6-Dideoxy-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 7 (1.5 g) in a mixture of tetrahydrofuran (30 ml) and methanol (15 ml) was added dropwise at room temperature a 1N solution of hydrochloric acid (15 ml) with vigorous stirring. Once the reaction was concluded (TLC control), saturated sodium bicarbonate (50 ml) and ethyl acetate (200 ml) were added and the mixture partitioned. The organic layer was washed with water (2×100 ml) and dried over magnesium sulfate. Elimination of the solvent gave a residue which was flash chromatographed over silica gel eluting with hexane:ethyl acetate (5:1) and (2:1) to give the title compound (1.1 g) as a white foam.

δ ($^1$H, CDCl$_3$): 9.73 (s, 1H, CHO), 7.5–7.2 (m, 10H, 2Ph), 6.99 (s, 1H, CHPh$_2$), 6.05 (dd, 1H, H-2, J=1.2 and 3.3 Hz), 4.64 (dd, 1H, H-1', J=2.1 and 9.6 Hz), 4.11 (m, 1H, H-3'), 4.06 (d, 1H, 8aCH$_2$, J$_{AB}$=9.3 Hz), 3.70 (m, 2H, H-5' and 8aCH$_2$), 3.34 (m, 1H, H-4'), 2.75 (t, 1H, H-1, J=3.6 Hz).

INTERMEDIATE 11

[1R-(1α, 3aβ, 4β, 4aβ, 7β, 7aα, 8aβ)] 8a-[(2,6-Dideoxy-3,4-O-thiocarbonyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A suspension of Intermediate 10 (160 mg) and dibutyltin oxide (124.5 mg) in dry toluene (15 ml) was heated under reflux for 2 hours in a flask fitted with a Dean-Stark condenser and then allowed to stand at room temperature under nitrogen atmosphere. To the resulting solution was added phenyl-chlorothionoformate (69 μl) in dry toluene (5 ml). TLC control showed that the reaction was complete after 6 hours. The solvent was removed under reduced pressure and the crude mixture was flash chromatographed over silica gel eluting with hexane:ethyl acetate (20:1) and (15:1) to give the title compound (150 mg) as a colourless oil.

δ ($^1$H, CDCl$_3$): 9.72 (s, 1H, CHO), 7.5–7.2 (m, 10H, 2Ph), 6.97 (s, 1H, CHPh$_2$), 6.05 (dd, 1H, H-2, J=1.5 and 3.6 Hz), 5.10 (m, 1H, H-3'), 4.61 (dd, 1H, H-1', J=2.4 and 8.4 Hz), 4.44 (dd, 1H, H-4', J=6.6 and 9.0 Hz), 4.04 and 3.67 (2d, 2H, 8aCH$_2$, J$_{AB}$=9 Hz), 3.62 (m, 1H, H-5'), 2.70 (t, 1H, H-1, J=2.0 Hz).

INTERMEDIATE 12

[1R-(1α,3aβ,4β,4aβ,7β,7aα,8aβ)] 8a-[(4-O-Allyl-2,6-Dideoxy-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A suspension of Intermediate 10 (400 mg) and tributyltin oxide (240 mg) in dry toluene (50 ml) was heated to reflux in a flask fitted with a Dean-Stark condenser and then allowed to stand at room temperature under nitrogen atmosphere (approximately 10 ml of azeotropic mixture was removed). Allyl bromide (71 µl) and tetrabutylammonium fluoride (1 M solution in tetrahydrofuran, 0.95 ml) were added consecutively and the mixture heated at 500° C. for 24 hours. Elimination of solvent gave a residue which was flash chromatographed over silica gel eluting with acetone:hexane (1:20) and (1:15) to give the title compound (300 mg) as a colourless oil.

$\delta$($^1$H, CDCl$_3$): 9.72 (s, 1H, CHO), 7.52–7.2 (m, 10H, 2Ph), 6.98 (s, H, CHPh$_2$), 6.05 (dd, 1H, H-2, J=1.5 and 3.6 Hz), 5.89 (m, 1H, C$\underline{H}$=CH$_2$), 5.30–5.20 (m, 2H, CH=C$\underline{H}_2$), 4.64 (dd, 1H, H-1', J=2.1 and 9.6 Hz), 4.19 (m, 1H, H-3'), 4.15–3.95 (m, 3H, C$\underline{H}_2$CH=CH$_2$+8aCH$_2$), 3.80–3.60 (m, 2H, H-5'+8aCH$_2$), 3.06 (dd, 1H, H-4', J=3.3 and 9.3 Hz), 2.75 (t, 1H, H-1, J=3.9 Hz), 2.38 (bd, 1H, OH).

INTERMEDIATE 13

[1R-(1α, 3aβ, 4β, 4aβ, 7β, 7aα, 8aβ)] 8a-[(2,6-Dideoxy-4-O-(2-methyl-2-propenyl)-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A suspension of Intermediate 10 (500 mg) and tributyltin oxide (300 mg) in dry toluene (50 ml) was heated to reflux in a flask fitted with a Dean-Stark condenser and then allowed to stand at room temperature under nitrogen atmosphere (approximately 10 ml of azeotropic mixture was removed). 3-Bromo-2-methyl-propene (202 µl) and tetrabutylammonium fluoride (1M solution in tetrahydrofuran, 0.90 ml) were added consecutively and the mixture heated at 50° C. for 24 hours. Elimination of the solvent gave a residue which was flash chromatographed over silica gel eluting with acetone:hexane (1:20) and (1:15) to give the title compound (340 mg) as a colourless oil.

$\delta$($^1$H, CDCl$_3$): 9.73 (s, 1H, CHO), 7.50–7.20 (m, 10H, 2Ph), 6.98 (s,1H, CHPh$_2$), 6.05 (dd, 1H, H-2, J=1.5 and 3.6 Hz), 4.96 and 4.91 (2m, 2H, =CH$_2$), 4.65 (dd, 1H, H-1', J=1.8 and 9.6 Hz), 4.20 (m, 1H, H-3'), 4.05 and 3.68 (2d, 2H, 8aCH$_2$, J$_{AB}$=9.3 Hz), 4.00 and 3.87 (2d, 2H, OCH$_2$, J$_{AB}$=12 Hz), 3.75 (m, 1H, H-5'), 3.06 (dd, 1H, H-4, J=3 and 9.6 Hz), 2.75 (t, 1H, H-1, J=3.6 Hz), 2.37 (bd, 1H, OH), 1.76 (bs,3H, C$\underline{H}_3$C=CH$_2$).

INTERMEDIATE 14

[1R-(1α, 3aβ, 4β, 4aβ, 7β, 7aα, 8aβ)] 8a-[(6-Trioxa-3,7-dimethyl-cis-bicyclo[4.4.0]-dec-9-yl-oxy-methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 12 (200 mg) in anhydrous tetrahydrofuran (10 ml) was added, at room temperature under nitrogen atmosphere, solid mercuric trifluoroacetate (213 mg) in small portions. The reaction mixture was allowed to stand at room temperature for 30 minutes and tributyltin hydride (135 µl) was added with vigorous stirring. After 30 minutes ethyl acetate (50 ml) was added and the suspension filtered through celite to give a colourless solution which was washed with water (3×100 ml) and dried over magnesium sulfate. Elimination of the solvent gave an oil which was flash chromatographed over silica gel eluting with acetone:hexane (1:15) to give the title compound (120 mg) as a 1:1 mixture of epimers at C-3'.

$\delta$ ($^1$H, CDCl$_3$) includes: 4.73 (dd, 1H, H-9', J=3.0 and 6.3 Hz), 4.62 (dd, 1H, H-9', J=2.1 and 9.9 Hz).

INTERMEDIATE 15

[1R-(1α, 3aβ, 4β, 4aβ, 7β, 7aα, 8aβ)] 8a-[[1S,7R,9S]-2,5,8-Trioxa-3,3,7-trimethyl-cis-bicyclo[4.4.0]-dec-9-yl-oxy-methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 13 (325 mg) in anhydrous tetrahydrofuran (10 ml) was added, at room temperature under nitrogen atmosphere, solid mercuric trifluoroacetate (303 mg) in small portions. The reaction mixture was allowed to stand at room temperature for 30 minutes and tributyltin hydride (192 µl) was added with vigorous stirring. After 30 minutes ethyl acetate (50 ml) was added and the suspension filtered through celite to give a colourless solution which was washed with water (3×100 ml) and dried over magnesium sulfate. Elimination of the solvent gave an oil which was flash chromatographed over silica gel eluting with acetone:hexane (1:20) and (1:15) to give the title compound (210 mg) as a colourless oil.

$\delta$ ($^1$H, CDCl$_3$): 9.73 (s, 1H, CHO), 7.50–7.20 (m, 10H, 2Ph), 6.98 (s, 1H, CHPh$_2$), 6.03 (dd, 1H, H-2, J=1.2 Hz, J=3.3 Hz), 4.54 (dd, 1H, H-9', J=2.1 and 9.6 Hz), 4.25 (m, 2H, H-7' and H-1'), 4.05 and 3.66 (2d, 2H, 8aCH$_2$, J$_{AB}$=9 Hz), 3.41 and 3.18 (2d, 2H, OCH$_2$, J$_{AB}$=11.7 Hz), 3.25 (dd, 1H, H-6', J=3.3 and 10.2 Hz), 2.75 (t, 1H, H-1, J=3.3 Hz), 1.25 and 1.16 (2s, 2CH$_3$).

INTERMEDIATE 16

[1R-(1α, 3aβ, 4β, 4aβ, 7β, 7aα, 8aβ)] 8a-[2,6-Dideoxy-4-O-p-methoxybenzyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A suspension of Intermediate 10 (500 mg) and tributyltin oxide (374 mg) in dry toluene (50 ml) was heated to reflux in a flask fitted with a Dean Stark condenser and then allowed to stand at room temperature under nitrogen atmosphere (approximately 10 ml of azeotropic mixture were removed). p-Methoxybenzyl chloride (135 µl) and tetrabutylammonium fluoride (1M solution in tetrahydrofuran, 1.5 ml) were added consecutively and the mixture heated at 60° C. for 24 hours. Elimination of the solvent gave a residue which was flash chromatographed over silica gel eluting with acetone:hexane (1:20) and (1:15) to give the title compound (300 mg) as a colourless oil.

$\delta$ ($^1$H, CDCl$_3$): 9.72 (s, 1H, CHO), 7.5–7.2 (m, 12H, 2Ph and 2Hortho), 6.97 (s, H, CHPh$_2$), 6.88 (m, 2H, 2Hmeta), 6.04 (dd, 1H, H-2, J=1.5 Hz, J=3.6 Hz), 4.64 (dd, 1H, H-1', J=2.4 and 9.9 Hz), 4.55 and 4.50 (2d, 2H, CH$_2$Ph, J$_{AB}$=11.2 Hz), 4.18 (m, 1H, H-3'), 4.04 and 3.66 (2d, 2H, 8aCH$_2$, J$_{AB}$=9 Hz), 3.80 (s, 3H, CH$_3$O), 3.74 (m, 1H, H-5'), 3.12 (dd, 1H, H-4', J=3.0 and 9.3 Hz), 2.75 (t, 1H, H-1, J=3.9 Hz).

INTERMEDIATE 17

[1R-(1α, 3aβ, 4β, 4aβ, 7β, 7aα, 8aβ)] 8a-[(3-O-Allyl-2,6-dideoxy-4-O-p-methoxybenzyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a vigorous stirred solution of Intermediate 16 (400 mg) in anhydrous tetrahydrofuran (10 ml) was added under nitrogen atmosphere at 0° C. sodium hydride (48 mg) in small portions. After the addition was concluded the mixture was allowed to stand at room temperature for 1 hour and allyl bromide (191 μl) was then added. After 24 hours the reaction was quenched by adding ammonium chloride (1N solution in water, 100 ml) and the mixture was extracted with ethyl acetate (200 ml). The organic layer was washed with water (1×100 ml), dried over magnesium sulfate and concentrated to dryness to give an oil which was flash chromatographed over silica gel eluting with ethyl acetate-:hexane (1:20) and (1:15) to give the title compound (400 mg) as a colourless oil.

δ ($^1$H, CDCl$_3$): 9.74 (s, 1H, CHO), 7.5–7.2 (m, 12H, 2Ph and 2Hortho), 6.98 (s, H, CHPh$_2$), 6.86 (m, 2H, 2Hmeta), 6.04 (dd, 1H, H-2, J=1.2 and 3.3 Hz), 5.95 (m, 1H, CH=CH$_2$), 5.28 and 5.15 (2m, 2H, CH=CH$_2$), 4.60 (m, 2H, H-1' and CH$_2$Ph), 4.42 (d, 1H, CH$_2$Ph, J$_{AB}$=11.4 Hz), 4.13 (m, 2H, CH$_2$—CH=), 4.02 and 3.68 (2d, 2H, 8aCH$_2$, J$_{AB}$=9.6 Hz), 3.89 (m, 2H, H-5' and H-3'), 3.80 (s, 3H, CH$_3$O), 3.09 (dd, 1H, H-4', J=3.0 and 9.3 Hz), 2.73 (t, 1H, H-1, J=3.9 Hz).

INTERMEDIATE 18

[1R-(1α, 3aβ, 4β, 4aβ, 7β, 7aα, 8aβ)] 8a-[(3-O-Allyl-2,6-dideoxy-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 17 (2.3 g) in dichloromethane (200 ml) was stirred with water (20 ml) and 2,3-dichloro-5,6-dicyanoquinone (0.79 g) was added. After overnight stirring at room temperature the mixture was filtered through a Celite pad with the aid of more dichloromethane. The dichloromethane phase was then washed with aqueous sodium bicarbonate followed by sodium chloride solution, then dried over anhydrous sodium sulfate, filtered and concentrated to dryness. The residue was chromatographed on silica gel using dichloromethane:methanol (49:1) as the eluent to yield the title compound (1.95 g) as a white foam.

δ ($^1$H, CDCl$_3$): 9.75 (s, 1H, CHO), 7.45–7.24 (m, 10H, Ph$_2$), 6.99 (s, 1H, CHPh$_2$), 6.05 (dd, 1H, H-2, J=1.5 and 3.3 Hz), 5.95 (m, 1H, CH=CH$_2$), 5.26 (m, 2H, CH=CH$_2$), 4.53 (dd, 1H, H-1', J=1.8 and 9.6 Hz), 4.19 and 3.96 (2m, 2H, CH$_2$CH=CH$_2$), 4.03 and 3.69 (2d, 2H, 8a-CH$_2$, J=9.3 Hz), 3.80 (q, 1H, H-3', J=3.3 Hz), 3.60 (dq, 1H, H-5', J=9.6 and 6.3 Hz), 3.23 (ddd, 1H, H-4', J=10.8, 9.6 and 3.3 Hz), 2.74 (t, 1H, H-1, J=3.6 Hz), 2.25 (d, 1H, OH, J=10.8 Hz).

INTERMEDIATE 19

[1R-(1α, 3aβ, 4β, 4aβ, 7β, 7aα, 8aβ)] 8a-[(3-O-Allyl-2,6-dideoxy-4-O-(methylthio)thiocarbonyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a cooled solution of Intermediate 18 (1.9 g) in anhydrous tetrahydrofuran (50 ml) under nitrogen atmosphere were added sodium hydride in small portions (240 mg) and a catalytic amount of imidazole. The ice bath was then removed and the reaction mixture was allowed to stand at room temperature under stirring for 1 hour. Carbon disulfide (1.5 ml) and methyl iodide (1.25 ml) were added consecutively. Once the reaction was completed (TCL control), the crude mixture was poured into ethyl acetate (500 ml) and quenched with 0.1 N aqueous ammonium chloride (250 ml). The organic layer was then washed with brine (1×500 ml) and water (1×500 ml), dried over anhydrous sodium sulfate and concentrated to dryness. The oily residue was flash chromatographed over silica gel using hexane:dichloromethane (3:5) as the eluent to obtain the title compound (1.85 g) as a white foam.

δ ($^1$H CDCl$_3$): 9.74 (s, 1H, CHO), 7.45–7.24 (m, 10H, Ph$_2$), 6.99 (s, 1H, CHPh$_2$), 6.06 (dd, 1H, H-2, J=1.2 and 3.3 Hz), 5.88 (m, 1H, CH=CH$_2$), 5.41 (dd, 1H, H-4', J=2.7 and 9.6 Hz), 5.22 (m, 2H, CH=CH$_2$), 4.70 (dd, 1H, H-1', J=2.1 and 9.3 Hz), 4.20–4.02 (m, 5H, H-5', CH$_2$—CH=CH$_2$, H-3' and 8a-CH$_2$ (1H)), 3.71 (d, 1H, 8a-CH$_2$, J=9.3 Hz), 2.75 (t, 1H, H-1, J=3.9 Hz), 2.58 (s, 3H, SCH$_3$).

INTERMEDIATE 20

(a) [1R-(1α, 3aβ, 4β, 4aβ, 7β, 7aα, 8aβ)] 8a-[[1S, 4S,6R,8R]-2,7-Dioxa-4,6-dimethyl-cis-bicyclo[3.4.0]-non-8-yl-oxy-methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester and (b) [1R-(1α, 3aβ, 4β, 4aβ, 7β, 7aα, 8aβ)] 8a-[[1S, 4R,6R,8R]-2,7-Dioxa-4,6-dimethyl-cis-bicyclo[3.4.0]-non-8-yl-oxy-methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 19 (1.8 g) in dry toluene (250 ml) was degassed with an argon stream for 1 hour and then heated to reflux. A catalytic amount of azobis (isobutyronitrile) and tributyltin hydride (0.95 ml) dissolved in dry toluene (50 ml) were added from a syringe in about 2 hours while heating and the argon stream were maintained. Once the addition was completed the reaction mixture was further refluxed for 1 hour and subsequently cooled, then concentrated to dryness and flash chromatographed on silica gel using hexane and then hexane:ethyl acetate (9:1) as the eluents. Intermediate 20(a) (680 mg; Rf=0.31 in hexane-:ethyl acetate 4:1) was obtained as a white foam and Intermediate 20(b) (180 mg; Rf=0.25 in hexane:ethyl acetate 4:1) was isolated as a white solid.

(a) δ ($^1$H, CDCl$_3$): 9.73 (s, 1H, CHO), 7.45–7.28 (m, 10H, Ph$_2$), 6.99 (s, 1H, CHPh$_2$), 6.05 (dd, 1H, H-2, J=1.2 and 3.6 Hz), 4.46 (dd, 1H, H-8', J=2.4 and 9.6 Hz), 4.14–4.05 (m, 3H, 8a-CH$_2$ (1H), H-1' and CH$_2$-3' (1H)), 3.67 (d, 1H, 8a-CH$_2$, J=9.3 Hz), 3.36–3.25 (m, 2H, H-6' and CH$_2$-3' (1 H)), 2.77 (t, $_1$H, H-1, J=3.9 Hz), 1.05 (d, 3H, 4'-CH$_3$, J=6.9 Hz).

(b) δ ($^1$H, CDCl$_3$): 9.72 (s, 1H, CHO), 7.45–7.24 (m, 10H, Ph$_2$), 6.99 (s, 1H, CHPh$_2$), 6.05 (dd, 1H, H-2, J=1.50 and 3.6 Hz), 4.42 (dd, 1H, H-8', J=2.1 and 9.6 Hz), 4.20 (m, 1H, H-1'), 4.07 and 3.67 (2d, 2H, 8a-CH$_2$, J=9.3 Hz), 3.97 (t, 1H, CH$_2$-3', J=8.4 Hz),3.54 (m, 1H, H-6'), 3.46 (dd, 1H, CH$_2$-3', J=10.5 Hz), 2.77 (t, 1H, H-1, J=3.9 Hz), 2.53 (m, 1H, H-4'), 1.02 (d, 3H, 6-CH$_3$).

INTERMEDIATE 21

[1R-(1α,3aβ,4β,4aβ,7β,7aα, 8aβ)]8a-[(4-O-Allyl-2,6-dideoxy-3-O-(methylthio)thiocarbonyl-β-D-allopyranosyloxy)methyl]-4-formyl-4-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 12 (380 mg) in anhydrous tetrahydrofuran (10 ml) were added, under nitrogen atmosphere at 0° C., solid sodium hydride (48 mg) in small portions and a catalytic amount of imidazole. Once the addition was concluded, the cool bath was removed and the reaction was allowed to stand at room temperature for 1 hour. Carbon disulfide (300 μl) and methyl iodide (250 μl) were added consecutively. After 4 hours the mixture was poured into ethyl acetate (100 ml) and quenched with aqueous 1N ammonium chloride (50 ml). The organic layer was washed with brine (1×100 ml) and water (1×100 ml), dried over magnesium sulfate and concentrated to dryness to give a yellow oil which was flash chromatographed over silica gel eluting with ethyl acetate:hexane (1:25) and (1:20) to afford the title compound (350 mg) as a white foam.

δ ($^1$H, CDCl$_3$): 9.73 (s, 1H, CHO), 7.50–7.20 (m, 10H, 2Ph), 6.98 (s, H, CHPh$_2$), 6.24 (m, 1H, H-3'), 6.05 (dd, 1H, H-2, J=1.5 and 3.6 Hz), 5.85 (m, 1H, C$\underline{H}$=CH$_2$), 5.30–5.20 (m, 2H, CH=C$\underline{H}_2$), 4.56 (dd, 1H, H-1', J=1.8 and 9.3 Hz), 4.15–3.75 (m, 4H, C$\underline{H}_2$CH=CH$_2$+8aCH$_2$+H-5'), 3.69 (d, 1H, 8aCH$_2$, J=9.3 Hz), 3.21 (dd, 1H, H-4', J=3.3 and 9.3 Hz), 2.72 (t, 1H, H-1, J=3.89 Hz), 2.59 (s, 3H, SCH$_3$).

INTERMEDIATE 22

[1R-(1α, 3aβ, 4β, 4aβ, 7β, 7aα, 8aβ)] 8a-[(2,6-Dideoxy-3-O-(methylthio)thiocarbonyl-4-O-(2-methyl-2-propenyl)-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a cooled solution of Intermediate 13 (700 mg) in anhydrous tetrahydrofuran (30 ml) under nitrogen atmosphere were added sodium hydride (85 mg) in small portions and a catalytic amount of imidazole. The ice bath was then removed and the reaction mixture was allowed to stand at room temperature under magnetical stirring for 1 hour. Carbon disulfide (0.54 ml) and methyl iodide (0.45 ml) were added consecutively. Once the reaction was completed (TLC control), the crude mixture was poured into ethyl acetate (200 ml) and quenched with 0.1 N aqueous ammonium chloride (120 ml). The organic layer was then washed with brine (1×200 ml) and water (1×200 ml), dried over anhydrous sodium sulfate and concentrated to dryness. The oily residue thus obtained was chromatographed on silica gel using hexane:ethyl acetate (19:1) as the eluent to give the title compound (600 mg).

δ ($^1$H, CDCl$_3$): 9.73 (s, 1H, CHO),7.45–7.26 (m, 10H, Ph$_2$), 6.98 (s, 1H, C$\underline{H}$Ph$_2$), 6.24 (m, 1H, H-3'), 6.05 (dd, 1H, H-2, J=1.5 and 3.6 Hz), 4.92 and 4.88 (2m, 2H, C=C$\underline{H}_2$), 4.55 (dd, 1H, H-1', J=2.1 and 9.6 Hz), 4.03 and 3.69 (2d, 2H, 8a-CH$_2$, J=9.3 Hz), 3.95 and 3.82 (2d, 2H, C$\underline{H}_2$—C=CH$_2$, J=12.3 Hz), 3.86 (m, 1H, H-5'), 3.19 (dd,1H, -H4', J=3 and 9.3 Hz), 2.72 (t, 1H, H-1, J=3–9 Hz), 2.58 (s, 3H, SCH$_3$), 1.70 (s, 3H, C$\underline{H}_3$C=CH$_2$).

INTERMEDIATE 23

(a) [1R-(1α,3aβ,4β,4aβ,7β,7aα,8aβ)] 8a-[[1S,4R,7R,9R]-2,8-Dioxo-4,9-dimethyl-cis-bicyclo[3.4.0]-non-7-yl-oxy-methyl]-4-formyl-4-4a,5,6,7,7a,8,8a-octahydro-7-methyl-3-(1-methylethyl)-1,4-methano-s-indacene-3a(1H)-carboxylic acid, diphenylmethyl ester and (b) [1R-(1α,3aβ,4β,4aβ,7β,7aα,8aβ)] 8a-[[1S,4S,7R,9R]-2,8-Dioxo-4,9-dimethyl-cis-bicyclo[3.4.0]-non-7-yl-oxy-methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester Method A A solution of Intermediate 21 (1.5 g) in dry toluene (150 ml) was degassed with argon for 90 minutes and then heated to reflux. To this boiling solution were added tributyltin hydride (847 μl) and azobis(isobutyronitrile) (33 mg). Heating was continued for an additional period of 30 minutes. Elimination of solvent gave a crude mixture which was flash chromatographed twice on silica gel eluting with hexane-:ethyl acetate (20:1) to give title compound (a) (150 mg; Rf=0.6 in hexane:ethyl acetate 4:1) and title compound (b) (260 mg; Rf=0.4 in hexane:ethyl acetate 4:1) both as colourless oils.

(a) δ ($^1$H, CDCl$_3$): 9.75 (s, 1H, CHO), 7.5–7.2 (m, 10H, 2Ph), 6.99 (s, 1H, CHPh$_2$), 6.06 (dd, 1H, H-2, J=1.5 and 3.6 Hz), 4.46 (dd, 1H, H-7', J=3 and 7.5 Hz), 4.06–3.95 (m, 2H, H-3' and 8aCH$_2$), 3.78–3.60 (m, 2H, H-1' and 8aCH$_2$), 3.38–3.26 (m, 2H, H-9' and H-3'), 2.75 (t, 1H, H-1, J=3.6 Hz), 0.98 (d, 3H, C$\underline{H}_3$, CH, J=6.9 Hz).

(b) δ ($^1$H, CDCl$_3$): 9.74 (s, 1H, CHO), 7.5–7.2 (m, 10H, 2Ph), 6.99 (S, 1H, CHPh$_2$), 6.04 (dd, 1H, H-1, J=1.5 and 3.6 Hz), 4.74 (t, 1H, H-7', J=3 Hz), 3.94 and 3.61 (2d, 2H, 8aCH$_2$, J$_{AB}$=9.3 Hz), 3.88 and 3.76 (2d, 2H, H-3'), 3.66 (m, 1H, H-9'), 3.43 (t, 1H, H-1', J=7.8 Hz), 2.72 (t, 1H, H-1, J=3.6 Hz), 2.46 (2m, 2H, C$\underline{H}$CH$_2$O and H-5'), 0.97 (d, 3H, C$\underline{H}_3$CH, J=6.9 Hz).

Method B

A solution of Intermediate 98 (685 mg) in o-xylene (15 ml) was degassed with argon for 60 minutes and then heated to reflux. Tributyltin hydride (379 μl) was added and heating continued for 15 minutes. After cooling the mixture was partitioned between diethyl ether (150 ml) and water (100 ml). The organic layer was washed with a saturated aqueous potassium fluoride solution until no more precipitation of tributyltin fluoride was observed, filtered and evaporated to dryness to give a residue which was flash chromatographed twice on silica gel eluting with hexane:ethyl acetate (20:1) to afford title compound (a) (103 mg) and title compound (b) (235 mg).

Method C

A solution of tributyltin hydride (684 μl) in dry toluene (25 ml) was degassed with an argon stream for 1 hour at reflux and then a solution of intermediate 98 (610 mg) in dry toluene (30 ml) was added over a period of 2 hours by means of a syringe. Heating was continued for 3.5 hours. Elimination of the solvent under reduced pressure gave a crude which was flash chromatographed over silica gel eluting with hexane and hexane:ethyl acetate (10:1) to (8:1) to afford the title compound (a) (357 mg).

INTERMEDIATE 24

[1R-(1α, 3aβ, 4β, 4aβ, 7β, 7aα, 8aβ] 8a-[[1S,7R,9R]-2,8-Dioxo-4,4,8-trimethyl-cis-bicyclo[3.4.0]-non-7-yl-oxy-methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 22 (580 mg) in dry toluene (150 ml) was degassed with an argon stream for one hour and then heated to reflux. A catalytic amount of azobis (isobutyronitrile) and tributyltin hydride (0.27 ml) dissolved in dry toluene (20 ml) were added from a syringe over about 2 hours while heating and the argon stream were maintained. Once the addition was completed, the reaction mixture was further refluxed for 3 hours and subsequently cooled, then concentrated and chromatographed on silica gel using hexane and then hexane:ethyl acetate (4:1) as eluents to give the title compound (100 mg) as a white foam.

δ ($^1$H, CDCl$_3$): 9.74 (s, 1H CHO), 7.45–7.26 (m, 10H, Ph$_2$), 6.99 (s, 1H, CHPh$_2$), 6.04 (dd, 1H, H-2, J=1.5 and 3.6 Hz), 4.71 (t, 1H, H-7', J=3.3 Hz), 3.93 and 3.61 (2d, 2H, 8a-CH$_2$, J=9.3 Hz), 3.85 (t, 1H, H-1', J=8.7 Hz), 3.56 (m, 1H, H-9'), 3.55 and 3.43 (2d, 2H, CH$_2$-3', J=8.4 Hz), 2.73 (m, 1H, H-1), 1.08 and 0.99 (2s, 6H, 4'-CH$_3$).

INTERMEDIATE 25

[1R-(1α, 3aβ, 4β, 4aβ, 7β, 7aα, 8aβ] 8a-[(6-Deoxy-β-D-altropyranosyloxy)methyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester To a stirred solution of Intermediate I (2.5 g) in dry acetonitrile (100 ml) were added at room temperature ethylene glycol (30 ml), trimethyl orthoformate (2 ml) and a catalytic amount of p-toluensulfonic acid. The reaction mixture was stirred for 3 hours, then diluted with ethyl acetate (300 ml) and washed sucessively with 5% aqueous sodium bicarbonate and brine. The organic layer was dried over anhydrous sodium sulfate, concentrated and purified by silica gel chromatography using hexane:ethyl acetate (3:1) as the eluent to give the title compound (2.6 g).

δ ($^1$H CDCl$_3$): 7.46–7.24 (m, 10H, Ph$_2$), 6.94 (s, 1H, CHPh$_2$), 5.83 (dd, 1H, H-2, J=1.2 and 3.6 Hz), 5.07 (s, 1H, CH beta), 4.65 (d, 1H, H-1', J=1.8 Hz), 4.07–4.04 (m, 2H, 8a-CH$_2$ (1H) and H-3'), 3.88–3.69 (m, 8H, OCH$_2$CH$_2$O,8a-CH$_2$(1H), H-2', H-4' and H-5'), 2.51 (t, 1H, H-1, J=4.5 Hz), 2.37 (d, 1H, OH, J=2.7 Hz), 2.28 (d, 1H, OH, J=3.6 Hz), 2.04 (d, 1H, OH, J=5.7 Hz).

INTERMEDIATE 26

[1R-(1α, 3aβ, 4β, 4aβ, 7β, 7aα, 8aβ] 8a-[(6-Deoxy-3,4-O-isopropylidene-β-D-altropyranosyloxy)methyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 25 (200 mg) in dry acetonitrile (6 ml) under nitrogen was treated with 2,2-dimethoxypropane (0.6 ml) and a catalytic amount of pyridinium p-toluenesulfonate. After 4 hours at room temperature the mixture was treated with saturated aqueous sodium hydrogen carbonate solution (20 ml) and extracted twice with ethyl acetate (20 ml). The combined organic phases were washed with water and brine, dried over magnesium sulphate, filtered and evaporated. The residue was purified by flash chromatography on silica gel eluting with hexane:ethyl acetate (4:1) and appropriate fractions were combined and evaporated to give the title compound (205 mg) as a white foam.

δ ($^1$H, CDCl$_3$): 7.47–7.2 (m, 10H,2Ph), 6.93 (s, 1H, CHPh$_2$), 5.83 (dd, 1H, H-2, J=1.2 and 3.6 Hz), 5.08 (s, 1H, 1,3-dioxolane), 4.56 (d, 1H, H-1', J=2.1 Hz), 4.3 (dd, 1H, H-3', J=3.6 and 5.7 Hz), 4.04 (d, 1H, A part of 8aCH$_2$, J$_{AB}$=9 Hz), 3.95–3.75 (m, 7H, H-2', H-4', OCH$_2$CH$_2$O and B part of 8aCH$_2$), 3.44 (dq, 1H, H-5', J=6 and 9 Hz), 2.65 (m, 1H, CHMe$_2$), 2.51 (bt, 1H, H-1, J=3.6 Hz), 2.35 (d, 1H, OH2'), 1.47, 1.36 (2s, 6H, 2CH$_3$ isopropylidene ketal).

INTERMEDIATE 27

[1R-(1α, 3aβ, 4β, 4aβ, 7β, 7aα, 8aβ] 8a-[(6-Deoxy-3,4-O-isopropylidene-β-D-allopyranosyloxy)methyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester Pyridine (0.67 ml) was added to a mixture of chromium oxide (CrO$_3$) (412 mg) in dichloromethane (25 ml) at 0° C. After 15 minutes, acetic anhydride (0.40 ml) was added followed after 10 minutes at the same temperature by a solution of Intermediate 26 (750 mg) in dichloromethane (25 ml). The mixture was stirred for 2 hours, filtered through a silica gel column with a top layer of magnesium sulfate and the filtrate was evaporated to dryness under reduced pressure to afford a syrup. This was dissolved in methanol:water (10:1, 11 ml), and then sodium borohydride (40 mg) was added at 0° C. The mixture was kept at 0° C. for 2 hours, acidified to pH 6–7 with a solution of 1N hydrochloric acid, and then evaporated to dryness under reduced pressure to afford a white solid, which was purified twice by flash column chromatography on silica gel eluting successively with hexane:ethyl acetate (6:1) then (2:1). The fractions which contained the desired product were combined and evaporated in vacuo to yield the title compound (585 mg).

δ ($^1$H, CDCl$_3$): 7.24–7.46 (m, 10H, 2Ph), 6.92 (s, 1H, CHPh$_2$), 5.87 (dd, 1H, H-2, J=3.9 and 1.5 Hz), 5.09 (s, 1H, CH-dioxolane), 4.52 (t, 1H, H-3', J=4.5 Hz), 4.45 (d, 1H, H-1', J=7.8 Hz, 4.07 (d, 1H, 8aCH$_2$, J=9 Hz), 3.74–3.86 (m, 6H, 2CH$_2$-dioxolane, H-4', 8aCH$_2$), 3.67 (m, 1H, H-2'), 2.65 (m, 1H, H-14), 2.58 (t, 1H, H-11).

INTERMEDIATE 28

[1R-(1α, 3aβ, 4β, 4aβ, 7β, 7aα, 8aβ)] 4-Formyl4, 4a,5,6,7,7a,8,8a-octahydro-8a-hydroxymethyl-7-methyl-3-(1-methylethyl)-1,4-methano-s-indacene-3a(1H)-carboxylic acid, 2-(trimethylsilyl)ethyl ester A solution of sordaricin (6.6 g) and O-[2-(trimethylsilyl)ethyl]-N,N'-diisopropylisourea[1] (9.3 g) in anhydrous tetrahydrofuran (150 ml) was heated under reflux for 3 hours. The mixture was then cooled to room temperature, filtered and concentrated to dryness. The residue was dissolved in ethyl acetate (750 ml) and washed successively with 1 N hydrochloric acid, 5% aqueous sodium bicarbonate and brine. The organic layer was dried over anhydrous sodium sulfate, concentrated in vacuo and purified by silica gel flash column chromatography using (10%) ethyl acetate in hexane as eluent to give the title compound (6.8 g) as a white foam.
[1]L. J. Mathias, Synthesis, (1979), 561.

δ ($^1$H, CDCl$_3$): 9.67 (s, 1H, CHO), 6.07 (dd, 1H, H-2, J=1.5 and 3.6 Hz), 4.27 (m, 2H, CH$_2$CH$_2$O), 3.93 and 3.49 (2m, 2H, 8a-CH$_2$), 2.75 (bs,1H, OH), 2.54 (t, 1H, H-1), 1.05 (m, 2H, CH$_2$CH$_2$Si), 0.07 (s, 9H, (CH$_3$)$_3$Si); δ ($^{13}$C, CDCl$_3$): 204.9 (CHO), 173.6 (COOTMSE), 148.2 (C-3), 130.6 (C-2), 66.9 (8a-CH$_2$O), 64.0 (CH$_2$CH$_2$O), 177.7 (CH$_2$CH$_2$Si), 1.6 (CH$_3$)$_3$Si).

INTERMEDIATE 29

[1R-(1α, 3aβ, 4β, 4aβ, 7β, 7aα, 8aβ)] 8a-[(3,4,6-Tri-O-acetyl-2-deoxy-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, trimethylsilylethyl ester To a solution of Intermediate 28 (63 mg) and 3,4,6-tri-O-acetyl D-allal[1] (20 mg) in dry toluene (1 ml) was added hydrobromic acid-triphenyl phosphine (9 mg). The reaction mixture was heated at 60° C. for 2 hours and poured into a 1M solution of sodium bicarbonate (100 ml). Ethyl acetate (100 ml) was added and the organic layer was washed with water, dried over anhydrous magnesium sulfate and filtered. The solvent was evaporated to dryness, and the residue was purified by silica gel flash column chromatography eluting with hexane:ethyl acetate (10:1). to give the title compound (16 mg) as a white foam.

1. M. D. Wittman, R. L. Halcomb and S. J. Danishefsky, J. Org. Chem. (1990), 55, 1979 –1981.

δ (¹H, CDCl₃): 9.73. (s, 1H, CHO), 6.03 (dd, 1H, H-2, J=1.5 and 3.6 Hz), 5.48 (m, 1H, H-3'), 4.89 (dd, 1H, H-4', J=3.3 and 9.6 Hz), 4.65 (dd, 1H, H-1', J=2.4 and 8.7 Hz), 4.23 (m, 4H, H-6', COOCH₂CH₂ Si), 4.02 (ddd, 1H, H-5', J=3, 5.4 and 9.6 Hz), 3.92 and 3.69 (2d, 2H, 8aCH₂, J=9.6 Hz), 2.75 (t, 1H, H-1), 2.28 (m, 1H, CH(CH₃)₂).

INTERMEDIATE 30

[1R-(1α, 3aβ, 4β, 4aβ, 7β, 7aα, 8aβ)] 8a-[(2-Deoxy-3,4-O-isopropylidene-6-O-methyl-β-D-allopyranosyloxy)methyl]-4-formyl-4,4a,5,6,7,7a,8,8a-octahydro-7-methyl-3-(1-methylethyl)-1,4-methano-s-indacene-3a[1H]-carboxylic acid,2-(trimethylsilyl)ethyl ester To a stirred solution of Intermediate 29 (275 mg) in absolute methanol (10 ml) was added 2 or 3 drops of 1 M solution of sodium methoxide in methanol. After stirring for 1.5 hours the reaction mixture was concentrated, diluted with toluene (10 ml) and concentrated to leave a yellow syrup. This was dissolved in acetone (5 ml) and 2,2-dimethoxypropane (60 µl) and p-toluensulfonic acid monohydrate (75 mg) were added. The reaction mixture was stirred at room temperature for 1 hour, neutralized with sodium carbonate, filtered and the filtrate concentrated to dryness. The oily residue was dissolved in ethyl acetate (20 ml), washed with water and brine, dried and concentrated to give an oil. A solution of this oil in dry tetrahydrofuran (5 ml) at 0° C. was treated with sodium hydride (10 mg) and stirred for 30 minutes before methyl iodide (100 µl) was added. The reaction mixture was gradually warmed to room temperature during 3 hours. The reaction was quenched with methanol (1 ml) and the mixture was then concentrated, the residue purified three times by flash column chromatography using successively hexane:ethyl acetate (10:1), (6:1) and (4:1) and the appropiate fractions were combined and the solvents evaporated to give the title compound (50 mg) as a colourless oil.

δ (¹H, CDCl₃): 9.73 (s, 1H, CHO), 6.04 (dd, 1H, H-2, J)1.2 and 3.6 Hz), 4.61 (dd, 1H, H-1', J=2.4 and 8.4 Hz), 4.43 (m, 1H, H-3'), 4.34–4.10 (m, 2H, CH₂—SEM protecting group), 3.66 and 3.89 (2d, 2H, 8aCH₂, J=9.3 Hz), 3.87 (m, 1H, H-4'), 3.48–3.64 (m, 3H, 2H-6' and H-5'), 3.24 (s, 3H,6'OMe), 2.73 (t, 1H, H-1, J=3.6 Hz), 1.34 and 1.35 (2s, 6H, methyl groups of isopropylidene).

INTERMEDIATE 31

[1R-(1α, 3aβ, 4β, 4aβ, 7β, 7aα, 8aβ)]8a-[(4-O-((E)-2-Butenyl)-2,6-dideoxy-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A suspension of intermediate 10 (1,5 g) and dibutyltin oxide (0.9 g) in dry toluene (150 ml) was heated under reflux for 2 hours in a flask fitted with a Dean-Stark condenser and then allowed to stand at room temperature under nitrogen atmosphere (approximately 20 ml of azeotropic mixture were removed). Crotyl bromide (predominantly trans, 0.37 ml), tetrabutylammonium fluoride (3.6 ml of 1M solution in tetrahydrofuran) and 4 Å molecular sieves (activated powder) were added consecutively and the mixture heated at 60° C. for 24 hours. Molecular sieves were filtered off. Elimination of the solvent gave a residue which was flash chromatographed over silica gel eluting with hexane:acetone (95:5) to give the title compound (1 g) as a white foam.

δ (¹H, CDCl₃): 9.73 (s, 1H, CHO), 7.44–7.23 (m, 10H, 2Ph), 6.98 (s, 1H, CHPh₂), 6.05 (dd, 1H, H-2, J=1.5 and 3.6 Hz), 5.75–5.52 (m, 2H, CH═CH), 4.64 (dd, 1H, H-1', J=2.1 and 9.6 Hz), 4.16 (m, 1H, H-3'), 4.98 (m, 3H, 8a-CH₂, (1H) and CH₂CH═CH(2H)), 3.74 (m, 1H, H-5'), 3.67 (d, 1H, 8a-CH₂ (1H), J=9.3 Hz), 3.05 (dd, 1H, H-4', J=3.0 and 9.6 Hz), 2.75 (t, 1H, H-1, J=3.6 Hz), 2.40 (d, 1H, OH, J=2.1 Hz), 1.72 (m, 3H, CH₃CH═CH).

INTERMEDIATE 32

[1R-(1α, 3aβ, 4β, 4aβ, 7β, 7aα, 8aβ)] 8a-[(2,6-Dideoxy-4-O-propargyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A suspension of intermediate 10 (2 g) and dibutyltin oxide (1.2 g) in dry toluene (150 ml) was heated under reflux for 2 hours in a flash fitted with a Dean-Stark condenser and then allowed to stand at room temperature under nitrogen atmosphere (approximately 20 ml of azeotropic mixture were removed). Propargyl bromide (0.55 ml of 80 wt % solution in toluene), tetrabutylammonium fluoride (4.8 ml of 1 M solution in tetrahydrofuran and 4 Å molecular sieves (activated powder) were added consecutively and the mixture heated at 60° C. for 24 hours. Molecular sieves were filtered off. Elimination of the solvent gave a residue which was twice flash chromatographed over silica gel eluting with hexane:acetone (96:4) to give the title compound (1.25 g) as a white foam.

δ (¹H, CDCl₃): 9.73 (s, 1H, CHO), 7.44–7.26 (m, 10H, 2Ph), 6.98 (s, 1H, CHPh₂), 6.05 (dd, 1H, H-2, J=1.2 and 3.3 Hz), 4.65 (dd, 1H, H-1', J=2.1 and 9.6 Hz), 4.29 (m, 1H, H-3'), 4.24 and 4.22 (2d, 2H, CH₂C≡CH, J=2.4 Hz), 4.05 and 3.68 (2d, 2H, 8a-CH₂, J=9.3 Hz), 3.75 (m, 1H, H-5'), 3.25 (dd, 1H, H-4', J=3.0 and 9.3 Hz), 2.75 (t, 1H, H-1, J=3.9 Hz), 2.46 (t, 1H, C≡CH, J=2.4 Hz).

INTERMEDIATE 33

[1R-(1α, 3aβ, 4β, 4aβ, 7β, 7aα, 8aβ)] 8a-[(4-O-(3-methyl-2-butenyl)-2,6-dideoxy-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A suspension of intermediate 10 (1 g) and tributyltin oxide (600 mg) in 150 ml of dry toluene was heated to reflux for 2 hours in a flask fitted with a Dean-Stark condenser (25 ml of azeotropic mixture was taken off) and then cooled to room temperature. 2-Methyl-4-bromo-2-butene (276 µl) and tetrabutylammonium fluoride (1M solution in tetrahydrofuran, 2.4 ml) were then added and the mixture heated to 50° C. for 24 hours. Elimination of the solvent gave a crude which was flash chromatographed (ethyl acetate:hexanes 1:20, 1:15 and 1:10) to afford 770 mg of the title compound as a foam (69% yield).

δ (¹H, CDCl₃): 9.73 (s, 1H, CHO), 7.5–7.2 (m, 10H, 2Ph), 6.98 (s, 1H, CHPh₂), 6.05 (dd, 1H, H2, J=1.5 and 3.3 Hz), 5.33 (m, 1H, OCH₂CH═), 4.64 (dd, 1H, H1', J=2.1 and 9.6 Hz), 4.20 (m, 1H, H3'), 4.25–3.95 (m, 3H, OCH₂C═+8aCH₂), 3.75–3.65 (m, 2H, H5'+8aCH₂), 3.03 (dd, 1H, H4', J=3.3 and 9.6 Hz), 2.75 (t, 1H, H1, J=3.9 Hz), 2.44 (d, 1H, OH, J=2.1 Hz).

INTERMEDIATE 34

[1R-(1α, 3aβ, 4β, 4aβ, 7β, 7aα, 8aβ)] 8a-[(4-O-((E)-2-Butenyl)-2,6-dideoxy-3-O-(methylthio)thiocarbonyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a cooled solution of intermediate 31 (1 g) in anhydrous tetrahydrofuran (20 ml) under nitrogen atmosphere were added sodium hydride in small portions (0.156 g) and a catalytic amount of imidazole. The ice bath was then removed and the reaction mixture was allowed to stand at room temperature under stirring for 1 hour. Carbon disulfide (0.58 ml) and methyl iodide (0.8 ml) were added consecutively. Once the reaction was completed (tlc control), the crude mixture was poured into ethyl acetate (400 ml) and quenched with 1N aqueous ammonium chloride (500 ml). The organic layer was then washed successively with 1N hydrochloric acid (200 ml), 5% aqueous sodium bicarbonate (200 ml) and brine (200 ml). The organic layer was dried over anhydrous sodium sulfate filtered and concentrated under vacuo. The residue thus obtained was flash chromatographed over silica gel eluting with dichloromethane:hexane (6:4) to give the title compound (1.04 9) as a white foam.

δ ($^1$H, CDCl$_3$): 9.73 (s, 1H, CHO), 7.45–7.26 (m, 10H, 2Ph), 6.98 (s, 1H, C$\underline{H}$Ph$_2$), 6.23 (dd, 1H, H-3', J=3.0 and 6.3 Hz), 6.05 (dd, 1H, H-2, J=1.5 and 3.3 Hz), 5.75–5.40 (m, 2H, C$\underline{H}$=C$\underline{H}$), 4.55 (dd, 1H, H-1', J=1.8 and 9.3 Hz), 4.05–3.80 (m, 4H, 8a-CH$_2$(1H), C$\underline{H}_2$CH=CH(2H) and H-5'), 3.75 (d, 1H, 8a-CH$_2$(1H), J=9.3 Hz), 3.20 (dd, 1H, H-4', J=3.0 and 9.3 Hz), 2.72 (t, 1H, H-1, J=3.9 Hz), 2.58 (s, 3H, CH$_3$S), 1.68 (m, 3H, C$\underline{H}_3$CH=CH).

INTERMEDIATE 35

[1R-(1α, 3aβ, 4β, 4aβ, 7β, 7aα, 8aβ)] 8a-[(2,6-Dideoxy-3-O-(methylthio)thiocarbonyl-4-O-propargyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a cooled solution intermediate 32 (1.25 g) in anhydrous tetrahydrofuran (25 ml) under nitrogen atmosphere were added sodium hydride in small portions (0.2 g) and a catalytic amount of imidazole. The ice bath was then removed and the reaction mixture was allowed to stand at room temperature under stirring for 1 hour. Carbon disulfide (0.6 ml) and methyl iodide (0.75 ml) were added consecutively. Once the reaction was complete (tlc control), the crude mixture was poured into ethyl acetate (400 ml) and quenched with 1N aqueous ammonium chloride (500 ml). The organic layer was then washed successively with 1N hydrochloric acid (200 ml), 5% aqueous sodium bicarbonate (200 ml) and brine (200 ml). The organic layer was dried over anhydrous sodium sulfate, filtered and concentrated. The residue was flash chromatographed over silica gel eluting with hexane:ethyl acetate 97:3 and 95:5 to give the title compound (1.2 g) as a white foam.

δ ($^1$H, CDCl$_3$): 9.73 (s, 1H, CHO), 7.45–7,26 (m, 10H, 2Ph), 6.99 (s, 1H, C$\underline{H}$Ph$_2$), 6.28 (q, 1H, H-3', J=3.3 Hz), 6.06 (dd, 1H, H-2, J=1.5 and 3.6 Hz), 4.57 (dd, 1H, H-1', J=1.8 and 9.3 Hz), 4.19 and 4.17 (2d, 2H, C$\underline{H}_2$C≡CH, J=2.4 Hz), 4.03 and 3.70 (2d, 2H, 8a-CH$_2$, J=9.3 Hz), 3.86 (dq, 1H, H-5', J=6.3 and 9.3 Hz), 3.50 (dd, 1H, H-4', J=3.0 and 9.3 Hz), 2.73 (t, 1H, H-1, J=3.9 Hz), 2.58 (s, 3H, CH$_3$S), 2.42 (t, 1H, C≡C$\underline{H}$).

INTERMEDIATE 36

[1R-(1α, 3aβ, 4β, 4aβ, 7β, 7aα, 8aβ)] 8a-[(4-O-(3-methyl-2-butenyl)-2,6-dideoxy-3-O-(methylthio)thiocarbonyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of intermediate 33 (770 mg) in dry tetrahydrofuran (15 ml) was added at 0° C. sodium hydride (105 mg) and imidazole (30 mg) under nitrogen. The mixture was stirred for 1 hour at room temperature, then carbon disulfide (300 μl) and methyl iodide (311 μl) were added consecutively. After stirring for 1 hour the reaction was quenched by adding 0.1N ammonium chloride (50 ml) and it was extracted twice with ethyl acetate (2×100 ml), dried over magnesium sulfate and concentrated to give an oil which was flash chromatographed (silica gel, ethyl acetate:hexanes 1:25 and 1:20) to afford 780 mg of the title compound (90%) as a white foam.

δ ($^1$H, CDCl$_3$): 9.73 (s, 1H, CHO), 7.5–7.2 (m, 10H, 2Ph), 6.98 (s, 1H, C$\underline{H}$Ph$_2$), 6.26 (m, 1H, H3'), 6.06 (dd, 1H, H2, J=1.2 and 3.3 Hz), 5.26 (m, 1H, OCH$_2$C$\underline{H}$=), 4.54 (dd, 1H, H1', J=1.8 and 9.6 Hz), 4.10–3.75 (m, 4H, 8aCH$_2$+OC$\underline{H}_2$C=+H5'), 3.69 (d, 1H, 8aCH$_2$, J=9.6 Hz), 3.18 (dd, 1H, H4', J=3 and 9.3 Hz), 2.72 (t, 1H, H1, J=3.9 Hz), 2.58 (s, 3H, SCH$_3$).

INTERMEDIATES 37 AND 38 a) [1R-(1α, 3aβ, 4β, 4aβ, 7β, 7aα, 8aβ)] 8a-[[1S, 4R, 7R, 9R]-2,8-Dioxa-4-ethyl-9-methyl-cis-bicyclo [3.4.0.]-non-7-yl-oxy-methyl]]-4-formyl-4,4a,5,6,7, 7a,8,8a-octahydro-7-methyl-3-(1-methylethyl)-1,4-methano-s-indacene-3a(1H)-carboxylic acid, diphenylmethyl ester b) [1R-(1a, 3ab, 4b, 4ab, 7b, 7aa, 8ab)] 8-[[1S, 4S, 7R, 9R]-2,8-Dioxa-4-ethyl-9-methyl-cis-bicyclo [3.4.0.]-non-7-yl-oxy-methyl]]-4-formyl-4,4a,5,6,7, 7a,8,8a-octahydro-7-methyl-3-(1-methylethyl)-1,4-methano-s-indacene-3a(1H)-carboxylic acid, diphenylmethyl ester A solution of intermediate 34 (1.04 g) in dry toluene (50 ml) was degassed with on argon stream for 1 hour under reflux. Tributyltin hydride (0.55 ml) and a catalytic amount of azobis(isobutyronitrile) were added. The reaction mixture was further refluxed for 20 minutes and subsequently cooled, concentrated and then twice flash chromatographed on silica gel using hexane and hexane:ethyl acetate (94:6) as the eluents. Intermediate 37 (220 mg, Rf=0.32 in hexane::ethyl acetate 4:1) was obtained a white foam and intermediate 38 (444 mg,. Rf=0.27 in hexane:ethyl acetate 4:1) was isolated as a white solid.

INTERMEDIATE 37

δ ($^1$H, CDCl$_3$): 9.75 (s, 1H$_1$ CHO), 7.45–7.26 (m, 10H, 2Ph), 6.99 (s; 1H, C$\underline{H}$Ph$_2$), 6.06 (dd, 1H, H-2, J=1.5 and 3.6 Hz), 4.50 (dd, 1H, H-7', J=2.7 and 6.9 Hz), 4.06 and 3.38 (2dd, 2H, CH$_2$-3', J=8.4 and 7.5 Hz),4.01 and 3.65 (2d, 2H, 8a-CH$_2$, J=9.0 Hz), 3.71 (dd, 1H, H-1', J=7.5 and 9.0 Hz), 3.34 (m, 1H, H-9'), 2.75 (t, 1H, H-1), 0.93 (t, 3H, C$\underline{H}_3$CH$_2$, J=7.5 Hz).

INTERMEDIATE 38

δ ($^1$H, CDCl$_3$): 9.74 (s, 1H, CHO), 7.45–7.26 (m, 10H, 2Ph), 6.99 (s, 1H, C$\underline{H}$Ph$_2$), 6.04 (dd, 1H, H-2, J=1.2 and 3.6 Hz), 4.73 (t, 1H, H-7', J=3.0 Hz), 3.92 (m, 2H, 8a-CH$_2$(1H) and CH$_2$-3' (1H)), 3.75 (m, 2H, H-9' and H-1'), 3.62 (d, 1H, 8a-CH$_2$, J=9.3 Hz), 3.48 (m, 1H, CH$_2$-3' (1H)), 2.71 (t, 1H, H-1, J=3.6 Hz), 2.55 and 2.23 (2m, 3H, H-4', H-5' and 3-CH), 0.96 (m, 3H, C$\underline{H}_3$CH$_2$).

INTERMEDIATES 39 AND 40

[1R-(1a, 3ab, 4b, 4ab, 7b, 7aa, 8ab)] 8a-[(1S,4R, 7R,9R)-2,8-Dioxa-4-(1-methylethyl)-9-methyl-cis-byciclo[3.4.0]-non-7-yl-oxymethyl)]-4-formyl-4,4a, 5,6,7,7a,8,8a-octahydro-7-methyl-3-(1-methylethyl)-1,4-methano-s-indacene-3a(1H)-carboxylic acid, diphenylmethyl ester and [1R-(1a, 3ab, 4b, 4ab, 7b, 7aa, 8ab)] 8a-[(1S,4S,7R,9R)-2,8-Dioxa-4-(1-methylethyl)-9-methyl-cis-byciclo[3.4.0]-non-7-yl-oxymethyl)]-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of intermediate 36 (780 mg) in dry toluene (50 ml) was degassed with argon for 1 hour and then heated to reflux. Tributyltin hydride (367 μl) and a catalytic amount of a,a'-azoisobutyronitrile (20 mg) were added and the mixture was refluxed for 2 hours, then cooled to room temperature. Elimination of solvent gave a residue which was flash chromatographed (silica gel, hexane:ethyl acetate 25:1, 20:1, 18:1 and 15:1) to obtain 280 mg of intermediate 39 (41% yield) and 300 mg of intermediate 40 (44% yield) as oils (Rf: 0.5 and 0.3 in hexanes:ethyl acetate v/v 3:1, respectively).

INTERMEDIATE 39

δ ($^1$H, CDCl$_3$): 9.75 (s, 1H, CHO), 7.5–7.2 (m, 10H, 2Ph), 6.99 (s, 1H, CHPh$_2$), 6.05 (dd, 1H, H2, J=1.2 and 3.6 Hz), 4.57 (dd, 1H, H7', J=2.7 and 5.7 Hz), 4.05–3.90 (m, 2H, H3'+8aCH$_2$), 3.73 (dd, 1H, H1', J=8.1 and 9.3 Hz), 3.62 (d, 1H, 8aCH$_2$, J=9 Hz), 3.50–3.45 (m, 2H, H3'+H9'), 2.74 (t, 1H, H1, J=3.9 Hz).

INTERMEDIATE 40

δ ($^1$H, CDCl$_3$): 9.74 (s, 1H, CHO), 7.5–7.2 (m, 10H, 2Ph), 6.99 (s, 1H, CHPh$_2$), 6.03 (dd, 1H, H2, J=1.5 and 3.3 Hz), 4.74 (t, 1H, H7', J=3 Hz), 4.0–3.8 (m, 8aCH$_2$+H9'+H3'), 3.73 (dd, 1H, H1', J=3.3 and 4.5 Hz), 3.63 (d, 1H, 8aCH$_2$, J=9.6 Hz), 3.52 (dd, 1H, H3', J=8.1 and 10.5 Hz), 2.70 (t, 1H, H1, J=3.9 Hz).

INTERMEDIATE 41

[1R-(1α, 3aβ, 4β, 4aβ, 7β, 7aα, 8aβ)] 8a-[[1S, 7R, 9R]-2,8-Dioxa-4-methylene,9-methyl-cis-bicyclo [3.4.0.]-non-7-yl-oxy-methyl]-4-formyl-4,4a,5,6,7, 7a,8,8a-octahydro-7-methyl-3-(1-methylethyl)-1,4-methano-s-indacene-3a(1H)-carboxylic acid, diphenylmethyl ester A solution of intermediate 35 (1.02 g) in dry toluene (50 ml) was degassed with an argon stream for 1 hour under reflux. Tributyltin hydride (0.55 ml) and a catalytic amount of azobis(isobutyronitrile) were added. The reaction mixture was further refluxed for 1 hour and subsequently cooled, concentrated and then twice flash chromatographed on silica gel using hexane and hexane:ethyl acetate (94:6) as the eluents. Pure title compound was thus obtained (380 mg) and isolated as a white foam.

δ ($^1$H, CDCl$_3$): 9.75 (s, 1H, CHO), 7.44–7.28 (m, 10H, 2Ph), 6.99 (s, 1H, CHPh$_2$), 6.05 (dd, 1H, H-2, J=1.5 and 3.6 Hz), 5.07 and 5.02 (2dd, 2H, CH$_2$=C, J=2.4 and 4.8 Hz), 4.49–4.31 (m, 3H, H-7' and CH$_2$-3'), 3.95 and 3.66 (2d, 2H, 8a-CH$_2$, J=9.3 Hz), 3.80 (dd, 1H, H-1', J=7.5 and 9.3 Hz), 3.26 (m, 1H, H-9'), 3.02 (m, 1H, H-5'), 2.76 (t, 1H, H-1, J=3.9 Hz); δ ($^{13}$C, CDCl$_3$): 204.4 (CHO), 171.0 (COODPM), 148.8 and 148.3 (C-3 and C-4'), 139.5 and 139.4 (2 CIV Ph), 130.7 (C-2), 128.6, 128.5, 128.2, 128.0, 127.7 and 127.0 (2×5CH(Ph)), 103.9 (CH$_2$=C), 98.3 (C-7'), 80.4 and 69.5 (C-1' and C-9'), 78.5 (CHPh$_2$), 73.9 and 70.6 (C8a-C and C-3').

INTERMEDIATE 42

[1R-(1α, 3aβ, 4β, 4aβ, 7β, 7aα, 8aβ)] 8a-[[1S, 7R, 9R]-2,8-Dioxa-9-methyl-4-methylene-3-oxo-cis-bicyclo[3.4.0]-non-7-yl-oxy-methyl]-4-formyl-4,4a, 5,6,7,7a,8,8a-octahydro-7-methyl-3-(1-methyl-ethyl)-1,4-methano-s-indacene-3a(1H)-carboxylic acid, diphenylmethyl ester To a stirred solution of chromium (VI) oxide (0.23 g) and dry pyridine (0.37 ml) in dry dichloromethane (20 ml) at 0° C., intermediate 41 (0.15 g) in dry dichloromethane (3 ml) was added. Stirring was maintained at room temperature for 6 hours and the reaction mixture was then directly flash chromatographed on silica gel using dichloromethane as the eluent to afford the title compound (65 mg) as a white foam.

δ ($^1$H, CDCl$_3$): 9.74 (s, 1H, CHO), 7.44–7.25 (m, 10H, 2Ph), 6.98 (s, 1H, CHPh$_2$), 6.37 and 5.64 (2d, 2H, CH$_2$=C), 6.04 (dd, 1H, H-2, J=1.2 and 3.3 Hz), 4.47 (dd, 1H, H-7', J=3.6 and 6.0 Hz), 4.29 (m, 1H, H-1'), 4.00 and 3.64 (2d, 2H, 8a-CH$_2$, J=9.3 Hz), 3.40 (m, 1H, H-5'), 3.30 (m, 1H, H-9'), 2.73 (t, 1H, H-1, J=3.9 Hz).

INTERMEDIATE 43

[1R-(1α, 3aβ, 4β, 4aβ, 7β, 7aα, 8aβ)] 8a-[[1S, 7R, 9R]-2,8-Dioxa-9-methyl-4-oxo-cis-bicyclo[3.4.0]-non-7-yl-oxy-methyl]-4-formyl-4,4a,5,6,7,7a,8,8a-octahydro-7-methyl-3-(1-methyl-ethyl)-1,4-methano-s-indacene-3a(1H)-carboxylic acid, diphenylmethyl ester Method A To an ice cold mixture of Intermediate 41 (105 mg) and N-methylmorpholine N-oxide (43 mg) in acetone:water (8:1, 9 ml) was added osmium tetroxide (2.5% wt solution in 2-methyl-2-propanol, 0.075 ml). The ice bath was removed and the mixture was stirred at room temperature for 24 hours. The reaction was quenched with sodium bisulfite, stirred for 1 hour and the solvent was evaporated. The crude residue was diluted with ethyl acetate (100 ml) and washed successively with water (30 ml), 1N hydrochloric acid (30 ml), sat aq. sodium bicarbonate (30 ml) and water (30 ml), then dried and evaporated. The crude product was dissolved in dioxane:water (2:1, 6 ml) and cooled to 0° C. Sodium periodate (0.13 g) was added in small portions and the mixture was stirred for 6 hours from 0° C. to room temperature, then concentrated and the crude product partitioned between water (60 ml) and ethyl acetate (60 ml). The organic phase was dried and concentrated and the residue thus obtained was purified by flash chromatography on silica gel (hexane:ethyl acetate 85:15) to give the title compound (0.045 g).

Method B

To a solution of trifluoroacetic anhydride (0.43 ml) in dry dichloromethane (2.5 ml) was added dimethylsulfoxide (0.22 ml) at −60° C. under nitrogen with vigorous stirring. After 10 minutes a solution of Intermediate 79 (470 mg) in dry dichloromethane (2.5 ml) was added and the mixture stirred at −60° C. for 2 hours. Triethylamine (1.4 ml) was added dropwise over a period of 10 minutes and the temperature was allowed to reach −20° C. Water (20 ml) was then added and the mixture stirred at room temperature for 1 hour. The mixture was partioned and the aqueous layer was extracted with dichloromethane (100 ml). The combined organic layers were washed with 1N hydrochloric acid (100 ml), saturated sodium bicarbonate (100 ml) and brine (100 ml), dried over magnesium sulfate and concentrated to dryness to afford an oil which was dissolved in dichloromethane and treated with triethylamine (1 ml) overnight. The solvent was removed and the resulting oil was flash chromatographed (silica gel, ethyl acetate:hexane 1:25, 1:20 and 1:15) to obtain 400 mg of the title compound (86% yield).

δ ($^1$H, CDCl$_3$): 9.71 (s, 1H, C$\underline{H}$O), 7.44–7.26 (m, 10H, 2Ph), 6.97 (s, 1H, C$\underline{H}$Ph$_2$), 6.06 (dd, 1H, H-2, J=1.5 and 3.6 Hz), 4.18–4.11 (m, 3H, H-7', H-1' and H-3'(1H), 4.00 and 3.62 (2d, 1H, 8a-CH$_2$, J=9.3 Hz), 3.91 (d, 1H, H-3', J=18 Hz), 3.30 (m, 1H, H-9'), 2.85 (bt, 1H, H-5', J=7.8 Hz), 2.75 (t, 1H, H-1, J=3.9 Hz).

INTERMEDIATE 44

[1R-(1α, 3aβ, 4β, 4aβ, 7β, 7aα, 8aβ)] 8a-{[4-O-(Trans-2-butenyl)-6-deoxy-β-D-altropyranosyloxy]methyl}-4-formyl-4,4a,5,6,7,7a,8,8a-octahydro-7-methyl-3-(1-methylethyl)-1,4-methano-s-indacene-3a(1H)-carboxylic acid, diphenylmethyl ester A suspension of intermediate 1 (5 g) and dibutyltin oxide (2.3 g) in dry toluene (300 ml) was refluxed for 3 hours in a flask fitted with a Dean-Stark condenser under nitrogen and then allowed to cool to 60° C. Molecular sieves (4 Å, powder), crotyl bromide (2.4 ml) and a 1M solution in tetrahydrofuran of tetrabutylammonium fluoride (23 ml) were added consecutively and the mixture heated at 60° C. for 1 hour and at room temperature for 12 hours. The solvent was evaporated to dryness and the residue chromatographed on a silica gel flash column eluting with hexane to hexane:acetone (9:1) to give the title compound (3.2 g) as a white foam.

δ ($^1$H, CDCl$_3$): 9.73 (s, 1H, CHO), 7.45–7.2 (m, 10H, 2Ph), 6.98 (s, 1H, C$\underline{H}$Ph$_2$), 6.05 (dd, 1H, H-2, J=1.5 and 3.6 Hz), 5.8–5.65 (m, 1H, C$\underline{H}$=CH), 5.65–5.5 (m, 1H, CH=C$\underline{H}$), 4.63 (d, 1H, H-1', J=0.9 Hz), 4.2–3.8 (m, 5H, H-2', H-3', 8aCHa and O—C$\underline{H}_2$—C=C), 3.8–3.65 (m, 2H, H-5', 8aCHb), 3.6 (dd, 1H, H4', J=3 and 9.3 Hz), 2.74 (t, 1H, H-1, J=3.9 Hz), 1.71 (dd, 3H, CH$_3$-C=C, J=1.2 and 6.3 Hz).

INTERMEDIATES 45, 46 AND 47 a) [1R-(1α, 3aβ, 4β, 4aβ, 7β, 7aα, 8aβ)] 8a-{[2,3-Anhydro-4-O-(trans-2-butenyl)-6-deoxy-β-D-mannopyranosyloxy]methyl}-4-formyl4,4a,5,6,7,7a,8,8a-octahydro-7-methyl-3-(1-methylethyl)-1,4-methano-s-indacene-3a(1H)-carboxylic acid, diphenylmethyl ester b) [1R-(1α, 3aβ, 4β, 4aβ, 7β, 7aα, 8aβ)] 8a-[(1S,4S,6S,7R,9R)-2,8-Dioxa-4-ethyl-6-hydroxy-9-methyl-cis-bicyclo[3.4.0]-non-7-yl-oxy-methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester c) [1R-(1a, 3ab, 4b, 4ab, 7b, 7aa, 8ab)] 8a-[(1S,4R,6S,7R,9R)-2,8-Dioxa-4-ethyl-6-hydroxy-9-methyl-cis-bicyclo[3.4.0]-non-7-yl-oxy-methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester Intermediate 44 (1.225 g), triphenylphosphine (1.38 g) and imidazole (0.36 g) were refluxed in toluene (35 ml) with stirring and then treated dropwise with a solution of iodine (0.89 g) in toluene (15 ml) during 2 hours. Tetrabutylammonium iodide (0.2 g) was added and reflux continued for 1 hour. The reaction mixture was cooled and partitioned between ethyl acetate (100 ml) and 1 N aqueous hydrochloric acid (50 ml). The organic layer was washed successively with 1 N aqueous hydrochloric acid, water, aqueous sodium metabisulfite solution, water and brine, then dried (Na$_2$SO$_4$), filtered and concentrated in vacuo. The residue was flash chromatographed on silica gel eluting with hexane:ethyl acetate (7:1) to obtain a 2:1 mixture of 2 compounds with a very similar Rf in hexane:ethyl acetate (1.08 g) (Rf=0.4 in hexane:ethyl acetate 4:1). The mixture was dissolved in dry toluene (25 ml) and the solution degassed with an argon stream for 1 hour and then heated to reflux. Tributyltin hydride (0.36 ml) was added and reflux continued for 20 minutes. After cooling carbon tetrachloride (2 ml) was added and the solution stirred at room temperature for 1 hour. A dilute solution of iodine in ether was then added until a faint coloration persisted. The solvent was then removed in vacuo and the residue taken up in diethyl ether and washed several times with a saturated aqueous solution of potassium fluoride until no more precipitation of tributyltin fluoride was observed. The organic layer was dried and evaporated to give a residue which was flash chromatographed twice on silica gel eluting with dichloromethane:ethyl acetate (95:5) and (9:1) to afford title compound (a) Intermediate 47 (230 mg, Rf=0.8 dichloromethane:ethyl acetate 9:1) title compound (b) intermediate 45 (275 mg, Rf=0.5 dichloromethane:ethyl acetate 9:1) and title compound (c) intermediate 46 (200 mg, Rf=0.4 dichloromethane:ethyl acetate 9:1).

INTERMEDIATE 45

δ ($^1$H, CDCl$_3$): 9.72 (s, 1H, CHO), 7.46–7.23 (m, 10H, 2Ph), 6.98 (s, 1H, C$\underline{H}$Ph$_2$), 6.05 (dd, 1H, H-2, J=1.2 and 3.3 Hz), 4.61 (d, 1H, H-7', J=3.3 Hz), 4.03 (d, 1H, 8a-CHa, J=9.3 Hz), 3.90 (dd, 1H, Ha-3', J=6.9 and 8.7 Hz), 3.82–3.69 (m, 3H, H-6', H-1' and H-9'), 3.66 (d, 1H, 8a-CHb, J=9.6 Hz), 3.61 (dd, 1H, Hb-3', J=6.6 and 8.4 Hz), 2.69 (t, 1H, H-1, J=3.9 Hz).

INTERMEDIATE 46

δ ($^1$H, CDCl$_3$): 9.74 (s, 1H, CHO), 7.45–7.22 (m, 10H, 2Ph), 6.99 (s, 1H, C$\underline{H}$Ph$_2$), 6.06 (dd, 1H, H-2, J=1.5 and 3.6 Hz), 4.50 (d, 1H, H-7', J=2.1 Hz); 4.1–4.02 (m, 2H, 8aCHa and Ha-3'), 3.84 (dd, 1H, H-1', J=7.5 and 8.7 Hz), 3.76–3.66 (m, 2H, 8aCHb and H6'), 3.5–3.38 (m, 2H, H-9' and Hb-3'), 2.72 (t, 1H, H-1, J=3.9 Hz), 0.94 (t, 3H, CH$_2$-C$\underline{H}_3$, J=7.5 Hz).

INTERMEDIATE 47

δ ($^1$H, CDCl$_3$): 9.75 (s, 1H, CHO), 7.45–7.2 (m, 10H, 2Ph), 6.99 (s, 1H, C$\underline{H}$Ph$_2$), 6.08 (dd, 1H, H-2, J=1.5 and 3.6 Hz), 5.85–5.7 (m, 1H, CH=CH), 5.65–5.5 (m, 1H, CH=C$\underline{H}$), 4.67 (s, 1H, H-1'), 4.2–4.05 (m, 2H, OCHa-C=C and 8aCHa), 4.05–3.9 (m, 1H, OCHb-C=C), 3.78 (d, 1H, 8aCHb, J=9 Hz), 3.3–3.15 (m, 3H, H-3', H-4' and H5'), 3.12 (d, 1H, H-2', J=3.9 Hz), 2.86 (t, 1H, H-1, J=3.9 Hz).

INTERMEDIATE 48

[1R-(1α, 3aβ, 4β, 4aβ, 7β, 7aα, 8aβ)] 8a-[(6-deoxy-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of sordarin (10.0 g) in dichloromethane (150 ml) was treated dropwise with a solution of diphenyldiazomethane in dichloromethane (0.35M, 85 ml). The resulting solution was stirred at room temperature for 24 hours. The solvent was removed under reduced pressure and the residue was purified by flash column chromatography on silica gel eluting with hexane:ethyl acetate (4:1) and (2:1). The fractions were combined and evaporated to yield the title compound (11.89 g) as a white foam.

δ ($^1$H, CDCl$_3$): 10.00 (s, 1H, CHO), 7.63 (m, 10H, 2Ph), 7.26 (s, 1H, CHPh$_2$), 6.30 (dd, 1H, H-2, J=1.2 and 3.3 Hz), 4.92 (d, 1H, H-1', J=0.9 Hz), 4.84 (t, 1H, H-3', J-3.3 Hz),4.03 and 4.35 (2d, 2H$_1$ 8aCH$_2$, J=9 Hz), 3.88 (m, 1H, H-2'), 3.70 (dq, 1H, H-5', J=6.3 and 9.3 Hz), 3.41 (s, 3H, 4'-OMe), 3.20 (dd, 1H, H4', J=3.3 and 9 Hz), 2.75 (t, 1H, H-1).

INTERMEDIATE 49

(a) [1R-(1α, 3aβ, 4β, 4aβ, 7β, 7aα, 8aβ)] 8a-[(6-Deoxy-4-O-methyl-2,3-di-O-tosyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester and (b) [1R-(1α, 3aβ, 4β, 4aβ, 7β, 7aα, 8aβ)] 8a-[(6-Deoxy-4-O-methyl-2-O-tosyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester Intermediate 48 (2 g) and 4-dimethylaminopyridine (500 mg) were dissolved in dry pyridine (30 ml). A solution of tosyl chloride (960 mg) in dry pyridine (20 ml) was added dropwise. The reaction mixture was stirred at room temperature for 4 days. The solvent was evaporated in vacuo to give a yellow residue, which was chromatographed on silica gel column, eluting with hexane:ethyl acetate (4:1) and (1:1) to afford title compound (a) with the higher Rf. as a white foam (1.65 g) and title compound (b) with the lower Rf. also obtained as a white foam (1.17 g).

(a) δ (1H, CDCl$_3$): 9.71 (s, 1H, CHO), 7.85–7.91 (m, 4H, ortho-Ts), 7.26–7.41 (m, 14H, meta-Ts and 2 Ph), 6.95 (s, 1H, CO$_2$CHPh$_2$), 5.87 (dd, 1H, H-2, J=1.2 and 3.3 Hz), 4.92 (dd, 1H, H-3', J=3.3 and 4.2 Hz), 4.65 (dd, 1H, H-2', J=1.2 and 4.5 Hz), 4.61 (d, 1H, H-1', J=1.2 Hz), 3.50 and 3.94 (2d, 2H, 8aCH$_2$, J=9 Hz), 3.68 (dq, 1H, H-5', J=6.6 and 9 Hz), 3.16 (dd, 1H, H4', J=3 and 9Hz), 2.78 (s, 3H, 4'-OMe), 2.45 and 2.47 (2s, 6H, 2Ts).

(b) δ ($^1$H, CDCl$_3$): 9.71 (s, 1H, CHO), 7.85 (m, 2H, ortho-Ts), 7.26–7.41 (m, 12H, meta-Ts and 2Ph), 6.95 (s, 1H, CHPh$_2$), 5.87 (dd, 1H, H-2, J=1.5 and 3.3 Hz), 4.61 (d, 1H, H-1', J=1.5 Hz), 4.55 (dd, 1H, H-2',J=1.2 and 4.2 Hz), 4.37 (m, 1H, H-3'), 3.50 and 3.95 (2d, 2H1, 8aCH$_2$, J=9Hz), 3.70 (dq, 11H, H-5', J=8.4 and 6.3 Hz), 3.23 (cd, $_1$H, H-4',J=3.3 and 8.7 Hz), 2.42 (s, 3H, Ts).

INTERMEDIATE 50

[1R-(1α, 3aβ, 4β, 4aβ, 7β, 7aα, 8aβ)] 8a-[(2,3-Anhydro-6-deoxy-4-O-methyl-β-D-mannopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester Sodium (0.5 g) was added to anhydrous methanol (50 ml) with cooling at 0° C., followed by Intermediate 49 a (670 mg) in dry dichloromethane (20 ml). The mixture was stirred for 5 days at room temperature and 4 days at reflux. The mixture was filtered off and the solvent removed. The residue was purified by flash chromatography eluting with hexane:ethyl acetate (3:1) to afford the title compound (330 mg).

δ ($^1$H, CDCl$_3$): 9.75 (s, 1H, CHO), 7.26–7.44 (m, 10H, 2Ph), 6.99 (s, 1H, CO$_2$CHPh$_2$), 6.08 (dd, 1H, H-2, J=1.5 and 3 Hz), 4.68 (s, 1H, H-1'), 3.78 and 4.11 (2d, 2H, 8aCH$_2$, J=9 Hz), 3.49 (s, 3H, 4'-OMe), 3.26 (d, 1H, H-2', J=3.9 Hz), 3.18 (m, 1H, H-5'), 3.12 (d, 1H, H-3', J=3.6 Hz), 3.08 (m, 1H, H-4'), 2.86 (m, 1H, H-1').

INTERMEDIATE 51

[1R-(1α, 3aβ, 4β, 4aβ, 7β, 7aα, 8aβ)] 8a-[(2,3-Anhydro-6-deoxy-4-O-methyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester Dry sodium hydride (25.9 mg) was suspended in dry dimethylformamide (5 ml). Intermediate 49(b) (470 mg) in dry dimethylformamide was added dropwise and the mixture stirred for 40 minutes at room temperature. The reaction mixture was poured with stirring into ice-cold water (20 ml) and the resulting solution was treated with ethyl acetate (3×20 ml). The organic layers were combined and dried over anhydrous magnesium sulphate. The gummy residue obtained upon evaporation of solvents was purified by flash column chromatography eluting with hexane:ethyl acetate (5:1) to yield the title compound as a white foam (332 mg).

δ ($^1$H, CDCl$_3$): 9.73 (s, 1H, CHO), 7.26–7.44 (m, 10H, 2Ph), 6.98 (s, 1H, CO$_2$CHPh$_2$), 6.08 (dd, 1H, H-2, J=1.5 and 3 Hz), 4.60 (s, 1H, H-1'), 3.76 and 4.03 (2d, 2H, 8aCH$_2$, J=9.3 Hz), 3.51 (m, 4H, H-4' and 4'-OMe), 3.33 (m, 3H, H-2', H-3' and H-5'), 2.80 (m, 1H, H-1).

INTERMEDIATE 52

[1R-(1α, 3aβ, 4β, 4aβ, 7β, 7aα, 8aβ)] 8a-[(2,3-Anhydro-6-deoxy-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 51 (100 mg) in ethyl acetate (15 ml) was added 10% palladium on charcoal (100 mg) under nitrogen. The mixture was shaken in a Parr apparatus under 15 psi hydrogen for 1 hour at room temperature. The catalyst was filtered off and the solvent evaporated to dryness. The residue was purified by flash chromatography on silica gel, eluting with hexane:ethyl acetate (3:1) and dichloromethane:methanol (15:1). The appropiate fractions were combined and the solvent removed to give the title compound (70 mg) as a foam.

δ ($^1$H, CDCl$_3$): 9.77 (s, 1H, CHO), 6.09 (dd, 1H, H-2, J=1.2 and 3.6 Hz), 4.67 (d, 1H, H-1', J=0.9 Hz), 3.58 and 4.17 (2d, 2H, 8aCH$_2$, J=9.6 Hz), 3.51 (m, 4H, H-3' and 4'-OMe), 3.38 (m, 1H, H-5'), 3.34 (d, 1H, H-2', J=4.2 Hz), 3.30 (dd, 1H, H-4', J=9 and 1.5 Hz), 2.65 (t, 1H, H-1, J=3.9 Hz).

INTERMEDIATE 53

[1R-(1α, 3aβ, 4β, 4aβ, 7β, 7aα, 8aβ)] 8a-[(4-O-Allyl-6-deoxy-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A suspension of Intermediate 1 (2 g) and dibutyltin oxide (870 mg) in dry toluene (25 ml) was refluxed for 2 h in a flask fitted with a Dean-Stark condenser, under nitrogen, and then allowed to stand at room temperature. Allyl bromide (0.3 ml) and a 1M solution of tetrabutylammonium fluoride (3.5 ml) were added consecutively and the mixture was heated at 40° C. for 24 h under nitrogen. The solvent was evaporated to dryness and the residue chromatographed on a silica gel flash column eluting with hexane:acetone (10:1) and (9:1) to give the title compound (1.7 g) as a white foam.

δ ($^1$H, CDCl$_3$): 9.73 (s, 1H, CHO), 6.98 (s, 1H, CHPh$_2$), 6.05 (dd, 1H, H-2, J=1.5 and 3.6 Hz), 5.89 (m, 1H, CH=CH$_2$), 5.25 (m, 2H, CH=CH$_2$), 4.64 (d, 1H, H-1', J=1.5 Hz), 4.15 (t, 1H, H-3', J=3.3 Hz), 4.09 (m, 3H, CH$_2$—CH=CH$_2$ and 8a-CH$_2$), 3.87 (m, 1H, H-2'), 3.74 (m, 2H, H-5' and 8a-CH$_2$), 3.38 (dd, 1H, H-4', J=3.3 and 9 Hz), 2.74 (t, 1H, H-1, J=3.9 Hz).

INTERMEDIATE 54

[1R-(1α, 3aβ, 4β, 4aβ, 7β, 7aα, 8aβ)] 8a-[(4-O-Benzyl-6-deoxy-β-D-altropyranosyloxy)methyl]-4formyl-4,4a,5,6,7,7a,8,8a-octahydro-7-methyl-3-(1-methylethyl)-1,4-methano-s-indacene-3a(1H)-carboxylic acid, diphenylmethyl ester A vigorous stirred mixture of Intermediate 1 (6.0 g) and dibutyltin oxide (3.55 g) in dry toluene (80 ml) was refluxed for 3 hours in a flask fitted with a Dean-Stark condenser under nitrogen atmosphere. The reaction mixture was cooled to 0° C. and then treated with benzyl bromide (1.2 ml) and tetrabutylammonium fluoride (1M in tetrahydrofuran, 10 ml). After heating at 40° C. for 18 hours under nitrogen, the reaction was concentrated under reduced pressure and the residue purified by flash chromatography, eluting with hexane:ethyl acetate (6:1) and (4:1). The appropriate fractions were combined and the solvents evaporated to give the title compound (3.73 g) as a white foam.

δ ($^1$H, CDCl$_3$): 9.73 (s, 1H, CHO), 7.24–7.44 (m, 15H, 3Ph), 6.98 (s, 1H, CO$_2$CHPh$_2$), 6.05 (dd, 1H, H-2, J=1.5 and 3.6 Hz), 4.65 (d, 1H, H-1', J=1.2 Hz), 4.57 (AB system, 4'OCH$_2$Ph, J=11.1 Hz), 4.21 (m, 1H, H-3'), 3.76 and 4.07 (2d, 2H, 8aCH$_2$, J=9 Hz), 3.87 (m, 1H, H-2'), 3.76 (m, 1H, H-5'), 3.49 (dd, 1H, H4', J=3.3 and 9 Hz), 2.74 (t, 1H, H-1, J=3.6 Hz).

INTERMEDIATE 55

[1R-(1α, 3aβ, 4β, 4aβ, 7β, 7aα, 8aβ)] 8a-[(2-O-Benzyloxycarbonyl-6-deoxy-4-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 48 (3 mmol) in dry dichloromethane (15 ml) at 0° C. under nitrogen atmosphere was added 4-dimethylaminopyridine (6.3 mmol). After stirring for 15 minutes, the mixture was cooled to −20° C. and a solution of benzylchloroformate (3.6 mmol) in dry dichloromethane (15 ml) was added dropwise. After two hours, the solvent was evaporated and the residue purified by flash chromatography using hexane:ethyl acetate (3:1) as eluent to give the title compound (1.2 g).

δ ($^1$H, CDCl$_3$): 9.70 (s, 1H, CHO), 7.35 (m, 15H, 3xPh), 6.96 (s, 1H, CHPh$_2$), 5.99 (dd, 1H, H-2, J=1.5 and 3.6 Hz), 5.18 (AB system, 2H, OCH$_2$Ph, J=12 Hz), 5.00 (dd, 1H, H-2', J=1.5 and 4.2 Hz), 4.70 (d, 1H, H-1', J=1.8 Hz), 4.13 (m, 1H, H-3'), 4.01 and 3.66 (d,d, 1H, 1H, 8a-CH$_2$, J=9 Hz), 3.75 (m, 1H, H-5'), 3.40 (s, 3H, OMe), 3.17 (dd, 1H, H4', J=3.3 and 8.4 Hz), 2.62 (t, 1H, H-1, J=3.6 Hz), 2.43 (d, 1H, OH, J=2.4 Hz), 2.21 (m, 1H, CH(CH$_3$)$_2$).

INTERMEDIATE 56

[1R-(1α, 3aβ, 4β, 4aβ, 7β, 7aα, 8aβ)] 8a-[(4-O-Allyl-2-O-benzyloxycarbonyl-6-deoxy-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 53 (1.4 g) in dry methylene chloride (30 ml) at 0° C. was added dimethylaminopyridine (513 mg) and the mixture was stirred for 15 minutes. Benzyl chloroformate (0.35 ml) in dry methylene chloride (15 ml) was then added dropwise for 15 minutes, and the mixture stirred for 4 h. The mixture was then diluted with methanol (1 ml) and methylene chloride (20 ml) and washed with water, 1 N hydrochloric acid and brine. The organic layer was dried over anhydrous magnesium sulphate, filtered and the solvent evaporated to dryness. The residue was purified by flash column chromatography eluting with hexane:ethyl acetate (7:1) and (5:1) to give the title compound (1.1 g).

δ ($^1$H, CDCl$_3$): 9.70(s, 1H, CHO), 6.96 (s, 1H, CHPh$_2$), 5.99 (dd, 1H, H-2, J=1.5 and 3.6 Hz), 5.88 (m, 1H, CH=CH$_2$), 5.20 (m, 4H, Ph—CH$_2$—O, CH$_2$—CH=CH$_2$), 4.99 (dd, 1H, H-2', J=1.5 and 4.2 Hz), 4.70 (d, 1H, H-1', J=1.5 Hz), 4.12 (m, 1H, H-3'), 4.03 (m, 3H, CH$_2$—CH=CH$_2$ and H-8a-CH$_2$), 3.76 (m, 1H, H-3'), 3.64 (d, 1H, 8a-CH$_2$, 8.7 Hz), 3.34 (dd, 1H, H-4', J=3.3 and 8.7 Hz), 2.61 (t, 1H, H-1, J=3.9 Hz).

INTERMEDIATE 57

[1R-(1α, 3aβ, 4β, 4aβ, 7β, 7aα, 8aβ)] 8a-[(4-O-Benzyl-2-O-benzyloxycarbonyl-6-deoxy-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 54 (3.7 g) in dry dichloromethane (25 ml) at 0° C. under nitrogen atmosphere was added 4-dimethylaminopyridine (1.85 g). After stirring for 15 minutes, the mixture was cooled to −20° C. and a solution of benzylchloroformate (0.68 ml) in dry dichloromethane (10 ml) was added dropwise until the product was detected by tlc (hexane:ethyl acetate 4:1). The solvent was then evaporated to dryness and the residue was purified by flash chromatography using hexane:ethyl acetate (6:1) as eluent to give the title compound (3.6 g) as a white foam.

δ ($^1$H, CDCl$_3$): 9.70 (s, 1H, CHO), 7.26–7.42 (m, 20H, 4Ph), 6.96 (s, 1H, CO$_2$CHPh$_2$), 5.99 (dd, 1H, H-2, J=1.2 and 3.3 Hz), 5.18 (AB system, 2'-OCO$_2$CH$_2$Ph, J=12.3 Hz), 5.00 (dd, 1H, H-2', J=1.5 and 4.2 Hz), 4.71 (d, 1H, H-1', J=1.5 Hz), 4.56 (AB system, 4-OCH$_2$Ph, J=11.1 Hz), 4.15 (m, 1H, H-3'), 3.66 and 4.00 (2d, 2H, 8aCH$_2$, J=9 Hz), 3.81 (dq, 1H, H-5', J=6.6 and 9 Hz), 3.43 (dd, 1H, H4', J=3.3 and 9 Hz), 2.60 (t, 1H, H-1, J=3.6 Hz).

INTERMEDIATE 58

[1R-(1α, 3aβ, 4β, 4aβ, 7β, 7aα, 8aβ)] 8a-[(2-O-Benzyloxycarbonyl-6-deoxy-4-O-methyl-3-O-tosyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 55 (3 mmol) and 4-dimethylaminopyridine (5.1 mmol) in dry dichloromethane (60 ml) was treated dropwise with a solution of tosyl chloride (4.5 mmol) in dry dichloromethane (20 ml). After 24 hours, the solvent was evaporated and the residue purified by flash chromatography using hexane:ethyl acetate (5:1) as eluent to give the title compound (1.8 g).

δ ($^1$H, CDCl$_3$): 9.70 (s, 1H, CHO), 7.84 and 7.32 (d, m, 2H, 17H, Ar), 6.96 (s, 1H, CHPh$_2$), 5.94 (dd, 1H, H-2, J=1.5 and 3.6 Hz), 5.17 (AB system, 2H, OCH$_2$Ph, J=12 Hz), 5.10 (m, 1H, H-3'), 4.88 (dd, 1H, H-2', J=3 and 5.4 Hz), 4.68 (d, 1H, H-1', J=2.1 Hz), 3.97 and 3.63 (2d, 2H, 8a-CH$_2$, J=9 Hz), 3.76 (dd, 1H, H-5', J=6.3 and 8.1 Hz), 3.18 (dd, 1H, H-4', J=3 and 8.1 Hz), 3.05 (s, 3H, OMe), 2.51 (t, 1H, H-1, J=3.6 Hz), 2.43 (s, 3H, CH$_3$Ar), 2.01 (m, 1H, CH(CH$_3$)$_2$).

INTERMEDIATE 59

1R-(1α, 3aβ, 4β, 4aβ, 7β, 7aα, 8aβ)] 8a-[(4-O-Allyl-2-O-benzyloxycarbonyl-6-deoxy-3-O-tosyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 56 (1.1 g) and dimethylaminopyridine (300 mg) in dry methylene chloride (40 ml) was added dropwise a solution of tosyl chloride (400 mg) in dry methylene chloride (20 ml) and the reaction mixture was stirred for 3 days at room temperature. The solvent was evaporated to dryness and the residue chromatographed on a silica gel flash column eluting with hexane:ethyl acetate (9:1) and (6:1) to give the title compound (820 mg).

δ ($^1$H, CDCl$_3$): 9.70 (s, 1H, CHO), 6.95 (s, 1H, CHPh$_2$), 5.94 (dd, 1H, H-2, J=1.5 and 3.9 Hz), 5.61 (m, 1H, CH=CH$_2$), 5.12 (m, 4H, Ph—CH$_2$—O, CH$_2$—CH=CH$_2$), 4.84 (dd, 1H, H-2', J=3 and 5.1 Hz), 4.69 (d, 1H, H-1', J=1.8 Hz), 3.96 and 3.63 (2d, 2H, 8a-CH$_2$, J=9.0 Hz), 3.76 (m, 4H, H-3', H-5', CH$_2$—CH=CH$_2$), 3.38 (dd, 1H, H4', J=3 and 8.1 Hz), 2.50 (t, 1H, H-1, J=3.9 Hz), 2.42 (s, 3H, CH$_3$—Ph).

INTERMEDIATE 60

[1R-(1α, 3aβ, 4β, 4aβ, 7β, 7aα, 8aβ)] 8a-[(4-O-Benzyl-2-O-benzyloxycarbonyl-6-deoxy-3-O-tosyl-β-D-altropyranosyloxy)methyl]-4-formyl-4,4a,5,6,7,7a,8,8a-octahydro-7-methyl-3-(1-methylethyl)-1,4methano-s-indacene-3a(1H)-carboxylic acid, diphenylmethyl ester To a solution of Intermediate 57 (3.5 g) and dimethylaminopyridine (1.3 g) in dry methylene chloride (80 ml) was added dropwise a solution of tosyl chloride (2 g) in dry methylene chloride (50 ml) and the mixture was stirred for 3 days at room temperature. The solvent was evaporated and the residue chromatographed on a silica gel flash column using hexane:ethyl acetate (9:1) as eluent to give the title compound (3.14 g).

δ ($^1$H, CDCl$_3$): 9.70 (s, 1H, CHO), 6.95 (s, 1H, CHPh$_2$), 5.95 (dd,1H, H-2, J=1.2 and 3.3 Hz), 5.16 (m, 3H, Ph—CH$_2$—O, H-2'), 4.93 (dd, 1H, H-3', J=3 and 4.8 Hz), 4.71 (d, 1H, H-1', J=1.8 Hz), 4.25 (AB system, 2H, O—CH$_2$Ph, J=11.5 Hz), 3.96, 3.63 (2d, 2H, 8a-CH$_2$, J=9.0 Hz), 3.83 (m, 1H, H-5'), 3.45 (dd, 1H, H-4', J=3 and 8.4 Hz), 2.51 (t, 1H, H-1, J=3.9 Hz), 2.35 (s, 3H, CH$_3$—Ph).

INTERMEDIATE 61

[1R-(1α, 3aβ, 4β, 4aβ, 7β, 7aα, 8aβ)] 8a-[(6-Deoxy-4-O-methyl-3-O-tosyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 58 (1.9 mmol) in ethyl acetate (60 ml) was added 10% palladium on charcoal (100 mg) under nitrogen. The mixture was shaken in a Parr apparatus under 15 psi of hydrogen for 1 hour at room temperature. The catalyst was filtered off and the solution was treated with a 0.35 M solution of diphenyldiazomethane (20 ml). After 2 hours, the solvent was evaporated and the residue purified by flash chromatography using hexane:ethyl acetate (3:1) as eluent to give the title compound (1.3 g).

δ ($^1$H, CDCl$_3$): 9.72 (s, 1H, CHO), 7.85 and 7.32 (d, m, 2H, 12H, Ar), 6.98 (s, 1H, CHPh$_2$), 6.06 (dd, 1H, H-2, J=1.2 and 3.3 Hz), 4.84 (dd, 1H, H-3', J=3 and 4.2 Hz), 4.64 (d, 1H, H-1', J=1.5 Hz), 4.06 and 3.75 (2d, 2H, 8a-CH$_2$, J=9.3 Hz), 4.02 (m, 1H, H-2'), 3.70 (m, 1H, H-5'), 3.16 (dd, 1H, H4', J=3 and 9 Hz), 2.93 (s, 3H, OMe), 2.69 (t, 1H, H-1, J=3.9 Hz), 2.45 (s, 3H, CH$_3$Ar), 2.30 (d, 1H, OH, J=3 Hz), 2.23 (m, 1H, CH(CH$_3$)$_2$).

INTERMEDIATE 62

1R-(1α, 3aβ, 4β, 4aβ, 7β, 7aα, 8aβ)] 8a-[(6-Deoxy-4-O-propyl-3-O-tosyl-β-D-altropyranosyloxy) methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 59 (800 mg) in ethyl acetate (200 ml) was added 10% palladium on charcoal (300 mg) under nitrogen. The mixture was shaken in a Parr apparatus under 20 psi of hydrogen for 1 hour at room temperature. The catalyst was filtered off and the solvent evaporated to dryness. The residue was dissolved in methylene chloride (50 ml) and a 0.35M solution of diphenyldiazomethane (6 ml) was added dropwise. The mixture was stirred at room temperature for 3 hours. The solvent was evaporated and the residue chromatographed on a silica gel flash column eluting with hexane:ethyl acetate (8:1) and (3:1) to give the title compound (630 mg).

δ ($^1$H, CDCl$_3$): 9.72 (s, 1H, CHO), 6.98 (s, 1H, CHPh$_2$), 6.06 (dd, 1H, H-2, J=1.2 and 3.3 Hz), 4.84 (dd 1H, H-2', J=3 and 4.2 Hz), 4.64 (d, 1H, H-1', J=1.5 Hz), 4.05 (m, 2H, H-3' and H-8a-CH$_2$), 3.73 (m, 2H, H-5' and H-8a-CH$_2$), 3.29 (dd, 1H, H-4', J=2.7 and 9 Hz), 3.01 (t, 2H, OCH$_2$CH$_2$CH$_3$, J=7 Hz), 2.68 (t, 1H, H-1, J=3.9 Hz), 2.44 (s, 3H, p-Ts).

INTERMEDIATE 63

[1R-(1α, 3aβ, 4β, 4aβ, 7β, 7aα, 8aβ)] 8a-[(4-O-Benzyl-6-deoxy-3-O-tosyl-β-D-altropyranosyloxy) methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 60 (1.0 g) in ethyl acetate (70 ml) was added 10% palladium on charcoal (600 mg) under nitrogen. The mixture was shaken in a Parr apparatus under 15 psi of hydrogen for 4 hours at room temperature. The catalyst was filtered off and the solvent evaporated to dryness. The residue was purified by flash chromatography on silica gel, eluting with hexane:ethyl acetate (3:1) and (1:1). The appropriate fractions were combined and the solvent was evaporated to give the title compound (530 mg).

δ (1H, CDCl$_3$): 9.70 (s, 1H, CHO), 7.81 and 7.10–7.30 (2m, 9H, Ts and Ph), 6.08 (dd, 1H, H-2, J=1.5 and 3.3 Hz), 4.91 (dd, 1H, H-3', J=3.3 and 4.5 Hz), 4.68 (d, 1H, H-1', J=1.5 Hz), 4.12 (m, 3H, CH$_2$Ph and H-2'), 4.06 and 3.64 (2d, 2H, 8aCH$_2$, J=9.3 Hz), 3.46 (m, 1H, H-4'), 2.65 (m, 1H, H-1), 2.36 (s, 3H, Ts).

INTERMEDIATE 64

[1R-(1α, 3aβ, 4β, 4aβ, 7β, 7aα, 8aβ)] 8a-[(2,3-Anhydro-6-deoxy-4-O-methyl-β-D-mannopyranosyloxy) methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A suspension of sodium hydride (3.2 mmol) in dry dimethylformamide (6 ml), under nitrogen atmosphere, was treated with a solution of Intermediate 61 (1.6 mmol) in dry dimethylformamide (6 ml). After 40 minutes, water ethyl acetate (1:1; 60 ml) was added. The organic phase was evaporated and the residue purified by flash chromatography using hexane:ethyl acetate (4:1) as eluent to give the title compound (960 mg), having the identical proton NMR spectrum as the compound of Intermediate 50.

INTERMEDIATE 65

1R-(1α, 3aβ, 4β, 4aβ, 7β, 7aα, 8aβ)] 8a-[(2,3-Anhydro-6-deoxy-4-O-propyl-β-D-mannopyranosyloxy) methyl]-4-formyl-4,4a,5,6,7, 7a,8,8a-octahydro-7-methyl-3-(1-methylethyl)-1,4-methano-s-indacene-3a(1H)-carboxylic acid, diphenylmethyl ester To a suspension of sodium hydride (35 mg) in dry dimethylformamide (10 ml) was added dropwise a solution of Intermediate 62 (600 mg) in dry dimethylformamide (15 ml). The mixture was stirred at room temperature under nitrogen for 1 h and was then treated with 1 N ammonium chloride (50 ml) and ethyl acetate (70 ml). The organic layer was washed with water and brine, dried over anhydrous magnesium sulphate and evaporated to dryness. The residue was chromatographed on a silica gel flash column eluting with hexane:ethyl acetate (8:1) and (6:1) to yield the title compound (450 mg) as a white foam.

δ ($^1$H, CDCl$_3$): 9.75 (s, 1H, CHO), 6.99 (s, 1H, CHPH$_2$), 6.08 (dd, 1H- H-2, J=1.5 and 4.8 Hz), 4.68 (s, 1H, H-1'), 4.11 and 3.79 (2d, 2H, 8a-CH$_2$, J=9.0 Hz), 3.68 (m, 1H, H-5'), 3.45 (m, 1H, H4'), 3.24 and 3.12 (2d, 2H, H-2', H-3', J=3.9 Hz), 3.19 (t, 2H, OCH$_2$CH$_2$CH$_3$, J=7 Hz), 2.86 (t, 1H, H-1, J=3.9 Hz).

INTERMEDIATE 66

[1R-(1α, 3aβ, 4β, 4aβ, 7β, 7aα, 8aβ)] 8a-[(6-Deoxy-3-O-tosyl-β-D-altropyranosyloxy)methyl]-4-formyl-4,4a,5,6,7,7a,8,8a-octahydro-7-methyl-3-(1-methylethyl)-1,4-methano-s-indacene-3a(1H) carboxylic acid To a suspension of 10% palladium on charcoal (800 mg) in ethyl acetate (60 ml) in a hydrogenation bottle under nitrogen were added a solution of Intermediate 60 (1.0 g) in ethyl acetate (30 ml) and a mixture of methanol:1 N hydrochloric acid (3:1; 4 ml). The bottle was shaken in a Parr hydrogenation apparatus at a pressure of 30 psi of hydrogen for 18 hours. The reaction mixture was filtered and the filtrate was evaporated to dryness. The residue was purified by flash column chromatography on silica gel, eluting with dichloromethane:methanol (20:1). The appropriate fractions were combined and the solvent was evaporated to give the title compound (380 mg).

δ (1H, CDCl$_3$): 9.70 (s, 1H, CHO), 7.84 and 7.38 (2d, 4H, Ts), 6.06 (dd, 1H, H-2, J=1.5 and 3.6 Hz), 4.75 (dd, 1H, H-3', J=3.3 and 4.5 Hz), 4.61 (d, 1H, H-1', J=1.2 Hz), 4.05 (d, 1H, H-8aCH$_2$a, J=9.3 Hz), 3.92 (dd, 1H, H-2', J=1.2 and 4.5 Hz), 3.65 (m, 3H, H-5', H-4' and H-8aCH$_2$b), 2.63 (m, 1H, H-1), 2.46 (s, 3H, Ts).

INTERMEDIATE 67

[1R-(1α, 3aβ, 4β, 4aβ, 7β, 7aα, 8aβ)] 8a-[(2,3-Anhydro-6-deoxy-β-D-mannopyranosyloxy)methyl]-4-formyl-4,4a,5,6,7,7a,8,8a-octahydro-7-methyl-3-(1-methylethyl)-1,4methano-s-indacene-3a(1H)-carboxylic acid, diphenylmethyl ester A solution of Example 55 (585 mg) in dry dichloromethane (20 ml) was treated dropwise with a purple solution of diphenyldiazomethane in dichloromethane (0.35 M, 8 ml). The resulting solution was stirred at room temperature for 14 hours. The solvent was removed under reduce pressure and the residue was purified by flash column chromatography on silica gel eluting with hexane:ethyl acetate (6:1) and (4:1). The appropriate fractions were combined and evaporated to yield the title compound (764 mg) as a white foam.

δ ($^1$H, CDCl$_3$): 9.75 (s, 1H, CHO), 7.26–7.44 (m, 10H, 2Ph), 7.00 (s, 1H, CO$_2$CHPh$_2$), 6.09 (dd, 1H, H-2, J=1.2 and 3.6 Hz), 4.71 (s, 1H, H-1'), 3.79 and 4.12 (2d, 2H, 8aCH$_2$, J=9.3 Hz), 3.63 (dd, 1H, H-4', J=5.7 and 8.7 Hz), 3.21 (m, 1H, H-5'), 3.15 and 3.24 (2d, 2H, H-2' and H-3', J=3.6 Hz), 2.86 (t, 1H, H-1, J=3.9 Hz).

INTERMEDIATE 68

[1R-(1α, 3aβ, 4β, 4aβ, 7β, 7aα, 8aβ)] 8a-[(2,3-Anhydro-4,6-dideoxy-4-fluoro-β-D-talopyranosyloxy) methyl]-4-formyl-4,4a,5,6,7,7a,8, 8a-octahydro-7-methyl-3-(1-methylethyl)-1, 4methano-s-indacene-3a(1H)-carboxylic acid, diphenylmethyl ester A solution of Intermediate 67 (300 mg) in dichloromethane (25 ml) was treated with diethylaminosulfur trifluoride (0.16 ml), and the resulting mixture was stirred overnight at room temperature. The mixture was cooled to 0° C., quenched by addition of methanol (15 ml) and then concentrated under reduced pressure. Flash chromatography of the residue on silica gel eluting with hexane:ethyl acetate (6:1) and (4:1) afforded the title compound (160 mg).

δ ($^1$H, CDCl$_3$): 9.73 (s, 1H, CHO), 7.45–7.26 (m, 10H, 2Ph), 6.98 (s, 1H, CHPh$_2$),6.09 (dd, 1H, H-2, J=1.5 and 3.9 Hz), 5.09 (d, 1H, H-1', J=1.5 Hz), 4.75 and 4.58 (2dq, 1H, H-5', J$_{5',F}$=48.6 Hz, J=6.6 Hz, J=3.9 Hz), 4.18 and 4.11 (2d, 1H, H-4', J$_{4'F}$=23.1 Hz, J=3.9 Hz), 3.97 and 3.81 (2d, 2H, 8aCH$_2$, J=9.3 Hz), 3.75 and 3.70 (2m, 2H, H-2' and H-3'), 2.84 (t, 1H, H-1).

INTERMEDIATE 69

[1R-(1α, 3aβ, 4β, 4aβ, 7β, 7aα, 8aβ)] 8a-[(2,3-Anhydro-6-deoxy-4-O-(2-methoxyethyl)-β-D-mannopyranosyloxy)methyl]-4-formyl-4,4a,5,6,7,7a, 8,8a-octahydro-7-methyl-3-(1-methylethyl)-1,4-methano-s-indacene-3a(1H)-carboxylic acid, diphenylmethyl ester To a suspension of sodium hydride (24 mg) in dry tetrahydrofuran (20 ml) at 0° C. under nitrogen was added Intermediate 67 (300 mg) and the mixture was stirred for 30 minutes. 2-Bromoethyl methyl ether (300 mg) and 1 N tetrabutylammonium iodide (2 ml) were added and the mixture was heated at 40° C. for 2 days. The reaction was quenched with 1 N ammonium chloride (10 ml) and the mixture diluted with ethyl acetate (30 ml). The organic layer was washed with water and brine, dried over anhydrous magnesium sulphate and the solvent evaporated to dryness. The residue was chromatographed on a silica gel flash column eluting with hexane:ethyl acetate (5:1) to give the title compound as a colourless oil.

δ ($^1$H, CDCl$_3$): 9.75 (s, 1H, CHO), 6.98 (s, 1H, CHPh$_2$), 6.08 (dd, 1H, H-2, J=1.2 and 3.3 Hz), 4.67 (s, 1H, H-1'), 4.10 and 3.78 (2d, 2H, 8a-CH$_2$, J=9.0 Hz) 4.09–4.00 (m, 2H, H-4', H-5'), 3.90–3.53 (m, 4H, OCH$_2$CH$_2$OCH$_3$), 3.40 (s, 3H, CH$_3$OCH$_2$CH$_2$), 3.29 and 3.11 (2d, 2H, H-3', and H-2', J=3.9 and 3.9 Hz), 2.86 (t, 1H, H-1, J=3.7 Hz).

INTERMEDIATE 70

[1R-(1α, 3aβ, 4β, 4aβ, 7β, 7aα, 8aβ)] 8a-[(2,3-Anhydro-6-deoxy-4-O-(2-methylprop-2-enyl)-β-D-mannopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A mixture of Intermediate 67 (0.3 mmol), cesium carbonate (0.3 mmol) and 3-bromo-2-methyl-propene (0.5 mmol) in dry dimethylformamide (1.5 ml) was stirred for three days at room temperature. After diluting with diethyl ether (30 ml) the mixture was washed with water. The solvent was evaporated and the residue was purified by flash chromatography using hexane:ethyl acetate (4:1) as eluent to give the title compound (62 mg).

δ ($^1$H, CDCl$_3$): 9.75 (s, 1H, CHO), 7.35 (m, 10H, 2xPh), 6.99 (s, 1H, CHPh$_2$), 6.08 (dd, 1H, H-2, J=1.5 and 3.6 Hz), 5.00 and 4.93 (m,m, 1H, 1H, CH$_2$=C), 4.70 (s, 1H, H-1'), 4.12 and 3.79 (2d, 2H, 8a-CH$_2$, J=9.3 Hz), 4.12 and 3.96 (d,d, 1H, 1H, CH$_2$O, J=12 Hz), 3.26 (m, 3H, H-3', H-4' and H-5'), 3.13 (d, 1H, H-2', J=3.9 Hz), 2.86 (t, 1H, H-1, J=3.9 Hz), 2.23 (m, 1H, CH(CH$_3$)$_2$).

INTERMEDIATE 71

[1R-(1α, 3aβ, 4β, 4aβ, 7β, 7aα, 8aβ)] 8a-[(2,3-Anhydro-6-deoxy-4-O-(1-methylethyl)carbonyl-β-D-mannopyranosyloxy)methyl]-4-formyl-4,4a,5,6,7,7a,8,8a-octahydro-7-methyl-3-(1-methylethyl)-1,4-methano-s-indacene-3a(1H)carboxylic acid, diphenylmethyl ester To a solution of Intermediate 67 (160 mg) in dry dichloromethane (5 ml) were added 4-dimethylaminopyridine (70 mg) and isobutyryl chloride (60 µl). The mixture was stirred overnight at room temperature and then concentrated to give a yellow oil, which was chromatographed on a silica gel flash column using hexane:ethyl acetate (5:1) as eluent to provide the title compound (162 mg) as a white foam.

δ ($^1$H, CDCl$_3$): 9.75 (s, 1H, CHO), 7.26–7.44 (m, 10H, 2Ph), 6.99 (s, 1H, CHPh$_2$), 6.08 (dd, 1H, H-2), 5.75 (s, 1H, H-1'), 4.68 (d, 1H, H-4', J=9 Hz), 4.12 and 3.80 (2d, 2H, 8aCH$_2$, J=9 Hz), 3.43 (dq, 1H, H-5', J=6.6 and 9 Hz), 3.15 (s, 2H, H-2' and H-3'), 2.86 (m, 1H, H-11), 2.59 (m, 1H, 4'-OCOCHMe$_2$).

INTERMEDIATE 72

[1R-(1α, 3aβ, 4β, 4aβ, 7β, 7aα, 8aβ)] 8a-[(2,3-Anhydro-6-deoxy-4-O-(2,2-dimethylpropionyl)-β-D-mannopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A mixture of Intermediate 67 (0.3 mmol) and 4-dimethylaminopyridine (0.6 mmol) in dry dichloromethane (15 ml) was treated with pivaloyl chloride (0.45 mmol). After 2.5 hours, the mixture was washed with water. The organic phase was evaporated and the residue was purified by flash column chromatography using hexane:ethyl acetate (5:1) as eluent to give the title compound (190 mg).

δ ($^1$H, CDCl$_3$): 9.76 (s, 1H, CHO), 7.83 (m, 10H, 2xPh), 7.00 (s, 1H, CHPh$_2$), 6.08 (dd, 1H, H-2, J=1.5 and 3.3 Hz), 4.77 (s, 1H, H-1'), 4.67 (d, 1H, H-4', J=9 Hz), 4.13 and 3.81 (d,d, 1H, 1H, 8a-CH$_2$, J=9 Hz), 3.43 (m, 1H, H-5'), 3.13 (m, 2H, H-2' and H-3'), 2.86 (t, 1H, H-1, J=3.9 Hz), 2.24 (m, 1H, CH(CH$_3$)$_2$).

INTERMEDIATE 73

[1R-(1α, 3aβ, 4β, 4aβ, 7β, 7aα, 8aβ)] 8a-[(2,3-Anhydro-4-O-benzyloxy-carbonyl-6-deoxy-β-D-mannopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 67 (0.3 mmol) and 4-dimethylaminopyridine (0.8 mmol) in dry dichloromethane (15 ml) was treated dropwise with benzyloxycarbonyl chloride (0.7 mmol) and stirred for 3 hours. After washing with water and brine, the solvent was evaporated and the residue was purified by flash chromatography using hexane:ethyl acetate (5:1) as eluent to give the title compound (185 mg).

δ ($^1$H, CDCl$_3$): 9.75 (s, 1H, CHO), 7.32 (m, 15H, 3xPh), 6.99 (s, 1H, CHPh$_2$), 6.08 (dd, 1H, H-2, J=1.2 and 3.3 Hz), 5.20 (m, 2H, OCH$_2$Ph), 4.72 (s, 1H, H-1'), 4.57 (d, 1H, H-4', J=8.4 Hz), 4.11 and 3.79 (2d, 2H, 8a-CH$_2$, J=9 Hz), 3.43 (m, 1H, H-5'), 3.27 and 3.15 (2d, 2H, H-2' and H-3', J=3.6 Hz), 2.85 (t, 1H, H-1, J=3.9 Hz), 2.24 (m, 1H, CH(CH$_3$)$_2$).

INTERMEDIATE 74

[1R-(1α, 3aβ, 4β, 4aβ, 7β, 7aα, 8aβ)] 8a-[(2,3-Anhydro-6-deoxy-4-oxy-β-D-mannopyranosyloxy)methyl]4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of trifluoroacetic anhydride (0.1 ml) in dry dichloromethane (5 ml) at –60° C. was treated dropwise with dimethylsulfoxide (0.06 ml) and a solution of Intermediate 67 (0.39 mmol) in dry dichloromethane (5 ml). After 60 minutes, triethylamine (0.24 ml) was added and the mixture was stirred at –20° C. for 2 hours. The mixture was diluted with dichloromethane (20 ml) and washed with water. After removal of the solvent, the residue was purified by flash chromatography using hexane:ethyl acetate (4:1) as eluent to give the title compound (171 mg).

δ ($^1$H, CDCl$_3$): 9.76 (s, 1H, CHO), 7.36 (m, 10H, 2xPh), 6.59 (s, 1H, CHPh$_2$), 6.09 (dd, 1H, H-2, J=1.5 and 3.6 Hz), 4.84 (s, 1H, H-1'), 4.11 and 3.84 (2d, 2H, 8a-CH$_2$, J=9 Hz), 3.92 (q, 1H, H-5', J=6.9 Hz), 3.59 and 3.37 (2d, H-2' and H-3', J=4.2 Hz), 2.86 (t, 1H, H-1, J=3.9 Hz), 2.26 (m, 1H, CH(CH$_3$)$_2$).

INTERMEDIATE 75

[1R-(1α, 3aβ, 4β, 4aβ, 7β, 7aα, 8aβ)] 8a-[2-O-Benzoyl-6-deoxy-4-methyl-β-D-altropyranosyloxy)methyl]4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 48 (15.88 g) and dimethylaminopyridine (8.83 g) in dry dichloromethane (200 ml) was added dropwise at –25° C. under nitrogen benzoyl chloride (2 ml) in dry dichloromethane (10 ml). After stirring for 45 minutes the cool bath was removed and 1 N hydrochloric acid (10 ml) was added carefully. The two phases were partioned and the organic layer was diluted with dichloromethane (600 ml) and washed with 1 N hydrochloric acid (500 ml) 10% sodium bicarbonate (500 ml) and brine (500 ml). The solvent was removed to dryness to give an oil which was flash chromatographed (silica gel, ethyl acetate:hexanes v/v 1:20 and 1:7) to obtain 8.75 g of the title compound (48% yield) as a foam.

δ ($^1$H, CDCl$_3$): 9.66 (s, 1H, CHO), 8.15–8.05, 7.60–7.2 (2m, 15H, 3Ph), 6.95 (s, 1H, CHPh$_2$), 5.93 (bd, 1H, H2, J=2.1 Hz), 5.35 (dd 1H, H2', J=1.5 and 4.8 Hz), 4.82 (d, 1H, H1', J=1.8 Hz), 4.25 (m, 1H, H3'), 3.99 (d, 1H, 8aCH$_2$, J=9 Hz), 3.86 (dq, 1H, H5', J=6.3 and 8.1 Hz), 3.68 (d, 1H, 8aCH$_2$, J=9 hz), 3.43 (s, 3H, OCH$_3$), 3.22 (dd, 1H, H4', J=3 and 8.1 Hz), 2.62 (t 1H, H1, J=3.9 Hz), 2.45 (d, 1H, OH, J=2.4 Hz), 2.19 (m, 1H, CH(CH$_3$)$_2$).

INTERMEDIATE 76

[1R-(1α, 3aβ, 4β, 4aβ, 7β, 7aα, 8aβ)] 8a-[(2-O-Benzoyl-3,6-dideoxy-4-O-methyl-3-oxo-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of trifluoroacetic anhydride (1.29 ml) in dry dichloromethane (15 ml) was added DMSO (0.66 ml) over a period of 10 minutes at −60° C. under nitrogen atmosphere. To the suspension thus formed was added a solution of Intermediate 75 (3.45 g) in dry dichloromethane (30 ml) and the mixture stirred at −60° C. for 1 hour. Triethylamine (5.76 ml) was added dropwise and the temperature was allowed to reach −20° C., then water (6 ml) was added to the resulting yellow solution and the mixture was stirred at room temperature for 1 hour. Dichloromethane (200 ml) and water (200 ml) were added and the two phases partioned. The organic layer was dried over magnesium sulfate and concentrated to dryness to give a crude which was dissolved in dichloromethane (10 ml) and treated with triethylamine (2 ml) overnight. Elimination of the solvent gave a oil which was flash chromatographed (silica gel, ethyl acetate:hexanes v/v 1:15 and 1:10) to afford 2.6 g of the title compound (76% yield) as a foam.

δ ($^1$H, CDCl$_3$): 9.68 (s, 1H, CHO), 8.2–8.0, 7.6–7.2 (2m, 15H, 3Ph), 6.96 (s, 1H, CHPh$_2$), 5.76 (dd, 1H, H2, J=1.2 and 3.3 Hz), 5.77 (dd, 1H, H2, J=1.2 and 3.3 Hz), 5.39 (dd, 1H, H2', J=1.2 and 8.1 Hz), 4.53 (d, 1H, H1', J=8.1 Hz), 4.09 (d, 1H, 8aCH$_2$, J=9 Hz), 3.75 (d, 1H, 8aCH$_2$, J=9 Hz), 3.7–3.4 (m, 5H, H4'+OCH$_3$+H5'), 2.63 (t, 1H, H1, J=4.2 Hz).

INTERMEDIATE 77

[1R-(1α, 3aβ, 4β, 4aβ, 7β, 7aα, 8aβ)] 8a-[(2,3,6-Trideoxy-4-O-methyl-3-oxo-β-D-allopyranosyloxy) methyl]-4-formyl-4a,5,6,7,7a,8,8a-octahydro-7-methyl-3-(1-methylethyl)-1,4-methano-s-indacene-3a(1H)-carboxylic acid, diphenylmethyl ester To a well degassed solution (Ar, 15 minutes) of tributyltin hydride (5.96 ml) in dry toluene (120 ml) was added via syringe a solution of Intermediate 76 (5.7 g) and a,a' azoisobutyronitrile (420 mg) in dry toluene (50 ml) at 90° C. over a period of 1 hour. The heating was continued until completion of the reaction and then it was cooled to room temperature. Water (40 ml) and potassium fluoride (1.5 g) were added and the mixture stirred overnight. The crude obtained after elimination of the solvents was stirred with diethyl ether for 1 hour and the solid was removed by filtration. The ethereal solution was concentrated to dryness and the resulting oil was flash chromatographed (silica gel, ethyl acetate:hexanes 1:15 and 1:10) to afford 2.22 g of the title compound (61% yield) as a foam when dried at vacuum.

δ ($^1$H, CDCl$_3$): 9.73 (s, 1H, CHO), 7.5–7.2 (m, 10H, 2Ph), 6.98 (s, 1H, CHPh$_2$), 6.04 (dd, 1H, H2, J=1.5 and 3.6 Hz), 4.45 (dd, 1H, H1', J=2.7 and 8.7 Hz), 4.06 (d, 1H, 8aCH$_2$, J=9 Hz), 3.70 (d, 1H, 8aCH$_2$, J=9 Hz), 3.52 (s, 3H, OCH$_3$), 3.5–3.3 (m, 2H, H4'+H5'), 2.7–2.5 (m, 3H, H1+H2'), 2.24 (m, 1H, CH(CH$_3$)$_2$).

INTERMEDIATE 78

[1R-(1α, 3aβ, 4β, 4aβ, 7β, 7aα, 8aβ)] 8a-[(1S,7R, 9R)-2,8-Dioxa-9-methyl-bicyclo [3,4,0]-non-4-ene-7-yl-oxymethyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a vigorous stirred solution of Intermediate 77 (260 mg) and diethyl diazomethyl phosphonate (110 mg) in dry tetrahydrofuran was added slowly at 0° C. under nitrogen a slurry of potassium tertbutoxide (112 mg) in dry tetrahydrofuran (1 ml) (gas evolution was observed immediately). After 10 minutes the mixture was diluted with dichloromethane (100 ml) and washed with 1 N hydrochloric acid (2×100 ml) saturated sodium bicarbonate (2×100 ml) brine (2×100 ml) and dried over magnesium sulfate. Removal of the solvent gave an oil which was flash chromatographed (silica gel, ethyl acetate:hexane v/v 1:15 and 1:12) to afford 200 mg of the title compound (77% yield) as a foam.

δ ($^1$H, CDCl$_3$): 9.75 (s, 1H, CHO), 7.5–7.2 (m, 10H, 2Ph), 6.99 (s, 1H, CHPh$_2$), 6.05 (dd, 1H, H2, J=1.2 and 3.3 Hz), 5.45 (m, 1H, H4'), 4.65 (m, 2H, H3'), 4.25–4.15(m, 2H, H7'+H1'), 4.07 (d, 1H, 8aCH$_2$, J=9 Hz), 3.71 (d, 1H, 8aCH$_2$, J=9 Hz), 3.19 (dq, 1H, H9', J=6 and 8.4 Hz), 2.77 (t, 1H, H1, J=3.9 Hz).

INTERMEDIATE 79

[1R-(1α, 3aβ, 4β, 4aβ, 7β, 7aα, 8aβ)] 8a-[(1S,4R, 7R,9R)-2,8-Dioxa-4-hydroxy-9-methyl-cis-bicyclo [3,4,0]-non-7-yl-oxymethyl]-4-hydroxymethyl-4,4a, 5,6,7,7a,8,8a-octahydro-7-methyl-3-(1-methyl-ethyl)-1,4-methano-s-indacene-3a(1H)-carboxylic acid, diphenylmethyl ester To a solution of Intermediate 78 (620 mg) in anhydrous tetrahydrofuran (5 ml) was added 9-borabicyclo [3.3.1] nonane (0.5 M solution in tetrahydrofuran, 6 ml) under nitrogen. The mixture was heated to 50° C. for 1 hour. An additional volume of 9-borabicyclo[3.3.1]nonane solution was added at 50° C. over a period of 3 hours to complete the reaction and it was allowed to stir at room temperature for 1 hour. Ethyl alcohol (2 ml) was added carefully (gas evolution) and the solution stirred for 1 hour. Then 3 N sodium hydroxide (5 ml) and hydrogen peroxide (35% v/v, 5 ml) were added consecutively at 0° C. and the mixture stirred at room temperature at 0° C. and at 70° C. overnight. The resulting solution was cooled to room temperature and concentrated to half the volume, then it was diluted with 1 N hydrochloric acid (100 ml) and extracted twice with ethyl acetate (2×100 ml). The organic layer was washed with 1 N hydrochloric acid (100 ml) sodium bicarbonate (2×100 ml) and brine (100 ml), dried over sodium sulfate and concentrated to dryness to give a syrup which was flash chromatographed (acetone:hexane 1:10 and 1:5) to obtain 475 mg of the title compound (74% yield) as a foam.

δ ($^1$H, CDCl$_3$): 7.5–7.2 (m, 10H, 2Ph), 7.04 (s, 1H, CHPh$_2$), 5.90 (dd, 1H, H2, J=1.5 and 3.6 Hz), 4.75 (d, 1H, HOCH$_2$, J=10.5 Hz), 4.62 (dd, 1H, H7', J=2.7 and 5.1 Hz), 4.27 (m, 1H, H4'), 4.16 (d, 1H, 8aCH$_2$, J=9 Hz), 4.09 (dd, 1H, H3', J=6 and 9.6 Hz), 3.91 (t, 1H, H3', J=6.9 Hz), 3.7–3.5 (m, 3H, 8aCH$_2$+H1'+H9'), 3.35 (d, 1H, HOCH$_2$, J=11.5 Hz), 3.22 (dd, 1H, HOCH$_2$, J=11.1 and 12 Hz), 2.57 (t, 1H, H1, J=4.5 Hz), 2.48 (m, 1H, H5'), 2.30 (m, 1H, CH(CH$_3$)$_2$).

INTERMEDIATE 80

[1R-(1α, 3aβ, 4β, 4aβ, 7β, 7aα, 8aβ)] 8a-[(1S,7R, 9R)-2,8-Dioxa-9-bicyclo[3,4,0]-non-4-ene-7-yl-oxymethyl]-4-[tert-butyl-dimethylsilyl-oxymethyl]-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 78 (200 mg) in tetrahydrofuran (5 ml) were added solid sodium borohydride (18.9 mg) and water (1 ml) and the mixture was stirred at 0° C. for 30 minutes and then for 1 hour at room temperature. The mixture was quenched carefully by adding water (2 ml) at 0° C. and partioned between ethyl acetate (100 ml) and water (100 ml). The organic layer was dried over magnesium sulfate and concentrated to dryness to give a syrup which was dissolved in dry dimethylformamide (5 ml) and treated at room temperature under nitrogen with imidazol (204 mg) and tert-butyl-dimethyl-silyl chloride (316 mg) overnight. The solution was poured into 100 ml of a mixture of 1 N ammonium chloride and ethyl acetate (v/v 1:1) and stirred for 1 hour. The organic layer was washed with 1 N ammonium chloride (100 ml) and brine (100 ml), dried over magnesium sulfate and concentrated to dryness to give a foam which was flash chromatographed (silica gel, ethyl acetate:hexanes v/v 1:20) to afford 215 mg of the title compound (92% overall yield).

δ ($^1$H, CDCl$_3$): 7.5–7.2 (m, 10H, 2Ph), 6.94 (s, 1H, CHPh$_2$), 5.96 (dd, 1H, H2, J=1.2 and 3.6 Hz), 5.54 (m, 1H, H4'), 4.65 (m, 2H, H3'), 4.25–4.15 (m, 3H, SiOCH$_2$+H7'+H1'), 4.1 (d, 1H, 8aCH$_2$, J=9.3 Hz), 3.69 (d, 1H, SiOCH$_2$, J=9 Hz), 3.30 (d, 1H, 8aCH$_2$, J=9.3 Hz), 3.19 (dq, 1H, H9', J=6 and 9 Hz), 2.68 (dd, 1H, H6', J=2 and 13.2 Hz), 2.57 (t, 1H, H1, J=4.2), 2.3 (m, 2H, CH(CH$_3$)$_2$+H6'), −0.017 and −0.031 (2s, 6H, (CH$_3$)$_2$Si).

INTERMEDIATE 81

[1R-(1α, 3aβ, 4β, 4aβ, 7β, 7aα, 8aβ)] 8a-[(1S,4R, 7R,9R)-2,8-Dioxa-4-hydroxy-9-methyl-cis-bicyclo [3,4,0]-non-7-yl-oxymethyl]-4-[tert-butyl-dimethylsilyl-oxymethyl]-4,4a,5,6,7,7a,8,8a-octahydro-7-methyl-3-(1-methylethyl)-1,4-methano-s-indacene-3a(1H)-carboxylic, acid, diphenylmethyl ester To a solution of Intermediate 80 (700 mg) in dry tetrahydrofuran (5 ml) was added 9-borabicyclo[3.3.1]nonane (0.5 M solution in tetrahydrofuran, 6 ml) under nitrogen. The mixture was heated to 50° C. for 1 hour. An additional volume of 9-borabicyclo[3.3.1]nonane solution was added at 50° C. over a period of 3 hours to complete the reaction, then it was cooled to room temperature and ethyl alcohol (2 ml) was added carefully. After 1 hour 3 N sodium hydroxide (5 ml) and hydrogen peroxide (35% v/V, 5 ml) were added consecutively at 0° C. and the mixture stirred at room temperature for 1 hour and at 70° C. overnight. The solution was cooled to room temperature and concentrated to half the volume, then it was diluted with 1 N hydrochloric acid (100 ml) and extracted twice with ethyl acetate (2×100 ml). The organic layer was washed with 1 N hydrochloric acid (100 ml), saturated sodium bicarbonate (100 ml) and brine (100 ml), dried over magnesium sulfate and concentrated to dryness to give a syrup which was flash chromatographed (acetone:hexanes 1:20 and 1:15) to afford 550 mg (77% yield) of the title compound as a white foam.

δ ($^1$H, CDCl$_3$): 7.5–7.2 (m, 10H, 2Ph), 6.94 (s, 1H, CHPh$_2$), 5.95 (m, 1H, H2), 4.57 (dd, 1H, H7', J=3 and 5.1 Hz), 4.30–4.15 (m, 2H, H4'+CH$_2$OSi), 4.10–3.95 (m, 2H, H3'+8aCH$_2$), 3.87 (t, 1H, H3', J=6.9 Hz), 3.7–3.5 (m, 3H, H1'+8aCH$_2$+H9'), 3.30 (d, 1H, CH$_2$OSi, J=9.3 Hz), 2.53 (t, 1H, H1, J=3.9 Hz), 2.46 (m, 1H, H5'), 2.32 (m, 1H, CH(CH$_3$)$_2$), −0.016 and −0.029 (2s, 6H, (CH$_3$)$_2$Si).

INTERMEDIATE 82

[1R-(1α, 3aβ, 4β, 4aβ, 7β, 7aα, 8aβ)] 8a-[(1S,4R, 7R,9R)-2,8-Dioxa-4-methoxy-9-methyl-cis-bicyclo [3,4,0]-non-7-yl-oxymethyl]-4-formyl-4,4a,5,6,7,7a, 8,8a-octahydro-7-methyl-3-(1-methylethyl)-1,4-methano-s-indacene-3a(1H)-carboxylic acid, diphenylmethyl ester To a solution of Intermediate 81 (537 mg) in anhydrous tetrahydrofuran (5 ml) was added sodium hydridre (75 mg) in small portions at 0° C. under nitrogen. After stirring for 10 minutes methyl iodide (374 µl) was added and the mixture kept at room temperature until completion of the reaction. The mixture was quenched by adding water (100 ml) and then it was extracted with ethyl acetate (100 ml). The organic layer was washed with brine (100 ml) and concentrated to dryness to give a foam which was dissolved in anhydrous THF (5 ml) and treated with tetrabutylammonium fluoride (1.1 M solution in tetrahydrofuran, 2 ml) at 40° C. for 24 hours. The resulting solution was concentrated to dryness and the residue dissolved in AcOEt and washed with water (2×100 ml), dried over magnesium sulfate and concentrated to give a syrup which was dissolved in dry dichloromethane 85 ml). Pyridinium chlorochromate (215 mg) was added and the mixture stirred at room temperature until completion of the reaction. The suspension was poured onto a well stirred mixture of dichloromethane and sodium metabisulfite (10% aqueous solution). The organic layer was washed with 1 N hydrochloric acid (200 ml) and 1 N sodium hydroxide (200 ml), dried over magnesium sulfate and concentrated to dryness to give an oil which was flash chromatographed on silica gel (ethyl acetate:hexane 1:15, 1:10 and 1:8) to obtain 255 mg of the title compound as an oil (57% overall yield).

δ ($^1$H, CDCl$_3$): 9.74 (s, 1H, CHO), 7.5–7.2 (m, 10H, 2Ph), 6.99 (s, 1H, CHPh$_2$), 6.04 (dd, 1H, H2, J=1.2 and 3.6 Hz), 4.60 (m, 1H, H7'), 4.10–3.95 (m, 2H, H4'+8aCH$_2$), 3.90–3.65 (m, 3H, H3'+H1'), 3.65–3.55 (m, 2H, 8aCH$_2$+H9'), 3.35 (s, 3H, OCH$_3$), 2.73 (t, 1H, H1, J=3.6 Hz), 2.54 (m, 1H, H5'), 22.4 (m, 1H, CH(CH$_3$)$_2$).

INTERMEDIATE 83

[1R-(1α, 3aβ, 4β, 4aβ, 7β, 7aα, 8aβ)] 8a-[(6-Deoxy-4-methyl-β-D-altropyranosyloxy)methyl]-4-(1,3-dioxolan-2-yl)-4,4a,5,6,7,7a,8,8a-octahydro-7-methyl-3-(1-methylethyl)-1,4methano-s-indacene-3a (1H)-carboxylic acid, diphenylmethyl ester A solution of Intermediate 48 (9.7 mmol) in dry methanol (40 ml) was treated with ethylene glycol (110 ml), trimethylorthoformate (3.25 ml) and a catalytic amount of p-toluenesulfonic acid. The mixture was heated at 40° C. for 3 hours. After cooling, the mixture was poured into ethyl acetate:aqueous sodium hydrogen carbonate (1:1; 500 ml) and the water layer was thoroughly extracted with ethyl acetate. The combined organic layers were washed with water and brine, and dried. After removal of the solvent, the residue was purified by flash chromatography using hexane-:ethyl acetate (6:1) as eluent to give the title compound (6.1 g).

δ (1H, CDCl$_3$): 7.43 and 7.30 (m,m, 4H, 6H, 2xPh), 6.94 (s, 1H, CHPh$_2$), 5.83 (dd, 1H, H-2, J=1.2 and 3.6 Hz), 5.07 (s, 1H, 4-CH), 4.63 (d, 1H, H-1', J=1.5 Hz), 4.20 (t, 1H, H-3', J=3.3 Hz), 4.07 (d, 1H, 8a-CHa, J=9.3 Hz), 3.84 (m, 6H, H-2', 8a-CHb and OCH$_2$CH$_2$O), 3.71 (m, 1H, H-5'), 3.42 (s, 3H, OCH$_3$), 3.21 (dd, 1H, H4', J=3 and 9 Hz), 2.63 (m, 1H, CH(CH$_3$)$_2$), 2.54 (t, 1H, H-1, J=3.9 Hz).

INTERMEDIATE 84

[1R-(1a, 3ab, 4b, 4ab, 7b, 7aa, 8ab)] 8a-[2-O-Benzoyl-6-deoxy-4-O-methyl-β-D-altropyranosyloxy) methyl]-4-[1,3-dioxolan-2-yl]]-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 83 (12.12 g) and dimethylaminopyridine (6.3 g) in dry dichloromethane (155 ml) was added dropwise at −20° C. benzoyl chloride (1.40 ml) in 50 ml of dry dichloromethane under nitrogen. After stirring for 2 hours, the mixture was allowed to reach the room temperature and the solution was washed with 0.1 N hydrochloric acid (500 ml), saturated sodium bicarbonate (500 ml) and brine (500 ml). Elimination of the solvent gave a residue which was flash chromatographed (silica gel, ethyl acetate-:hexanes v/v 1:4) to obtain 5.89 g of the title compound (42%) as a white foam.

δ ($^1$H, CDCl$_3$): 8.14–8.05, 7.6–7.2 (2m, 15H, 3Ph), 6.91 (s, 1H, CHPh$_2$), 5.70 (bd, 1H, H2, J=2.1 Hz), 5.34 (dd, 1H, H2', J=2.1 and 5.1 Hz), 5.01 (s, 1H, OCHO), 4.82 (d, 1H, H1', J=1.8 Hz), 4.26 (m, 1H, H3'), 3.98 (d, 1H, 8aCH$_2$, J=9.3 Hz), 3.92–3.74 (m, 5H, H5'+OCH$_2$CH$_2$O), 3.72 (d, 1H, 8aCH$_2$, J=9.3 Hz), 3.42 (s, 3H, OCH$_3$), 3.23 (dd, 1H, H4', J=3.3 and 8.1 Hz), 2.57 (m, 1H, CH(CH$_3$)$_2$), 2.44–2.38 (m, 2H, OH+H1).

INTERMEDIATE 85

[1R-(1α, 3aβ, 4β, 4aβ, 7β, 7aα, 8aβ)] 8a-[(2-O-Benzoyl-3,6-dideoxy-4-O-methyl-3-oxo-β-D-allopyranosyloxy)methyl]-4-[1,3-dioxolan-2-yl]-4,4a,5,6,7,7a,8,8a-octahydro-7-methyl-3-(1-methylethyl)-1,4-methano-s-indacene-3a(1H)-carboxylic acid, diphenylmethyl ester To a solution of trifluoroacetic anhydride (0.45 ml) in dry dichloromethane (5 ml) was added DMSO (0.23 ml) over a period of 10 minutes at −60° C. under nitrogen atmosphere. To the suspension thus formed was added a solution of Intermediate 84 (1.2 g) in dry dichloromethane (5 ml) and the mixture stirred at −60° C. for 1 hour. Triethylamine (1.24 ml) was added dropwise and the temperature was allowed to reach −20° C., then water (2 ml) was added to the resulting yellow solution and the mixture was stirred at room temperature for 1 hour. Dichloromethane (200 ml) and water (250 ml) were added and the two phases partioned. The organic layer was dried over magnesium sulfate and concentrated to dryness to give a crude which was dissolved in dichloromethane (10 ml) and treated with triethylamine (2 ml) overnight. Elimination of the solvent gave a oil which was flash chromatographed (silica gel, ethyl acetate:hexanes v/v 1:15 and 1:10) to afford 1.1 g of the title compound (92% yield) as a foam when dried at vacuum.

δ ($^1$H, CDCl$_3$): 8.2–8.0, 7.6–7.2 (2m, 15H, 3Ph), 6.90 (s, 1H, CHPh$_2$), 5.57 (dd, 1H, H2, J=1.2 and 3.6 Hz), 5.37 (dd, 1H, H2', J=1.5 and 8.1 Hz), 5.05 (s, 1H, OCHO), 4.52 (d, 1H, H1', J=8.1 Hz), 4.08 (d, 1H, 8aCH$_2$, J=8.7 Hz), 3.9–3.7 (m, 5H, OCH$_2$CH$_2$O+8aCH$_2$), 3.6–3.4 (m, 5H, H4'+OCH$_3$+ H5'), 2.62 (m, 1H, CH(CH$_3$)$_2$), 2.43 (t, 1H, H1, J=3.9 Hz).

INTERMEDIATE 86

[1R-(1α, 3aβ, 4β, 4aβ, 7β, 7aα, 8aβ)] 8a-[(2,3,6-Trideoxy-4-O-methyl-3-oxo-β-D-allopyranosyloxy) methyl]-4-[1,3-dioxolan-2-yl]-4,4a,5,6,7,7a,8,8a-octahydro-7-methyl-3-(1-methylethyl)-1,4-methano-s-indacene-3a(1H)-carboxylic acid, diphenylmethyl ester To a well degassed solution (Ar, 15 minutes) of tributyltin hydride (263 μl) in dry toluene (10 ml) was added via syringe a solution of Intermediate 85 (250 mg) and a,a'-azoisobutyronitrile (16 mg) in dry toluene (5 ml) at 90° C. over a period of 1 hour. The heating was continued until completion of the reaction, then it was cooled to room temperature. Water (5 ml) and potassium fluoride (100 mg) were added and the mixture stirred overnight. The crude obtained after elimination of the solvents was stirred with diethyl ether for 1 hour and the solid was removed by filtration. The ethereal solution was concentrated to dryness and the resulting oil was flash chromatographed (silica gel, ethyl acetate:hexanes 1:15 and 1:10) to afford 168 mg of the title compound (80% yield) as a foam when dried at vacuum.

δ ($^1$H, CDCl$_3$): 7.6–7.1 (m, 10H, 2Ph), 6.92 (s, 1H, CHPh$_2$), 5.80 (dd, 1H, H2, J=0.9 and 3.6 Hz), 5.08 (s, 1H, OCHO), 4.44 (dd, 1H, H1', J=2.7 and 8.7 Hz), 4.05 (d, 1H, 8aCH$_2$, J=9.3 Hz), 3.9–3.7 (m, 5H, OCH$_2$CH$_2$O+8aCH$_2$), 3.50–3.30 (mn, 2H, H5'+H4'), 2.5–2.1 (m, 3H, H2'+CH (CH$_3$)$_2$), 2.50 (t, 1H, H1, J=4.5 Hz).

INTERMEDIATE 87

[1R-(1a, 3ab, 4b, 4ab, 7b, 7aa, 8ab)] 8a-[(1S,7R, 9R)-2,8-Dioxa-9-methyl-bicyclo [3,4,0]-non-4-ene-7-yl-oxymethyl]-4-[1,3-dioxolan-2-yl]-4,4a,5,6,7,7a, 8,8a-octahydro-7-methyl-3-(1-methylethyl)-1,4-methano-s-indacene-3a(1H)-carboxylic acid, diphenylmethyl ester To a vigorous stirred solution of Intermediate 86 (160 mg) and diethyl-diazomethyl-phosphonate (63 mg) in dry tetrahydrofuran was added slowly at 0° C. under nitrogen a slurry of potassium tert-butoxide (100 mg) in dry tetrahydrofuran (2.3 ml) (gas evolution was observed immediately). After 10 minutes the mixture was diluted with dichloromethane (100 ml) and washed with 1 N hydrochloric acid (2×100 ml), saturated sodium bicarbonate (2×100 ml), brine (2×100 ml) and subsequently dried over magnesium sulfate. Removal of the solvent gave a oil which was flash chromatographed (silica gel, ethyl acetate:hexane v/v 1:15 and 1:12) to afford 110 mg of the title compound (70% yield) as a foam.

δ ($^1$H, CDCl$_3$): 7.5–7.2 (m, 10H, 2Ph), 6.94 (s, 1H, CHPh$_2$), 5.83 (dd, 1H, H2, J=1.2 and 3.3 Hz), 5.53 (m, 1H, H4'), 5.06 (s, 1H, OCHO), 4.65 (m, 2H, H3'), 4.25–4.10 (m, 2H, H7'+H1'), 4.05 (d, 1H, 8aCH$_2$, J=9.3 Hz), 3.90–3.70 (m, 5H, OCH$_2$CH$_2$O+8aCH$_2$), 3.18 (dq, 1H, H9', J=6 and 8.7 Hz), 2.75–2.50 (m, 3H, H6'+CH(CH$_3$)$_2$+H1).

INTERMEDIATE 88

[1R-(1α, 3aβ, 4β, 4aβ, 7β, 7aα, 8aβ)] 8a-(4-O-Allyl-3,6-dideoxy-3-iodo-β-D-mannopyranosyloxy) methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 53 (GM 2008) (103 mg), triphenylphosphine (197 mg) and imidazole (51 mg) in dry tetrahydrofuran (5 ml) was treated with iodine (95 mg) portionwise. After stirring for 1 hour at room temperature the solution was refluxed until all the starting material was consumed tlc analysis hexane:ethyl acetate 4:1). The reaction mixture was cooled and partitioned between ethyl acetate (50 ml) and 1 N aqueous hydrochloric acid (30 ml). The organic layer was washed successively with 1 N aqueous hydrochloric acid, water, aqueous sodium metabisulfite solution, water and brine, then dried ($Na_2SO_4$), filtered and concentrated. The residue was flash chromatographed on silica gel eluting with hexane:ethyl acetate (9:1) to give the title compound (70 mg).

δ ($^1$H, $CDCl_3$): 9.73 (s, 1H, CHO), 7.46–7.22 (m, 10H, 2Ph), 6.98 (s, 1H, $CHPh_2$), 6.03 (dd, 1H, H-2, J=1.5 and 3.6 Hz), 6.02–5.9 (m, 1H, O—C—CH=C), 5.35–5.15 (m, 2H, O—C—C=$CH_2$), 4.4–4.32 (m, 1H, O—CHa—C=C), 4.35 (d, 1H, H-1', J=0.6 Hz), 4.18–3.96 (m, 4H, O—CHb-C=C, H-2', H-3', 8aCHa), 3.75 (d, 1H, 8a-CHb, J=9 Hz), 3.45 (dd, 1H, H-4', J=9 and 10.2 Hz), 3.34 (dq, 1H, H-5', J=5.7 and 8.7 Hz), 2.72 (t, 1H, H-1, J=3.9 Hz).

INTERMEDIATES 89a and 89b a) [1R-(1α, 3aβ, 4β, 4aβ, 7β, 7aα, 8aβ)] 8a-[(1S, 4S,6S,7R,9R)-2,8-Dioxa-4,9-dimethyl-6-hydroxy-cis-bicyclo[3.4.0]-non-7-yl-oxy-methyl]-4-formyl-4, 4a,5,6,7,7a,8,8a-octahydro-7-methyl-3-(1-methylethyl)-1,4-methano-s-indacene-3a(1H)-carboxylic acid, diphenylmethyl ester b) [1R-(1a, 3ab, 4b, 4ab, 7b, 7aa, 8ab)] 8a-[(1S,4R, 6S,7R,9R)-2,8-Dioxa-4,9-dimethyl-6-hydroxy-cis-bicyclo[3.4.0]-non-7-yl-oxy-methyl]-4-formyl-4,4a, 5,6,7,7a,8,8a-octahydro-7-methyl-3-(1-methylethyl)-1,4-methano-s-indacene-3a(1H)-carboxylic acid, diphenylmethyl ester A solution of intermediate 88 (80 mg) in dry toluene (2 ml) was degassed with an argon stream for 60 minutes and then heated to reflux. Tributyltin hydride (41 μl) was added and reflux continued for 15 minutes. The solvent was removed in vacuo and the residue taken up in diethyl ether (50 ml) and washed several times with a saturated aqueous solution of potassium fluoride until no more precipitation of tributyltin fluoride was observed. The organic layer was dried and evaporated to give a residue which was purified by preparative TLC (silica gel, dichloromethane:ethyl acetate 95:5) to afford title compound (a) Intermediate 89a (35 mg, Rf=0.4 dichloromethane:ethyl acetate 9:1) and title compound (b) Intermediate 89b (24 mg, Rf=0.3 dichloromethane:ethyl acetate 9:1).

INTERMEDIATE 89a

δ ($^1$H, $CDCl_3$): 9.73 (s, 1H, CHO), 7.46–7.22 (m, 10H, 2Ph), 6.99 (s, 1H, $CHPh_2$), 6.05 (dd, 1H, H-2, J=1.2 and 3.3 Hz), 4.63 (d, 1H, H-7', J=3.3 Hz), 4.02 (d, 1H, 8aCHa, J=9 Hz), 3.86 (dd, 1H, Ha-3', J=6.6 and 8.7 Hz), 3.83–3.6 (m, 4H, H-6', H-1', H-9' and 8a-CHb),3.52 (dd, 1H, Hb-3', J=5.7 and 8.7 Hz), 2.69 (t, 1H, H-1, J=3.9 Hz).

INTERMEDIATE 89b

δ ($^1$H, $CDCl_3$): 9.74 (s, 1H, CHO), 7.45–7.22 (m, 10H, 2Ph), 6.99 (s, 1H, $CHPh_2$), 6.06 (dd, 1H, H-2, J=1.2 and 3.6 Hz), 4.48 (d, 1H, H-7', J=2.1 Hz), 4.1–4.0 (m, 2H, 8a-CHa and Ha-3'), 3.85 (dd, 1H, H-1', J=7.8 and 9 Hz), 3.76–3.68 (m, 2H, 8a-CHb and H-6'), 3.46–3.3 (m, 2H, H-9' and Hb-3'), 2.73 (t, 1H, H-1, J=3.9 Hz).

INTERMEDIATE 90

[1R-(1α, 3aβ, 4β, 4aβ, 7β, 7aα, 8aβ)] 8a-[(6-Deoxy-β-D-altropyranosyloxy)methyl]-4-formyl-4, 4a,5,6,7,7a,8,8a-octahydro-7-methyl-3-(1-methylethyl)-1,4-methano-s-indacene-3a(1H)-carboxylic acid, diphenylmethyl ester To a solution of 4'-demethylsordarin (10 g) in methanol (20 ml) was added dropwise at room temperature a solution of diphenyldiazomethane (90 ml) in methylene chloride, and the mixture was stirred for 6 hours. The solvent was evaporated to dryness and the residue chromatographed in a silica gel flash column with n-hexane:ethyl acetate (3:1) as eluent to give the title compound (12.6 g) as a pale yellow foam:

δ ($^1$H, $CDCl_3$): 9.73 (s, 1H, CHO), 6.98 (s, 1H, $CHPh_2$), 6.05 (dd, 1H, H-2, J=1.5 and 3.6 Hz), 4.65 (d, 1H, H-1', J=1.5 Hz), 4.09, 3.76 (2d, 2H, 8a-$CH_2$, J=9 Hz), 4.01 (m, 1H, H-2'), 3.84 (m, 1H, H-3'), 3.75 (m, 1H, H-5'), 3.69 (m, 1H, H-4'), 2.73 (t, 1H, H-1, J=4.2 Hz).

INTERMEDIATE 91

[1R-(1α, 3aβ, 4β, 4aβ, 7β, 7aα, 8aβ)] 8a-[(6-Deoxy-3,4-O-isopropylidene-β-D-altropyranosyloxy)methyl]-4-formyl-4,4a,5,6,7,7a,8, 8a-octahydro-7-methyl-3-(1-methylethyl)-(1H)-1,4-methano-s-indacene-3a(1H)-carboxylic acid, diphenylmethyl ester To a solution of Intermediate 90 (650 mg) in 15 ml of 2,2-dimethoxypropane:acetone (1:2) was added p-toluensulphonic acid (10 mg). The solution was stirred at room temperature for 1.5 hours, then potassium carbonate (1.0 g) was added, the stirring continued for 30 minutes and the solvent evaporated to dryness. The crude mixture was partitioned between ethyl acetate (50 ml) and water (25 ml), the aqueous phase was extracted with ethyl acetate (2×50 ml), the organic phase was washed with brine, dried over magnesium sulphate and evaporated to dryness. The residue was flash chromatographed on silica gel eluting with ethyl acetate:hexane (1:3) to give the title compound (600 mg) as a white foam.

δ ($^1$H, $CDCl_3$): 9.73 (s, 1H, CHO), 7.45–7.24 (m, 10H, 2Ph), 6.98 (s, 1H, $CHPh_2$), 6.06 (dd, 1H, H-2, J=1.5 and 3.3 Hz), 4.57 (d, 1H, H-1', J=3.0 Hz), 4.30 (dd, 1H, H-3', J=3.6 and 5.7 Hz), 4.07 (d, 1H, 8a$CH_2$, J=9.0 Hz), 3.95–3.93 (m, 1H, H-2'), 3.85 (dd, 1H, H-4', J=5.7 and 9.3 Hz), 3.75 (d, 1H, 8a$CH_2$, J=9.0 Hz), 3.44 (dq, 1H, H-5', $J_d$=9.3 Hz, $J_q$=6.3 Hz), 2.73 (t, 1H, H-1, J=3.6 Hz).

INTERMEDIATE 92

[1R-(1α, 3aβ, 4β, 4aβ, 7β, 7aα, 8aβ)] 8a-[(6-Deoxy-3,4-O-isopropylidene-2-O-(methylthio) thiocarbonyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester Intermediate 91 (100 mg) and imidazole (1 mg) were dissolved in dry tetrahydrofuran (4 ml) under nitrogen atmosphere. Sodium hydride (5 mg) was added and the suspension was stirred at room temperature for 0.5 hours. Carbon disulfide (2.7 ml) was added, the stirring continued for 20 minutes and methyl iodide (18 ml) was added. After 2 hours the reaction was stopped by addition of 1 N ammonium chloride (20 ml). The mixture was extracted with ethyl acetate (3×25 ml), the organic phase was washed with brine, dried over magnesium sulphate and the solvent evaporated to dryness. The residue was purified in a flash chromatography column on silica gel eluting with ethyl acetate:hexane (1:9) to give the title compound (110 mg).

δ ($^1$H, CDCl$_3$): 9.71 (s, 1H, CHO), 7.44–7.25 (m, 10H, 2Ph), 6.96 (s, 1H, CHPh$_2$), 6.01 (dd, 1H, H-2, J=1.2 and 3.6 Hz), 6.90 (dd, 1H, H-2', J=2.4 and 5.4 Hz), 4.85 (d, 1H, H-1', J=2.4 Hz), 4.53 (dd, 1H, H-3', J=5.4 and 6.3 Hz), 4.00 (dd, 1H, H4', J=6.3 and 8.7 Hz), 3.93 (d, 1H, 8aCH$_2$, J=9.3 Hz), 3.65 (dq, 1H, H-5', J$_d$=8.7, J$_q$=6.3 Hz), 2.68 (t, 1H, H-1, J=3.9 Hz), 2.59 (s, 3H, CH$_3$S).

INTERMEDIATE 93

[1R-(1α, 3aβ, 4β, 4aβ, 7β, 7aα, 8aβ)] 8a-[(2,6-Dideoxy-3,4-O-isopropylidene-β-D-allopyranosyloxy)methyl]-4-formyl4,4a,5,6,7,7a,8,8a-octahydro-7-methyl-3-(1-methylethyl)-1,4-methano-s-indacene-3a(1H)-carboxylic acid, diphenylmethyl ester Intermediate 92 (95 mg) was dissolved in dry toluene (5 ml) under nitrogen atmosphere and heated at 110° C. A solution of tributyltin hydride (64 ml) in dry toluene (5 ml) was added dropwise over 1.5 hours with stirring. The heating was continued for another 1:5 hours, methanol (2 ml) was added and the solvent evaporated to dryness. Flash chromatography of the residue on silica gel eluting with ethyl acetate:hexane (1:9) gave the title compound (42 mg).

δ ($^1$H, CDCl$_3$): 9.73 (s, 1H, CHO), 7.44–7.25 (m, 10H, 2Ph), 6.98 (1H, s, CHPh$_2$), 6.05 (dd, 1H, H-2, J=1.2 and 3.3 Hz), 4.54 (dd, 1H, H-1', J=2.7 and 9.3 Hz), 4.39 (dt, 1H, H-3', J$_d$=2.7 Hz, J$_t$=3.6 Hz), 4.04 (d, 1H, 8aCH$_2$, J=9.0 Hz),3.67 (d, 1H, 8aCH$_2$, J=9.0 Hz), 3.65 (dd, 1H, H-4', J=3.6 and 8.7 Hz), 3.44 (dq, 1H, H-5', J$_d$=6.3 Hz, J$_q$=8.7 Hz), 2.75 (t, 1H, J=3.9 Hz).

INTERMEDIATE 94

[1R-(1α, 3aβ, 4β, 4aβ, 7β, 7aα, 8aβ)] 8a-[(2,6-Dideoxy-β-D-allopyranosyloxy)methyl]-4-formyl-4, 4a,5,6,7,7a,8,8a-octahydro-7-methyl-3-(1-methylethyl)-1,4-methano-s-indacene-3a(1H)-carboxylic acid, diphenylmethyl ester To a solution of Intermediate 93 (1.5 g) in a mixture of tetrahydrofuran (30 ml) and methanol (15 ml) was added dropwise at room temperature a 1 N solution of hydrochloric acid (15 ml) with vigorous stirring. Once the reaction was concluded (TLC control), saturated sodium bicarbonate (50 ml) and ethyl acetate (200 ml) were added and the mixture partitioned. The organic layer was washed with water (2×100 ml) and dried over magnesium sulfate. Elimination of the solvent gave a residue which was flash chromatographed over silica gel eluting with hexane:ethyl acetate (5:1) and (2:1) to give the title compound (1.1 g) as a white foam.

δ ($^1$H, CDCl$_3$): 9.73 (s, 1H, CHO), 7.5–7.2 (m, 10H, 2Ph), 6.99 (s, 1H, CHPh$_2$), 6.05 (dd, 1H, H-2, J=1.2 and 3.3 Hz), 4.64 (dd, 1H, H-1', J=2.1 and 9.6 Hz), 4.11 (m, 1H, H-3'), 4.06 (d, 1H, 8aCH$_2$, J$_{AB}$=9.3 Hz), 3.70 (m, 2H, H-5' and 8aCH$_2$), 3.34 (m, 1H, H-4'), 2.75 (t, 1H, H-1, J=3.6 Hz).

INTERMEDIATE 95

[1R-(1α, 3aβ, 4β, 4aβ, 7β, 7aα, 8aβ)] 8a-[(2,3,6-Trideoxy-3-iodo-β-D-glucopyranosyloxy)methyl]-4-formyl-4,4a,5,6,7,7a,8,8a-octahydro-7-methyl-3-(1-methylethyl)-1,4-methano-s-indacene-3a(1H) carboxylic acid, diphenylmethyl ester Intermediate 94 (2.0 g), triphenylphosphine (3.4 g) and imidazole (186 mg) were refluxed in toluene (50 ml) with stirring and then treated with iodine (610 mg), added in small portions. Refluxing was continued for 4 hours. The reaction mixture was cooled, decanted into excess aqueous sodium hydrogen carbonate and sodium thiosulfate in a separating funnel. The mixture was shaken until the iodine was consumed. The toluene phase was washed with water, dried over magnesium sulfate and concentrated. The residue was purified by flash column chromatography eluting with hexane:ethyl acetate (15:1) and (5:1) to give the title compound (1.65 g).

δ ($^1$H, CDCl$_3$): 9.73 (s, 1H, CHO), 7.26–7.44 (m, 10H, 2Ph), 6.98 (s, 1H, CHPh$_2$), 6.04 (dd, 1H, H-2, J=1.2 and 3.3 Hz), 4.25 (dd, 1H, H-1', J=1.8 and 9.3 Hz), 4.08 (m, 1H, H-4'), 3.67 and 4.01 (2d, 2H, 8aCH$_2$, J=9 Hz), 3.40 (m, 1H, H-3'), 3.32 (m 1H, H-5'), 2.74 (t, 1H, H-1, J=4.2 Hz), 2.32 and 2.53 (2m, 2H, 2H-2').

INTERMEDIATE 96

[1R-(1a, 3ab, 4b, 4ab, 7b, 7aa, 8ab)] 8a-(((2,3,6-Trideoxy-3-ethylamino-3-N,4-O-carbonyl-β-D-allopyranosyl)oxy)methyl)-4-formyl-4,4a,5,6,7,7a,8,8a-octahydro-7-methyl-3-(1-methylethyl)-1,4-methano-s-indacene-3a(1H)-carboxylic acid, diphenylmethyl ester A solution of intermediate 95 (200 mg) in dry tetrahydrofuran (15 ml) was treated with sodium hydride (24 mg, 1.0 mmol). After 15 minutes, ethyl isocyanate (0.04 ml) was added, and the reaction mixture was stirred at reflux for 6 hours. After being quenched with water (3 ml), the mixture was extracted with ethyl acetate (3×5 ml), the combined organic solutions were treated with brine (1×5 ml) and dried over magnesium sulphate, filtered and concentrated in vacuo to a syrup. This was purified by flash column chromatography on silica gel, eluting with hexane:ethyl acetate 3:1, to yield pure title compound (75 mg).

δ ($^1$H, CDCl$_3$): 9.74 (s, 1H, CHO), 7.44–7.26 (m, 10H, 2Ph), 6.98 (s, 1H, —CHPh$_2$), 6.03 (dd, 1H, H-2, J=3.3 and 1.2 Hz), 4.60 (dd, 1H, H-1', J=5.1 and 3.9 Hz), 4.12 (m, 2H, H-3', H4'), 4.01 (d, 1H, H-8a, J=9.3 Hz), 3.64 (d, 1H, H-8a, J=9.3 Hz), 3.61 (dq, 1H, H-5', J=8.7 and 6.3 Hz), 3.49 (m, 1H, CH$_2$—CH$_3$), 3.13 (m, 1H, CH$_2$—CH$_3$), 2.70 (t, 1H, H-1, J=3.9 Hz), 2.24 (m, 1H, CH(CH$_3$)$_2$), 1.14 (t, 3H, CH$_3$, J=7.2 Hz).

INTERMEDIATE 97

[1R-(1α, 3aβ, 4β, 4aβ, 7β, 7aα, 8aβ)] 8a-[(1S,4R, 6S,7R,9R)-2,8-Dioxa-4,9-dimethyl-6-(methylthio)-thiocarbonyloxy-cis-bicyclo[3.4.0]-non-7-yl-oxymethyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester Intermediate 89b (250 mg) and imidazole (catalytic amount) were dissolved in dry tetrahydrofuran (10 ml) under argon atmosphere. Sodium hydride (45 mg) was added and the suspension stirred at room temperature for 20 minutes. Carbon disulfide (140 μl) was added, the stirring continued for 20 minutes and methyl iodide (150 μl) was added. After 2 hours the reaction was quenched by addition of ethyl acetate (10 ml) and then water dropwise (5 ml). The mixture was partitioned between ethyl acetate (50 ml) and water (50 ml), the organic layer washed with water and brine, then dried and evaporated. The residue was purified by flash chromatography on silica gel eluting with hexane:ethyl acetate (10:1) to (8:1) to give the title compound (211 mg).

δ (¹H, CDCl₃): 9.72 (s, 1H, CHO), 7.46–7.22 (m, 10H, 2Ph), 6.97 (s, 1H, CHPh₂), 6.02 (dd, 1H, H-2, J=1.2 and 3.3 Hz), 5.80 (dd, 1H, H-6', J=2.1 and 6.3 Hz), 4.72 (d, 1H, H-7', J=2.1 Hz), 4.05 (dd, 1H, Ha-3', J=7.2 and 8.4 Hz), 3.98–3.86 (m, 2H, 8aCHa and H1'), 3.66–3.55 (m, 2H, 8aCHb and H-9'), 3.34 (t, 1H, Hb-3', J=8.4 Hz), 2.73 (t, 1H, H1, J=3.9 Hz), 2.59 (s, 3H, SCH₃).

INTERMEDIATE 98

[1R-(1α, 3aβ, 4β, 4aβ, 7β, 7aα, 8aβ)] 8a-[(4-O-Allyl-3-iodo-2,3,6-trideoxy-b-D-glucopyranosyloxy)methyl]-4-formyl-4,4a,5,6,7,7a 8,8a-octahydro-7-methyl-3-(1-methylethyl)-1,4-methano-s-indacene-3a(1H)-carboxylic acid, diphenylmethyl ester A solution of Intermediate 12 (67 mg), triphenylphosphine (105 mg) and imidazole (28 mg) in dry tetrahydrofuran (5 ml) was treated with iodine (51 mg) portionwise. The mixture was stirred at room temperature for 1.5 hours and partitioned between ethyl acetate (30 ml) and 1 N aqueous hydrochloric acid (30 ml). The organic layer was washed successively with 1 N aqueous hydrochloric acid, water, aqueous sodium metabisulfite solution, water and brine, then dried, filtered and concentrated. The residue was flash chromatographed on silica gel eluting with hexane:ethyl acetate (9:1) to give the title compound (68 mg).

δ (¹H, CDCl₃): 9.73 (s, 1H, CHO), 7.45–7.22 (m, 10H, 2Ph), 6.97 (s, 1H, CHPh₂), 6.07–5.9 (m, 2H, H-2 and OC—CH=C), 5.37–5.14 (m, 2H, O—C—C=CH₂), 4.45–4.35 (m, 1H, O—CHa—C=C), 4.25–4.1 (m, 2H, H-1' and O—CHb—C=C), 4.1–3.95 (m, 2H, H-3' and 8a-CHa), 3.66 (d, 1H, 8a-CHb, J=9 Hz), 3.29 (dq, 1H, H-5', J=6 and 8.7 Hz), 3.15 (dd, 1H, H4', J=8.7 and 9.9 Hz), 2.73 (t, 1H, H-1, J=3.9 Hz).

INTERMEDIATE 99

[1R-(1α, 3aβ, 4β, 4aβ, 7β, 7aα, 8aβ)] 8a-(2,3-Anhydro-6-deoxy-β-D-mannopyranosyloxy)methyl-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester A solution of intermediate 67 (3.2 mmol) in dry acetonitrile (40 ml) was treated with ethylene glycol (39 ml), trimethylorthoformate (1.1 ml) and p-toluenesulfonic acid (30 mg). After 5 hours, the mixture was thoroughly extracted with ethyl acetate. After removal of the solvent, the residue was purified by flash chromatography using hexane:ethyl acetate 3:1 as eluent to give the title compound (2.08 g).

δ (¹H, CDCl₃): 7.43 and 7.29 (m, m, 4H, 6H, 2xPh), 6.95 (s, 1H, CHPh₂), 5.86 (d, 1H, H-2, J=3.3 Hz), 5.08 (s, 1H, 4-CH), 4.69 (s, 1H, H-1'), 4.11 (d, 1H, 8a-CHa, J=9.3 Hz), 3.81 (m, 5H, 8a-CHb and O—CH₂CH₂—O), 3.63 (m, 1H, H-5'), 3.23 and 3.15 (d, d, 1H, 1H, H-2' and H-3', J=3.6 Hz), 3.20 (m, 1H, H-4'), 2.63 (m, 2H, H-1 and CH(CH₃)₂).

INTERMEDIATE 100

[1R-(1α, 3aβ, 4β, 4aβ, 7β, 7aα, 8aβ)] 8a-(2,3-Anhydro-4-oxo-deoxy-β-D-mannopyranosyloxy)methyl-4-(1,3-dioxolan-2-yl)-4,4a,5,6,7,7a,8,8a-octahydro-7-methyl-3-(methylethyl)-1,4-methano-s-indacene-3a(1H)-carboxylic acid, diphenylmethyl ester A solution of trifluoroacetic anhydride (230 μl) in dry dichloromethane (10 ml) at −60° C. was treated dropwise with dimethylsulfoxide (138 μl) and a solution of Intermediate 99 (0.9 mmol) in dry dichloromethane (10 ml). After 60 minutes, triethylamine (554 μl) was added and the mixture was stirred at −20° C. for 2 hours. After this time, was diluted with dichloromethane and washed with water. After removal of the solvent, the residue was purified by flash chromatography using hexane:ethyl acetate 4:1 as eluent to give the title compound (214 mg).

δ (¹H, CDCl₃):. 7.44 and 7.30 (m, m, 4H, 6H, 2xPh), 6.94 (s, 1H, CHPh₂), 5.87 (dd, 1H, H-2, J=1.5 and 3.6 Hz), 5.10 (s, 1H, 4-CH), 4.81 (s, 1H, H-1'), 4.09 (d, 1H, 8a-CHa, J=8.7 Hz), 3.88 (m, 5H, 8a-CHb and OCH₂CH₂—O), 3.58 and 3.36 (d, d, 1H, 1H, H-2' and H-3', J=3.9 Hz), 2.65 (m, 2H, H-1 and CH(CH₃)₂).

INTERMEDIATE 101

[1R-(1a, 3ab,4b,4ab,7b,7aa,8ab)] 8a-(2,3-Anhydro-4,6-dideoxy-4-methylene-β-D-mannopyranosyloxy)methyl-4-(1,3-dioxolan-2-yl)-4,4a 5,6,7,7a,8,8a-octahydro-7-methyl-3-(1-methylethyl)-1,4methano-s-indacene-3a(1H)-carboxylic acid, diphenylmethyl ester A solution of methyltriphenylphosphonium bromide (0.3 mmol) in dry tetrahydrofuran (10 ml) under nitrogen atmosphere at −78° C. was treated with n-Butyllithium 2.44M (0.15 ml). After 15 minutes, a solution of Intermediate 100 (0.21 mmol) in dry tetrahydrofuran (5 ml) was slowly added and the mixture was slowly warmed at room temperature. The mixture was diluted with ethyl acetate and washed with ammonium chloride (1 N) and brine. After removal of the solvent, the residue was purified by flash chromatography using hexane:ethyl acetate 4:1 as eluent to give the title compound (91 mg):

δ (¹H, CDCl₃): 7.45 and 7.29 (m, m, 4H, 6H, 2xPh), 6.95 (s, 1H, CHPh₂), 5.87 (m, 1H, H-2), 5.35 and 5.22 (d, d, 1H, 1H, CH₂=C, J=2.4 Hz), 5.08 (s, 1H, 4-CH), 4.68 (s, 1H, H-1'), 4.10 (m, 2H, 8a-CHa and H-5'), 3.82 (m, 5H, 8a-CHb and O—CO₂CH₂O), 3.57 and 3.35 (d, d, 1H, 1H, H-2' and H-3', J=3.9 Hz), 2.63 (m, 2H, H-1 and CH(CH₃)₂).

INTERMEDIATE 102

[1R-(1α, 3aβ, 4β, 4aβ, 7β, 7aα, 8aβ)] 8a-(2,3-Anhydro-6-deoxy-β-D-talopyranosyloxy)methyl-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester To solution of Intermediate 100 (1.13 mmol) in dry tetrahydrofuran (45 ml), under nitrogen atmosphere at −78° C., L-selectride 1 N (2 ml) was slowly added. After 1 hour, the mixture was diluted with ethyl acetate (100 ml), warmed at room temperature and washed with ammonium chloride (1 N), water and brine. After removal of the solvent, the residue was purified by flash chromatography using hexane:ethyl acetate 3:1 as eluent to give the title compound (431 mg).

δ (¹H, CDCl₃): 7.44 and 7.31 (m, m, 4H, 6H, 2xPh), 6.95 (s, 1H, CHPh₂), 5.85 (dd, 1H, H-2, J=1.2 and 3.6 Hz), 5.08 (s, 1H, 4-CH), 4.92 (s, 1H, H-1'), 4.11 (d, 1H, 8a-CHa, J=9.3 Hz), 3.83 (m, 5H, 8a-CHb and OCH₂CH₂O), 3.62 (m, 1H, H-4'), 3.54 (dd, 1H, H-3', J=3.6 and 5.1 Hz), 3.40 (m, 1H, H-5'), 3.24 (d, 1H, H-2', J=3.9 Hz).

INTERMEDIATE 103

[1R-(1a, 3ab,4b,4ab,7b,7aa,8ab)] 8a-2,3-Anhydro-4-O-tertbutylcarbonyl-6-deoxy-β-D-talopyranosyloxy)methyl-4-(1 3-dioxolan-2-yl)4,4a,5,6,7,7a 8 8a-octahydro-7-methyl-3-(1-methylethyl)-1,4-methano-s-indacene-3a(1H)-carboxylic acid, diphenylmethyl ester A mixture of Intermediate 102 (0.2 mmol) and 4-dimethylaminopyridine (0.4 mmol) in dry dichloromethane (15 ml) was treated with pivaloyl chloride (0.3 mmol). After 30 minutes, was washed with water and purified by flash chromatography using hexane:ethyl acetate 5:1 as eluent to give the title compound (95 mg).

δ ($^1$H, CDCl$_3$): 7.44 and 7.30 (m, m, 4H, 6H, 2xPh), 6.95 (s, 1H, CHPh$_2$), 5.85 (dd, 1H, H-2, J=1.2 and 3.6 Hz), 5.08 (s, 1H, 4-CH), 4.82 (t, 1H, H4', J=3.9 Hz), 4.60 (s, 1H, H-1'), 4.12 (d, 1H, 8a-CHa, J=9.6 Hz), 3.83 (m, 5H, 8a-CHb and O—CH$_2$CH$_2$—O), 3.65 (m, 1H, H-5'), 3.53 (t, 1H, H-3', J=4.2 Hz), 3.17 (d, 1H, H-2', J=4.2 Hz), 2.63 (m, 2H, H-1 and CH(CH$_3$)$_2$).

INTERMEDIATE 104

[1R-(1α, 3aβ, 4β, 4aβ, 7β, 7aα, 8aβ)] 8a-(4-O-Allyl-2,3-anhydro-6-deoxy-β-D-talopyranosyloxy) methyl-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester To a solution of Intermediate 102 (0.3 mmol) in dry tetrahydrofuran (10 ml) under nitrogen atmosphere, sodium hydride (0.6 mmol) and a catalytic amount of tetrabutylammonium iodide were added. After 30 minutes, allyl bromide (0.9 mmol) was added and the mixture was stirred overnight at room temperature. Then, was diluted with ethyl acetate (10 ml) and washed with ammonium chloride (1 N) and brine. After removal of the solvent, the residue was purified by flash chromatography using hexane:ethyl acetate 4:1 as eluent to give the title compound (163 mg).

δ ($^1$H, CDCl$_3$): 7.44 and 7.29 (m, m, 4H, 6H, 2xPh), 6.95 (s, 1H, CHPh$_2$), 5.96 (m, 1H, H-2"), 5.85 (dd, 1H, H-2, J=1.2 and 3.6 Hz), 5.30 and 5.12 (m, m, 1H, 1H, CH$_2$-3"), 5.06 (s, 1H, 4-CH), 4.58 (s, 1H, H-1'), 4.31 (m, 1H, H-4'), 4.10 (m, 2H, H-5' and 8a-CHa), 3.83 (m, 5H, 8a-CHb and O—CH$_2$CH$_2$—O), 3.53 (m, 2H, CH$_2$O), 4.23 (t, 1H, H-3', J=4.2 Hz), 3.19 (d, 1H, H-2', J=4.2 Hz), 2.65 (t, 1H, H-1, J=4.2 Hz), 2.61 (m, 1H, CH(CH$_3$)$_2$).

INTERMEDIATE 105

[1R-(1α, 3aβ, 4β, 4aβ, 7β, 7aα, 8aβ)] 8a-(2,3-Anhydro-6-deoxy-4-O-tosyl-β-D-talopyranosyloxy) methyl-4-(1,3-dioxolan-2-yl)-4,4a,5,6,7,7a,8,8a-octahydro-7-methyl-3-(1-methylethyl)-1,4-methano-s-indacene-3a(1H)carboxylic acid, diphenylmethyl ester A solution of Intermediate 102 (0.45 mmol) in dry dichloromethane (7 ml) was treated with 4-dimethylaminopyridine (1.35 mmol) and tosyl chloride (0.9 mmol) and was stirred overnight at room temperature. After this time, was washed with water and brine. After removal of the solvent, the residue was purified by chromatography using hexane:ethyl acetate 3:1 as eluent. Appropriate fractions were evaporated to give the title compound (277 mg).

δ ($^1$H, CDCl$_3$): 7.86, 7.42 and 7.29 (m, m, 10H, Ar), 6.93 (S, 1H, CHPh$_2$), 5.82 (m, 1H, H-2), 5.06 (s, 1H, 4-CH), 4.68 (t, 1H, H-3', J=4.2 Hz), 4.55 (s, 1H, H-1'), 4.07 (d, 1H, 8a-CHa, J=8.7 Hz), 3.81 (m, 5H, 8a-CHb and O—CH$_2$CH$_2$—O), 3.62 (m, 1H, H-5'), 3.30 (t, 1H, H-2', J=4.2 Hz), 3.15 (d, 1H, H-4', J=3.9 Hz), 2.61 (m, 2H, H-1 and CH(CH$_3$)$_2$).

INTERMEDIATE 106

[1R-(1α, 3aβ, 4β, 4aβ, 7β, 7aα, 8aβ)] 8a-(2,3-Anhydro-4-azido-4,6-dideoxy-β-D-mannopyranosyloxy) methyl-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester A solution of Intermediate 105 (0.15 mmol) and lithium azide (0.45 mmol) in dry dimethylformamide (3 ml) was heated overnight at 100° C. The mixture reaction was diluted with ethyl acetate (20 ml) and washed with water and brine. After removal of the solvent, the residue was purified by flash chromatography using hexane:ethyl acetate 4:1 as eluent. Appropriate fractions were evaporated to give the title compound (53 mg).

δ ($^1$H, CDCl$_3$): 7.46–7.23 (m, 1OH, Ph$_2$), 6.94 (s, 1H, CHPh$_2$), 5.86 (dd, 1H, H-2, J=1.2 and 3.6 Hz), 5.08 (s, 1H, 4-CH), 4.67 (s, 1H, H-1'), 4.10 (d, 1H, 8a-CHa, J=8.7 Hz), 3.83 (m, 4H, 8a-CHb and O—C$_2$CH$_2$—O), 3.40 (d, 1H, H-4', J=9.3 Hz), 3.31 and 3.15 (d, d, H-2' and H-3', J=3.6 Hz), 3.23 (m, 1H, H-5'), 2.65 (m, 2H, H-1 and CH(CH$_3$)$_2$).

INTERMEDIATE 107

[1R-(1α, 3aβ, 4β, 4aβ, 7β, 7aα, 8aβ)] 8a-[(4-O-Allyl,2,3-anhydro, 6-deoxy-β-D-mannopyranosyl) oxy methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester

PROCEDURE A

To a solution of Intermediate 21 (650 mg) in 50 ml of dry THF at 0° C., 90 mg of sodium hydride were added. The mixture was stirred under nitrogen at 0° C. for 30 minutes. Then, 875 mg of allyl bromide and a catalytic amount of tetrabutylammonium iodide (50 mg) were added. The reaction was complete after 5 hours stirring at room temperature. The crude was treated with ammonium chloride 1 N and ethyl acetate. The organic layer was washed with water and brine, dried over anhydrous MgSO$_4$ and evaporated to dryness. The residue was chromatographed in a silica gel column with n-hexane:ethyl acetate 7:1 to yield 590 mg of the title compound as a white foam

PROCEDURE B

To a solution of Intermediate 53 (3 g) in dry methylene chloride (200 ml), 2.35 g of dimethylaminopyridine were added at room temperature. Then a solution of 3.66 g of tosyl chloride in 100 ml of methylene chloride was added slowly, under stirring. The mixture was stirred for three days at room temperature until the reaction was complete. The crude was washed with 1 N hydrochloric acid, a saturated solution of sodium bicarbonate and brine. The organic layer was dried over anhydrous magnesium sulphate, filtered and treated with 20 ml of a solution of sodium methoxide in methanol (25 wt. %). This mixture was stirred at room temperature for 1 day. The crude was treated with 1 N hydrochloric acid and washed with water and brine. The organic layer was dried over anhydrous magnesium sulphate and evaporated. The residue was purified by flash chromatography with n-hexane:ethyl acetate 8:1 to give the title compound as a white foam (45% overall yield).

δ ($^1$H, CDCl$_3$): 9.75 (s, 1H, CHO), 6.99 (s, 1H, CHPh$_2$), 6.08 (dd, 1H, H-12, J=1.2 and 3.3 Hz), 5.90 (m, 1H, CH=CH$_2$), 5.28 (m, 2H, CH=CH$_2$), 4.69 (d, 1H, H-1, J=1.2 Hz), 4.23 (m, 1H, H-5'), 4.11 (d, 1H, H-19a, J=9 Hz), 4.06 (m, 1H, H- 4'), 3.79 (d, 1H, H-19b, J=9 Hz), 3.26 (d, 1H, H-2', J=3.9 Hz), 3.21 (m, 2H, CH$_2$—CH=CH$_2$), 3.13 (d, 1H, H-3', J=3.9 Hz), 2.86 (t, 1H, H-11, J=3.6 Hz).

INTERMEDIATE 108

[1R-(1α, 3aβ, 4β, 4aβ, 7β, 7aα, 8aβ)] 8a-[2,3-Anhydro,6-deoxy-4-O-(2,3-dihydroxypropyl)-b-D-mannopyranosyl)oxymethyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of intermediate 107 (2 g) in 50 ml of acetone and 5 ml of water at 0° C., 1 g of N-oxide of N-methylmorpholine was added. To this mixture, 0.2 ml of solution of osmium tetroxide (2.5 wt % in isobutanol) was added slowly. The hydroxylation of GM 218045X was complete after stirring for 3 days at room temperature. The crude was treated with sodium hydrosulfide, filtered over celite and evaporated to dryness. The residue was solved in ethyl acetate and washed with water and brine. The organic layer was dried over anhydrous magnesium sulphate, evaporated to dryness and chromatographed in silica gel column with n-hexane:ethyl acetate, 1:1 and methylene chloride:methanol, 50:1. The title compound (mixture of enantiomers 50:50) was obtained as a white foam (1.75 g).

δ ($^1$H, CDCl$_3$): 9.75 (s, 1H, CHO), 6.99 (s, 1H, CHPh$_2$), 6.08 (dd, 1H, H-12, J=1.5 and 3.6 Hz), 4.69 (s, 1H, H-1'), 4.10 (d, 1H, H-19a, J=9.3 Hz), 3.90–3.58 (m, 5H, CH$_2$OH, CHOH, OCH$_2$—CHOH in 4'), 3.79 (d, 1H, H-19b, J=9.3 Hz), 3.27, 3.13 (d, d, 1H, 1H, H-2' and H-3', J=3.9 Hz), 3.28–3.22 (m, 2H, H-4' and H-5'), 2.85 (t, 1H, H-11, J=3.6 Hz).

INTERMEDIATE 109

[1R-(1a,3ab,4b,4ab,7b,7aa,8ab)] 8a-[(2,3-Anhydro, 6-deoxy-4-O-[(2,3-O-isopropylidene)-2,3-dihydroxypropyl]-b-D-mannopyranosyl)oxymethyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester To a solution of intermediate 108 (350 mg) in dry acetone (20 ml), 250 μl of 2,2,dimethoxypropane and a catalytic amount of p-toluenesulfonic acid (30 mg) were added. The mixture was stirred at room temperature for 2 hours under nitrogen. The crude was evaporated to dryness and the residue solved again in ethyl acetate (70 ml) and washed with water and brine. The organic layer was concentrated and purified by a silica gel column with n-hexane:ethyl acetate 6:1 to give the title compound (mixture of isomers 50:50) as a white foam (290 mg, 80% yield).

δ ($^1$H, CDCl$_3$): 9.74 (s, 1H, CHO), 6.99 (s, 1H, CHPh$_2$), 6.08 (dd, 1H, H-12, J=0.9 and 3.3 Hz), 4.67 (d, 1H, H-1', J=2.1 Hz), 4.32–4.22 (m, 1H, CHOH in 4'), 4.12–4.03 (m, 2H, H-19a and OCH$_2$ in 4'), 3.82–3.51 (m, 4H, H-19b, OCH$_2$—CHOH—CH$_2$O), 3.29 and 3.12 (d, d, 1H, 1H, H-2' and H-3', J=3.9 Hz), 3.26–3.20 (m, 2H, H-4' and H-5'), 2.85 (t, 1H, H-11, J=3.9 Hz), 1.42 and 4.36 (d,d, 3H, 3H, (CH$_3$)$_2$-C of isopropylidene).

EXAMPLE 1

[1R-(1α, 3aβ, 4β, 4aβ, 7β, 7aα, 8aβ)] 8a-[(6-Deoxy-3,4-O-isopropylidene-β-D-altropyranosyloxy)methyl]-4-formyl-4, 4a,5,6,7,7a,8,8a-octahydro-7-methyl-3-(1-methylethyl)-1,4-methano-s-indacene-3a(1H)-carboxylic acid To a suspension of 10% palladium on charcoal (80 mg) in ethyl acetate (10 ml) under nitrogen was added a solution of Intermediate 2 (180 mg) in ethyl acetate (10 ml) and the mixture was hydrogenated at room temperature under 30 psi of hydrogen for 1 hour. The catalyst was filtered off and the solvent evaporated to dryness. Flash chromatography of the residue on silica gel eluting with dichloromethane:methanol (20:1) gave the title compound (128 mg).

δ ($^1$H, CDCl$_3$): 9.73 (s, 1H, CHO), 6.08 (dd, 1H, H-2, J=1.5 and 3.3 Hz), 4.61 (d, 1H, H-1', J=2.1 Hz), 4.30 (dd, 1H, H-3', J=3.6 and 5.4 Hz), 4.04 (d, 1H, 8aCH$_2$, J=9.3 Hz), 3.95 (dd, 1H, H-2', J=2.1 and 3.6 Hz), 3.85 (dd, 1H, H-4', J=5.4 and 9.0 Hz), 3.66 (d, 1H, J=9.3 Hz), 3.49 (dq, 1H, H-5', J$_d$=9.0 Hz, J$_q$=6.3 Hz), 2.69 (t, 1H, H-11, J=3.6 Hz); δ ($^{13}$C, CDCl$_3$): 204.8 (CHO), 175.4 (CO$_2$H), 148.3 (C-3), 130.7 (C-2), 109.3 (Cq.isop), (98.9 (C-1'), 76.9 (C-4'), 75.8 (C-2'), 74.2 (8aCH$_2$), 71.7 (C-3'), 68.6 (C-5'), 65.6 (C-8a), 58.9 (C-4).

EXAMPLE 2

[1R-(1α, 3aβ, 4β, 4aβ, 7β, 7aα, 8aβ)] 8a-[(6-Deoxy-3,4-isopropylidene-β-D-altropyranosyloxy)methyl]-4-formyl-4, 4a,5,6,7,7a,8,8a-octahydro-7-methyl-3-(1-methylethyl)-1,4-methano-s-indacene-3a(1H)-carboxylic acid, sodium salt Example 1 (246 mg) was dissolved in dioxane (2 ml) and 0.5 M sodium bicarbonate (0.99 ml) was added. The solution was stirred for 15 minutes and freeze-dried to obtain the title compound (256 mg).

δ ($^1$H, CDCl$_3$): 9.88 (s, 1H, CHO), 5.95 (dd, 1H, H-2, J=1.5 and 3.3 Hz), 4.51 (d, 1H, H-1', J=1.8 Hz), 4.26 (dd, 1H, H-3', J=4.8 and 6.0 Hz), 4.01 (d, 1H, 8aCH$_2$, J=9.6 Hz), 3.87–3.80 (m, 2H, H-2' and H-4'), 3.74 (d, 1H, 8aCH$_2$, J=9.6 Hz), 3.50–3.42 (m, 1H, H-5'), 2.66 (t, 1H, H-1, J=3.9 Hz).

EXAMPLE 3

[1R-(1α, 3aβ, 4β, 4aβ, 7β, 7aα, 8aβ)] 8a-[(6-Deoxy-3,4-O-2-pentylidene)-β-D-altropyranosyloxy)methyl]-4-formyl-4, 4a,5,6,7,7a,8,8a-octahydro-7-methyl-3-(1-methylethyl)-1,4-methano-s-indacene-3a(1H)-carboxylic acid To a suspension of 10% palladium on charcoal (30 mg) in ethyl acetate (10 ml) under nitrogen, was added a solution of Intermediate 3 (140 mg) in ethyl acetate and the mixture was hydrogenated under 30 psi of hydrogen for 45 minutes. The catalyst was filtered off and the solvent evaporated to dryness. Flash chromatography on silica gel using dichloromethane:methanol (30:1) as eluent afforded the title compound (75 mg) in a epimer ratio of 26:74.

δ ($^1$H, CDCl$_3$): 9.82 (s, 1H, CHO), 6.08 (dd, 1H, H-2, J=1.5 and 3.3 Hz), 4.60 (d, 1H, H-1', J=1.8 Hz), 4.30 (dd, 1H, H-3', J=4.2 and 6.0 Hz), 3.98 (d, 1H, 8aCH$_2$, J=9.3 Hz), 3.94 (dd, 1H, H-2', J=1.8 and 4.2 Hz), 3.87 (dd, 1H, H-4', J=6.0 and 9.3 Hz), 3.65 (d, 1H, 8aCH$_2$, J=9.3 Hz), 3.47 (dq, 1H, H-5', J$_d$=9.3 Hz, J$_q$=6.3 Hz), 2.70 (t, 1H, H-1, J=3.9 Hz); δ ($^{13}$C, CDCl$_3$): 204.5 (CHO), 176.5 (CO$_2$H), 148.2 (C-3), 130.6 (C-2), 110.8 (Cq acetal), 98.8 (C-1'), 76.6 (C-4'), 75.6 (C-2'),73.9 (8aCH$_2$), 71.3 (C-3'), 68.9 (C-5'), 65.5 (C8a), 58.8 (C-4).

EXAMPLE 4

[1R-(1α, 3aβ, 4β, 4aβ, 7β, 7aα, 8aβ)] 8a-[(6-Deoxy-3,4-O-(4-ethoxy-2-butylidene)-β-D-altropyranosyloxy)methyl] formyl-4,4a,5,6,7,7a,8,8a-octahydro-7-methyl-3-(1-methylethyl)-1,4methano-s-indacene-3a(1H)-carboxylic acid To a suspension of 10% palladium on charcoal (100 mg) in ethyl acetate (15 ml) was added a solution of Intermediate 4 (260 mg) in ethyl acetate (10 ml) and the mixture was hydrogenated at room temperature under 30 psi of hydrogen for 45 minutes. The catalyst was filtered off and the solvent evaporated to dryness. The residue was flash chromatographed on silica gel eluting with dichloromethane:methanol (30:1) to give the title compound (172 mg).

δ ($^1$H, CDCl$_3$): 9.71 (s, 1H, CHO), 6.08 (dd, 1H, H-2, J=1.5 and 3.6 Hz), 4.60 (d, 1H, H-1', J=2.4 Hz), 4.31 (dd, 1H, H-3', J=4.2 and 6.0 Hz), 3.98 (d, 1H, 8aCH$_2$, J=9.3 Hz), 3.94 (dd, 1H, H-2', J=2.4 and 4.2 Hz), 3.88 (dd, 1H, H-4', J=6.0 and 9.3 Hz), 3.65 (d, 1H, 8aCH$_2$, J=9.3 Hz), 3.50 (t, 1H, CH$_2$O, J=7.2 Hz), 3.50–3.40 (m, 1H, H-5'), 2.69 (t, 1H, H-1, J=3.9 Hz); δ ($^{13}$C, CDCl$_3$): 204.5 (CHO), 176.2 (CO$_2$H), 148.2 (C-3), 130.6 (C-2), 109.8 (C-2''), 98.8 (C-1'), 76.7 (C-4'), 75.7 (C-2'), 73.8 (8aCH$_2$), 71.2 (C-2'), 68.8 (C-5'), 68.4 (CH$_2$O), 65.6 (C8a), 58.9 (C-4), 58.5 (CH$_3$O).

EXAMPLE 5

[1R-(1α, 3aβ, 4β, 4aβ, 7β, 7aα, 8aβ)] 8a-[(6-Deoxy-3,4-O-cyclopentylidene-β-D-altropyranosyloxy) methyl]-4- formyl-4,4a,5,6,7,7a,8,8a-octahydro-7-methyl-3-(1-methylethyl)-1,4-methano-s-indacene-3a(1H)-carboxylic acid To a suspension of 10% palladium on charcoal (50 mg) in ethyl acetate (10 ml) was added a solution of Intermediate 5 (232 mg) in ethyl acetate and the mixture was hydrogenated at room temperature under 35 psi of hydrogen for 1.5 hours. The catalyst was filtered off and the solvent evaporated to dryness. The residue was flash chromatographed on silica gel eluting with dichloromethane:methanol (30:1) to give the title compound (67 mg).

δ ($^1$H, CDCl$_3$): 9.71 (s, 1H, CHO), 6.07 (dd, 1H, H-2, J=1.5 and 3.3 Hz), 4.59 (d, 1H, H-1', J=2.1 Hz), 4.17 (dd, 1H, H-3', J=3.6 and 5.4 Hz), 4.54 (d, 1H, 8aCH$_2$, J=9.3 Hz), 3.97 (dd, 1H, H-2', J=2.1 and 3.6 Hz), 3.81 (dd, 1H, H-4', J=5.4 and 9.0 Hz), 3.70 (d, 1H, 8aCH$_2$, J=9.3 Hz), 3.44 (dq, 1H, H-5', J$_d$=9.0 Hz, J$_q$=6.3 Hz), 2.69 (t, 1H, H-1, J=3.3 Hz).

EXAMPLE 6

[1R-(1α, 3aβ, 4β, 4aβ, 7β, 7aα, 8aβ)] 8a-[(2,6-Dideoxy-3,4-O-isopropylidene-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 7 (1.2 g) in ethyl acetate (60 ml) was added 10% palladium on charcoal (600 mg) in portions, under nitrogen. The mixture was shaken in a Parr apparatus under 40 psi of hydrogen for 1 hour at room temperature. The catalyst was filtered off and washed with more ethyl acetate. The solvent was evaporated to dryness and the residue was flash chromatographed on silica gel eluting with dichloromethane:methanol (25:1) to give the title compound (0.79 g).

δ ($^1$H, CDCl$_3$): 9.81 (s, 1H, CHO), 6.05 (dd, 1H, H-2, J=1.2 and 3.3 Hz). 4.63 (dd, 1H, H-1', J=2.4 and 8.4 Hz), 4.38 (dt, 1H, H-3', J$_d$=3.0 Hz, J$_t$=5.1 Hz), 4.29 (d, 1H, 8aCH$_2$, J=9.3 Hz), 3.64 (dd, 1H, H-4', J=5.1 and 9.3 Hz), 4.43 (dq, 1H, H-5', J$_d$=9.3 Hz, J$_q$=6.0 Hz), 3.40 (d, 1H, 8aCH$_2$, J=9.3 Hz), 2.53 (t, 1H, H-1, J=3.9 Hz); δ ($^{13}$C, CDCl$_3$): 204.7 (CHO), 174.6 (CO$_2$H), 148.2 (C-3), 130.6 (C-2), 108.9 (C(CH$_3$)$_2$), 98.3 (C-1'), 76.6 (C-4'), 73.7 (8aCH$_2$), 72.5 (C-3'), 71.7 (C-5'), 67.0 (C8a), 65.2, 59.0 (C-4).

EXAMPLE 7

[1R-(1α, 3aβ, 4β, 4aβ, 7β, 7aα, 8aβ)] 8a-[(2,6-Dideoxy-3,4-O-(4-methoxy-2-butylidene)-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a suspension of 10% palladium on charcoal (300 mg) in ethyl acetate (10 ml) was added a solution of Intermediate 8 (246 mg) in ethyl acetate (10 ml) and the mixture was hydrogenated at room temperature under 45 psi of hydrogen for 1 hour. The catalyst was filtered off and the solvent evaporated to dryness. The residue was purified by flash chromatography on silica gel eluting with dichloromethane and dichloromethane:methanol (30:1) to give the title compound (182 mg) as a white foam in an epimer ratio of 4:1.

δ ($^1$H, CDCl$_3$) signals of the major component: 9.81 (s, 1H, CHO), 6.06 (dd, 1H, H-2, J=1.5 and 3.6 Hz), 4.62 (dd, 1H, H-1', J=2.7 and 8.1 Hz), 4.41 (dt, 1H,H-3', J$_d$=3.3 Hz, J$_t$=2.5 Hz), 4.24 (d, 1H, 8aCH$_2$, J=9.0 Hz), 3.68 (dd, 1H, H-4', J=5.7 and 9.0 Hz), 3.50 (t, 2H, CH$_2$, J=7.5 Hz), 3.46–3.38 (m, 1H, H-5'), 3.33 (s, 3H, CH$_3$O), 2.54 (t, 1H, H-1, J=4.2 Hz),; δ ($^{13}$C, CDCl$_3$): 204.5 (CHO), 175.1 (CO$_2$H), 148.2 (C-3), 130.7 (C-2), 109.4 (C-2"), 98.3 (C-1'), 76.4 (C-4'), 73.6 (8aCH$_2$), 71.9 (C-3'), 71.4 (C-5'), 68.6 (CH$_2$O), 65.2 (C8a), 58.9 (C-4), 58.6 (CH$_3$O).

EXAMPLE 8

[1R-(1α, 3aβ, 4β, 4aβ, 7β, 7aα, 8aβ)] 8a-[(2,6-Dideoxy-3,4-O-isopropylidene-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, sodium salt Example 6 (376 mg) was dissolved in dioxane (3 ml) and 0.5 N sodium bicarbonate (1.50 ml) was added. The resulting solution was stirred for 30 minutes at room temperature and then freeze-dried to give the title compound (392 mg).

δ ($^1$H, CDCl$_3$): 9.84 (s, 1H, CHO), 5.94 (dd, 1H, H-2, J=1.5 and 3.6 Hz), 4.52 (dd, 1H, H-1', J=2.4 and 9.0 Hz), 4.41–4.37 (m, 1H, H-3'), 4.02 (d, 1H, 8aCH$_2$, J=9.6 Hz), 3.74 (d, 1H, 8aCH$_2$, J=9.6 Hz), 3.57 (dd, 1H, H-4', J=5.4 and 10.0 Hz), 3.42 (dq, 1H, H-5', J$_d$=6.3 Hz, J$_q$=6.3 Hz), 2.56 (t, 1H, H-1, J=3.6 Hz).

EXAMPLE 9

[1 R-(1α, 3aβ, 4β, 4aβ, 7β, 7aα, 8aβ)] 8a-[(6-Deoxy-3,4-O-thionocarbonyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid A 2% solution of trifluoroacetic acid in dichloromethane (20 ml) was added to a solution of Intermediate 9 (0.220 g) in dichloromethane (5 ml) at 0° C. The reaction mixture was stirred at 0° C. for 1 hour and then washed with water (2×20 ml) and dried (magnesium sulfate). The solvent was evaporated to give a residue which was chromatographed on silica gel column eluting with dichloromethane:methanol (40:1 to 20:1) to give the title compound (0.1 g).

δ ($^1$H, CDCl$_3$): 9.68 (s, 1H, CHO), 6.09 (dd, 1H, H-2, J=1.5 and 3.6 Hz), 4.94 (dd, 1H, H-3', J=3.9 and 7.2 Hz), 4.62 (m, 2H, H-1' and H-4'), 4.14 (dd, 1H, H-2', J=2.1 and 3.9 Hz), 4.00 (d, 1H, 8aCH$_2$, J$_{AB}$=9.3 Hz), 3.72 (d, 1H, 8aCH$_2$, J$_{AB}$=9.3 Hz), 3.68 (m, 1H, H-5'), 2.71 (m, 1H, H-1); δ ($^{13}$C, CDCl$_3$): 204.4 (CHO), 190.2 (CS), 176.4 (CO$_2$H), 148.4 (C-3), 130.6 (C-2), 98.2 (C-1'), 82.3 and 80.1 (C-3' and C-4'), 74.5 (8aCH$_2$), 71.7 (C-3a), 69.2 and 66.4 (C-2' and C-5'); 65.5 (C-8a), 58.8 (C-4), 46.0 (C-1).

EXAMPLE 10

[1R-(1α, 3aβ, 4β, 4aβ, 7β, 7aα, 8aβ)] 8a-[(2,6-Dideoxy-3,4-carbonyl-β-D-allopyranosyloxy)methyl]-4-formyl-4,4a,5,6,7,7a,8,8a-octahydro-7-methyl-3-(1-methylethyl)-1,4-ethano-s-indacene-3a(1H)-carboxylic acid To a solution of Intermediate 10 (125 mg) in refluxing dry toluene (15 ml) was added, under nitrogen atmosphere, excess carbonyldimidazole in small portions. Once the reaction was completed (TLC control), the solvent was removed under reduced pressure and the crude mixture dissolved in dichloromethane (200 ml), washed with 1 N hydrochloric acid (3×100 ml), brine (1×100 ml) and water (1×100 ml), then dried over magnesium sulfate and concentrated to dryness to give an oil which was used without further purification. The oil was dissolved in ethyl acetate (15 ml) and shaken in a Parr apparatus under 20 psi of hydrogen in the presence of 10% palladium on activated charcoal (50 mg) for 1 hour at room temperature. Filtration of the catalyst and elimination of the solvent gave a syrup which was purified by preparative TLC (silica gel, methanol:dichloromethane 1:15) to give the title compound (50 mg) obtained from the fraction at Rf 0.5.

δ ($^1$H, CDCl$_3$): 9.70 (s, 1H, CHO), 6.07 (dd, 1H, H-2, J=1.2 and 3.3 Hz), 4.93 (m, 1H, H-3'), 4.63 (dd, 1H, H-1', J=2.4 and 7.8 Hz), 4.24 (dd, 1H, H-4', J=6.6 and 9.3 Hz), 4.05 and 3.57 (2d, 2H, 8aCH$_2$, J$_{AB}$=9 Hz), 3.63 (m, 1H, H-5'), 2.66 (t, 1H, H-1, J=3.9 Hz); δ ($^{13}$C, CDCl$_3$): 204.6

(COH), 176.0 (COOH), 154.0 (OCO), 148.2 (C-3), 130.7 (C-2), 97.5 (C-1'), 76.6 (C-4'), 74.7 (C-3'), 69.9 (C-5'), 31.7 (C-2').

EXAMPLE 11

[1R-(1α, 3aβ, 4β, 4aβ, 7β, 7aα, 8aβ)] 8a-[(2,6-Dideoxy-3,4-O-thiocarbonyl-β-D-allopyranosyloxy)methyl]-4-formyl-4,4a,5,6,7,7a,8,8a-octahydro-7-methyl-3-(1-methylethyl)1,4-methano-s-indacene-3a(1H)-carboxylic acid To a solution of Intermediate 11 (130 mg) in dry dichloromethane (5 ml) was added trifluoroacetic acid (250 μl) at 0° C. After 2 hours the solution was diluted with dichloromethane (50 ml), washed with water (2×100 ml), dried over magnesium sulfate and concentrated to dryness to give an oil which was purified by preparative TLC (silica gel, methanol:dichloromethane 1:15) to give the title compound (68 mg) obtained from the fraction at Rf 0.6.

δ ($^1$H, CDCl$_3$): 9.70 (s, 1H, CHO), 6.07 (dd, 1H, H-2, J=1.2 and 3.3 Hz), 5.08 (m, 1H, H-3'), 4.63 (dd, 1H, H-1', J=2.7 and 8.4 Hz), 4.45 (dd, 1H, H-4', J=6.6 and 9.0 Hz), 4.03 and 3.59 (2d, 2H, 8aCH$_2$, J$_{AB}$=9.3 Hz), 3.64 (m, 1H, H-5'), 2.67 (t, 1H, H-1, J=3.0 Hz); δ ($^{13}$C, CDCl$_3$): 204.5 (COH), 190.9 (CS), 176.3 (COOH), 148.2 (C-3), 130.7 (C-2), 97.5 (C-1), 80.3 (C-4'), 79.6 (C-3'), 69.5 (C-5'), 31.3 (C-2').

EXAMPLE 12

[1R-(1α, 3aβ, 4β, 4aβ, 7β, 7aα, 8aβ)] 8a-[(2,6-Dideoxy-3,4-O-methylene-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 10 (450 mg) in dibromomethane (10 ml) were added, with vigorous stirring, tetrabutylammonium bromide (40 mg) and 50% aqueous sodium hydroxide (100 ml). After 12 hours, the mixture was quenched by adding of 1 N hydrochloric acid (100 ml) and extracted with dichloromethane (100 ml). The organic layer was washed with 1 N hydrochloric acid (1×100 ml), dried over magnesium sulfate and concentrated to dryness to give a white solid which was used without further purification. This solid was dissolved in ethyl acetate (15 ml) and shaken in a Parr apparatus under 20 psi of hydrogen in the presence of 10% palladium on activated charcoal (50 mg) for 1 hour at room temperature. After filtration of the catalyst and elimination of the solvent, the oily residue was flash chromatographed over silica gel eluting with acetone:hexane (1:10) and (1:5) to give the title compound (130 mg) as an oil.

δ ($^1$H, CDCl$_3$): 9.80 (s, 1H, CHO), 6.05 (dd, 1H, H-2, J=1.2 and 3.3 Hz), 5.12 and 4.86 (2m, 2H, OCH$_2$O), 4.60 (dd, 1H, H-1', J=2.4 and 8.7 Hz), 4.20 and 3.44 (2d, 2H, 8aCH$_2$, J$_{AB}$=9.3 Hz), 4.13 (m, 1H, H-3'), 3.67 (dd, 1H, H-4', J=5.1 and 8.7 Hz), 3.38 (m, 1H, H-5'), 2.58 (t, 1H, H-1, J=3.9 Hz); δ ($^{13}$C, CDCl$_3$): 204.6 (COH), 174.8 (COOH), 148.3 (C-3), 130.6 (C-2), 98.1 (C-1'), 94.9 (OCH$_2$O), 75.4 (C-4'), 73.9 C-3'), 70.3 (C-5'), 32.3 (C-2').

EXAMPLE 13

[1R-(1α, 3aβ, 4β, 4aβ, 7β, 7aα, 8aβ)] 8a-[(2,6-Dideoxy-3,4-O-methylene-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, sodium salt To a solution of Example 12 (200 mg) in methanol (5 was was added dropwise a 0.106 N solution of sodium hydroxide in water (3.98 ml). After 30 minutes the solvent was removed under reduced pressure and the residue dissolved in dioxane (5 ml) and lyophilized to give the title compound (209 mg).

δ ($^1$H, CD$_3$OD): 9.87 (s, 1H, CHO), 6.54 (dd, 1H, H-2, J=1.5 and 3.6 Hz), 5.10 and 4.82 (2m, 2H, OCH$_2$O), 4.51 (dd, 1H, H-1', J=2.4 and 8.7 Hz), 4.12 (m, 1H, H-3'), 4.03 and 3.73 (2d, 2H, 8aCH$_2$, J$_{AB}$=9.9 Hz), 3.61 (m, 1H, H-3'), 3.35 (m. 1H, H-5'), 2.56 (t, 1H, H-1); δ ($^{13}$C, CD$_3$OD): 200.2 (COH), 169.0 (COOH), 142.9 (C-2), 120.6 (C-2), 90.3 (C-1'), 86.4 (OCH$_2$O), 67.5 (C-4'), 66.2 (C-3'), 61.8 (C-5').

EXAMPLE 14

(a) [1R-(1α, 3aβ, 4β, 4aβ, 7β, 7aα, 8aβ)] 8a-[[1S,3R,7R,9R]-2,5,8-Trioxa-3,7-dimethyl-cis-bicyclo[4.4.0]-dec-9-yl-oxy-methyl]-4-formyl-4,4a,5,6,7,7a,8,8a-octahydro-7-methyl-3-(1-methylethyl)-1,4-methano-s-indacene-3a(1H)-carboxylic acid and (b) [1R-(1a, 3aβ, 4β, 4aβ, 7β, 7aα, 8aβ)] 8a-[[1S,3S,7R,9R]-2,5,8-Trioxa-3,7-dimethyl-cis-bicyclo[4.4.0]-dec-9-yl-oxy-methyl]-4-formyl-4,4a,5,6,7,7a,8,8a-octahydro-7-methyl-3-(1-methylethyl)-1,4-methano-s-indacene-3a(1H)-carboxylic acid Intermediate 14 (120 mg) in ethyl acetate (15 ml) was shaken in a Parr apparatus under 20 psi of hydrogen in the presence of 10% palladium on charcoal (50 mg) for 1 hour at room temperature. Filtration of the catalyst and evaporation of the solvent under reduced pressure gave a syrup which was flash chromatographed over silica gel using as eluent acetone:hexane (1:10), (1:7) and (1:5) to give title compound (a) (35 mg; Rf=0.5 in hexane:acetone 4:1) and title compound (b) (40 mg; Rf=0.4 in hexane:acetone 4:1) both as colourless oils.

(a) δ ($^1$H, CDCl$_3$): 9.80 (s, 1H, CHO), 6.04 (dd, 1H, H-2, J=1.2 and 3.3 Hz), 4.62 (dd, 1H, H-9', J=2.1 and 9.9 Hz), 4.20 (m, 2H, 8aCH$_2$+H-7'), 3.97 (m, 1H, H-1'), 3.73 (m, 1H, OCHCH$_3$), 3.40 (m, 2H, 8aCH$_2$+OCH$_2$), 3.27 (d, 1H, OCH$_2$, J$_{AB}$=10.8 Hz), 3.18 (dd, 1H, H-6', J=3.3 and 10.2 Hz); δ ($^{13}$C, CDCl$_3$): 204.6 (COH), 174.6 (COOH), 148.3 (C-3), 130.6 (C-2), 97.9 (C-9'), 73.5 (OCH$_2$), 73.2 (C-6'), 72.1 (C-1'), 71.9 (OCHCH$_3$), 65.4 (C-7'), 31.9 (C-10'), 22.7 (OCHCH$_3$).

(b) δ ($^1$H, CDCl$_3$): 9.79 (s, 1H, CHO), 6.05 (dd, 1H, H-2, J=1.5 and 3.6 Hz), 4.73 (dd, 1H, H-9', J=3.0 and 6.3 Hz), 4.26 (m, 1H, H-1'), 4.15 (m, 2H, 8aCH$_2$+H-7'), 3.98 (m, 1H, OCHCH$_3$), 3.79 (dd, 1H, OCH$_2$, J=3.1 and 11.4 Hz), 3.41 (d, 1H, 8aCH$_2$, J=9.6 Hz), 3.35 (m, 1H, OCH$_2$, J=3.1 and 6.3 Hz), 3.27 (dd, 1H, H-6', J=5.7 and 11.7 Hz), 2.55 (t, 1H, H-1); δ ($^{13}$C, CDCl$_3$): 204.6 (COH), 174.6 (COOH), 148.3 (C-3), 130.6 (C-2), 99.2 (C-9'), 74.7 (OCHCH$_3$), 73.6 (OCH$_2$), 69.3 (C-6'), 66.3 (C-1'), 65.4 (C-7'), 31.9 (C-10'), 22.6 (OCHCH$_3$).

EXAMPLE 15

[1R-(1α, 3aβ, 4β, 4aβ, 7β, 7aα, 8aβ)] 8a-[[1S,7R,9R]-2,5,8-Trioxa-3,3,7-trimethyl-cis-bicyclo[4.4.0]-dec-9-yl-oxy-methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 15 (200 mg) in ethyl acetate (15 ml) was added 10% palladium on charcoal (50 mg) under nitrogen. The mixture was shaken in a Parr apparatus under 20 psi of hydrogen for 1 hour at room temperature. Filtration of the catalyst and evaporation of the solvent gave a residue which was flash chromatographed over silica gel eluting with acetone:hexane (1:10) and (1 :15) to give the title compound (140 mg) as a white foam.

δ ($^1$H, CDCl$_3$): 9.81 (s, 1H, CHO), 6.03 (dd, 1H, H-2, J=1.5 Hz), 4.62 (dd, 1H, H-1', J=2.1 Hz, J=9.6 Hz), 4.35–4.15 (m, 3H, 8aCH$_2$, H-7' and H-1'), 3.40 (m, 2H, 8aCH$_2$ and OCH$_2$), 3.25–3.15 (m, 2H, H-6' and OCH$_2$), 2.52 (t, 1H, H-1), 1.33 and 1.13 (2s, 2CH$_3$); δ ($^{13}$C, CDCl$_3$):

204.7 (COH), 174.1 (COOH), 148.3 (C-3), 130.6 (C-2), 98.0 C-9'), 73.4 (OCH$_2$), 73.3 (C-6'), 65.1 (C-1'), 64.7 (C-7), 31.9 (C-10'), 21.1 (2CH$_3$).

EXAMPLE 16

[1R-(1α, 3aβ, 4β, 4aβ, 7β, 7β, 8aβ)] 8a-[[1S,4S,6R,8R]-2,7-Dioxa-4,6-dimethyl-cis-bicyclo[3.4.0]-non-8-yl-oxymethyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 20(a) (680 mg) in ethyl acetate (100 ml) was added 10% palladium on charcoal (200 mg) under nitrogen. The mixture was shaken in a Parr apparatus under 25 psi of hydrogen for 2 hours at room temperature. The catalyst was filtered off and the solvent evaporated to dryness. The residue was purified by flash chromatography eluting with dichloromethane:methanol (49:1) to afford the title compound (450 mg) as a white foam.

δ ($^1$H, CDCl$_3$): 9.86 (s, 1H, CHO), 6.04 (dd, 1H, H-2, J=1.5 and 3.6 Hz), 4.57 (dd, 1H, H-8', J=2.4 and 9.3 Hz), 4.40 (d, 1H, 8a-CH$_2$, J=9.6 Hz), 4.08 (m, 2H, H-1' and CH$_2$-3' (1H)), 3.27 (m, 3H, H6', CH$_2$-3' (1H), 8a-CH$_2$ (1H)), 2.47 (t, 1H, H-1, J=3.9 Hz), 1.02 (d, 3H, 4'-CH$_3$, J=6.6 Hz); δ ($^{13}$C, CDCl$_3$): 204.7 (CHO), 173.8 (COOH), 148.4 (C-3), 130.5 (C-2), 98.5 (C-8'), 75.2 (C-1'), 74.3 (8a-CH$_2$), 73.3 (C-3'), 71.9 (C-6'), 51.2 (C-5'), 36.0 (C-4'), 32.9 (C-9'), 19.4 (4'-CH$_3$).

EXAMPLE 17

[1R-(1α, 3aβ, 4β, 4aβ, 7β, 7aα, 8aβ)] 8a-[[1S,4S,6R,8R]-2,7-Dioxa-4,6-dimethyl-cis-bicyclo [3.4.0]non-8-yl-oxymethyl]-4-formyl-4,4a,5,6,7,7a,8,8a-octahydro-7-methyl-3-(1-methylethyl)-1,4-methano-s-indacene-3a(1H)-carboxylic acid, sodium salt To a solution of Example 16 (450 mg) in methanol (100 ml) was added dropwise aqueous sodium hydroxide (0.099 N, 9.5 ml). The solvent was removed under reduced pressure and the residue was dissolved in water (80 ml) and lyophilized to give the title compound (470 mg).

δ ($^1$H, CD$_3$OD): 9.86 (s, 1H, CHO), 5.94 (dd, 1H, H-2, J=1.5 and 3.6 Hz), 4.43 (dd, 1H, H-8', J=2.1 and 9.3 Hz), 4.13–4.02 (m, 3H, 8a-CH$_2$ (1H), H-1', CH$_2$-3' (1H)), 3.74 (d, 1H, 8a-CH$_2$, J=9.9 Hz), 3.34–3.23 (m, 2H, CH$_2$-3 (1H), H-6'), 2.56 (t, 1H, H-1, J=3.9 Hz), 2.34 (m, 1H, H-4') 0.99 (d, 3H, 4'-CH$_3$, J=6.9 Hz); δ ($^{13}$C, CD$_3$OD): 209.7 (CHO), 178.4 (COO—Na$^+$), 152.4 (C-3), 130.1 (C-2), 100.1 (C-8'), 77.2 (C-1'), 77.0 (C-3'), 75.3 (8a-CH$_2$), 73.0 (C-6'), 52.8 (C-5'), 37.2 (C-4'), 34.5 (C-9'), 19.6 (4'-CH$_3$).

EXAMPLE 18

[1R-(1α, 3aβ, 4β, 4aβ, 7β, 7aα, 8aβ)] 8a-[[1S,4R,6R,8R]-2,7-Dioxa,4,6-dimethyl-cis-bicyclo [3.4.0]-non-8-yl-oxymethyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 20(b) (180 mg) in ethyl acetate (60 ml) was added 10% palladium on charcoal (100 mg) under nitrogen. The suspension was shaken in a Parr apparatus under 25 psi of hydrogen for two hours at room temperature. The catalyst was filtered off and the solvent evaporated to dryness. The residue was twice flash chromatographed on silica gel, using successively dichloromethane:methanol (49:1) and hexane:acetone (4:1) as the eluents to give the title compound (90 mg) as a white foam.

δ ($^1$H, CDCl$_3$): 11.5 (bs, 1H, COOH), 9.87 (s, 1H, CHO), 6.04 (dd, 1H, H-2, J=1.2 and 3.3 Hz), 4.53 (dd, 1H, H-8', J=2.4 and 9.9 Hz), 4.45 and 3.26 (2d, 2H, 8a-CH$_2$, J=9.3 Hz), 4.19 (q, 1H, H-1', J=3.3 Hz), 3.96 (t, 1H, CH$_2$-3', J=8.4 Hz), 3.58 (m, 1H, H-4'), 3.43 (dd, 1H, CH$_2$-3', J=10.2 Hz), 2.55 (m, 1H, H-4'); δ ($^{13}$C, CDCl$_3$): 204.6 (CHO), 174.4 (COOH), 148.3 (C-3), 130.6 (C-2), 97.9 (C-8'), 78.7 (C-1'), 73.3 (C-3'), 72.9 (8a-CH$_2$), 68.7 (C-6'), 46.1 (C-5'), 36.6 (C-4'), 34.02 (C-9'), 21.8 (6'-CH$_3$), 13.6 (4'-CH$_3$).

EXAMPLE 19

[1R-(1α, 3aβ, 4β, 4aβ, 7β, 7aα, 8aβ)] 8a-[[1S,4R,7R,9R]-2,8-Dioxa-4,9-dimethyl-cis-bicyclo[3.4.0]-non-7-yl-oxymethyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 23(a) (150 mg) in ethyl acetate (15 ml) was added 10% palladium on charcoal (50 mg) under nitrogen. The mixture was shaken in a Parr apparatus under 20 psi of hydrogen for 1 hour at room temperature. The catalyst was filtered off and the solvent evaporated to dryness. The residue thus obtained was purified by flash chromatography eluting with acetone:hexane (1:3) to afford the title compound (100 mg) as a crystalline solid.

δ ($^1$H, CDCl$_3$): 9.86 (s, 1H, CHO), 6.05 (dd, 1H, H-2, J=1.2 and 3.3 Hz), 4.63 (dd, 1H, H-7', J=3.3 and 6.6 Hz), 4.37 (d, 1H, 8aCH$_2$, J$_{AB}$=9.6 Hz), 3.98 and 3.67 (2dd, 2H, H-3', J=6.6 and 8.1 Hz), 3.40–3.20 (m, 3H, 8aCH$_2$, H-9' and H-1'), 2.46 (t,1H, H-1, J=3.9 Hz), 1.04 (d, 3H, CH$_3$CH).

EXAMPLE 20

[1R-(1α, 3aβ, 4β, 4aβ, 7β, 7aα, 8aβ)] 8a-[[1S,4R,7R,9R]-2,8-Dioxa-4,9-dimethyl-cis-bicyclo-[3.4.0]-7-yl-oxymethyl]-4-formyl-4,4a,5,6,7,7a,8,8a-octahydro-7-methyl-3-(1-methylethyl)-1,4-methano-s-indacene-3a(1H)-carboxylic acid, sodium salt To a solution of Example 19 (100 mg) in methanol (5 ml) was added dropwise sodium hydroxide (0.106 N solution in water, 1.88 ml). After 30 minutes the solvent was removed under reduced pressure and the residue dissolved in water (3 ml) and lyophilized to afford the title compound (104 mg).

δ ($^1$H, CD$_3$OD): 9.88 (s, 1H, CHO), 5.93 (dd, 1H, H-2, J=1.2 and 3.3 Hz), 4.49 (m, 1H, H-7'), 4.02 (m, 2H, H-3' and 8a CH$_2$), 3.72 (d, 1H, 8aCH$_2$, J$_{AB}$=9.3 Hz), 2.56 (t, 1H, H-1, J=3.6 Hz); δ ($^{13}$C, CD$_3$OD): 209.7 (CHO), 178.4 (COOH), 152.4 (C-3), 130.1 (C-2), 99.9 (C-7'), 82.1 (C-1'), 76.5 (8aCH$_2$), 72.2 (C-9'), 37.5 (C-5'), 15.2 (CH$_3$-CH).

EXAMPLE 21

[1R-(1α, 3aβ, 4β, 4aβ, 7β, 7aα, 8aβ)] 8a-[[1S,4S,7R,9R]-2,8-Dioxa-4,9-dimethyl-cis-bicyclo[3.4.0]-non-7-yl-oxymethyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 23(b) (260 mg) in ethyl acetate (15 ml) was added 10% palladium on charcoal (50 mg). The mixture was shaken in a Parr apparatus under 20 psi of hydrogen for 1 hour at room temperature. The catalyst was filtered off and the solvent evaporated to dryness. The residue thus obtained was purified by preparative T(C (silica gel, methanol:dichloromethane 1:20) to afford the title compound (185 mg) as an oil at Rf=0.6.

δ ($^1$H, CDCl$_3$): 9.85 (s, 1H, CHO), 6.04 (dd, 1H, H-2, J=1.5 and 3.6 Hz), 4.88 (t, 1H, H-7', 2.7 Hz), 4.27 and 3.28 (2d, 2H, 8aCH$_2$, J$_{AB}$=9.9 Hz), 3.85 and 3.73 (2m, 2H, OCH$_2$), 3.60 (m, 1H, H-9'), 3.37 (dd, 1H, H-1', J=7.2 and 8.4 Hz), 2.47 (m, 3H, H-5'+CHCH$_3$+H1); δ ($^{13}$C, COCl$_3$): 204.4 (CHO), 173.7 (COOH), 148.2 (C-3), 130.5 (C-2), 98.7 (C-7'), 81.2 (C-1'), 72.8 (8aCH$_2$+OCH$_2$), 69.9 (C-9'), 25.4 (C-6'), 12.4 (CH$_3$CH).

EXAMPLE 22

[1R-(1α, 3aβ, 4β, 4aβ, 7β, 7aα, 8aβ)] 8a-[[1S,7R,9R]-2,8-Dioxa-4,4,9-trimethyl-cis-bicyclo[3.4.0]-non-7-yl-oxy-methyl]-4-formyl-4,4a,5,6,7,7a,8,8a-octahydro-7-methyl-3-(1-methylethyl)-(1,4-methano-s-indacene-3a(1H))-carboxylic acid To a solution of Intermediate 24 (100 mg) in ethyl acetate (40 ml) was added 10% palladium on charcoal (50 mg) under nitrogen. The mixture was shaken in a Parr apparatus under 25 psi of hydrogen for 2 hours at room temperature. The catalyst was filtered off and the solvent evaporated to dryness. The residue was twice flash chromatographed using successively 1.5% methanol in dichloromethane and 15% acetone in hexane as the eluents to afford the title compound (40 mg) as a white foam.

δ ($^1$H, CDCl$_3$): 9.85 (s, 1H, CHO), 6.05 (dd, 1H, H-2, J=1.2 and 3.6 Hz), 4.84 (t, 1H, H-7', J=3 Hz, 4.23 and 3.29 (2d, 2H, 8a-CH$_2$, J=9.6 Hz), 3.81 (t, 1H, H-1', J=8.7 Hz), 3.52 (dq, 1H, H-9', J=9.3 and 6.3 Hz), 3.50 and 3.42 (2d, 2H, CH$_2$-3', J=8.4 Hz), 2.48 (t, 1H, H-1, J=4.2 Hz), 1.09 and 0.98 (2s, 6H, 4'-CH$_3$); δ ($^{13}$C, CDCl$_3$): 204.5 (CHO), 174.0 (COOH), 148.2 (C-3), 130.5 (C-2), 98.7 (C-7'), 81.01 (C-1'), 78.8 (C-3'), 72.7 (8a-CH$_2$), 70.2 (C-9'), 41.3 (C-4'), 40.4 (C-5'), 27.3 (4'-CH$_3$), 26.5 (C-6'), 22.8 (4'-CH$_3$).

EXAMPLE 23

[1R-(1α, 3aβ, 4β, 4aβ, 7β, 7aα, 8aβ)] 8a-[(6-Deoxy-3,4-O-isopropylidene-β-D-allopyranosyloxy)methyl]-4-formyl-4,4a,5,6,7,7a,8 8a-octahydro-7-methyl-3-(1-methylethyl)-1,4-methano-s-indacene-3a(1H)-carboxylic acid To a solution of Intermediate 27 (125 mg) in methanol (25 ml) was added 10% palladium on charcoal (100 mg) under nitrogen. The mixture was shaken in a Parr apparatus under 15 psi of hydrogen for 1.5 hours at room temperature. The catalyst was filtered off and to the filtrate was added 1 N hydrochloric acid (0.5 ml) at 0° C. After stirring for 1hour, the mixture was neutralized with 10% sodium hydrogen carbonate. The solvents were evaporated to dryness and the oily residue was purified by flash column chromatography eluting with hexane:ethyl acetate (4:1) and dichloromethane:methanol (20:1) to give the title compound (62 mg).

δ ($^1$H, CDCl$_3$): 9.73 (s, 1H, CHO), 6.10 (dd, 1H, H-2, J=1.2 and 3.3 Hz), 4.51 (t, 1H, H-2', J=4.5 Hz), 4.48 (d, 1H, H-1', J=7.5 Hz), 3.65 and 4.07 (2d, 2H, 8aCH$_2$, J=9.3 Hz), 3.78 (dd, 1H, H-4', J=9 and 5.1 Hz), 3.69 (dd, 1H, H-3', J=7.5 and 5.1 Hz), 3.50 (m, 1H, H-5', J=6 and 9 Hz), 2.59 (t, 1H, H-1, J=3.9 Hz), 2.32 (m, 1H, CHMe$_2$); δ ($^{13}$C, CDCl$_3$): 204.6 (CHO), 176.1 (CO$_2$H), 148.2 (C-3), 130.8 (C-2), 110.4 (quaternary C Isopilidene), 100.9 (C-1'), 78.34 (C-4'), 75.1 (C-2'), 74.7 (8aCH$_2$), 72.5 (C-4a), 71.7 (C-3'), 69.3 (C-5'), 65.6 (C-8a), 58.9 (C-4), 46.3 (C-1).

EXAMPLE 24

[1R-1α, 3aβ, 4β, 4aβ, 7β, 7aα, 8aβ)] 8a-[(2-Deoxy-3,4-O-isopropylidene-6-O-methyl-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid A solution of Intermediate 30 (50 mg) in tetrahydrofuran (5 ml) at room temperature was treated with tetrabutylammonium fluoride (1.0 M solution in tetrahydrofuran, 200 μl). After 24 hours, the reaction mixture was concentrated to dryness and the resulting yellow oil was purified by flash column chromatography eluting with dichloromethane:methanol (15:1) to give the title compound (18 mg).

δ ($^1$H, CDCl$_3$): 9.80 (s, 1H, CHO), 5.98 (dd, 1H, H-2, J=1.2 and 3.3 Hz), 4.64 (dd, 1H, H-1', J=2.7 and 8.1 Hz), 4.42 (m, 1H, H-3'), 3.68 and 4.01 (2d, 2H, 8aCH$_2$, J=9 Hz), 3.90 (m, 1H, H-4'), 3.45–3.65 (m, 3H, H-5' and 2H-6'), 3.22 (s, 3H, 6'-OCH$_3$), 2.60 (m, 1H, H-1'), 1.34 and 1.35 (2s, 6H, methyl groups of isopropilidene); δ ($^{13}$C, CDCl$_3$): 206.3 (CHO), 175.7 (CO$_2$H), 149.7 (C-3), 129.7 (C-2), 108.9 (C-quaternary of isopropilidene), 98.2 (C-1'), 74.8 (C-3a), 74.8 (C-4), 74.4 (8aCH$_2$), 72.6 (C-3'), 71.3 (C-5'), 65.1 (C-8a), 61.1 (C-6'), 58.4 (C-4), 48.4 (6'-OMe), 46.1 (C-1), 32.8 (C-2').

EXAMPLE 25

[1R-(1α, 3aβ, 4β, 4aβ, 7β, 7aα, 8aβ)] 8a-[[1S,4R,7R,9R]-2,8-Dioxa-4-ethyl-9-methyl-cis-bicyclo[3.4.0]-non-7-yl-oxy-methyl]-4-formyl-4,4a,5,6,7,7a,8,8a-octahydro-7-methyl-3-(1-methyl-ethyl)-1,4-methano-s-indacene-3a(1H)-carboxylic acid To a solution of intermediate 37 (200 mg) in ethyl acetate (40 ml), 10% palladium on charcoal (50 mg) was added under nitrogen. The mixture was shaken in a Parr apparatus under 30 psi of hydrogen at room temperature for 2 hours. The catalyst was filtered off and the solvent evaporated to dryness. The residue thus obtained was flash chromatographed over silica gel using dichloromethane:methanol (98:2) as the eluent to afford the title compound (125 mg).

δ ($^1$H, CDCl$_3$): 9.86 (s, 1H, CHO), 6.05 (dd, 1H, H-2, J=1.5 and 3.3 Hz), 4.66 (dd, 1H, H-7', J=3.0 and 6.0 Hz), 4.32 and 3.29 (2d, 2H, 8a-CH$_2$, J=9.6 Hz), 4.02 (dd, 1H, CH$_2$-3',(1H), J=7.2 and 8.4 Hz), 3.67 (dd, 1H, H-1', J=7.8 and 9.3 Hz), 3.41–3.22 (m, 2H, H-9' and CH$_2$-3' (1H)), 2.48 (t, 1H, H-1, J=3.9 Hz), 0.92 (t, 3H, CH$_3$CH$_2$, J=7.5 Hz); δ ($^{13}$C, CDCl$_3$): 204.5 (CHO), 174.2 (COOH), 148.3 (C-3), 130.5 (C-2), 98.5 (C-7'), 80.3 (C-1'), 73.0 and 73.0 (8a-C and C-3'), 70.9 (C-9').

EXAMPLE 26

[1R-(1α, 3aβ, 4β, 4aβ, 7β, 7aα, 8aβ)] 8a-[[1S,4R,7R,9R]-2,8-Dioxa-4-ethyl-9-methyl-cis-bicyclo[3.4.0]-non-7-yl-oxy-methyl]-4-formyl-4,4a,5,6,7,7a,8,8a-octahydro-7-methyl-3-(1-methyl-ethyl)-1,4-methano-s-indacene-3a (1H)-carboxylic acid, sodium salt To a solution of Example 25 (88 mg) in methanol (10 ml), 0.099 N aqueous sodium hydroxide (1.8 ml) was added dropwise. The solvent was removed under reduced pressure and the residue was dissolved in water (50 ml) and lyophilized to give the title compound (92 mg).

δ ($^1$H, DMSO-d$_6$): 9.77 (s, 1H, CHO), 5.78 (m, 1H, H-2), 4.40 (brdd, 1H, H-7'), 3.92 (m, 1H, H-3'), 3.87 (d, 1H, 8a-CH$_2$ (1H), J=9.6 Hz), 3.50 (m, 2H, 8a-CH$_2$ (1H) and H-1'), 3.38–3.21 (m, 2H, H-3' and H-9').

EXAMPLE 27

[1R-(1α, 3aβ, 4β, 4aβ, 7β, 7aα, 8aβ)] 8a-[[1S,4S,7R,9R]-2,8-Dioxa-4-ethyl-9-methyl-cis-bicyclo[3.4.0]-non-7-yl-oxy-methyl]-4-formyl-4,4a,5,6,7,7a,8,8a-octahydro-7-methyl-3-(1-methyl-ethyl)-1,4-methano-s-indacene-3a (1H)-carboxylic acid To a solution of intermediate 38 (420 mg) in ethyl acetate (80 ml), 10% palladium on charcoal (100 mg) was added under nitrogen. The mixture was shaken in a Parr apparatus under 30 psi of hydrogen at room temperature for 1.5 hour. The catalyst was filtered off and the solvent evaporated to dryness. The residue thus obtained was purified by flash chromatography on silica gel using dichloromethane:methanol (98:2) as the eluent to give the title compound (280 mg).

δ ($^1$H, CDCl$_3$): 9.86 (s, 1H, CHO), 6.05 (dd, 1H, H-2, J=1.5 and 3.6 Hz), 4.89 (m, 1H, H-7'), 4.29 and 3.29 (2d, 2H, 8a-CH$_2$, J=9.9 Hz), 3.90 (dd, 1H, H-3', J=7.5 and 8.7 Hz), 3.75 (m, 1H, H-1'), 3.64 (m,1H, H-9'), 3.43 (t, 1H, H-3', J=8.7 Hz), 2.46 (t, 1H, H-1, J=3.6 Hz), 0.93 (t, 3H, CH$_3$-CH$_2$, J=7.2 Hz); δ ($^{13}$C, CDCl$_3$): 204.4 (CHO), 173.7 (COOH), 148.2 (C-3), 130.5 (C-2), 98.8 (C-7'), 81.3 (C-1'), 72.8 and 70.9 (8a-C and C-3'), 69.8 (C-9').

EXAMPLE 28

[1R-(1α, 3aβ, 4β, 4aβ, 7β, 7aα, 8aβ)] 8a-[[1S,4S,7R,9R]-2,8-Dioxa-4-ethyl-9-methyl-cis-bicyclo[3.4.0]-non-7-yl-oxy-methyl]-4-formyl-4,4a,5,6,7,7a,8,8a-octahydro-7-methyl-3-(1-methyl-ethyl)-1,4-methano-s-indacene-3a(1H)-carboxylic acid, sodium salt To a solution of Example 27 (262 mg) in methanol (20 ml), 0.099N aqueous sodium hydroxide (5.3 ml) was added dropwise. The solvent was removed under reduced pressure and the residue was dissolved in water (100 ml) and lyophilized to give the title compound (272 mg).

δ ($^1$H, DMSO-d$_6$): 9.77 (s, 1H, CHO), 5.79 (dd, 1H, H-2, J=1.2 and 3.6 Hz), 4.57 (m, 1H, H-7'), 3.83 and 3.45 (2d, 2H, 8a-CH$_2$, J=9.6 Hz), 3.76 and 3.33 (2m, 2H, CH$_2$-3'), 3.52 (m, 2H, H-1' and H-9').

EXAMPLE 29

[1R-(1α, 3aβ, 4β, 4aβ, 7β, 7aα, 8aβ)] 8a-[[1S,4R,7R,9R)-2,8-Dioxa-4-(1-methylethyl)-9-methyl-cis-bicyclo[3.4.0]-non-7-yl-oxymethyl)]-4-formyl-4,4a,5,6,7,7a,8,8a-octahydro-7-methyl-3-(1-methylethyl)-1,4-methano-s-indacene-3a(1H)-carboxylic acid To a solution of intermediate 39 (280 mg) in ethyl acetate (15 ml) Palladium (10%) on charcoal was added (50 mg) under nitrogen. The mixture was shaken in a Parr apparatus (PH$_2$=20 psi) for 1 hour at room temperature. Filtration of catalyst and evaporation of the solvent gave a residue which was purified by flash chromatography (silica gel, hexanes:acetone v/v 10:1 and 5:1 to give 180 mg of the title compound as an oil (84% yield).

δ ($^1$H, CDCl$_3$): 12-11 (b, 1H, COOH), 9.88 (s, 1H, CHO), 6.053 (dd, 1H, H2, J=1.5 and 3.6 Hz), 4.77 (m, 1H, H7'), 4.37 (d, 1H, 8aCH2, J=9.3 Hz), 3.95 (dd, 1H, H3', J=7.2 and 8.7 Hz), 3.67 (dd, 1H, H1', J=8.7 and 9 Hz), 3.5–3.36 (m, 2H, H3'+H9'), 3.23 (d, 1H, 8aCH$_2$, J=9.3 Hz), 2.43 (t, 1H, H1, J=3.9 Hz).

EXAMPLE 30

[1R-(1α, 3aβ, 4β, 4aβ, 7β, 7aα, 8aβ)] 8a-[(1S,4R,7R,9R)-2,8-Dioxa-4-(1-methylethyl)-9-methyl-cis-bicyclo[3.4.0]-non-7-yl-oxymethyl)]-4-formyl-4,4a,5,6,7,7a,8,8a-octahydro-7-methyl-3-(1-methylethyl)-1,4-methano-s-indacene-3a(1H)-carboxylic acid, sodium salt To a solution of Example 29 (170 mg) in methanol (15 ml) was added 0.0956 N solution of sodium hydroxide (3.45 ml). After stirring for 1 hour the solvent was removed to dryness to give a solid which was dissolved in 3 ml of water and freeze dried.

δ ($^1$H, DMSO-d$_6$): 9.78 (s, 1H, CHO), 5.80 (dd, 1H, H2, J=1.2 and 3.6 Hz), 4.46 (dd, 1H, H7', J=2.7 and 5.1 Hz), 3.9–3.8 (m, 2H, H3'+8aCH$_2$), 3.54 (dd, 1H, H1', J=8.1 and 9 Hz), 3.47 (d, 1H, 8aCH$_2$, J=9.3 Hz); δ ($^{13}$C, DMSO-d$_6$): 206.4 (CHO), 174.3 (COO$^-$), 151.3 (C3), 127.6 (C2), 97.1 (C7'), 80.7 (C1').

EXAMPLE 31

[1R-(1α, 3aβ, 4β, 4aβ, 7β, 7aα, 8aβ)] 8a-[(1S,4S,7R,9R)-2,8-Dioxa-4-(1-methylethyl)-9-methyl-cis-bicyclo[3.4.0]-non-7-yl-oxymethyl)]-4-formyl-4,4a,5,6,7,7a,8,8a-octahydro-7methyl-3-1-methylethyl)-1,4methano-s-indacene-3a(1H)-carboxylic acid To a solution of intermediate 40 (280 mg) in ethyl acetate (15 ml), palladium (10%) on charcoal was added (50 mg) under nitrogen. The mixture was shaken in a Parr apparatus (PH$_2$=20 psi) for 1 hour at room temperature. Filtration of catalyst and evaporation of the solvent gave a residue which was flash chromatographed (silica gel, hexanes:acetone v/v 10:1 and 5:1) to give 190 mg of the title compound as a crystalline solid (89% yield).

δ ($^1$H, CDCl$_3$): 9.88 (s, 1H, CHO), 6.05 (dd, 1H, H2, J=1.5 and 3.3 Hz), 4.92 (t, 1H, H7', J=2.7 Hz, 4.33 (d, 1H, 8aCH$_2$, J=10.2 Hz), 3.94 (t, 1H, H3', J=8.1 Hz), 3.8–3.7 (m, 2H, H1'+H9'), 3.47 (dd, 1H, H3', J=8.4 and 10.8 Hz), 3.29 (d, 1H, 8aCH$_2$, J=10.5 Hz).

EXAMPLE 32

[1R-(1α, 3aβ, 4β, 4aβ, 7β, 7aα, 8aβ)] 8a-[(1S,4S,7R,9R)-2,8-Dioxa-4-(1-methylethyl)-9-methyl-cis-bicyclo[3.4.0]-non-7-yl-oxymethyl)]-4-formyl-4,4a,5,6,7,7a,8,8a-octahydro-7-methyl-3-(1-methylethyl)-1,4-methano-s-indacene-3a(1H)carboxylic acid, sodium salt To a solution of Example 31 (165 mg) in methanol (15 ml) were added 0.0956 N solution of sodium hydroxide (3.35 ml). After stirring for 1 hour the solvent was removed to dryness to give a solid which was dissolved in 3 ml of water and freeze dried.

δ ($^1$H, CDCl$_3$): 9.77 (s, 1H, CHO), 5.79 (dd, 1H, H2, J=0.9 and 3.3 Hz), 4.58 (bs, 1H, H7'), 3.85–3.72 (m, 2H, H3'+8aCH$_2$), 3.71–3.56 (m, 2H, H9'+H1'), 3.45 (d, 1H, 8aCH$_2$, J=9.9 Hz); δ ($^{13}$C, CDCl$_3$): 206.3 (CHO), 174.3 (COO$^-$), 151.4 (C3), 127.5 (C2), 96.7 (C7'), 80.8 (C1').

EXAMPLE 33

[1R-(1α, 3aβ, 4β, 4aβ, 7β, 7aα, 8aβ] 8a-[[1S,7R,9R]-2,8-Dioxa-9-methyl-4-methylene-cis-bicyclo [3.4.0]-non-7-yl-oxy-methyl]-4-formyl-4,4a,5,6,7,7a,8,8a-octahydro-7-methyl-3-(1methylethyl)-1,4-methano-s-indacene-3a(1H-carboxylic acid To an ice cooled solution of intermediate 41 (330 mg) in dichloromethane (4 ml) was added trifluoroacetic acid (0.2 ml). The mixture was stirred for 20 minutes at 0° C. and subsequently diluted with dichloromethane (150 ml) and washed three times with water (100 ml). The organic layer was dried over anhydrous sodium sulfate and concentrated to dryness to give an oil which was flash chromatographed on silica gel using dichloromethane:methanol (98:2) as the eluent. The appropriate fractions were then collected and RP-18 chromatographed under medium pressure (about 10 bars) using a linear gradient of acetonitrile (60 to 75%) in water to give the title compound.

δ ($^1$H, CDCl$_3$): 9.87 (s, 1H, CHO), 6.04 (d, 1H, H-2, J=3.3 Hz), 5.08 and 5.02 (2m, 2H, H$_2$C═), 4.50 (dd, 1H, H-7', J=2.7 and 8.4 Hz), 4.48–4.29 (m, 3H, CH$_2$-3' and 8a-CH$_2$ (1H)), 3.76 (dd, 1H, H-1', J=7.2 and 9.3 Hz), 3.27 (m, 1H, H-9'), 3.02 (m, 1H, H-5'), 2.45 (m, 1H, H-1); δ ($^{13}$C, CDCl$_3$): 205.1 (CHO), 176.0 (COOH), 148.6 (C-3), 130.4 (C-2), 104.2 (CH$_2$═), 98.2 (C-7'), 80.1 (C-1'), 73.4 and 70.6 (8a-CH$_2$ and C-3'), 69.8 (C-9').

EXAMPLE 34

[1R-(1α, 3aβ, 4β, 4aβ, 7β, 7aα, 8aβ)] 8a-[[1S,7R,9R]-2,8-Dioxa-9-methyl-4-methylene-cis-bicyclo[3.4.0]-non-7-yl-oxy-methyl]-4-formyl-4,4a,5,6,7,7a,8,8a-octahydro-7-methyl-3-(1-methylethyl)-1,4-methano-s-indacene-3a(1H)-carboxylic acid, sodium salt To a solution of Example 33 (140 mg) in methanol (15 ml), 0.945 N aqueous sodium hydroxide (3.06 ml) was added dropwise. The solvent was removed under reduced pressure and the residue was dissolved in water (60 ml) and lyophilized to give the title compound (145 mg).

δ ($^1$H, DMSO-$_6$): 9.76 (s, 1H, CHO), 5.76 (d, 1H, H-2, J=3.3 Hz), 5.04 (m, 2H, H$_2$C═), 4.34–4.20 (m, 3H, H-7' and CH₂-3'), 3.84 and 3.50 (2d, 2H, 8a-CH₂, J=9.9 Hz), 3.62 (dd, 1H, H-1', J=7.5 and 9.3 Hz), 3.15 (m, 1H1, H-9'), 2.89 (m, 1H, H-5').

EXAMPLE 35

[1R-(1α, 3aβ, 4β, 4aβ, 7β, 7aα, 8aβ)] 8a-[[1S,7R,9R]-2,8-Dioxa-9-methyl-4-methylene-3-oxo-cis-bicyclo[3.4.0]-non-7-yl-oxy-methyl]-4-formyl-4,4a,5,6,7,7a,8,8a-octahydro-7-methyl-3-(1-methyl-ethyl)-1,4-methano-s-indacene-3a(1H) carboxylic acid To a solution of intermediate 42 (62 mg) in dry dichloromethane (1.1 ml) was added trifluoroacetic acid (0.05 ml). The mixture was stirred at 0° C. for 20 minutes, then diluted with dichloromethane (50 ml) and washed with water (3×25 ml). The organic layer was dried over anhydrous sodium sulfate and concentrated to give an oil which was twice flash chromatographed on silica gel using dichloromethane:methanol (98:2) as the eluent. The title compound was thus obtained (25 mg) as a pale yellow foam.

δ ($^1$H, CDCl₃): 9.75 (s, 1H, CHO), 6.35 and 5.63 (2d, 2H, H₂C=C, J=3.3 Hz), 6.04 (dd, 1H, H-2, J=1.2 and 3.3 Hz), 4.52 (t, 1H, H-7', J=4.8 Hz), 4.24 (t, 1H, H-4', J=8.7 Hz), 4.09 and 3.46 (2d, 2H, 8a-CH₂, J=9.3 Hz), 3.38 (m, 1H, H-5'), 3.30 (m, 1H, H-9'), 2.59 (t, 1H, H-1, J=3.9 Hz); δ ($^{13}$C, CDCl₃): 204.5 (CHO), 175.3 (COOH), 169.7 (C-3'), 148.2 (C-3), 136.8 (C-4'), 130.6 (C-2), 122.4 (C=CH2), 97.7 (C-7'), 77.8 (C-1') and 71.2 (C-9').

EXAMPLE 36

[1R-(1α, 3aβ, 4β, 4aβ, 7β, 7aα, 8aβ)] 8a-[[1S,7R,9R]-2,8-Dioxa-9-methyl-4-methylene-3-oxo-cis-bicyclo[3.4.0]-non-7-yl-oxy-methyl]-4-formyl-4,4a,5,6,7,7a,8,8a-octahydro-7-methyl-3-(1-methyl-ethyl)-1,4-methano-s-indacene-3a (1H)-carboxylic acid, sodium salt To a solution of Example 35 (25 mg) in methanol (10 ml), 0.0945 N aqueous sodium hydroxide (0.53 ml) was added dropwise. The solvent was removed under reduced pressure and the residue was dissolved in water (25 ml) and lyophilized to give the title compound (26 mg).

δ ($^1$H, DMSO-d₆): 9.75 (s, 1H, CHO), 6.15 and 5.82 (2d, 2H, H₂C=C, J=3.3 Hz), 5.76 (brd, 1H, H-2), 4.31 (dd, 1H, H-7', J=2.4 and 7.8 Hz), 4.24 (t, 1H, H-1', J=8.7 Hz), 3.84 and 3.52 (2d, 2H, 8a-CH₂, J=9.9 Hz), 3.38 (m, 1H, H-5), 3.21 (ml 1H, H-9').

EXAMPLE 37

[1R-(1α, 3aβ, 4β, 4aβ, 7β, 7aα, 8aβ)] 8a-[[1S,7R,9R]-2,8-Dioxa-9-methyl-4-oxo-cis-bicyclo[3.4.0]-non-7-yl-oxy-methyl]-4-formyl-4,4a,5,6,7,7a,8,8a-octahydro-7-methyl-3-(1-methyl-ethyl)-1,4methano-s-indacene-3a(1H)-carboxylic acid To a solution of intermediate 43 (45 mg) in ethyl acetate (15 ml) was added 10% palladium on charcoal (25 mg) under nitrogen. The mixture was shaken in a Parr apparatus under 25 psi of hydrogen for 1 hour at room temperature. The catalyst was filtered off and the solvent evaporated to dryness. The residue thus obtained was purified by flash chromatography on silica gel using hexane:ethyl acetate (65:35) as the eluent to afford the title compound (25 mg).

δ ($^1$H, CDCl₃): 9.77 (s, 1H, CHO), 6.05 (dd, 1H, H-2, J=1.5 and 3.6 Hz), 4.17 (m, 4H, H-3' (1H), 8a-CH₂ (1H), H-7' and H-1'), 3.90 (d, 1H, H-3' (1H), J=17.7 Hz), 3.42 (d, 1H, 8a-CH₂ (1H), J=9 Hz), 3.31 (m, 1H, H-9'), 2.85 (m, 1H, H-5'), 2.58 (t, 1H, H-3, J=3.9 Hz); δ ($^{13}$C, CDCl₃): 214.4 (C-4), 204.8 (CHO), 148.3 (C-3), 130.6 (C-2), 98.9 (C-7'), 78.6 and 70.3 (C-1' and C-9'), 73.6 and 69.1 (C8a-C and C-3').

EXAMPLE 38

[1R-(1α, 3aβ, 4β, 4aβ, 7β, 7aα, 8aβ)] 8a-[[1S,4S,6S,7R,9R]-2,8-Dioxa-4-ethyl-6-hydroxy-9-methyl-cis-bicyclo[3.4.0]-non-7-yl-oxy-methyl]-4-formyl-4,4a,5,6,7,7a,8,8a-octahydro-7-methyl-3-(methylethyl)-1,4-methano-s-indacene-3a(1H)-carboxylic acid To a solution of Intermediate 45 (123 mg) in ethyl acetate (50 ml) 10% palladium on charcoal (65 mg) was added under nitrogen and the mixture hydrogenated under 15 psi of hydrogen for 1 hour at room temperature. The catalyst was filtered off and the solvent evaporated to dryness. The residue was flash chromatographed on silica gel eluting with dichloromethane:methanol (19:1) to (18:2) to give the title compound (90 mg).

δ ($^1$H, CDCl₃): 9.67 (s, 1H, CHO), 6.07 (d, 1H, H-2, J=3.3 Hz), 4.64 (d, 1H, H-7', J=3.6 Hz), 4.02 (d, 1H, 8aCHa, J=9.9 Hz), 3.89 (dd, 1H, Ha-3', J=6.9 and 9 Hz), 3.85–3.7 (m, 3H, H-6', H-1' and H-9'), 3.68–3.5 (m, 2H, Hb-3' and 8a-CHb), 2.65 (t, 1H, H-1, J=3.6 Hz); δ ($^{13}$C, CDCl₃): 204.9 (CHO), 176.3 (CO₂H), 148.9 (C-3), 130.1 (C-2), 99.2 (C-7'), 80.5, 70.1 and 65.5 (C-6', C-1' and C-9'), 73.7 and 71.0 (8a-CH₂ and C-3'), 13.4 (CH₂—CH₃).

EXAMPLE 39

[1R-(1α, 3aβ, 4β, 4aβ, 7β, 7aα, 8aβ)] 8a-[[1S,4R,6S,7R,9R]-2,8-Dioxa-4-ethyl-6-hydroxy-9-methyl-cis-bicyclo[3.4.0]-non-7-yl-oxy-methyl]4-formyl-4,4a,5,6,7,7a,8,8a-octahydro-7-methyl-3-(1-methylethyl)-1,4-methano-s-indacene-3a(1H)-carboxylic acid To a solution of intermediate 46 (102 mg) in ethyl acetate (25 ml) 10% palladium on charcoal (60 mg) was added under nitrogen and the mixture hydrogenated under 15 psi of hydrogen for 1 hour at room temperature. The catalyst was filtered off and the solvent evaporated to dryness. The residue was flash chromatographed on silica gel eluting with dichloromethane:methanol (25:1) to give the title compound (75 mg).

δ (1H, CDCl₃): 9.73 (s, 1H, CHO), 6.08 (dd, 1H, H-2, J=1.2 and 3.6 Hz), 4.53 (d, 1H, H-7', J=1.8 Hz), 4.05 (dd, 1H, Ha-3', J=7.2 and 8.4 Hz), 4.02 (d, 1H, 8a-CHa, J=9.3 Hz), 3.83 (dd, 1H, H-1', J=7.2 and 8.7 Hz), 3.72 (dd, 1H, H-6', J=2.1 and 4.8 Hz), 3.64 (d, ₁H, 8a-CHb, J=9.3 Hz), 3.54–3.36 (m, 2H, H-9' and Hb-3'), 2.68 (t, 1H, H-1, J=3.9 Hz), 0.96 (t, 3H, CH₃—CH₂, J=7.5 Hz); δ ($^{13}$C, CDCl₃): 204.7 (CHO), 176.1 (CO₂H), 148.5 (C-3), 130.5 (C-2), 98.8 (C-7'), 79.2, 70.7 and 69.1 (C-6', C-1' and C-9'), 73.7 and 72.7 (8a-CH₂ and C-3'), 12.7 (CH₂-CH₃).

EXAMPLE 40

[1R(1α, 3aβ, 4β, 4aβ, 7β, 7aα, 8aβ)] 8a-[(1S,4R,6S,7R,9R]-2,8-Dioxa-4-ethyl-6-hydroxy-9-methyl-cis-bicyclo[3.4.0]-non-7-yl-oxy-methyl]-4-formyl-4,4a,5,6,7,7a,8,8a-octahydro-7-methyl-3-(1-methylethyl-1,4-methano-s-indacene-3a(1H)carboxylic acid, sodium salt To a solution of Example 39 (490 mg) in methanol (50 ml) was added dropwise 0.095 N aqueous sodium hydroxide solution (10 ml). After 30 minutes the solvent was removed under reduced pressure and the residue dissolved in water (10 ml) and lyophilized to give the title compound (475 mg).

δ ($^1$H, (CD₃)₂SO): 9.77 (s, 1H, CHO), 5.8 (d, 1H, H-2, J=2.4 Hz), 4.41 (bs, 1H, —OH), 4.31 (d, 1H, H-7', J=2.1 Hz), 3.94–3.82 (m, 2H, 8aCHa and Ha-3'), 3.66 (t, 1H, H-1', J=8.1 Hz), 3.54–3.34 (m, 3H, 8aCHb, H-6' and H-9'), 3.24 (t, 1H, Hb-3', J=8.1 Hz), 2.55 (t, 1H, H-1, J=3.6 Hz).

EXAMPLE 41

[1R-(1α, 3aβ, 4β, 4aβ, 7β, 7aα, 8aβ)] 8a-[[1S,7R,9R]-2,8-Dioxa-9-methyl-4-oxo-cis-bicyclo[3.4.0]-non-7-yl-oxymethyl]-4-formyl-4,4a,5,6,6,7,7a,8,8a-octahydro-7-methyl-3-(1-methylethyl)-1,4-methano-s-indacene-3a(1H)-carboxylic acid, sodium salt To a solution of intermediate 43 (350 mg) in ethyl acetate (15 ml), palladium (10%) on charcoal was added (50 mg) under nitrogen. The mixture was shaken in a Parr apparatus ($PH_2$=25 psi) for 1 hour at room temperature. Filtration of catalyst and evaporation of the solvent gave a residue which was flash chromatographed (silica gel, dichloromethane:methanol v/v 100:1, 70:1 and 50:1) to obtain 200 mg of a foam which was dissolved in methanol (10 ml) and treated with 0.0947 M sodium hydroxide (4.54 ml). the solvent was removed under vacuum and the resulting solid dissolved in water (15 ml) and freeze dried.

δ ($^1$H, DMSO-d6): 9.76 (s, 1H, CHO), 5.80 (dd, 1H, H2, J=0.9 and 3.3 Hz), 4.20–3.95 (m, 4H, H7'+H1'+H3'), 3.89 (d, 1H, $8aCH_2$, J=9.6 Hz), 3.47 (d, 1H, $8aCH_2$, J=9.6 Hz), 2.92 (m, 1H, H5').

EXAMPLE 42

[1R-(1α, 3aβ, 4β, 4aβ, 7β, 7aα, 8aβ)] 8a-[(1S,4R,7R,9R)-2,8-Dioxa-4-methoxy-9-methyl-cis-bicyclo[3,4,0]-non-7-yl-oxymethyl]-4-formyl-4,4a,5,6,7,7a,8,8a-octahydro-7-methyl-3-(1-methylethyl)-1,4-methano-s-indacene-3a(1H)-carboxylic acid, sodium salt To a solution of intermediate 82 (250 mg) in ethyl acetate (15 ml), palladium (10%) on charcoal was added (50 mg) under nitrogen. The mixture was shaken in a Parr apparatus ($PH_2$=25 psi) for 1 hour at room temperature. Filtration of catalyst and evaporation of the solvent gave a residue which was flash chromatographed (silica gel, dichloromethane:methanol 100:1, 70:1, 50:1 and 40:1) to obtain 120 mg of a syrup which was dissolved in methanol (15 ml) and treated with 0.0947 M sodium hydroxide (2.51 ml). Elimination of the solvent gave a semisolid which was dissolved in water (15 ml) and freeze dried.

δ ($^1$H, DMSO-d6): 9.77 (s, 1H, CHO), 5.80 (dd, 1H, H2, J=1.2 and 3.3 Hz), 4.47 (t, 1H, H7', J=3.9 Hz), 3.96–3.84 (m, 2H, H3'+$8aCH_2$), 3.80 (m, 1H, H4'), 3.65– 3.40 (m, 4H, H9'+$8aCH_2$+H3'+H1'), 3.23 (s, 3H, $OCH_3$), 2.46–2.2 (m, 4H, H1+H6'+H5'+$CH(CH_3)_2$); δ ($^{13}$C, DMSO-d6): 206.4 (CHO), 174.4 (COO$^-$), 151.3 (C3), 127.6 (C2), 96.9 C7'), 84.1 (C4'), 56.6 ($OCH_3$).

EXAMPLE 43

[1R-(1α, 3aβ, 4β, 4aβ, 7β, 7aα, 8aβ)] 8a-[(1S,7R,9R)-2,8-Dioxa-9-methyl-bicyclo [3,4,0]-non-4-ene-7-yl-oxymethyl] 4-formyl-4,4a,5,6,7,7a,8,8a-octahydro-7-methyl-3-(1-methylethyl)-1,4methano-s-indacene-3a(1H)-carboxylic acid To a solution of intermediate 87 (120 mg) in dry dichloromethane (20 ml) was added at 0° C. under nitrogen atmosphere trifluoroacetic acid (100 μl). After 5 minutes the mixture was diluted with dichloromethane (100 ml) and washed with water (100 ml) and brine (100 ml), then dried over magnesium sulfate and concentrated to give a crude which was dissolved in a mixture tetrahydrofuran:methanol (v/v 2:1, 15 ml) and treated with 1 N hydrochloric acid (5 ml). After completion of the reaction it was diluted with water (100 ml) and extracted twice with dichloromethane. The organic layer was dried over magnesium sulfate to give an oil which was purified by preparative TLC (silica gel; acetone:hexanes 1:3) to afford 62 mg of the title compound (73% yield) as a white foam.

δ ($^1$H, $CDCl_3$): 9:79 (s, 1H, CHO), 6.06 (dd, 1H, H2, J=1.2 and 3.3 Hz), 5.56 (m, 1H, H4'), 4.65–4.65 (m, 2H, H3'), 4.3–4.0 (m, 3H, H7'+$8aCH_2$+H1'), 3.50 (d, 1H, $8aCH_2$, J=9 Hz), 3.18 (dq, 1H, H9', J=6.3 and 9 Hz), 2.72 (m, 1H, H6'), 2.62 (t, 1H, H1, J=3 Hz); δ ($^{13}$C, $CDCl_3$): 204.6 (CHO), 175.2 (COOH), 148.3(C3), 136.3 (C5'), 130.6 (C2), 119.15 (C4'), 101.5 (C7'), 86.5 (C1').

EXAMPLE 44

[1R-(1α, 3aβ, 4β, 4aβ, 7β, 7aα, 8aβ)] 8a-[(1S,7R,9R)-2,8-Dioxa-9-methyl-bicyclo [3.4.0]-non-4-ene-7-yl-oxymethyl]-4-formyl-4,4a,5,6,7,7a,8,8a-octahydro-7-methyl-3-(1-methylethyl)-1,4methano-s-indacene-3a(1H)-carboxylic acid, sodium salt To a solution of Example 43 (50 mg) in methanol (5 ml) was added 0.0966 N sodium hydroxide (1.09 ml). The mixture was stirred for 15 minutes and the solvent removed to dryness. The residue was dissolved in water (1 ml) and freeze dried.

δ ($^1$H, DMSO-d6): 9.78 (s, 1H, CHO), 5.80 (bd, 1H, H2, J=3.6 Hz), 5.64 (bs, 1H, H4'), 4.6–4.4 (m, 2H, H3'), 4.1 (dd, 1H, H7', J=2.7 and 9.3 Hz), 4.05–3.90 (m, 2H, H1'+$8aCH_2$), 3.56 (d, 1H, $8aCH_2$, J=9.6 Hz), 3.06 (dq, 1H, H9', J=6.3 and 8.7 Hz); δ ($^{13}$C, DMSO-d6): 215.9 (CHO), 183.9 (COO$^-$), 160.9 (C3), 146.1 (C5'), 137.2 (C2), 128.3 (C4'), 110.9 (C7'), 95.7 (C1').

EXAMPLE 45

[1R-(1α, 3aβ, 4β, 4aβ, 7β, 7aα, 8aβ)] 8a-[(1S,7R,9R)-Dioxa-9-methyl-cis-bicyclo [3,4,0]-non-7-yl-oxymethyl]-4-formyl4,4a,5,6,7,7a,8,8a-octahydro-7-methyl-3-(1-methylethyl)-1,4-methano-s-indacene-3a(1H)-carboxylic acid To a solution of intermediate 87 (100 mg) in ethyl acetate (15 ml), palladium (10%) on charcoal was added (50 mg) under nitrogen. The mixture was shaken in a Parr apparatus ($PH_2$=20 psi) for 1 hour at room temperature. Filtration of catalyst and evaporation of the solvent gave a residue which was dissolved in a mixture tetrahydrofuran:methanol (v/v 2:1, 15 ml) and treated with 1 N hydrochloric acid (5 ml). After completion of the reaction dichloromethane (100 ml) and water (100 ml) were added and the 2 layers partionated. The organic layer was dried over magnesium sulfate and concentrated to give an oil which was purified by preparative TLC (hexanes:acetone, v/v 3:1) to afford 20 mg of the title compound as a transparent oil (30% overall yield).

δ ($^1$H, $CDCl_3$): 9.86 (s, 1H, CHO), 6.05 (dd, 1H, H2, J=1.5 and 3.6 Hz), 4.07 (dd, 1H, H7', J=3 and 5.4 Hz), 4.33 (d, 1H, $8aCH_2$, J=9.6 Hz), 3.90 (m, 1H, H3)', 3.69 (m, 1H, H3'), 3.61 (dd, 1H, H1', J=8.1 and 9 Hz), 3.39 (dq, 1H, H9', J=6 and 9 Hz), 3.28 (d, 1H, $8aCH_2$, J=9.6 Hz), 2.6–2.4 (m, 2H, H5'+H1), 2.32 (m, 1H, $CH(CH_3)_2$).

EXAMPLE 46

[1R-(1α, 3aβ, 4β, 4aβ, 7β, 7aα, 8aβ)] 8a-[(1S,4R,6S,7R,9R)-2,8-Dioxa-4,9-dimethyl-6-hydroxy-cis-bicyclo[3.4.0]-non-7-yl-oxy-methyl]]-4-formyl-4,4a,5,6,7,7a,8,8a-hydro-7-methyl-3-(1-methyl-ethyl)-1,4-methano-s-indacene-3a (1H)-carboxylic acid To a solution of Intermediate 89b (90 mg) in ethyl acetate (25 ml) 10% palladium on charcoal (50 mg) was added under nitrogen and the mixture hydrogenated under 40 psi of hydrogen for 45 minutes at room temperature. The catalyst was filtered off and the solvent evaporated to dryness. The residue was flash chromatographed on silica gel eluting with dichloromethane:ethyl acetate (10:1) to give the title compound (60 mg).

δ ($^1$H, $CDCl_3$): 9.74 (s, 1H, CHO), 6.08 (dd, 1H, H-2, J=1.5 and 3.6 Hz), 4.53 (d, 1H, H-7', J=2.1 Hz), 4.09 (d, 1H, 8a-CHa, J=9.6 Hz), 4.02 (dd, 1H, Ha-3', J=7.5 and 8.4 Hz), 3.84 (dd, 1H, H-1', J=7.8 and 9 Hz), 3.74 (dd, 1H, H-6', J=2.1 and 5.1 Hz), 3.60 (d, 1H, 8a-CHb, J=9.3 Hz), 3.42 (dq, 1H, H-9', J=6 and 9 Hz), 3.34 (t, 1H, Hb-3', J=8.7 Hz), 2.66 (t, 1H, H-1, J=3.9 Hz).

EXAMPLE 47

[1R-(1α, 3aβ, 4β, 4aβ, 7β, 7aα, 8aβ)] 8a-[(1S,4R,6S,7R,9R)-2,8-Dioxa-4,9-dimethyl-6-hydroxy-cis-bicyclo[3.4.0]- non-7-yl-oxy-ethyl]-4-formyl-4,4a,5,6,7,7a,8,8a-octahydro-7-methyl-3-(1-methyl-ethyl)-1,4-methano-s-indacene-3a(1H)-carboxylic acid, sodium salt To a solution of Example 46 (258 mg) in methanol (20 ml) was added dropwise 0.103 N aqueous sodium hydroxide solution (4.98 ml). After 15 minutes the solvent was removed under reduced pressure and the residue dissolved in water (10 ml) and lyophilized to give the title compound (250 mg).

δ ($^1$H, (CD$_3$)$_2$SO): 9.77 (s, 1H, CHO), 5.79 (d, 1H, H-2, J=3.6 Hz), 4.29 (d, 1H, H-7', J=1.8 Hz), 3.94–3.8 (m, 2H, 8a-CHa and Ha-3'), 3.67 (t, 1H, H-1', J=8.4 Hz), 3.55–3.25 (m, 3H, 8a-CHb, H-6', H-9'), 3.14 (t, 1H, Hb-3', J=8.4 Hz), 2.54 (t, 1H, H-1, J=3.6 Hz).

EXAMPLE 48

[1R-(1α, 3aβ, 4β, 4aβ, 7β, 7aα, 8aβ)] 8a-(((2,3,6-Trideoxy-3-ethylamino-3-N,4-O-carbonyl-β-D-allopyranosyl)oxy)methyl-4-formyl-4,4a,5,6,7,7a,8,8a-octahydro-7-methyl-3-(1-methylethyl)-1,4-methano-s-indacene-3a(1H)-carboxylic acid To a solution of intermediate 96 (180 mg) in ethyl acetate (15 ml), palladium (10%) on charcoal was added (30 mg) under nitrogen. The mixture was shaken in a Parr apparatus (PH$_2$=20 psi) for 2 hours at room temperature. The catalyst was filtered and the solvent evaporated to dryness. The residue was purified by flash column chromatography on silica gel eluting with hexane:ethyl acetate 1:1 to give pure GM 233039X (70 mg).

δ ($^1$H, CDCl$_3$): 9.76 (s, 1H, CHO), 6.05 (dd, 1H, H-2, J=3.0 and 1.2 Hz), 4.64 (dd, 1H, H-1', J=5.7 and 3.3 Hz), 4.11 (m, 2H, H-3', H-4'), 4.04 (d, 1H, H-8a, J=9.3 Hz), 3.62 (dq, 1H, H-5', J=8.4 and 6.0 Hz), 3.51 (d, 1H, H-8a, J=9.3 Hz), 3.49 (m, 1H, CH$_2$—CH$_3$), 3.13 (m, 1H, CH$_2$—CH$_3$), 2.62 (t, 1H, H-1, J=3.6 Hz), 2.32 (m, 1H, CH(CH$_3$)$_2$), 1.15 (t, 3H, CH$_3$, J=7.2 Hz); δ ($^{13}$C, CDCl$_3$): 204.4 (CHO), 175.7 (COOH), 157.6(N—COO), 148.3 (C-3), 130.5 (C-2), 97.2 (C-1'), 74.2 (C-4'), 73.4 (8a-CH$_2$), 69.4 (C-5'), 51.2 (C—N).

EXAMPLE 49

[1R-(1α, 3aβ, 4β, 4aβ, 7β, 7aα, 8aβ)] 8a-[(2,3-Anhydro-6-deoxy-4-O-methyl-β-D-mannopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 50 (140 mg) in ethyl acetate (20 ml) was added 10% palladium on charcoal (100 mg) under nitrogen. The mixture was shaken in a Parr apparatus under 15 psi hydrogen for 1 hour at room temperature. The catalyst was filtered off and the solvent evaporated to dryness. The residue was purified by flash chromatography on silica gel, eluting with hexane:ethyl acetate (5:1) and dichloromethane:methanol (20:1). The appropriate fractions were combined and the solvent removed to give the title compound (85 mg) as a foam.

δ ($^1$H, CDCl$_3$): 9.76 (s, 1H, CHO), 6.08 (dd, 1H, H-2, J=1.2 and 3.3 Hz), 4.74 (s, 1H, H-1'), 3.63 and 4.13 (2d, 2H, 8aCH$_2$, J=9.3 Hz), 3.48 (m, 4H, H-4' and 4'-OMe), 2.26 (d, 1H, H-2', J=3.9 Hz), 3.19 (m, 1H, H-5'), 3.13 (d, 1H, H-3', J=3.9 Hz), 3.06 (d, 1H, H-4', J=8.7 Hz), 2.74 (t, 1H, H-1, J=3.6 Hz); δ ($^{13}$C, CDCl$_3$): 204.8 (CHO), 175.6 (CO$_2$H), 148.2. (C-3), 130.8 (C-2), 98.0 (C-1'), 76.5 (C-4'), 74.3 (8aCH$_2$), 74.4 (C-3a), 72.5 (C-5'), 65.6 (C-8a), 59.0 (C-4), 58.2 (4'-OMe), 53.6 (C-2'), 50.3 (C-3'), 46.4 (C-1).

EXAMPLE 50

[1R-(1α, 3aβ, 4β, 4aβ, 7β, 7aα, 8aβ)] 8a-[(2,3-Anhydron-6-deoxy-4-O-methyl-β-D-mannopyranosyloxy)methyl]-4-formyl-4,4a,5,6,7,7a8,8a-octahydro-7-methyl-3-(1-methylethyl)-1,4-methano-s-indacene-3a(1H)-carboxylic acid, sodium salt Example 49 (310 mg) was dissolved in methanol (10 ml) and an sodium hydroxide solution (0.0976 N, 6.69 ml) was added. The mixture was stirred for 2 hours at room temperature. The solvent was removed and the residue was dissolved in water (2 ml) and freeze-dried to yield the title compound (324 mg) of as white solid.

δ ($^1$H, CDCl$_3$): 9.87 (s, 1H, CHO), 5.98 (dd, 1H, H-2, J=1.5 and 3.6 Hz), 4.69 (s, 1H, H-1'), 3.85 and 4.07 (2d, 2H, 8aCH$_2$, J=9.6 Hz), 3.47 (s, 3H, 4'-OMe), 3.26 (d, 1H, H-2', J=3.9 Hz), 3.19 (dq, 1H, H-5', J=5.7 and 9 Hz), 3.12 (d, 1H, H-3', J-3.9 Hz), 2.97 (dd, 1H, H-4', J=0.6 and 8.7 Hz), 2.66 (t, 1H, H-1, J=3.6 Hz); δ ($^{13}$C, CDCl$_3$): 209.6,(CHO), 178.6 (CO$_2$H), 152.4 (C-3), 130.2 (C-2), 100.1 (C-1'), 78.2 (C-4'), 77.9 (8aCH$_2$), 73.8 (C-3a), 73.9 (C-5'), 65.6 (C-8a), 59.2 (C-4), 58.2 (4'-OMe), 54.6 (C-2'), 51.9 (C-3'), 46.4 (C-1).

EXAMPLE 51

[1R-(1α, 3aβ, 4β, 4aβ, 7β, 7aα, 8aβ)] 8a-[(2,3-Epithio-4-O-methyl-2,3,6-trideoxy-β-D-mannopyranosyloxy)methyl]-4-formyl-4,4a,5,6,7,7a,8,8a-octahydro-7-methyl-3-(1-methylethyl)-1,4-methano-s-indacene-3a(1H)-carboxylic acid A mixture of Intermediate 52 (0.67 mmol), 5,5-dimethyl-2-thiolo-2-thioxo-1,3,2-dioxaphosphorinane[1] (3.37 mmol) and triethylamine (4.02 mmol) in dry dimethylformamide (5 ml) was heated for 48 hours at 100° C. After cooling, the mixture was poured into aqueous ether. The organic phase was evaporated and the residue purified by flash chromatography using dichloromethane:methanol (30:1) as eluent to give the title compound (180 mg).

[1]R. S. Edmundson; Tetrahedron, 21, 2379 (1965).

δ ($^1$H, CDCl$_3$): 9.77 (s, 1H, CHO), 6.08 (dd, 1H, H-2, J=1,2 and 3.3 Hz), 4.95 (d, 1H, H-1', J=1.8 Hz), 4.15 and 3.65 (d,d, 1H, 1H, 8a-CH$_2$), J=9.3 Hz), 3.33 (d, 1H, H-4', J=8.7 Hz), 3.18 (m, 1H, H-5'),3.14 (m, 2H, H-2' and H-3'), 2.70 (m, 1H, H-1),2.30 (m, 1H, CH(CH$_3$)$_2$); δ ($^{13}$C, CDCl$_3$): 204.7 (CHO), 175.6 (CO$_2$H), 148.3 (C-3),130.7 (C-2),98.5 (C-1'), 79.1 (C-4'), 74.1 (8a-CH$_2$), 73.5 (C-5'), 46.6 (C-1), 35.6 (C-2'),35.2 (C-3'),27.5 (CH(CH$_3$)$_2$).

EXAMPLE 52

[1R-(1α, 3aβ, 4β, 4aβ, 7β, 7aα, 8aβ)] 8a-[(2,3-Anhydro-6-deoxy-4-O-propyl-β-D-mannopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 65 (400 mg) in ethyl acetate (100 ml) was added 10% palladium on charcoal (200 mg) under nitrogen. The mixture was shaken in a Parr apparatus under 20 psi of hydrogen for 1 hour at room temperature. The catalyst was filtered off and the solvent evaporated to dryness. The residue was purified on a silica gel flash column eluting with methylene chloride and methylene chloride:methanol (25:1) to obtain the title compound (300 mg) as a white foam.

δ ($^1$H, CDCl$_3$): 9.76 (s, 1H, CHO), 6.08 (dd, 1H, H-2, J=1.5 and 3.6 Hz), 4.72 (s, 1H, H-1'), 4.13 and 3.65 (2d, 2H, 8a-CH$_2$, J=9 Hz), 3.67 (m, 1H, H-5'), 3.44 (m, 1H, H-4'), 3.25 and 3.12 (2d, 2H, H-2', H-3', J=4.2 Hz), 3.20 (m, 2H, OCH$_2$CH$_2$CH$_3$), 2.74 (t, 1H, H-1, J=3.9 Hz); δ ($^{13}$C, CDCl$_3$): 204.8 (CHO), 175.8 (CO$_2$H), 130.8 (C-2), 148.2 (C-3), 98.0 (C-1'), 74.9 (C-4'), 74.3 (C-8a-CH$_2$), 72.6 (C-5'), 72.4 (OCH$_2$CH$_2$CH$_3$ en C-4'), 65.6 (C-8a), 59.0 (C-3), 54.2 (C-2'), 50.3 (C-3'), 18.6 (C-6').

EXAMPLE 53

[1R-(1α, 3aβ, 4β, 4aβ, 7β, 7aα, 8aβ)] 8a-[(2,3-Anhydro-6-deoxy-4-O-propyl-β-D-mannopyranosyloxy) methyl]-4- formyl-4,4a,5,6,7,7a,8,8a-octahydro-7-methyl-3-(1-methylethyl)-1,4-methano-s-indacene-3a(1H)-carboxylic acid, sodium salt To a solution of Example 52 (400 mg) in dry methanol (30 ml) was added dropwise 0.0976 N sodium hydroxide solution (8.15 ml) at room temperature. The mixture was stirred for 1 hour. The solvent was evaporated to dryness and the solid residue dissolved in the minimum volume of water (10–15 ml). This solution was lyophilized to obtain the title compound (417 mg) as a white solid.

δ ($^1$H, CDCl$_3$): 9.89 (s, 1H, CHO), 5.97 (dd, 1H, H-2, J=1.5 and 3.6 Hz), 4.70 (s, 1H, H-1'), 4.09 and 3.86 (2d, 2H, 8a-CH$_2$, J=9.7 Hz); 3.70 (m, 1H, H-5'), 3.44 (m, 1H, H-4'), 3.24 and 3.12 (2d, 2H, H-2' and H-3', J=4 Hz), 3.20 (m, 2H, OCH$_2$CH$_2$CH$_3$), 2.65 (t, 1H, H-1, J=3.9 Hz); δ ($^{13}$C, CDCl$_3$): 209.6 (CHO), 178.38 (CO$_2$Na), 152.4 (C-3), 130.1 (C-2), 100.1 (C-1'), 77.9 (OCH$_2$CH$_2$CH$_3$ en C-4'), 76.6 (C-4'), 73.5 (C-5'), 73.1 (C-8a-CH$_2$), 66.6 (C-3'), 18.9 (C-6').

EXAMPLE 54

[1R-(1α, 3aβ, 4β, 4aβ, 7β, 7aα, 8aβ)] 8a-[(2,3-Anhydro-4-O-benzyl-6-deoxy-β-D-mannopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a suspension of sodium hydride (22 mg) in dry dimethylformamide (5 ml) was added dropwise a solution of Intermediate 63 (200 mg) in dry dimethylformamide (7 ml) and the mixture was stirred for 1 hour at room temperature. The reaction mixture was neutralized with 1 N hydrochloric acid and ethyl acetate (30 ml) was added. The organic layer was washed with water and brine, dried over anhydrous magnesium sulphate, filtered and evaporated to dryness. The residue was chromatographed on a silica gel flash column using methylene chloride:methanol (50:1) and (35:1) as eluents to give the title compound as a white foam (150 mg).

δ ($^1$H, CDCl$_3$): 9.86 (s, 1H, CHO), 7.31 (m, 5H, PhCH$_2$O), 6.08 (dd, 1H, H-2, J=1.2 and 3.3 Hz), 4.75 (d, 1H, OCH$_2$Ph, J=11.4 Hz), 4.73 (s, 1H, H-1'), 4.56 (d, 1H, OCH$_2$Ph, J=11.4 Hz), 4.17 and 3.62 (2d, 2H, 8a-CH$_2$, J=9.0 Hz), 3.32 and 3.14 (2d, 2H, H-3' and H-2', J=3.7 Hz), 3.30 (m, 2H, H-4', H-5'), 2.71 (t, 1H, H-1); δ ($^{13}$C, CDCl$_3$): 204.9 (CHO), 175.8 (COOH), 137.2, 128.14, 128.11 (6C-Ph), 148.3 (C-3), 130.8 (C-2), 98.0 (C-1'), 74.4 (C8a-CH$_2$), 74.3 (C-4'), 72.6 (OCH$_2$Ph), 72.5 (C-5'), 65.5 (C-8a), 54.0 (C-2'), 50.3 (C-3'), 18.6 (C-6').

EXAMPLE 55

[1R-(1α, 3aβ, 4β, 4aβ, 7β, 7aα, 8aβ)] 8a-[(2,3-Anhydro-6-deoxy-β-D-mannopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a suspension of dry sodium hydride (75 mg) in dry dimethylformamide (5 ml) under nitrogen was added a solution of Intermediate 66 (500 mg) in dry dimethylformamide (5 ml). The reaction mixture was stirred under nitrogen for 3 hours and the reaction was then quenched by water addition and neutralized to pH 6.5–7 with 0.5 M aqueous hydrochloric acid. The mixture was concentrated and the residue partitionated in water:ethyl acetate (1:1;100 ml). The aqueous phase was extracted with ethyl acetate (2×20 ml), and the organic phases were combined and treated with brine and dried over magnesium sulphate, filtered and concentrated in vacuo to a syrup. This was purified by flash column chromatography on silica gel eluting with dichloromethane:methanol (40:1) to give the title compound (172 mg) as a white foam.

δ ($^1$H, CDCl$_3$): 9.76 (s, 1H, CHO), 6.09 (dd, 1H, H-12, J=1.5 and 3.6 Hz), 4.77 (s, 1H, H-1'), 3.61 and 4.21 (2d, 2H, 8aCH$_2$, J=9 Hz), 3.60 (d, 1H, H-4', J=8.7 Hz), 3.21 (dq, 1H, H-5', J=9 and 6 Hz), 3.16 and 3.27 (2d, 2H, H-2' and H-3' J=3.6 Hz), 2.70 (t, 1H, H-1); δ ($^{13}$C, CDCl$_3$): 205.5 (CHO), 174.6 (CO$_2$H), 148.4 (C-3), 130.8 (C-2), 97.8 (C-1'), 74.1 (8aCH$_2$), 73.9 (C-4'), 73.7 (C-3a), 67.2 (C-5'), 65.5 (C-8a), 59.0 (C-4), 56.5 (C-2'), 50.4 (C-3'), 46.5 (C-1).

EXAMPLE 56

[1R-(1α, 3aβ, 4β, 4aβ, 7β, 7aα, 8aβ)] 8a-[(2,3-Anhydro-4,6-dideoxy-4-fluoro-β-D-talopyranosyloxy)methyl]formyl-4,4a,5,6,7,7a,8,8a-octahydro-7-methyl-3-(1-methylethyl)-1,4-methano-s-indacene-3a(1H)-carboxylic acid To a solution of Intermediate 68 (130 mg) in ethyl acetate (30 ml) was added 10% palladium on charcoal (100 mg) under nitrogen. The mixture was shaken in a Parr apparatus under 15 psi of hydrogen for 1 hour at room temperature. The catalyst was filtered off and the solvent evaporated to dryness. The residue was chromatographed on a silica gel flash column using hexane:ethyl acetate (4:1) and dichloromethane:methanol (20:1) as eluents to give the title compound as a white foam (82 mg).

δ ($^1$H, CDCl$_3$): 9.79 (s, 1H, CHO), 6.08 (dd, 1H, H-2, J=1.2 and 3.6 Hz), 5.13 (s, 1H, H-1'), 4.75 and 4.58 (2dq, 1H, H-5', J$_{5'F}$=48.3 Hz, J=6.6 Hz, J=3.9 Hz), 4.18 and 4.11 (2d, 1H, H-4', J=3.9 Hz and J$_{4'F}$=23.1 Hz ), 4.07 and 3.61 (2d, 2H, 8aCH$_2$, J=9.3 HZ), 3.77 (m, 2H, H-2' and H-3'), 2.67 (t, 1H, H-1); δ ($^{13}$C, CDCl$_3$): 204.6 (CHO), 175.3 (CO$_2$H), 148.2 (C-3), 130.7 (C-2), 101.7 (C-1'), 90.2 (d, C-4', J$_{C4'-F}$=157 Hz), 80.3 (d, C-5', J$_{C5'-F}$=21.4 Hz), 74.3 (C-8aCH$_2$), 73.4 (C-3a), 65.4 (C-8a), 58.9 (C-4), 55.9 (C-2'), 55.1 (d, C-3', J$_{C3'-F}$=6.3 Hz), 16.4 (d, C-6', J$_{C6'-F}$=21 Hz).

EXAMPLE 57

[1R-(1α, 3aβ, 4β, 4aβ, 7β, 7aα, 8aβ)] 8a-[(2,3-Anhydro-6-deoxy-4-O-(2-methoxyethyl)-β-D-mannopyranosyloxy) methyl]-4-formyl-4,4a,5,6,7,7a,8,8a-octahydro-7-methyl-3-(1methylethyl)-1,4-methano-s-indacene-3a(1H)-carboxylic acid To a solution of Intermediate 69 (140 mg) in ethyl acetate (50 ml) was added 10% palladium on charcoal (70 mg) under nitrogen. The mixture was shaken in a Parr apparatus under 20 psi of hydrogen for 1 hour at room temperature. The catalyst was filtered off and the solvent evaporated to dryness. The residue was purified on a silica gel flash column eluting with dichloromethane and dichloromethane:methanol (40:1) to give the title compound (74 mg) as a white foam.

δ ($^1$H, CDCl$_3$): 9.78 (s, 1H, CHO), 6.08 (dd, 1H, H-2, J=1.2 and 3.3 Hz), 4.74 (s, 1H, H-1'), 4.23 and 3.60 (2d, 2H, 8a-CH$_2$, J=9 Hz), 3.86–3.50 (m, 4H, OCH$_2$CH$_2$OCH$_3$), 3.38 (s, 3H, CH$_3$OCH$_2$CH$_2$O), 3.30 and 3.13 (2d, 2H, H-2' and H-3', J=3.9 Hz), 3.26–3.22 (m, 2H, H-4' and H-5'), 2.68 (t, 1H, H-1, J=3.7 Hz); δ ($^{13}$C, CDCl$_3$): 204.8 (CHO), 175.2 (COOH), 148.3 (C-3), 130.8 (C-2), 97.9 (C-1'), 74.2 (C-8aCH$_2$), 72.4 (C-5'), 71.7 and 69.9 (OCH$_2$CH$_2$OCH$_3$), 54.1 (C-2'), 50.3 (C-3'), 46.5 (CH$_3$OCH$_2$CH$_2$),18.5 (C-6').

EXAMPLE 58

[1R-(1α, 3aβ, 4β, 4aβ, 7β, 7aα, 8aβ)] 8a-[(2,3-Anhydro-6-deoxy-4-O-(2-methylpropyl)-β-D-mannopyranosyloxy) methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 70 (0.14 mmol) in ethyl acetate (30 ml) was added 10% palladium on charcoal (50 mg) under nitrogen. The mixture was shaken in a Parr apparatus under 25 psi of hydrogen for 30 minutes at room temperature. The catalyst was filtered off and the solvent evaporated to dryness. The residue was purified by flash chromatography using dichloromethane:methanol (40:1) as eluent to give the title compound (49 mg).

δ ($^1$H, CDCl$_3$): 9.76 (s,1H, CHO), 6.09 (dd, 1H, H-2, J=1.2 and 3.3 Hz), 4.73 (s, 1H, H-1'), 4.12 and 3.65 (2d, 2H, 8a-CH$_2$, J=9.3 Hz), 3.49 (m, 1H, H-5'), 3.22 (m, 3H, H-2' and CH$_2$—O), 3.13 (m, 2H, H-3' and H-4'), 2.75 (t, 1H, H-1, J=3.9 Hz), 2.33 (m, 1H, CH(CH$_3$)$_2$); δ ($^{13}$C, CDCl$_3$): 204.8 (CHO), 176.0 (CO$_2$H), 148.2 (C-3), 130.8 (C-2), 98.0 (C-1'), 77.6 (C-1''), 75.2 (C-4'), 74.3 (8a-CH$_2$), 72.9 (C-3a), 72.6 (C-5'), 65.6 (C-8a), 59.0 (C-4), 54.1 (C-2'), 50.4 (C-3'), 46.4 (C-1), 41.7 (C-4a), 41.3 (C-7a):

EXAMPLE 59

[1R-(1α, 3aβ, 4β, 4aβ, 7β, 7aα, 8aβ)] 8a-[(2,3-Anhydro-6-deoxy-4-O-(1-methylethyl)carbonyl-β-D-mannopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 71 (140 mg) in ethyl acetate (20 ml) was added 10% palladium on charcoal (120 mg) under nitrogen. The mixture was shaken in a Parr apparatus under 20 psi of hydrogen for 1 hour at room temperature. The catalyst was filtered off and the solvent evaporated to dryness. The residue was purified by flash column chromatography on silica gel eluting with hexane:ethyl acetate (4:1) and dichloromethane:methanol (20:1) to afford the title compound (103 mg) as a white foam.

δ ($^1$H, CDCl$_3$): 9.74 (s, 1H, CHO), 6.09 (dd, 1H, H-2, J=1.5 and 3.6 Hz), 4.78 (s, 1H, H-1'), 4.66 (d, 1H, H-4', J=9 Hz), 4.10 and 3.60 (2d, 2H, 8aCH$_2$, J=9 Hz), 3.42 (dq, 1H, H-5', J=9 and 3 Hz), 3.15 (s, 2H, H-2' and H-3'), 2.78 (m, 1H, H-1), 2.58 (m, 1H, 4'-OCOCHMe$_2$); δ ($^{13}$C, CDCl$_3$): 204.9 (CHO), 176.1, 175.9 (CO$_2$H and 4'OCOR), 148.2 (C-3), 130.9 (C-2), 97.9 (C-1'), 74.5 (C-8aCH$_2$), 72.6 (C-3a), 71.4 (C-4'), 67.8 (C-5'), 66.0 (C-8a), 59.0 (C-4), 18.5 and 18.8 (2CH$_3$ of 4'-OCOCHMe$_2$).

EXAMPLE 60

[1R-(1α, 3aβ, 4β, 4aβ, 7β, 7aα, 8aβ)] 8a-[(2,3-Anhydro-6-deoxy-4-O-(2,2-dimethylpropionyl)-β-D-mannopyranosyloxy)methyl]-4-formyl-4,4a,5,6,7,7a,8,8a-octahydro-7-methyl-3-(1-methylethyl)-1,4methano-s-indacene-3a(1H)-carboxylic acid To a solution of Intermediate 72 (0.21 mmol) in ethyl acetate (60 ml) was added 10% palladium on charcoal (50 mg) under nitrogen. The mixture was shaken in a Parr apparatus under 20 psi of hydrogen for 30 minutes at room temperature. The catalyst was filtered off and the solvent evaporated to dryness. The residue was purified by flash chromatography using dichloromethane:methanol (40:1) as eluent to give the title compound (101 mg).

δ ($^1$H, CDCl$_3$): 9.75 (s, 1H, CHO), 6.10 (dd, 1H, H-2, J=1.2 and 3.3 Hz), 4.80 (s, 1H, H-1'), 4.64 (d, 1H, H-4', J=9 Hz), 4.11 and 3.70 (2d, 2H, 8a-CH$_2$, J=9.3 Hz), 3.43 (m, 1H, H-5'), 3.13 (m, 2H, H-2' and H-3'), 2.78 (t, 1H, H-1, J=3.9 Hz), 2.34 (m, 1H, CH(CH$_3$)$_2$); δ ($^{13}$C, CDCl$_3$): 204.9 (CHO), 177.3 and 176.5 (2xCO$_2$), 148.2 (C-3), 130.9 (C-2), 98.0 (C-1'), 74.5 (8a-CH$_2$), 72.6 (C-2), 71.3 (C-5'), 67.9 (C-4'), 65.7 (C-8a), 59.0 (C-4), 54.3 (C-2'), 50.1 (C-3'), 46.3 (C-1), 41.8 (C-4a), 41.3 (C-8), 38.8 (C-$^t$Bu), 32.0 (C-5), 30.9 (C-7), 18.5 ($^t$Bu).

EXAMPLE 61

[1R-(1α, 3aβ, 4β, 4aβ, 7β, 7aα, 8aβ)] 8a-[(2,3-Anhydro-4-O-benzyloxycarbonyl-6-deoxy-β-D-mannopyranosyloxy)methyl]-4-formyl-4,4a,5,6,7,7a,8,8a-octahydro-7-methyl-3-(1-methylethyl)-1,4-methano-s-indacene-3a(1H)-carboxylic acid A solution of Intermediate 73 (0.22 mmol) in dichloromethane (10 ml) at 0° C. was treated with trifluoroacetic acid (0.1 ml). After two hours, the mixture was washed with water and the organic phase was evaporated. The residue was purified by flash chromatography using dichloromethane:methanol (40:1) as eluent to give the title compound (60 mg).

δ ($^1$H, CDCl$_3$): 9.74 (s, 1H, CHO), 7.37 (m, 5H, Ph), 6.09 (dd, 1H, H-2, J=1.5 and 3.6 Hz), 5.20 (m, 2H, CH$_2$Ph), 4.75 (s, 1H, H-1'), 4.55 (d, 1H, H-4', J=9 Hz), 4.08 and 3.70 (2d, 2H, 8a-CH$_2$, J=9 Hz), 3.47 (m, 1H, H-5'), 3.28 and 3.16 (d,d, 1H, 1H, H-2' and H-3', J=3.6 Hz), 2.79 (t, 1H, H-1, J=3.9 Hz), 2.33 (m, 1H, CH(CH$_3$)$_2$); δ ($^{13}$C, CDCl$_3$): 204.8 (CHO), 176.4 (CO$_2$H), 154.1 (CO$_3$), 148.1 (C-3), 134.6 (Cipso), 130.9 (C-2), 128.8, 128.7, 128.5, 128.4 (Ph), 97.8 (C-1'), 74.5 (8a-CH$_2$), 72.5 (C-3a), 71.6 (C-5'), 71.1 8C-4'), 70.3 (CH$_2$Ph), 65.7 (C-8a), 58.9 (C-4), 53.9 (C-2'), 50.0 (C-3'), 46.2 (C-1), 41.7 (C-4a), 41.3 (C-7a).

EXAMPLE 62

[1R-(1α, 3aβ, 4β, 4aβ, 7β, 7aα, 8aβ)] 8a-[(2,3-Anhydro-6-deoxy-4-oxo-β-D-mannopyranosyloxy)methyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 74 (0.26 mmol) in ethyl acetate (30 ml) was added 10% palladium on charcoal (50 mg) under nitrogen. The mixture was shaken in a Parr apparatus under 25 psi of hydrogen for 1.5 h at room temperature. The catalyst was filtered off and the solvent evaporated to dryness. The residue was purified by flash chromatography using dichloromethane:methanol (40:1) as eluent and appropriate fractions were collected and evaporated to give the title compound (38 mg).

δ ($^1$H, CDCl$_3$): 9.72 (s, 1H, CHO), 6.12 (dd, 1H, H-2, J=1.5 and 3.6 Hz), 4.87 (s, 1H, H-1'), 4.10 and 3.76 (2d, 2H, 8aCH$_2$, J=9 Hz), 3.83 (q, 1H, H-5', J=6.6 Hz), 3.60 and 3.38 (d,d, 1H, 1H, 3' and 2', J=3.9 Hz), 2.82 (t, 1H, H-1, J=3.6 Hz),. 2.36 (m, 1H, CH(CH$_3$)$_2$); δ ($^{13}$C, CDCl$_3$): 204.9 (CHO), 202.9 (CO-4'), 176.2 (CO$_2$H), 148.2 (C-3), 130.9 (C-2), 96.1 (C-1'), 76.6 (C-5'), 74.7 (8aCH$_2$), 72.1 (C-3a), 65.7 (C-8a), 58.9 (C-4), 54.2 and 53.5 (C-2' and C-3'), 46.1 (C-1), 41.8 (C-4a), 41.3 (C-7a).

EXAMPLE 63

[1R-(1α, 3aβ, 4β, 4aβ, 7β, 7aα, 8aβ)] 8a-(2,3-Anhydro-4,6-dideoxy-4-methylene-β-D-mannopyranosyloxy)methyl-4-formyl-4,4a,5,6,7,7a,8,8a-octahydro-7-methyl-3-(1-methylethyl)-1,4-methano-s-indacene-3a(1H)-carboxylic acid A solution of intermediate 101 (0.17 mmol) in dichloromethane (15 ml) at 0° C. was treated with trifluoroacetic acid (0.15 ml). After 2 hours, was treated with water (10 ml). The organic phase was evaporated and the residue was dissolved in ethanol (15 ml) and 1 N hydrochloric acid (1.5 ml) and stirred at 0° C. for other 2 hours. The solvent was removal of and the residue purified using dichloromethane:methanol 20:1 as eluent. Appropriate fractions were evaporated to give the title compound (24 mg).

δ ($^1$H, CDCl$_3$): 9.75 (s, 1H, CHO), 6.08 (dd, 1H, H-2, J=1.2 and 3.3 Hz), 5.20 and 5.10 (s, s, 1H, 1H, CH$_2$=C), 4.82 (d, 1H, H-1, J=2.1 Hz), 4.42 (m, 2H, H-5' and H-3'), 4.19 and 3.56 (d, d, 1H, 1H, 8a-CH$_2$, J=9.6 Hz), 3.65 (m, 1H, H-2'), 2.63 (t, 1H, H-1, J=3.9 Hz), 2.36 (m, 1H, CH(CH$_3$)$_2$); δ ($^{13}$C, CDCl$_3$): 204.7 (CHO), 175.0 (CO$_2$H), 148.5 (C-3), 145.6 (C-4'), 130.5 (C-2), 112.1 (CH$_2$=C), 99.5 (C-1'), 74.0 (8a-CH$_2$), 73.0 (C-5'), 72.8 (C-3a), 72.2 and 71.6 (C-2' and C-3').

EXAMPLE 64

[1R-(1α, 3aβ, 4β, 4aβ, 7β,7aα, 8aβ)] 8a-(2,3-Anhydro-4-O-tertbutylcarbonyl-6-deoxy-β-D-talopyranosyloxy)

methyl-4-formyl-4,4a,5,6,7,7a,8,8a-octahydro-7-methyl-3-(1-methylethyl)-1,4-methano-s-indacene-3a(1H)-carboxylic acid A mixture of intermediate 103 (0.1 mmol) in water (2 ml) at 0° C. was treated with trifluoroacetic acid (3 ml). After 90 minutes the mixture was poured into ethyl ether:water 1:1 (30 ml). The organic phase was evaporated and the residue purified by chromatography using dichloromethane:methanol 40:1 as eluent to give the title compound (32 mg).

δ ($^1$H, CDCl$_3$): 9.77 (s, 1H, CHO), 6.08 (dd, 1H, H-2, J=1.5 and 3.6 Hz), 4.75 (dd, 1H, H-4', J=3.6 and 4.8 Hz), 4.68 (s, 1H, H-1'), 4.17 (d, 1H, 8a-CHa, J=9.3 Hz), 3.66 (m, 2H, 8a-CHb and H-5'), 3.57 (t, 1H, H-3', J=4.2 Hz), 3.17 (d, 1H, H-2', J=3.6 Hz), 2.73 (t, 1H, H-1, J=3.9 Hz), 2.33 (m, 1H, CH(CH$_3$)$_2$); δ ($^{13}$C, CDCl$_3$): 204.8 (CHO), 178.5 and 175.7 (2xCO$_2$), 148.3 (C-3), 130.8 (C-2), 97.9 (C-1'), 74.1 (8a-CH$_2$), 73.0 (C-3a), 71.5 (C-5'), 66.0 (C-4'), 65.6 (C-8a), 59.0 (C-4), 51.3 (C-2'), 50.7 (C-3').

EXAMPLE 65

[1R-(1α, 3aβ, 4β, 4aβ, 7β, 7aα, 8aβ)] 8a-[[2,3-Anhydro-4-O-(trans-2-butenyl)-6-deoxy-β-D-mannopyranosyloxy]methyl]-4-formyl-4,4a,5,6,7,7a,8,8a-octahydro-7-methyl-3-(1-methylethyl)-1,4-methano-s-indacene-3a(1H)-carboxylic acid A solution of intermediate 47 (103 mg) in dry dichloromethane (5 ml) at 0° C. was treated with trifluoroacetic acid (100 μl). After 1 hour, the mixture was partitioned between ethyl acetate (50 ml) and saturated aqueous sodium sulfate solution (50 ml). The organic layer was washed with saturated aqueous sodium sulfate solution, water and brine, then dried and evaporated. The residue was chromatographed twice on silica gel eluting with hexane:ethyl acetate (2:1) to (1:1) to give the title compound (50 mg).

δ ($^1$H, CDCl$_3$): 9.76 (s, 1H, CHO), 6.08 (dd, 1H, H-2, J=1.5 and 3.6 Hz), 5.82–5.68 (m, 1H, CH=CH), 5.62–5.48 (m, 1H, CH=CH), 4.72 (s, 1H, H-1'), 4.2–4.1 (m, 2H, O—CHa—C=C and 8a-CHa), 4.02–3.92 (m, 1H, OCHb-C=C), 3.63 (d, 1H, 8a-CHb, J=9.3 Hz), 3.3–3.15 (m, 3H, H-3', H-4' and H-5'), 3.12 (d, 1H, H-2', J=3.9 Hz), 2.73 (t, 1H, H-1, J=3.9 Hz), 1.72 (dd, 3H, H$_3$C—C=C, J=1.2 and 6.6 Hz); δ ($^{13}$C, CDCl$_3$): 204.8 (CHO), 175.6 (CO$_2$H), 148.2 (C-3),130.8 (C-2), 131.1 and 126.6 (O—CH$_2$—C=C—CH$_3$), 97.9 (C-1'), 74.2 (8a-CH$_2$), 71.2 (O—CH$_2$—C=C—CH$_3$), 73.5 and 72.5 (C-4' and C-5').

EXAMPLE 66

[1R-(1α, 3aβ, 4β, 4aβ, 7β, 7aα, 8aβ)] 8a-(2,3-Anhydro-6-deoxy-4-O-propyl-β-D-talopyranosyloxy) methyl-4-formyl-4,4a,5,6,7,7a,8,8a-octahydro-7-methyl-3-(1-methylethyl)-1,4-methano-s-indacene-3a(1H)-carboxylic acid To a solution of intermediate 104 (150 mg, 0.21 mmol) in ethanol (50 ml), ethyl acetate (10 ml) and 1 N hydrochloric acid (1 ml), palladium (10%) on charcoal was added (30 mg) under nitrogen. The mixture was shaken in a Parr apparatus (PH$_2$=35 psi) for 3,5 hours at room temperature. The catalyst was filtered and the solvent evaporated to dryness. The residue was purified by chromatography using dichloromethane:methanol 30:1 as eluent to give the title compound (60 mg).

δ ($^1$H, CDCl$_3$): 9.83 (s, 1H, CHO), 6.06 (dd, 1H, H-2, J=1.2 and 3.6 Hz), 4.75 (s, 1H, H-1'), 4.44 and 3.42 (dd, 2H, 8a-CH$_2$; J=9.3 Hz), 4.37 (t, 1H, H-3', J=2.7 Hz), 4.10 (m, 1H, H-4'), 3.74–3.65 (m, 2H, CH$_2$O), 3.91 (m, 1H, H-5'), 3.19 (m, 1H, H-2'), 2.51 (t, 1H, H-1, J=3.6 Hz); δ ($^{13}$C, CDCl$_3$): 204.7 (CHO), 174.9 (CO$_2$H), 148.6 (C-3), 130.4 (C-2), 97.9 (C-1'), 78.7 (C-4'), 73.9 (8a-CH$_2$), 73.3 (CH$_2$O), 69.8 (C-5'), 69.3 (C-3'), 65.3 (C-8a), 59.0 (C-4), 54.6 (C-2'), 47.0 (C-1).

EXAMPLE 67

[1R-(1α, 3aβ, 4β, 4aβ, 7β, 7aα, 8aβ)] 8a-(2,3-Anhydro-4-azido-4,6-dideoxy-β-D-mannopyranosyloxy) methyl-4-formyl-4,4a,5,6,7,7a,8,8a-octahydro-7-methyl-3-(1-methylethyl)-1,4-methano-s-indacene-3a(1H)-carboxylic acid A solution of intermediate 106 (0.06 mmol) in dry dichloromethane (5 ml) at 0° C. was treated with trifluoroacetic acid (70 μl). After 2 hours, was washed with water and brine. The solvent was evaporated and the residue purified by chromatography using dichloromethane:methanol 30:1 as eluent to give the title compound (12 mg).

δ ($^1$H, CDCl$_3$): 9.73 (s, 1H, CHO), 6.09 (d, 1H, H-2, J=3.6 Hz), 4.73 (s, 1H, H-1'), 4.12 and 3.67 (d, d, 1H, 1H, 8a-CH$_2$, J=9 Hz), 3.39 (d, 1H, H-4', J=9 Hz), 3.33 and 3.17 (d, d, 1H, 1H, H-2' and H-3', J=3.6 Hz), 3.22 (m, 1H, H-5'), 2.76 (t, 1H, H-1, J=3.6 Hz), 2.34 (m, 1H, CH(CH$_3$)$_2$); δ ($^{13}$C, CDCl$_3$): 205.1 (CHO), 175.3 (CO$_2$H), 148.4 (C-3), 130.8 (C-2), 97.8 (C-1'), 74.6 (8a-CH$_2$), 72.7 (C-5'), 68.0 (C-3a), 65.7 (C-8a), 59.0 (C4), 58.7 (C-4), 54.4 (C-2'), 50.1 (C-3'), 46.3 (C-1).

EXAMPLE 68

[1R-(1α, 3aβ, 4β, 4aβ, 7β, 7aα, 8aβ)] 8a-[(4-O-Allyl,2,3-anhydro, 6deoxy-β-D-mannopyranosyl)oxy-methyl]4-formyl-4,4a,5,6,7,7a,8,8a-octahydro-7-methyl-3-(1-methylethyl)-1,4-methano-s-indacene-3a(1H)-carboxylic acid A solution of intermediate 107 (250 mg) in a mixture of 10 ml of methylene chloride and 0.2 ml of trifluoroacetic acid, was stirred at 0° C. for 4 hours. The crude was evaporated to dryness and the residue purified by flash chromatography with methylene chloride:methanol 50:1, to yield 140 mg of the title compound as a white foam.

δ ($^1$H, CDCl$_3$): 9.77 (s, 1H, CHO), 6.08 (dd, 1H, H-12, J=1.2 and 3.3 Hz), 5.90 (m 1H, CH=CH$_2$), 5.28 (m, 2H, CH=CH$_2$), 4.75 (s, 1H, H-1'), 4.28 (m, 1H, H-5'), 4.21 (d, 1H, H-19a, J=9.6 Hz), 4.05 (m, 1H, H-4'), 4.05 (m, 1H, H-4'), 3.60 (d, 1H, H-19b, J=9.6 Hz), 3.27, 3.14 (d, d, 1H, 1H, H-2', H-3', J=3.9 Hz), 3.25 (m, 2H, CH$_2$—CH=CH$_2$), 2.68 (t, 1H, H-11, J=4.2 Hz); δ ($^{13}$C, CDCl$_3$): 205.07(CHO), 174.6 (CO$_2$H), 148.4 (C-13), 133.7 (CH=CH$_2$), 129.7 (C-12), 118.0 (CH$_2$=CH), 97.8 (C-1'), 74.17 (C-19), 74.04 (C-4'), 72.5 (C-5'), 71.0 (O—CH$_2$—CH=CH$_2$), 54.1 (C-2'), 50.2 (C-3'), 27.5 (C-14), 22.7 (C-20), 21.2 (C-15), 18.6 (C-6'), 17.4 (C-17).

EXAMPLE 69

[1R-(1α, 3aβ, 4β, 4aβ, 7β, 7aα, 8aβ)] 8a-[(2,3-Anhydro,6-deoxy,4-O-tert-butoxycarbonylmethyl-β-D-mannopyranosyl)oxymethyl-4-formyl-4,4a,5,6,7,7a,8,8a-octahydro-7-methyl-3-(1-methylethyl)-1,4-methano-s-indacene-3a(1H)-carboxylic acid To a solution of Intermediate 21 (200 mg) in 15 ml of dry THF at 0° C., 30 mg of sodium hydride were added. The mixture was stirred at 0° C. under nitrogen for 30 minutes. Then, 260 μl of tert-butyl-bromoacetate were added and the mixture was stirred at room temperature under nitrogen for 3 days. The crude was treated with ammonium chloride 1 N and ethyl acetate. The organic layer was washed with water and brine and evaporated to dryness. The residue was hydrogenated following the standard procedure and the crude was purified by flash chromatographic with methylene chloride:methanol, 50:1 to give 140 mg of the title compound as a white foam.

δ ($^1$H, CDCl$_3$): 9.74 (s, 1H, CHO), 6.08 (dd, 1H, H-12, J=1.5 and 3.9 Hz), 4.74 (s, 1H, H-1'), 4.21 (dd, 1H, H-4', J=3.6 and 6.0 Hz), 4.16 (d, 1H, H-19a, J=9 Hz), 4.12 (s, 2H, CH$_2$,—CO$_2$C(CH$_3$)$_3$), 3.63 (d, 1H, H-19b, J=9 Hz), 3.36, 3.14 (d, d, 1H, 1H, H-2', H-3', J=3.9 Hz), 3.30 (m, 1H, H-5'), 2.71 (t, 1H, H-11, J=3.9 Hz); δ ($^{13}$C, CDCl$_3$): 205.7 (CHO), 174.9 (CO$_2$C(CH$_3$)$_3$), 168.8 (CO$_2$H), 148.4 (C-13), 130.8 (C-12), 97.8 (C-1'), 82.2 (C(CH$_3$)$_3$), 75.6 (C-4'), 72.4 (C-5'), 68.2 (OCH$_2$—CO), 59.0 (C-3), 53.9 (C-2'), 50.3 (C-3'), 27.5 (C-14), 22.7 (C-20), 21.2 (C-15),18.6 (C-6'), 17.4 (C-17).

EXAMPLE 70
[1R-(1α, 3αβ, 4β, 4αβ, 7β, 7αα, 8αβ)] 8a-[(2,3-Anhydro-6-deoxy-4-O-ethyl-β-D-mannopyranosyl)oxy-methyl]4,4a,5,6,7,7a,8,8a-octahydro-7-methyl-3-(1-methylethyl)-1,4-methano-s-indacene-3a(1H) carboxylic acid To a solution of Intermediate 21 (290 mg) in 5 ml of dry dimethylformamide at 0° C., 25 mg of sodium hydride were added under nitrogen. The mixture was stirred for 30 minutes at 0° C. and then, 1 mmol of ethyl iodide was added. After 16 hours stirring at room temperature the reaction was complete. The crude was treated with ammonium chloride 1 N and ethyl acetate. The organic layer was washed with water and brine, dried over anhydrous magnesium sulphate and evaporated to dryness. The residue was hydrogenated following the standard procedure and the crude was purified by flash chromatography with methylene chloride:methanol, 50:1, to give 180 mg of the title compound as a white foam.

δ ($^1$H, CDCl$_3$): 9.73 (s, 1H, CHO), 6.08 (d, 1H, H-12, J=3.3 Hz), 4.73 (s, 1H, H-1'), 4.16 (d, 1H, H-19a, J=9.3 Hz), 3.78, 3.54 (m, m, 1H, 1H, O—CH$_2$—CH$_3$), 3.63 (s, 1H, H-19b, J=9.3 Hz), 3.25, 3.13 (d, d, 1H, 1H, H-2', H-3', J=3.9 Hz), 3.19 (m, 2H, H-4', H-5'), 2.71 (t, 1H, H-11, J=3.3 Hz); δ ($^{13}$C, CDCl$_3$): 201.8 (CHO), 175.0 (CO$_2$H), 148.2 (C-13), 130.7 (C-12), 97.9 (C-1'), 74.6 (C-4'), 74.3 (C-19), 72.5 (C-5'), 54.3 (C-2'), 50.3 (C-3'), 27.5 (C-14), 22.7 (C-20), 21.2 (C-15), 18.6 (C-6'), 17.4 (C-17).

EXAMPLE 71
[1R-(1α, 3αβ, 4β, 4αβ, 7β, 7αα, 8αβ)] 8a-[(2,3-Anhydro,6-deoxy-4-O-(2,3-dihydroxypropyl)-β-D-mannopyranosyl)oxymethyl]]-4-formyl-4,4a,5,6,7,7a,8,8a-octahydro-7-methyl-3-(1-methylethyl)-1,4-methano-s-indacene-3a(1H)-carboxylic acid To a solution of Intermediate 108 (700 mg) in ethanol (100 ml), palladium (10%) on charcoal was added (350 mg) under nitrogen. The mixture was shaken in a Parr apparatus (PH$_2$=20 psi) for 1 hour at room temperature. The catalyst was filtered and the solvent evaporated to dryness. The residue was purified on a silica gel column eluting with methylene chloride and methylene chloride:methanol 25:1 to obtain 425 mg of the title compound (mixture of isomers 50:50) as a white powder.

δ ($^1$H, CDCl$_3$): 9.75 (s, 1H, CHO), 6.08 (dd, 1H, H-12, J=1.2 and 3.6 Hz), 4.73 (s, 1H, H-1'), 3.98 (d, 1H, H-19a, J=9.6 Hz), 3.81 (d, 1H, H-19b, J=9.6 Hz), 3.81–3.68 (m, 2H, —OCH$_2$—CHOH— in C-4'), 3.55–3.31 (m, 3H, —CHOH—CH$_2$OH in C-4'), 3.30–3.11 (m, 4H, H-2', H-3', H-4', H-5'), 2.76 (t, 1H, H-11, J=3.6 Hz); δ ($^{13}$C, CDCl$_3$): 207.70 (CHO), 178.2 (CO$_2$H), 150.49 (C-13), 131.44 (C-12), 99.81 (C-1'), 77.07 and 76.96 (CH—CH$_2$OH in C-4'), 76.57 (C-19), 73.55 (C-4'), 72.86 and 72.69 (O—CH$_2$—CHOH in C-4'), 72.24 (C-5'), 55.01 (C-3'), 51.89 (C-2'), 23.2 (C-20), 21.6 (C-15), 19.4 (C-6'), 17.9 (C-17).

EXAMPLE 72
[1R-(1α, 3αβ, 4β, 4αβ, 7β, 7αα, 8αβ)] 8a-[(2,3-Anhydro,6-deoxy-4-O-(2,3-dimethoxypropyl)-β-D-mannopyranosyl)oxymethyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 108 (350 mg) in dry THF (20 ml) at 0° C., sodium hydride (40 mg) was added under nitrogen, and the mixture was stirred for 30 minutes. Then, methyl iodide (0.5 ml) was added and the reaction was kept at room temperature stirring over nitrogen for two days. The crude was treated with 1 N ammonium chloride and ethyl acetate. The organic layer was washed with water and brine and evaporated to dryness. The residue was hydrogenated following the standard procedure without previous purification to give the title compound (mixture of isomers 50:50) as a white foam (225 mg).

δ ($^1$H, CDCl$_3$): 9.75 (s, 1H, CHO), 6.08 (d, 1H, H-12, J=3.3 Hz), 4.73 (d, 1H, H-1', J=1.5 Hz), 4.18 (d, 1H, H-19b, J=9 Hz), 3.62 (d, 1H, H-19b, J=9 Hz), 3.48 and 3.47(s, s, 3H, 3H, CH$_2$OMe CHOMe), 3.36–3.20 (m, 4H, H-2', H-3', H-4', H-5'), 2.70 (t, 1H, H-11, J=3.6 Hz); δ ($^{13}$C, CDCl$_3$): 205.2 (CHO), 174.7 (CO$_2$H), 148.2 (C-11), 130.7 (C-12), 97.9 (C-1'), 79.0 (CHOMe in C-4'), 75.6 and 75.7 (C-4'), 72.4 (C-5'), 71.6 and 71.5 (OCH$_2$—CHOMe in C-4'), 70.1 and 69.8 (—CH$_2$OMe in C-4'), 59.2, 57.9 and 57.8 (—CHOMe and —CH$_2$OMe in C-4'), 53.9 and 50.2 (C-2' and C-3'), 22.7 (C-20), 21.2 (C-15), 18.6 (C-6'), 17.4 (C-17).

EXAMPLE 73
[1R-(1α, 3αβ, 4β, 4αβ, 7β, 7αα, 8αβ)] 8a-[(2,3-Anhydro,6-deoxy-4-O-[(2,3-O-isopropylidene)-2,3-dihydroxypropyl]-β-D-mannopyranosyl)oxymethyl]-4-formyl-4,4a,5,6,7,7a,8 8a-octahydro-7-methyl-3-(1-methylethyl)-1,4-methano-s-indacene-3a(1H) carboxylic acid To a solution of Intermediate 109 (250 mg) in ethyl acetate (50 ml), palladium (10%) on charcoal was added (100 mg) under nitrogen. The mixture was shaken in a Parr apparatus (PH$_2$=20 psi) for 1 hour at room temperature. The catalyst was filtered and the solvent evaporated to dryness. The residue was purified by flash chromatographic with n-hexane:ethyl acetate 1:1 and methylene chloride:methanol 50:1 to give the title compound (mixture of isomers 50:50) as a white foam (150 mg).

δ ($^1$H, CDCl$_3$): 9.75 (s, 1H, CHO), 6.08 (dd, 1H, H-12, J=1.5 and 3.6 Hz), 4.71 (d, 1H, H-1', J=0.9 Hz), 4.29–4.24 (m, 1H, CHOH in 4'), 4.15–4.01 (m, 3H, H-19a and —OCH$_2$), 3.82–3.49 (m, 4H, H-19b, OCH$_2$—CHOH—CH$_2$O), 3.29 and 3.13 (d, d, 1H, 1H, H-2' and H-3', J=3.9 Hz), 3.27–3.18 (m, 2H, H4' and H-5'), 2.74 (t, 1H, H-11, J=3.6 Hz), 1.41 and 1.35 (d, d, 3H, 3H, (CH$_3$)$_2$C of isopropilidene); δ ($^{13}$C, CDCl$_3$): 204.8 (CHO), 165.7 (CO$_2$H), 148.2 (C-11), 130.8 (C-12), 97.9 (C-1'), 75.7 and 75.6 (—CHO—CH$_2$O in C-4'), 74.4 (C-4'), 72.8 and 72.4 (C-5'), 72.0 and 71.6 (O—CH$_2$—O in C-4'), 54.0 and 53.8 (C-3'), 50.3 (C-2'), 22.6 (C-20), 21.1 (C-15), 18.6 (C-6'), 17.4 (C-17).

EXAMPLE 74
Characteristics of IMI 362184

IMI 362184 is a mutant of *Sordaria araneosa* (ATCC 36386, NRRL 3196) isolated following N-methyl-N'-nitro-N-nitrosoguanidine mutagenesis of ascospores of this strain. The characteristics of IMI 362184 are essentially similar to those described in British Patent Specification No 1,162,027 for NRRL 3196, except that IMI 362184 produces 4'-demethylsordarin as a major product under the same conditions used for sordarin production by NRRL 3196.

EXAMPLE 75
Characteristics of IMI 362947

IMI 362947 is a mutant of *Sordaria araneosa* (ATCC 36386, NRRL 3196) isolated following N-methyl-N'-nitro-N-nitrosoguanidine mutagenesis of ascospores of this strain. The characteristics of IMI 362947 are essentially similar to those described in British Patent Specification No. 1,162, 027 for NRRL 3196, except that IMI 362947 does not produce ascospores readily on agar. The strain also differs from NRRL 3196 in that it produces sordaricin as a major product under the same conditions used for sordarin production by NRRL 3196.

EXAMPLE 76

Characteristics of NCIMB 40675

NCIMB 40675 is an aerobic, Gram-positive, non-motile irregular rod that produces lemon yellow, translucent, round, entire, convex colonies with a diameter of between 0.5–1 mm when grown on tryptic soy agar supplemented with 2% (w/v) yeast extract for 48 hours at 28° C. The organism grows well at temperatures up to 37° C., but not at 45° C. Metachromatic granules were not observed and the strain is catalase positive, oxidase negative and does not metabolise glucose fermentatively. The strain can utilise the following sources of carbon: α-D-glucose, D-fructose, p-hydroxyphenyl-acetic acid, D-mannitol, methylpyruvate, lactamide, D-trehalose and sucrose. The organism can only weakly utilise D-gluconic acid, pyruvic acid and salicin as sole carbon sources. Colony and microscopic morphology resembles that of coryneform bacteria. The genus Corynebacterum was excluded on the grounds that the peptidoglycan of NCIMB 40675 contains ornithine rather than the mesoisomer of 2,6-diaminopimelic acid or diaminobutyric acid. Also, the organism contains a complex mixture of branch chain fatty acids atypical of Corynebacterum species, namely, 12-methyltetradecanoic, 14-methylhexadecanoic and 14-methylpentadecanoic acids. The presence of α-branched-β-hydroxylated fatty acids was not determined. On the basis of these results NCIMB 40675 most closely resembles one of the following aminobacterial genera: Aureobacterium, Curtobacterium or Cellulomonas.

To clarify the taxonomic position of NCIMB 40675, a 1100 base pair partial sequence of the 16S rRNA gene was compared against 24 other species representing a range of actinobacteria and related genera. Results from this analysis indicate a close relationship between NCIMB 40675 and the genera Aureobacterium and Curtobacterium, but not Cellulomonas or Corynebacterium. More precise identification for the strain could be obtained by performing a phylogenetic analysis comparing variable regions of the 16S rRNA gene for a range of Aureobacterium and Curtobacterium species in addition to further chemotaxonomic and physiological tests.

Pharmacy Examples

1. Conventional oral tablet

| | |
|---|---|
| Drug substance | 100 mg |
| Microcrystalline cellulose | 160 mg |
| Crosscarmellose sodium | 20 mg |
| Magnesium stearate | 5 mg |

The drug substance is blended with microcrystalline cellulose, crosscarmellose sodium and magnesium stearate, then compressed into tablets.

2. Chewable oral tablet

| | |
|---|---|
| Drug substance | 100 mg |
| Xylitol | 865 mg |
| Peppermint flavour | 5 mg |
| Aspartame | 10 mg |
| Polyvinylpyrollidone | 15 mg |
| Magnesium stearate | 5 mg |

The drug substance, xylitol, aspartame and polyvinylpyrollidone are blended together and granulated with water, then dried. This granule is mixed with the peppermint flavour and magnesium stearate, then compressed into tablets.

3. Aqueous Oral Solution

| | |
|---|---|
| Drug substance | 100 mg |
| Hydroxypropylmethyl cellulose | 150 mg |
| Sodium propylhydroxybenzoate | 1 mg |
| Sodium methylhydroxybenzoate | 2 mg |
| Orange flavour | 10 mg |
| Sodium saccharin | 5 mg |
| Sucrose | 800 mg |
| Suitable buffers | qs |
| Purified water to | 5 mls |

Dissolve the drug substance and all the excipients in most of the purified water and mix. Make to volume and mix Suitable buffers may be added to control the pH in the region of maximum stability.

4. Non-Aqueous Oral Suspension

| | |
|---|---|
| Drug substance | 100 mg |
| Aspartame | 50 mg |
| Grapefruit flavour | 25 mg |
| Mannitol | 800 mg |
| Colloidal silica | 10 mg |
| Fractionated coconut oil | 5 mls |

Disperse the drug substance and mannitol in the bulk of the fractionated coconut oil by high shear mixing. Add the remaining ingredients and mix. Make to volume with fractionated coconut oil and mix.

5. Ointment

| | |
|---|---|
| Drug substance | 200 mg |
| White Soft Paraffin | 9800 mg |

Melt the white soft paraffin, add the drug and mix. Continue to mix until the ointment starts to congeal.

6. Injection

| | |
|---|---|
| Drug substance | 40 mg |
| Suitable buffers | qs |
| Suitable antioxidants | qs |
| Suitable chelating agents | qs |
| Water for injections to | 2 mls |

Dissolve the drug substance in most of the water for injections. Suitable buffering agents may be added to control the pH to the region of optimum stability. Suitable antioxidants and chelating agents may be added to improve the stability of the injection. Make to mark with water for injections. Fill into ampoules or vials, then sterilise by autoclaving. Alternatively, sterilise by filtration and fill aseptically.

Antifungal Activity

Compounds of formula (I) have been tested for anti fungal activity in a standard in vitro screen and the minimum inhibiting concentration (MIC; μg/ml) determined for each compound against a variety of clinically relevant pathogens. The results obtained with representative compounds of the invention are given below.

The compounds of the invention are essentially non-toxic at therapeutically useful levels. For example the compound of example 8 when administered at a dose of 50 mg/kg po was active in protecting male mice infected with C. albicans 4711E. The $LD_{50}$ value for the compound of example 8, in male mice is >1000 mg/kg po.

|  | MICs μg/ml Example No. | | | | | | | | | | | | | |
|---|---|---|---|---|---|---|---|---|---|---|---|---|---|---|
| ORGANISM | 1 | 6 | 13 | 14 | 16 | 20 | 34 | 37 | 43 | 51 | 52 | 4 | 59 | 68 |
| C. albicans 1208E | 0.500 | 0.008 | 0.015 | 0.030 | 0.001 | ≦0.001 | 0.001 | 0.060 | 0.001 | 0.120 | 0.004 | ≦0.001 | 0.015 | 0.060 |
| C. albicans 2005E | 0.120 | 0.001 | 0.008 | 0.015 | 0.001 | ≦0.001 | 0.001 | 0.001 | 0.001 | 0.030 | 0.001 | ≦0.001 | ≦0.001 | 0.060 |
| C. albicans 2402E | 0.500 | 0.008 | 0.015 | 0.060 | 0.001 | ≦0.001 | 0.001 | 0.060 | 0.001 | 0.120 | 0.008 | ≦0.001 | 0.008 | 0.002 |
| C. albicans 4711 | 0.250 | 0.004 | 0.015 | 0.030 | 0.001 | ≦0.001 | 0.001 | 0.030 | 0.001 | 0.120 | 0.004 | ≦0.001 | 0.002 | 0.030 |
| C. tropicalis 2808E | 1.000 | 0.120 | 0.120 | 16.00 | 0.008 | 0.008 | 0.150 | 0.500 | 0.500 | 0.500 | 0.030 | ≦0.001 | 0.015 | 0.250 |
| C. psuedotropicalis 2371E | 0.060 | 0.004 | 0.008 | 0.060 | <0.001 | 0.004 | <0.001 | 0.060 | <0.001 | 0.008 | 0.001 | ≦0.01 | 0.015 | 0.015 |
| C. glabrata 2375E | 31.00 | 31.00 | 8.00 | 8.00 | 8.00 | 0.500 | 1.000 | 4.00 | 4.00 | 16.00 | 8.00 | 8.00 | 16.0 | 31.00 |
| C. glabrata 2376E | 31.00 | 31.00 | 8.00 | 16.00 | 8.00 | 0.500 | 1.000 | 8.00 | 4.00 | 16.00 | 8.00 | 8.00 | 16.0 | 31.00 |
| C. neoformans 2867E | >125 | 8.00 | 0.500 | 31.00 | 1.00 | 0.250 | <0.250 | <0.250 | 2.00 | >125 | 1.00 | 2.00 | 1.00 | 1.00 |

We claim:

1. A method of treating a fungal infection which comprises administering a therapeutically effective amount of a compound of the formula:

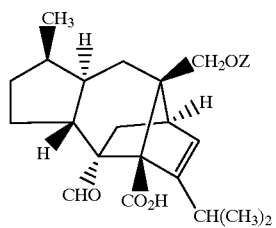

(I)

wherein Z is a tetrahydro-pyrano group selected from

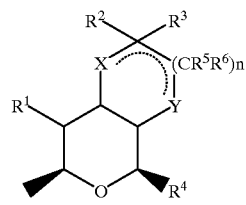

(a)

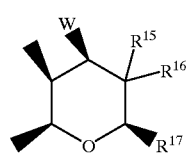

(b)

and pharmaceutically acceptable salts and solvates or metabolically labile derivatives thereof,
wherein $R^1$ represents hydrogen, halogen, hydroxyl, $C_{1-4}$-alkoxy or acyloxy;
$R^2$ and $R^3$ may each independently represent hydrogen, $C_{1-6}$alkyl or $C_{1-4}$alkoxy $C_{1-4}$alkyl or $R^2$ and $R^3$ may together with the carbon atom to which they are attached represent C=O, C=S or $C_{3-8}$cycloalkyl;
$R^4$ represents hydrogen or $CH_2R^7$ where $R^7$ is hydrogen, hydroxyl, $C_{1-4}$alkoxy or a group $OCOR^8$ in which $R^8$ is $C_{1-4}$alkyl or aryl;
$R^5$ and $R^6$ may each independently represent hydrogen, $C_{1-6}$alkyl or $C_{1-4}$alkoxy $C_{1-4}$alkyl or $R^5$ and $R^6$ may together with the carbon atom to which they are attached represent C=O, C=S or $C_{3-8}$cycloalkyl;
n represents zero or 1;
X and Y may each independently represent oxygen, sulphur or $CR^9R^{10}$ where $R^9$ and $R^{10}$ may each independently represent hydrogen, $C_{1-6}$alkyl, $C_{1-4}$alkoxy or $C_{1-4}$alkoxyC$_{1-4}$alkyl or $R^9$ and $R^{10}$ may together with the carbon atom to which they are attached represent C=O, C=S, $C_{3-8}$cycloalkyl or C=CHR$^{11}$ where $R^{11}$ represents hydrogen or $C_{1-4}$alkyl; or when X or Y is oxygen and n is zero then —Y—$CR^2R^3$ or —X—$R^2R^3$— respectively may also represent —N=CR$^3$— or —NR$^{12}$—CR$^2R^3$— where $CR^2$ and $R^3$ are C=O and $R^{12}$ is $C_{1-4}$alkyl an acyl group COR$^{13}$ where $R^{13}$ is $C_{1-6}$alkyl or when Y is oxygen and n is zero X may be represent the group CR$^{11}$ which is attached to the pyran ring by a double bond;
$R^{15}$ represents hydrogen, halogen, azido, $C_{1-6}$alkyl, hydroxy, $C_{1-6}$alkoxy optionally substituted by 1 or 2 hydroxy or a ketal thereof or 1 or 2 $C_{1-3}$ alkoxy groups arylC$_{1-4}$alkoxy, $C_{3-6}$ alkenyloxy, a group OCOR$^{18}$ where $R^{18}$ is arylC$_{1-4}$alkoxy or a $C_{1-10}$alkyl group optionally containing one or two double bonds or $C_{1-6}$ alkoxycarbonyl $C_{1-4}$alkoxy, and $R^{16}$ represents hydrogen or $R^{15}$ and $R^{16}$ may together with the carbon atom to which they are attached represent C=O or C=CH$_2$;
$R^{17}$ represents $CH_2R^{19}$ where $R^{19}$ is hydrogen, hydroxyl, $C_{1-14}$alkoxy or a group $OCOR^{20}$ in which $R^{20}$ is $C_{1-4}$alkyl; and
W represents an oxygen or sulphur atom or a $CH_2$ group; and the dotted line in group (a) indicates the optional presence of an additional bond;
together with one or more other antifungal agents.

2. The method of claim 1 wherein the other antifungal agent is polienic derivative.

3. The method of claim 1 wherein the other antifungal agent is an azole derivative.

4. The method of claim 1 wherein the other antifungal agent is 5-Flurocytosine.

5. The method of claim 1 wherein the other antifungal agent is a Pneumoncandin or Echinocandine derivative.

6. The method of claim 1 wherein the other antifungal agent is Intraconzaole, Flucytosine, Fluconazole or Amphotericin B.

* * * * *